US009582877B2

(12) United States Patent
Fu et al.

(10) Patent No.: US 9,582,877 B2
(45) Date of Patent: Feb. 28, 2017

(54) METHODS AND SYSTEMS FOR DIGITALLY COUNTING FEATURES ON ARRAYS

(71) Applicant: Cellular Research, Inc., Palo Alto, CA (US)

(72) Inventors: Glenn Fu, Menlo Park, CA (US); Roger Rudoff, Menlo Park, CA (US); David Stern, Menlo Park, CA (US); George T. Wu, Menlo Park, CA (US); Stephen P. A. Fodor, Menlo Park, CA (US); Geoffrey Facer, Menlo Park, CA (US)

(73) Assignee: Cellular Research, Inc., Menlo Park, CA (US)

( * ) Notice: Subject to any disclaimer, the term of this patent is extended or adjusted under 35 U.S.C. 154(b) by 0 days.

(21) Appl. No.: 14/508,911

(22) Filed: Oct. 7, 2014

(65) Prior Publication Data

US 2016/0055632 A1    Feb. 25, 2016

Related U.S. Application Data

(60) Provisional application No. 61/887,853, filed on Oct. 7, 2013.

(51) Int. Cl.
| | |
|---|---|
| G06K 9/00 | (2006.01) |
| G06T 7/00 | (2006.01) |
| G01N 21/27 | (2006.01) |
| G01N 21/64 | (2006.01) |
| G06T 7/20 | (2006.01) |

(52) U.S. Cl.
CPC ......... *G06T 7/0012* (2013.01); *G01N 21/274* (2013.01); *G01N 21/6452* (2013.01); *G06T 7/208* (2013.01); *G06T 2207/10056* (2013.01); *G06T 2207/10064* (2013.01); *G06T 2207/30072* (2013.01); *G06T 2207/30242* (2013.01)

(58) Field of Classification Search
USPC .................................................. 382/128–134
See application file for complete search history.

(56) References Cited

U.S. PATENT DOCUMENTS

| | | |
|---|---|---|
| 4,725,536 A | 2/1988 | Fritsch et al. |
| 5,124,246 A | 6/1992 | Urdea et al. |
| 5,149,625 A | 9/1992 | Church et al. |
| 5,200,314 A | 4/1993 | Urdea |

(Continued)

FOREIGN PATENT DOCUMENTS

| | | |
|---|---|---|
| EP | 0799897 A1 | 10/1997 |
| EP | 1647600 A2 | 4/2006 |

(Continued)

OTHER PUBLICATIONS

Casbon, et al. A method for counting PCR template molecules with application to next-generation sequencing. Nucleic Acids Res. Jul. 2011;39(12):e81. doi: 10.1093/nar/gkr217. Epub Apr. 13, 2011

(Continued)

*Primary Examiner* — Alex Liew
(74) *Attorney, Agent, or Firm* — Knobbe, Martens, Olson & Bear, LLP

(57) ABSTRACT

Methods, systems and platforms for digital imaging of multiple regions of an array, and detection and counting of the labeled features thereon, are described.

44 Claims, 28 Drawing Sheets

(56) References Cited

U.S. PATENT DOCUMENTS

| | | |
|---|---|---|
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,117,631 A | 9/2000 | Nilsen |
| 6,124,092 A | 9/2000 | O'Neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,235,475 B1 | 5/2001 | Brenner et al. |
| 6,268,152 B1 | 7/2001 | Fodor et al. |
| 6,284,460 B1 | 9/2001 | Fodor et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,395,491 B1 | 5/2002 | Fodor et al. |
| 6,406,848 B1 | 6/2002 | Bridgham et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,489,114 B2 | 12/2002 | Laayoun et al. |
| 6,492,121 B2 | 12/2002 | Kurane et al. |
| 6,512,105 B1 | 1/2003 | Hogan et al. |
| 6,514,699 B1 | 2/2003 | O'Neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,849,404 B2 | 2/2005 | Park et al. |
| 6,852,488 B2 | 2/2005 | Fodor et al. |
| 6,858,412 B2 | 2/2005 | Willis et al. |
| 7,155,050 B1* | 12/2006 | Sloge ............ G06K 9/00127 382/133 |
| 7,424,368 B2 | 9/2008 | Huang et al. |
| 7,537,897 B2 | 5/2009 | Brenner et al. |
| 7,544,473 B2 | 6/2009 | Brenner |
| 7,635,566 B2 | 12/2009 | Brenner |
| 7,822,555 B2 | 10/2010 | Huang et al. |
| 7,824,889 B2 | 11/2010 | Vogelstein et al. |
| 7,915,015 B2 | 3/2011 | Vogelstein et al. |
| 8,148,068 B2 | 4/2012 | Brenner |
| 8,168,385 B2 | 5/2012 | Brenner |
| 8,241,850 B2 | 8/2012 | Brenner |
| 8,298,767 B2 | 10/2012 | Brenner et al. |
| 8,318,433 B2 | 11/2012 | Brenner |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,563,274 B2 | 10/2013 | Brenner et al. |
| 8,603,749 B2 | 12/2013 | Gillevet |
| 8,679,756 B1 | 3/2014 | Brenner et al. |
| 8,685,678 B2 | 4/2014 | Casbon et al. |
| 8,835,358 B2 | 9/2014 | Fodor et al. |
| 2002/0072058 A1 | 6/2002 | Voelker et al. |
| 2002/0168665 A1* | 11/2002 | Okawa ............ G01N 33/54373 435/6.1 |
| 2003/0003490 A1 | 1/2003 | Fan et al. |
| 2003/0049616 A1 | 3/2003 | Brenner et al. |
| 2003/0104436 A1 | 6/2003 | Morris et al. |
| 2003/0186251 A1 | 10/2003 | Dunn et al. |
| 2003/0207300 A1 | 11/2003 | Matray et al. |
| 2004/0096892 A1 | 5/2004 | Wang et al. |
| 2004/0146901 A1 | 7/2004 | Morris et al. |
| 2004/0157243 A1 | 8/2004 | Huang et al. |
| 2004/0259118 A1 | 12/2004 | Macevicz |
| 2005/0019776 A1 | 1/2005 | Callow et al. |
| 2005/0170373 A1 | 8/2005 | Monforte |
| 2005/0250147 A1 | 11/2005 | Macevicz |
| 2006/0035258 A1 | 2/2006 | Tadakamalla et al. |
| 2006/0041385 A1* | 2/2006 | Bauer ...................... G01N 1/30 702/19 |
| 2006/0073506 A1 | 4/2006 | Christians et al. |
| 2006/0211030 A1 | 9/2006 | Brenner |
| 2007/0020640 A1 | 1/2007 | McCloskey et al. |
| 2007/0065823 A1 | 3/2007 | Dressman et al. |
| 2008/0299609 A1 | 12/2008 | Kwon et al. |
| 2009/0105959 A1 | 4/2009 | Braverman et al. |
| 2009/0137407 A1 | 5/2009 | Church et al. |
| 2009/0226891 A2 | 9/2009 | Nova et al. |
| 2009/0252414 A1* | 10/2009 | Suzuki ............... G01N 21/6456 382/170 |
| 2009/0283676 A1* | 11/2009 | Skoglund ............ G01N 23/046 250/307 |
| 2009/0298709 A1 | 12/2009 | Ma |
| 2010/0069250 A1 | 3/2010 | White et al. |
| 2010/0105886 A1 | 4/2010 | Woudenberg et al. |
| 2010/0291666 A1 | 11/2010 | Collier et al. |
| 2010/0323348 A1 | 12/2010 | Hamady et al. |
| 2011/0038507 A1* | 2/2011 | Hager ..................... G01N 21/33 382/100 |
| 2011/0059436 A1 | 3/2011 | Hardin et al. |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0294689 A1 | 12/2011 | Namsaraev |
| 2012/0071331 A1 | 3/2012 | Casbon |
| 2012/0163681 A1* | 6/2012 | Lohse ................ G01N 21/6428 382/128 |
| 2012/0220494 A1 | 8/2012 | Samuels |
| 2012/0316074 A1 | 12/2012 | Saxonov |
| 2013/0005585 A1 | 1/2013 | Anderson et al. |
| 2013/0022977 A1 | 1/2013 | Lapidus et al. |
| 2013/0116130 A1 | 5/2013 | Fu et al. |
| 2013/0210643 A1 | 8/2013 | Casbon et al. |
| 2013/0224743 A1 | 8/2013 | Casbon et al. |
| 2013/0237458 A1 | 9/2013 | Casbon et al. |
| 2013/0267424 A1 | 10/2013 | Casbon et al. |
| 2014/0155295 A1 | 6/2014 | Hindson et al. |
| 2014/0206547 A1 | 7/2014 | Wang |
| 2014/0227684 A1 | 8/2014 | Hindson et al. |
| 2014/0228255 A1 | 8/2014 | Hindson et al. |
| 2014/0235506 A1 | 8/2014 | Hindson et al. |
| 2014/0287963 A1 | 9/2014 | Hindson et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005185 A1 | 1/2015 | Fodor et al. |
| 2015/0005199 A1 | 1/2015 | Hindson et al. |

(56) References Cited

U.S. PATENT DOCUMENTS

| | | |
|---|---|---|
| 2015/0005200 A1 | 1/2015 | Hindson et al. |
| 2015/0066385 A1 | 3/2015 | Schnall-Levin et al. |
| 2015/0298091 A1 | 10/2015 | Weitz |
| 2015/0307874 A1 | 10/2015 | Jaitin |
| 2016/0222378 A1 | 8/2016 | Fodor et al. |
| 2016/0244828 A1 | 8/2016 | Mason |
| 2016/0253584 A1 | 9/2016 | Fodor et al. |
| 2016/0257993 A1 | 9/2016 | Fu et al. |
| 2016/0265069 A1 | 9/2016 | Fan et al. |
| 2016/0289669 A1 | 10/2016 | Fan et al. |
| 2016/0289740 A1 | 10/2016 | Fu et al. |
| 2016/0312276 A1 | 10/2016 | Fu et al. |

FOREIGN PATENT DOCUMENTS

| | | |
|---|---|---|
| EP | 1 845 160 | 10/2007 |
| EP | 2 805 769 | 11/2014 |
| WO | WO 97/10365 A1 | 3/1997 |
| WO | WO 99/28505 A1 | 6/1999 |
| WO | WO 00/58516 A2 | 10/2000 |
| WO | WO 02/056014 A2 | 7/2002 |
| WO | WO 2005/080604 A2 | 9/2005 |
| WO | WO 2005/111242 A2 | 11/2005 |
| WO | WO 2006/071776 A2 | 7/2006 |
| WO | WO 2006/102264 A1 | 9/2006 |
| WO | WO 2009/152928 A2 | 12/2009 |
| WO | WO 2009/152928 A3 | 2/2010 |
| WO | WO 2010/117620 A2 | 10/2010 |
| WO | WO 2011/143659 A2 | 11/2011 |
| WO | WO 2011/155833 | 12/2011 |
| WO | WO 2012/042374 A2 | 4/2012 |
| WO | WO 2012/048341 A1 | 4/2012 |
| WO | WO 2012/083225 A2 | 6/2012 |
| WO | WO 2012/129363 A2 | 9/2012 |
| WO | WO 2012/142213 A2 | 10/2012 |
| WO | WO 2012/148477 A1 | 11/2012 |
| WO | WO 2013/019075 A2 | 2/2013 |
| WO | WO 2013/130674 A1 | 9/2013 |
| WO | WO 2013/176767 | 11/2013 |
| WO | WO 2014/018460 A1 | 1/2014 |
| WO | WO 2014/028537 A1 | 2/2014 |
| WO | WO 2014/093676 A1 | 6/2014 |
| WO | WO 2014/124336 A2 | 8/2014 |
| WO | WO 2014/124338 A1 | 8/2014 |
| WO | WO 2014/210353 A2 | 12/2014 |
| WO | WO 2015/031691 A1 | 3/2015 |

OTHER PUBLICATIONS

Fan, et al. Expression profiling. Combinatorial labeling of single cells for gene expression cytometry. Science. Feb. 6, 2015;347(6222):1258367. doi: 10.1126/science.1258367.

Gunderson, et al. Decoding Randomly Ordered DNA Arrays. Genome Research pp. 871-878.

International search report and written opinion dated Feb. 3, 2015 for PCT Application No. US2014/053301.

International search report dated Aug. 6, 2014 for PCT Application No. GB1408829.8.

Lee, et al. Highly Multiplexed Subcellular RNA Sequencing in Situ. Sciencexpress, Feb. 27, 2014, p. 1-6.

Lovatt, et al. Trancriptome in vivo analysis (TIVA) of spatially defined single cells in live tissue. Nature Methods, vol. 11, No. 2, Feb. 2014, pp. 190-195.

Office action dated Feb. 18, 2015 for U.S. Appl. No. 14/540,007.
Office action dated Feb. 26, 2015 for U.S. Appl. No. 14/540,029.
Office action dated Mar. 19, 2015 for U.S. Appl. No. 14/540,018.
U.S. Appl. No. 14/281,706, filed May 19, 2014, Fodor et al.
U.S. Appl. No. 14/326,424, filed Jul. 8, 2014, Fodor et al.
U.S. Appl. No. 14/326,434, filed Jul. 8, 2014, Fodor et al.
U.S. Appl. No. 14/326,443, filed Jul. 8, 2014, Fodor et al.
U.S. Appl. No. 14/326,448, filed Jul. 8, 2014, Fodor et al.
U.S. Appl. No. 14/326,452, filed Jul. 8, 2014, Fodor et al,.
U.S. Appl. No. 14/326,454, filed Jul. 8, 2014, Fodor et al.
U.S. Appl. No. 14/381,488, filed Aug. 27, 2014, Fu.
U.S. Appl. No. 14/472,363, filed Aug. 28, 2014, Fan et al.
U.S. Appl. No. 14/540,007, filed Nov. 12, 2014, Fu et al.
U.S. Appl. No. 14/540,018, filed Nov. 12, 2014, Fu et al.
U.S. Appl. No. 14/540,029, filed Nov. 12, 2014, Fu et al.
U.S. Appl. No. 61/384,001, filed Sep. 17, 2010, Hopping et al.
U.S. Appl. No. 61/432,119, filed Jan. 12, 2011, Casbon et al.

Alkan, et al. Personalized copy number and segmental duplication maps using next-generation sequencing. Nat Genet. Oct. 2009;41(10):1061-7. doi: 10.1038/ng.437. Epub Aug. 30, 2009.

Ansorge. Next-generation DNA sequencing techniques. New Biotechnology, 25(4): 195-203 (2009).

Atanur, et al. The genome sequence of the spontaneously hypertensive rat: Analysis and functional significance. Genome Res. Jun. 2010;20(6):791-803. doi: 10.1101/gr.103499.109. Epub Apr. 29, 2010.

Audic, et al. The Significance of Digital Gene Expression Profiles. Genome Research, 7: 986-995 (1997).

Bendall, et al. Single-cell mass cytometry of differential immune and drug responses across a human hematopoietic continuum. Science, May 6, 2011;332(6030):687-96. doi: 10.1126/science.1198704.

Bonaldo, et al. Normalization and subtraction; two approaches to facilitate gene discovery. Genome Res. Sep. 1996;6(9):791-806.

Braha, et al. Simultaneous stochastic sensing of divalent metal ions. Nature Biotechnology, 18: 1005-1007 (2000).

Bratke, et al. Differential expression of human granzymes A, B, and K in natural killer cells and during CD8+ T cell differentiation in peripheral blood. Eur J Immunol. Sep. 2005;35(9):2608-14.

Brenner, et al. Gene expression analysis by massively parallel signature sequencing (MPSS) on microbead arrays. Nature Biotechnology, 18: 630-634 (2000).

Brenner, et al. In vitro cloning of complex mixtures of DNA on microbeads; physical separation of differentially expressed cDNAs. Proc Natl Acad Sci U S A. Feb. 15, 2000;97(4):1665-70.

Carr, et al. Inferring relative proportions of DNA variants from sequencing electropherograms. Bioinformatics. Dec. 15, 2009;25(24):3244-50. doi: 10.1093/bioinformatics/btp583. Epub Oct. 9, 2009.

Casbon, et al. A method for counting PCR template molecules with application to next-generation sequencing. Nucleic Acids Res. Jul. 2011;39(12):e81. doi: 10.1093/nar/gkr217. Epub Apr. 13, 2001.

Castle, et al. DNA copy number, including telomeres and mitochondria, assayed using next-generation sequencing. BMC Genomics. Apr. 16, 2010;11:244. doi: 10.1186/1471-2164-11-244.

Chang, et al. Detection of allelic imbalance in ascitic supernatant by digital single nucleotide polymo ahism analysis. Clin Cancer Res, Aug. 2002;8(8):2580-5.

Chee, et al. Accessing genetic information with high-density DNA arrays. Science, 274: 610-6 14 (1996).

Chee. Enzymatic multiplex DNA sequencing. Nucleic Acids Research, 19(12): 3301-3305 (1991).

Church, et al. Multiplex DNA sequencing. Science, 240: 185-188 (1988).

Costello, et al. Discovery and characterization of artifactual mutations in deep coverage targeted capture sequencing data due to oxidative DNA damage during sample preparation. Nucleic Acids Res, Apr. 1, 2013;41(6):e67. doi: 10.1093/narigks1443. Epub Jan. 8, 2013.

Cox. Bar coding objects with DNA. Analyst. May 2001;126(5):545-7.

Craig, et al. Identification of genetic variants using bar-coded multiplexed sequencing. Nat Methods. Oct. 2008;5(10):887-93. doi: 10.1038/nmeth.1251. Epub. Sep. 14, 2008.

Daines, et al. High-throughput multiplex sequencing to discover copy number variants in *Drosophila*. Genetics. Aug. 2009;182(4):935-41. doi: 10.1534/genetics.109.103218. Epub Jun. 15, 2009.

D'Antoni, et al. Rapid quantitative analysis using a single molecule counting approach. Anal Biochem. May 1, 2006;352(1):97-l09. Epub Feb. 10, 2006.

(56) References Cited

OTHER PUBLICATIONS

Daser, et al. Interrogation of genomes by molecular copy-number counting (MCC) Nature Methods, 3(6): 447-453 (2006).
De Saizieu, et al. Bacterial transcript imaging by hybridization of total RNA to oligonucleotide arrays. Nature Biotechnology, 16: 45-48 (1998).
Fan, et al. Microfluidic digital PCR enables rapid prenatal diagnosis of fetal aneuploidy. Am Obstet Gynecol. 2009; 200:543.e1-543.e7.
Fan, et al. Non-invasive prenatal measurement of the fetal genome. Nature. Jul. 19, 2012;487(7407):320-4. doi: 10.1038/nature11251.
Fan, et al. Parallel Genotyping of Human SNPs Using Generic High-density Oligonucleotide Tag Arrays. Genome Research, 10: 853-860 (2000).
Fu, et al. Counting individual DNA molecules by the stochastic attachment of diverse labels. Proc Natl Acad Sci U S A. May 31, 2011;108(22):9026-31. Epub May 11, 2011.
Fu, et al. Digital encoding of cellular mRNAs enabling precise and absolute gene expression measurement by single-molecule counting. Anal Chem. Mar. 18, 2014;86(6):2867-70. doi: 10.1021/ac500459p. Epub Mar. 4, 2014.
Gerry, et al. Universal DNA microarray method for multiplex detection of low abundance point mutations. Journal of Molecular Biology, 292(2): 251-262 (1999).
Gillespie, D. Exact stochastic simulation of coupled chemical reactions, The Journal of Physical Chemistry, 81(25): 2340-2361 (1977).
Grant, et al. SNP genotyping on a genome-wide amplified DOP-PCR template. Nucleic Acids Res. Nov. 15, 2002;30(22):e125.
Gundry, et al. Direct mutation analysis by high-throughput sequencing: from germline to low-abundant, somatic variants. Mutat Res. Jan. 3, 2012;729(1-2):1-15. doi: 10.1016/turfmmm.2011.10.001. Epub Oct. 12, 2011.
Gundry, et al. Direct, genome-wide assessment of DNA mutations in single cells. Nucleic Acids Res. Mar. 2012;40(5):2032-40. doi: 10.1093/nar/g,kr949. Epub Nov. 15, 2011.
Hacia, et al. Determination of ancestral alleles for human single-nucleotide polymorphisms using high-density oligonucleotide arrays. Nature Genetics, 22: 164-167 (1999).
Hamady, et al. Error-correcting barcoded primers for pyrosequencing hundreds of samples in multiplex. Nat Methods. Mar. 2008;5(3):235-7. doi: 10.1038/nmeth.1184. Epub Feb. 10, 2008.
Hensel, et al. Simultaneous identification of bacterial virulence genes by negative selection. Science. Jul. 21, 1995;269(5222):400-3.
Hiatt, et al. Parallel, tag-directed assembly of locally derived short sequence reads. Nat Methods. Feb. 2010;7(2):119-22. doi: 10.1038/nmeth,1416. Epub Jan. 17, 2010.
Hiatt, et al. Single molecule molecular inversion probes for targeted, high-accuracy detection of low-frequency variation. Genome Res. May 2013;23(5):843-54. doi: 10.1101/gr.147686.112. Epub Feb. 4, 2013.
Hollas, et al. A stochastic approach to count RNA molecules using DNA sequencing methods. Lecture Notes in Computer Science, 2812: 55-62 (2003).
Hug, et al. Measurement of the number of molecules of a single mRNA species in a complex mRNA preparation. J Theor Biol. Apr. 21, 2003;221(4):615-24.
Ingolia, et al. Genotne-wide analysis in vivo of translation with nucleotide resolution using ribosome profiling. Science. Apr. 10, 2009;324(5924):218-23. Epub Feb. 12, 2009.
International search report and written opinion dated Jun. 6, 2012 for PCT/US2011/065291.
International search report and written opinion dated Aug. 16, 2013 for PCT/US2013/027891.
International search report and written opnion dated May 7, 2012 for PCT/IB2011/003160.
Islam, et al. Characterization of the single-cell transcriptional landscape by highly multiplex RNA-seq. Genome Res. Jul. 2011;21(7):1160-7. doi: 10.1101/gr.110882.110. Epub May 4, 2011.

Jabara, et al. Accurate sampling and deep sequencing of the HIV-1 protease gene using a Primer ID, Dec. 3, 2011, PNAS, vol. 108, No. 50, p. 20166-20171.
Kanagawa. Bias and artifacts in multitemplate polymerase chain reactions (PCR), 2003, Journal of Bioscience and Bioengineering, vol. 96, No. 4, p. 317-323.
Kinde, et al. Detection and quantification of rare mutations with massively parallel sequencing, Jun. 7, 2011, PNAS, vol. 108, No. 23, p. 9530-9535.
Kivioja, et al. Counting absolute numbers of molecules using unique molecular identifiers. Nat Methods. Nov. 20, 2011;9(1):72-4. doi: 10.1038/nmeth.1778.
Koboldt, et al. VarScan: variant detection in massively parallel sequencing of individual and pooled samples. Bioinformatics. Sep. 1, 2009;25(17):2283-5. doi: 10.1093/bioinfoimatics/btp373. Epub Jun. 19, 2009.
Konig, et al. iCLIP reveals the function of hnRNAP particles in splicing at individual nucleotide resolution, Jul. 2010, Nature Structural & Molecular Biology, 17(7):909-916.
Larson, et al. A single molecule view of of gene expression. Trends Cell Biol. Nov. 2009;19(11):630-7. Epub Oct. 8, 2009.
Lizardi, et al. Mutation detection and single-molecule counting using isothermal rolling-circle amplification. Nat Genet. Jul. 1998;19(3):225-32.
Lockhart, et al. Expression monitoring by hybridization to high-density oligonucleotide arrays. Nature Biotechnology, 14: 1675-1680 (1996).
Lucito, et al. Representational Oligonucleotide Microarray Analysis: A High-Resolution Method to Detect Genome Copy Number Variation. Genome Research, 13: 2291-2305.
Maamar, et al. Noise in Gene Expression Determines Cell Fate in Bacillus subtilis. Science, 317: 526-529 (2007).
Makrigiorgos, et al. A PCR-based amplification method retaining the quantitative difference between two complex genomes. Nat Biotechnol. Sep. 2002;20(9):936-9. Epub Aug. 5, 2002.
McCloskey, et al. Encoding PCR products with batch-stamps and barcodes. Biochem Genet. Dec. 2007;45(11-12):761-7. Epub Oct. 23, 2007.
Medvedev, et al. Detecting copy number variation with mated short reads. Genome Res. Nov. 2010,20(11):1613-22. doi: 10.1101/gr.106344.110. Epub Aug. 30, 2010.
Mei, et al. Identification of recurrent regions of Copy-Number Variants across multiple individuals. BMC Bioinformatics. Mar. 22, 2010;11:147. doi: 10.1186/1471-2105-11-147.
Mortazavi, et al. Mapping and quantifying mammalian transcriptomes by RNA-Seq. Nat. Methods. 2008; 5, 621-628.
Newell, et al. Cytometry by time-of-flight shows combinatorial cytokine expression and virus-specific cell niches within a continuum of CD8+ T cell phenotypes. Immunity. Jan. 27, 2012;36(1):142-52. doi: 10.1016/j.immuni.2012.01.002.
Notice of allowance dated Mar. 21, 2014 for U.S. Appl. No. 12/969,581.
Notice of allowance dated Jun. 19, 2014 for U.S. Appl. No. 12/969,581.
Notice of allowance dated Aug. 22, 2014 for U.S. Appl. No. 12/969,581.
Office action dated Oct. 3, 2013 for U.S. Appl. No. 12/969,581.
Ogino, et al. Quantification of PCR bias caused by a single nucleotide polymorphism in SMN gene dosage analysis. J Mol Diagn. Nov. 2002;4(4):185-90.
Park, et al. Discovery of common Asian copy number variants using integrated high-resolution array CGH and massively parallel DNA sequencing, Nat Genet. May 2010;42(5):400-5, doi: 10.1038/ng.555. Epub Apr. 4, 2010.
Pihlak, et al. Rapid genome sequencing with short universal tiling probes. Nature Biotechnology, 26: 676-684 (2008).
Pinkel, et al, Comparative Genomic Hybridization. Annual Review of Genomics and Human Genetics, 6: 331-354 (2005).
Pleasance, et al. A small-cell lung cancer genome with complex signatures of tobacco exposure. Nature. Jan. 14, 2010;463(7278):184-90. doi: 10.1038/nature08629. Epub Dec. 16, 2009.

(56) References Cited

OTHER PUBLICATIONS

Qiu, et al. DNA sequence-based "bar codes" for tracking the origins of expressed sequence tags from a maize cDNA library constructed using multiple mRNA sources Plant Physiol. Oct. 2003;133(2):475-81.
Response with alllowed claims dated Mar. 4, 2014 for U.S. Appl. No. 12/969,581.
Schmitt, et al. Detection of ultra-rare mutations by next-generation sequencing. Proc Natl Acad Sci U S A. Sep. 4, 2012;109(36):14508-13. doi: 10.1073/pnas.1208715109. Epub Aug. 1, 2012.
Sebat, et al. Large-Scale Copy Number Polymorphism in the Human Genome. Science, 305: 525-528 (2004).
Shalek, et al. Single-cell transcriptomics reveals bimodality in expression and splicing in immune cells. Nature. Jun. 13, 2013;498(7453):236-40. doi: 10.1038/nature12172. Epub May 19, 2013.
Shiroguchi, et al. Digital RNA sequencing minimizes sequence-dependent bias and amplification noise with optimized single-molecule barcodes, PNAS, Jan. 24, 2012; 109(4):1347-52.
Shoemaker, et al. Quantitative phenotypic analysis of yeast deletion mutants using a highly parallel molecular bar-coding strategy. Nature Genetics, 14: 450-456 (1996).
Simpson, et al. Copy number variant detection in inbred strains from short read sequence data. Bioinformatics. Feb. 15, 2010;26(4):565-7. doi: 10.1093/bioinformatics/btp693. Epub Dec. 18, 2009.
Smith, et al. Highly-multiplexed barcode sequencing: an efficient method for parallel analysis of pooled samples. Nucleic Acids Research, 38(13): e142 (2010).
Tan, et al. Genome-wide comparison of DNA hydroxymethylation in mouse embryonic stem cells and neural progenitor cells by a new comparative hMeDIP-seq method. Nucleic Acids Res. Apr. 2013;41(7):e84. doi: 10.1093/nar/gkt091. Epub Feb. 13, 2013.
Taudien, et al. Haplotyping and copy number estimation of the highly polymorphic human beta-defensin locus on 8p23 by 454 amplicon sequencing. BMC Genomics. Apr. 19, 2010;11:252. doi: 10.1186/1471-2164-11-252.
Tomaz, et al. Differential methylation as a cause of allele dropout at the imprinted GNAS locus. Genet Test Mol Biomarkers. Aug. 2010;14(4):455-60. doi: 10.1089/glinb.2010.0029.
Treutlein, et al. Reconstructing lineage hierarchies of the distal lung epithelium using single-cell RNA-seq. Nature. May 15, 2014;509(7500):371-5. doi; 10.1038/nature13173. Epub Apr. 13, 2014.
Velculescu, et al. Characterization of the Yeast Transcriptome. Cell, 88: 243-251 (1997).
Velculescu, et al. Serial Analysis of Gene Expression. Science, 270: 484-487 (1995).
Vogelstein, et al. Digital PCR. Proc. Natl. Acad. Sci., 96(16): 9236-9241 (1999).
Walker, et al. Isothermal in vitro amplification of DNA by a restriction enzyme/DNA polymerase system, Proc Nati Acad Sci U S A. Jan. 1, 1992;89(1):392-6.
Walsh, et al. Detection of inherited mutations for breast and ovarian cancer using genomic capture and massively parallel sequencing. Proc Natl Acad Sci U S A. Jul. 13, 2010;107(28):12629-33. doi: 10.1073lpnas.1007983107. Epub Jun. 28, 2010.
Wang, et al. iCLIP predicts the dual splicing effects of TIA-RNA interactions, Oct. 2010, PLoS Biol, 8(10):e1000530.
Wang, et al. RNA-Seq: a revolutionary tool for transcriptomics. Nature Reviews Genetics, 10: 57-63 (2009).
Weber, et al. A real-time polymerase chain reaction assay for quantification of allele ratios and correction of amplification bias. Anal Biochem. Sep. 15, 2003;320(2):252-8.
Wittes, et al. Searching for Evidence of Altered Gene Expression: a Comment on Statistical Analysis of Microarray Data. Journal of the National Cancer Institute, 91(5): 400-401 (1999).
Wodicka, et al. Genome-wide expression monitoring in *Saccharomyces cerevisiae*. Nature Biotechnology, 15: 1359-1367 (1997).
Wojdacs, et al. Primer design versus PCR bias in methylation independent PCR amplifications. Epigenetics. May 16, 2009;4(4):231-4. Epub May 14, 2009.
Wood, et al. Using next-generation sequencing for high resolution multiplex analysis of copy number variation from nanogram quantities of DNA from formalin-fixed paraffin-embedded specimens. Nucleic Acids Res. Aug. 2010;38(14):e151. doi: 10.1 093/nar/gkq510. Epub Jun. 4, 2010.
Wu, et al. Quantitative assessment of single-cell RNA-sequencing methods. Nat Methods. Jan. 2014;11(1):41-6. doi: 10.1038/inmeth.2694. Epub Oct. 20, 2013.
Yandell, et al. A probabilistic disease-gene finder for personal genomes. Genome Res. Sep. 2011;21(9):1529-42. doi: 10.1101/gr.123158.111. Epub Jun. 23, 2011.
Ye, et al. Fluorescent microsphere-based readout technology for multiplexed human single nucleotide polymorphism analysis and bacterial identification. Human Mutation, 17(4): 305-316 (2001).
Yoon, et at Sensitive and accurate detection of copy number variants using read depth of coverage. Genome Res, Sep. 2009;19(9):1586-92. doi: 10.1101/gr.092981.109. Epub Aug. 5, 2009.
Zhang, et al. The impact of next-generation sequencing on genomics. J Genet Genomics. Mar. 20, 2011;38(3):95-109. doi: 10.1016/j.jgg.2011.02.003. Epub Mar. 15, 2011.
Zhao, et al. Homozygous Deletions and Chromosome Amplifications in Human Lung Carcinomas Revealed by Single Nucleotide Polymorphism Array Analysis. Cancer Research, 65: 5561-5570 (2005).
Zhou, et al. Counting alleles reveals a connection between chromosome 18q loss and vascular invasion. Nature Biotechnology, 19: 78-81 (2001).
Anderson, Feb. 11, 2014, Study describes RNA sequencing applications for molecular indexing methods, genomeweb.com, 5 pp.
Bioscribe, Feb. 5, 2015, Massively parallel sequencing technology for single-cell gene expression published (press release), 3 pp.
Brisco et al., Jun. 25, 2012, Quantification of RNA integrity and its use for measurement of transcript number, Nucleic Acids Research, 40(18):e144.
Butkus, Feb. 6, 2014, Cellular research set to laUnch first gene expression platform using 'molecular indexing' technology, genomeweb.com, 5 pp.
Gong et al., 2010, Massively parallel detection of gene expression in single cells using subnanolitre wells, Lab Chip, 10:2334-2337.
Junker et al., May 21, 2015, Single-cell transcriptomics enters the age of mass production, Molecular Cell, 58:563-564.
Klein et al., May 21, 2015, Droplet barcoding for single-cell transcriptomics applied to embryonic stem cells, Cell, 161:1187-1201.
Kolodziejczyk et al., May 21, 2015, The technology and biology of single-cell RNA sequencing, Molecular Cell, 58:610-620.
Lamble et al., Nov. 20, 2013, Improved workflows for high throughput library preparation using the transposome-based nextera system, BMC Biotechnology, 13(1):104.
Lee et al., 2010, Large-scale arrays of picolitre chambers for single-cell analysis of large cell populations, Lab Chip, 10:2952-2958.
Liu et al., Single-cell transcriptome sequencing: recent advances and remaining challenges, F1000Research 2016, 5(F1000 Faculty Rev):182, 9 pp.
Marcus et a., 2006, Microfluidic single-cell mRNA isolation and analysis, Ana. Chem. 78:3084-3089.
Martinez et al., Jul. 2012, A microfluidic approach to encapsulate living cell sin uniform alginate hydrogel microparticles, Marcomol. Biosci, 12(7):946-951.
Nadai et al., 2008, Protocol for nearly full-length sequencing of HIV-1 RNA from plasma, PLoS ONE, 3(1):e1420.
Nagai et al., 2001, Development of a microchamber array for picoleter PCR, Anal. Chem., 73:1043-1047.
Navin, 2015, The first five years of single-cell cancer genomics and beyond, Genome Research, 25:1499-1507.
Pfaffl et al., Mar. 2004, Determination of stable housekeeping genes, differentially regulated target genes and sample integrity: BestKeeper—Excel-based tool using pair-wise correlations, Biotechnology Letters, 26(6):505-515.

(56) References Cited

OTHER PUBLICATIONS

Rajeevan et al., Oct. 2003, Global amplification of sense RNA: a novel method to replicate and archive mRNA for gene expression analysis, Genomics, 82(4):491-497.
Stratagene 1998 Catalog, Gene Characterization Kits, p. 39.
Vandesompele et al., Jun. 18, 2002, Accurate normatlizaiton of real-time quantitative RT-PCR data by geometric averaging of multiple internal control genes, Genome Biology, 3(7).
Warren et al., Nov. 21, 2006, Transcription factor profiling in individual hematopoietic progenitors by digital RT-PCR, PNAS, 103(47):17807-17812.
Weiner et al., Apr. 2008, Kits and their unique role in molecular biology: a brief retrospective, BioTechniques, 44:701-704.
White et al., Aug. 23, 2011, High-throughput microfluidic single-cell RT-qPCR, PNAS, 108(34):13999-14004.
Office Action dated Oct. 11, 2016 in U.S. Appl. No. 15/224,460.
Office Action dated Aug. 12, 2016 in U.S. Appl. No. 14/381,488.
Office action dated Aug. 17, 2016 for U.S. Appl. No. 14/800,526.
Office Action dated Oct. 25, 2015 in U.S. Appl. No. 14/872,337.
Office action dated Sep. 26, 2016 in U.S. Appl. No. 15/167,807.
Written Opinion dated Sep. 27, 2016 in PCT/US16/019962.
International Search Report and Written Opinion dated Aug. 9, 2016 in PCT/US16/019971.
International Search Report and Written Opinion dated Sep. 28, 2016 in PCT/US16/028694.
International Search Report and Written Opinion dated Sep. 27, 2016 in PCT/US16/034473.

\* cited by examiner

```
                          SEQUENCE LISTING

<160> NUMBER OF SEQ ID NOS: 961

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 1
tcctgaacgg tagcatcttg acgac                                          25

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 2
cccaaagggt accagagctt aaggtcaa                                       28

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 3
cccaaagcgt taaggtttct tgtcacaa                                       28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 4
cccaagtcgt acgaactcac cacatgaa                                       28

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 5
```
cccaaacttg ttcccttgag accagtaa                                              28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 6
cccaagactt ctaccctagg ttccagaa                                              28

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 7
cccaaccaga cttgggtacg tgaaacaa                                              28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 8
cccaacgact ggttctgaag tggaacaa                                              28

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 9
cccaatttag cttcgtgagt cagaccaa                                              28

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 10
cccaactcga agagtggtca gtctttaa                                              28

```
<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 11
cccaatcgca aggagacata gtctttaa                                              28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 12
cccaagtcct agtgagagca acgtttaa                                              28

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 13
cccaaggaac ctactgtcct tgtcagaa                                              28

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 14
cccaaactag aagacgagtt cgagtcaa                                              28

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 15
cccaaggaca tactcaacgt agctcaaa                                              28

<210> SEQ ID NO 16
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 16
cccaaggcat tgcaacctc acatgaaa                                              28

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 17
cccaagtacc catccactgt cgagtaaa                                             28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 18
cccaaagcgt ttgtgtaaca gaccataa                                             28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 19
cccaaatggt ctggttcgac agtcacaa                                             28

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 20
cccaagaggt acaacgactc tagggtaa                                             28

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
```

```
<223> OTHER INFORMATION: 5' amino modifier C6

<400> SEQUENCE: 21
cccaagaact tctacttgct tcgtgaaa                                            28

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 22
cccaagcact ttctgttaac tagctgaa                                            28

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 23
cccaagaacc tctctctagt gctagtaa                                            28

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 24
cccaagcctt taagcctaaa gtcctgaa                                            28

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 25
cccaatctgg tagctcaaca tccttgaa                                            28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 26
```

```
cccaaaggac tccatggaga agtgtcaa                                              28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 27
cccaagaacc ctttctggaa gcttccaa                                              28

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 28
cccaaattcg cttcctagta gtggacaa                                              28

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 29
cccaaccgta cgaagaccta gtttctaa                                              28

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 30
cccaatcacg aagagagtca ctgtttaa                                              28

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 31
cccaagaaac ataaactcga gttgcgaa                                              28

<210> SEQ ID NO 32
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 32
cccaaccagt tacgtgagtg ttgctaaa                                        28

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 33
cccaaactcg tgactcctgt ttcagaaa                                        28

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 34
cccaacggtt gaagagactc ctgaaaaa                                        28

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 35
cccaaattgc tctggtcaca tcgaaaaa                                        28

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 36
cccaacagga cttgtgctac gtgttaaa                                        28

<210> SEQ ID NO 37
<211> LENGTH: 28
<212> TYPE: DNA
<213> ORGANISM: Artificial Sequence
<220> FEATURE:
```

<223> OTHER INFORMATION: Description of Artificial Sequence: Synthetic
      probe
<220> FEATURE:
<223> OTHER INFORMATION: 5' amino modifier C6

<400> SEQUENCE: 37
cccaaatttc gtgtgtcaac catgccaa                                          28

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 38
cccaacgtga aggcttaaca acattgaa                                          28

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 39
cccaatgaac acaactacga agctgtaa                                          28

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 40
cccaaacttc cgttgttact agtcgaaa                                          28

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 41
cccaaggagt acaagcttcc tagggtaa                                          28

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 42
cccaagtgct aaactgctct ttacgtaa                                28

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 43
cccaaagaaa ctgcatctcc tttggaaa                                28

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 44
cccaaggact aagttccact cacctgaa                                28

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 45
cccaaagttg tctggttcac tcgagaaa                                28

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 46
cccaacgttc taagtttgct tcgaagaa                                28

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 47
cccaactaaa ggttgtgcat ccaagcaa                                28

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 48
cccaaaggct tcacgacatg tcatttaa                                          28

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 49
cccaactgct aggttcctac acaagtaa                                          28

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 50
cccaaatcag tagctacacc acaggtaa                                          28

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 51
cccaagactg caagctcact acattgaa                                          28

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 52
cccaagctac tcctctaaga gcatagaa                                          28

<210> SEQ ID NO 53
<211> LENGTH: 28

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 53
cccaatggaa cgctaaggtg taaaccaa                                      28

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 54
cccaagaaac taaccttggc ttgccaaa                                      28

<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 55
cccaaccatt agaccttgtg ttgccaaa                                      28

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 56
cccaaggtct gacagtaggt gttccaaa                                      28

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 57
cccaatttcg caagccttgg tacataaa                                      28

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence: Synthetic
```

```
        probe
<220> FEATURE:
<223> OTHER INFORMATION: 5' amino modifier C6

<400> SEQUENCE: 58
cccaagtttc tagcctacca ctacggaa                                              28

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 59
cccaaataga cctaacggaa gctgtgaa                                              28

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 60
cccaaggagt catccatgca tctttgaa                                              28

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 61
cccaaccgta ctagcttggg ttaaacaa                                              28

<210> SEQ ID NO 62
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 62
cccaaaaagg ctagccttct gactttaa                                              28

<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6
```

```
<400> SEQUENCE: 63
cccaaagagc tctgcactac aagtttaa                                              28

<210> SEQ ID NO 64
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 64
cccaacagct aacggtagta aaggtcaa                                              28

<210> SEQ ID NO 65
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 65
cccaaagctt tccgtttcaa agtgacaa                                              28

<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 66
cccaagtcca tgcttccagt gacaaaaa                                              28

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 67
cccaagtagc tttgctctac tcgtaaaa                                              28

<210> SEQ ID NO 68
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 68
cccaacttcg aactaaggag tagagcaa                                              28
```

<210> SEQ ID NO 69
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 69
cccaattcag tcctagagga gagactaa                                      28

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 70
cccaataggt ctgtcttacc caacgtaa                                      28

<210> SEQ ID NO 71
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 71
cccaacgtga ggaaagttct gctaacaa                                      28

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 72
cccaagttgg caacttgctc tctaagaa                                      28

<210> SEQ ID NO 73
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 73
cccaagacat ctctctcaga gctagaaa                                      28

<210> SEQ ID NO 74
<211> LENGTH: 28
<212> TYPE: DNA

```
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 74
cccaatttcg catgtctcat caggacaa                                            28

<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 75
cccaaagcct tccttggtac tgaaagaa                                            28

<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 76
cccaaacttg ccttgcgtac tgtaaaaa                                            28

<210> SEQ ID NO 77
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 77
cccaacactt tgtacggtag agacgtaa                                            28

<210> SEQ ID NO 78
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 78
cccaagtttc catcaaccga agcttgaa                                            28

<210> SEQ ID NO 79
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
```

```
<220> FEATURE:
<223> OTHER INFORMATION: 5' amino modifier C6

<400> SEQUENCE: 79
cccaagcatt accaaactgg aacctgaa                                        28

<210> SEQ ID NO 80
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 80
cccaaccgta caacttgttc gtttgaaa                                        28

<210> SEQ ID NO 81
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 81
cccaacagct agtagcacac catttgaa                                        28

<210> SEQ ID NO 82
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 82
cccaacctca cgaaagcatc attgtgaa                                        28

<210> SEQ ID NO 83
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 83
cccaaacaaa gtgaggtcat ctcgacaa                                        28

<210> SEQ ID NO 84
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 84
```
cccaagaaac cttcttgtag gactcgaa                                        28

<210> SEQ ID NO 85
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 85
cccaaaagcc taagctctgt cagtttaa                                        28

<210> SEQ ID NO 86
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 86
cccaaacgtt cccttcatgt cgaaagaa                                        28

<210> SEQ ID NO 87
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 87
cccaagtagc actgacacca agcattaa                                        28

<210> SEQ ID NO 88
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 88
cccaagtttg actccaagcc tacgtcaa                                        28

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 89
cccaaaccgt tggtgaagcc ttaaagaa                                        28

<210> SEQ ID NO 90
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 90
cccaagccta caccttcagt gaacagaa                                           28

<210> SEQ ID NO 91
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 91
cccaacagct caagcagtta gtaaacaa                                           28

<210> SEQ ID NO 92
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 92
cccaatacgc aagcatgtag gtttacaa                                           28

<210> SEQ ID NO 93
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 93
cccaacacga gtcgttagtt gtttcaaa                                           28

<210> SEQ ID NO 94
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 94
cccaattcgg aagacctact aacctgaa                                           28

<210> SEQ ID NO 95
<211> LENGTH: 28
<212> TYPE: DNA
<213> ORGANISM: Artificial Sequence -continued

```
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 95
cccaaaggtc tctacgaaag gaacataa                                              28

<210> SEQ ID NO 96
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 96
cccaagtgct agacgtctgt gtcaaaaa                                              28

<210> SEQ ID NO 97
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 97
cccaaaccag tggacttctc tcctagaa                                              28

<210> SEQ ID NO 98
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 98
cccaacatgt aggagacgta gttcccaa                                              28

<210> SEQ ID NO 99
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 99
cccaagaact ctctggttag gcttgaaa                                              28

<210> SEQ ID NO 100
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
```

<223> OTHER INFORMATION: 5' amino modifier C6

<400> SEQUENCE: 100
cccaaggaca tccacatcgt ctgacaaa                                           28

<210> SEQ ID NO 101
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 101
cccaaacttg ttgggttcag ctaacaaa                                           28

<210> SEQ ID NO 102
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 102
cccaacacgt gtcctgtcat gtcaaaaa                                           28

<210> SEQ ID NO 103
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 103
cccaatcgga aaccaacgtt agctttaa                                           28

<210> SEQ ID NO 104
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 104
cccaaggact taggtacctg ttcggaaa                                           28

<210> SEQ ID NO 105
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 105
cccaagactt aacaacctgt gacgagaa					28

<210> SEQ ID NO 106
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 106
cccaagttaa catgcagacg aacggtaa					28

<210> SEQ ID NO 107
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 107
cccaagcgta caactcttgt cagtttaa					28

<210> SEQ ID NO 108
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 108
cccaagtaac accttctgag cagtggaa					28

<210> SEQ ID NO 109
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 109
cccaagacct acctctcagg aacagtaa					28

<210> SEQ ID NO 110
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 110
cccaaacctg accttaggaa gagcataa					28

<210> SEQ ID NO 111

```
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 111
cccaacaaag tttgtctcag ttagcgaa                                        28

<210> SEQ ID NO 112
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 112
cccaacggta gcattgttcc tgtagaaa                                        28

<210> SEQ ID NO 113
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 113
cccaactagg tttgttctag acagctaa                                        28

<210> SEQ ID NO 114
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 114
cccaagtctc tacgttccat cgaaagaa                                        28

<210> SEQ ID NO 115
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 115
cccaaacctt cgttcttgag tacagcaa                                        28

<210> SEQ ID NO 116
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      probe
<220> FEATURE:
<223> OTHER INFORMATION: 5' amino modifier C6

<400> SEQUENCE: 116
cccaagaaca ctcctcatgt gactgcaa                                          28

<210> SEQ ID NO 117
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 117
cccaaacgct tggtaacaaa gacagtaa                                          28

<210> SEQ ID NO 118
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 118 cccaaccta gagtagtact acggttaa                                           28

<210> SEQ ID NO 119
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 119
cccaacctga ggtagtgact gaaacaaa                                          28

<210> SEQ ID NO 120
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 120
cccaagctac gaacttggtt gtttcaaa                                          28

<210> SEQ ID NO 121
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6
```

```
<400> SEQUENCE: 121
cccaagcaag tcctaggttg tgttcaaa                                          28

<210> SEQ ID NO 122
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 122
cccaactcca tgtcaaggaa gggtacaa                                          28

<210> SEQ ID NO 123
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 123
cccaatccga acacgaagta caagttaa                                          28

<210> SEQ ID NO 124
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 124
cccaacacgt tgacattgtt ggcttaaa                                          28

<210> SEQ ID NO 125
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 125
cccaacctct aggaacgtag tacaccaa                                          28

<210> SEQ ID NO 126
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 126
cccaatagga caccacagtt catcgaaa                                          28
```

<210> SEQ ID NO 127
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 127
cccaaatgtc gttcggttag ctcaaaaa                                   28

<210> SEQ ID NO 128
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 128
cccaaatcgg ttgtgtctag ctcaaaaa                                   28

<210> SEQ ID NO 129
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 129
cccaataaga acgaaacgta ccttgcaa                                   28

<210> SEQ ID NO 130
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 130
cccaatcgca agaaccgtta gtcaaaaa                                   28

<210> SEQ ID NO 131
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 131
cccaagtcac acgtctccac aggtttaa                                   28

<210> SEQ ID NO 132
<211> LENGTH: 28

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 132
cccaagagct tacatcgttc tagggtaa                                          28

<210> SEQ ID NO 133
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 133
cccaagacct tctccttgac agaggtaa                                          28

<210> SEQ ID NO 134
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 134
cccaaaaggc ttagctctct ttactgaa                                          28

<210> SEQ ID NO 135
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 135
cccaagtcgt aacagaggtg tccacaaa                                          28

<210> SEQ ID NO 136
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 136
cccaaactac tgcaagtggt aggttcaa                                          28

<210> SEQ ID NO 137
<211> LENGTH: 28
<212> TYPE: DNA
<213> ORGANISM: Artificial Sequence
<220> FEATURE:
<223> OTHER INFORMATION: Description of Artificial Sequence: Synthetic
``` probe
<220> FEATURE:
<223> OTHER INFORMATION: 5' amino modifier C6

<400> SEQUENCE: 137
cccaatttcg gaaccagtac catgggaa                                              28

<210> SEQ ID NO 138
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 138
cccaatcgag aagcaacttc cttgtaaa                                              28

<210> SEQ ID NO 139
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 139
cccaatggag acttccgtac tgttgaaa                                              28

<210> SEQ ID NO 140
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 140
cccaaacatg cgtttcgtag tcttcaaa                                              28

<210> SEQ ID NO 141
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 141
cccaagaacc tcagctcttt cgaaagaa                                              28

<210> SEQ ID NO 142
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

```
<400> SEQUENCE: 142
cccaagtcct taagctgttc gagagtaa                                            28

<210> SEQ ID NO 143
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 143
cccaatctcg aaactcttgt gtgaccaa                                            28

<210> SEQ ID NO 144
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 144
cccaaccatt agaggaacta agagctaa                                            28

<210> SEQ ID NO 145
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 145 cccaaccta gagtgagtca ggaactaa                                             28

<210> SEQ ID NO 146
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 146
cccaatgaac cataagagca acggttaa                                            28

<210> SEQ ID NO 147
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 147
cccaagaacc ttcccttagt cgttgaaa                                            28
```

```
<210> SEQ ID NO 148
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 148
cccaagtggt cagtaaccct ttccgaaa                                        28

<210> SEQ ID NO 149
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 149
cccaaagcat gtacgtctcc tactagaa                                        28

<210> SEQ ID NO 150
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 150
cccaaggact tcacctacgt tcgaacaa                                        28

<210> SEQ ID NO 151
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 151
cccaacgaac tttaccttgt ccatggaa                                        28

<210> SEQ ID NO 152
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 152
cccaacaggt tcttacgcaa cacatgaa                                        28

<210> SEQ ID NO 153
<211> LENGTH: 28
<212> TYPE: DNA
```

```
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 153
cccaacttgt tagggtagct gactcaaa                                              28

<210> SEQ ID NO 154
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 154
cccaactgga gaagagacta cctgttaa                                              28

<210> SEQ ID NO 155
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 155
cccaactaag gtttggtcag tcctgaaa                                              28

<210> SEQ ID NO 156
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 156
cccaagcaca ctagcctttc tgaaagaa                                              28

<210> SEQ ID NO 157
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 157
cccaagtcct gacgagagtt tggtacaa                                              28

<210> SEQ ID NO 158
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
```

```
<220> FEATURE:
<223> OTHER INFORMATION: 5' amino modifier C6

<400> SEQUENCE: 158
cccaatccca agagtctctg gttgacaa                                          28

<210> SEQ ID NO 159
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 159
cccaaggcat tcagcattca ttcttgaa                                          28

<210> SEQ ID NO 160
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 160
cccaagtttg actaccaagc aactgcaa                                          28

<210> SEQ ID NO 161
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 161
cccaacctta agctaagtgt gagacgaa                                          28

<210> SEQ ID NO 162
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 162
cccaacttac agctagtttg aagtgcaa                                          28

<210> SEQ ID NO 163
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 163
```
cccaactagt ctcttagagt ttggcaaa                                      28

<210> SEQ ID NO 164
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 164
cccaataaag ctctaggaga acacgtaa                                      28

<210> SEQ ID NO 165
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 165
cccaaagcgt agtagtgact aacgacaa                                      28

<210> SEQ ID NO 166
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 166
cccaagacgt aaacgcttcc ttctagaa                                      28

<210> SEQ ID NO 167
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 167
cccaaagctg tagtaccctt tcctagaa                                      28

<210> SEQ ID NO 168
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 168
cccaactcgt acagcatacc tagaagaa                                      28

```
<210> SEQ ID NO 169
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 169
cccaatcgct acatagcaac tgaaagaa                                            28

<210> SEQ ID NO 170
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 170
cccaacttgg caacgtgtgt agtacaaa                                            28

<210> SEQ ID NO 171
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 171
cccaaacctg ttacgcttgt gctaaaaa                                            28

<210> SEQ ID NO 172
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 172
cccaaagctt ggttgtaact ttaccgaa                                            28

<210> SEQ ID NO 173
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 173
cccaagagac cttagcaaca accttgaa                                            28

<210> SEQ ID NO 174
<211> LENGTH: 28
<212> TYPE: DNA
<213> ORGANISM: Artificial Sequence
```

-continued

```
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 174
cccaataccg aagagtgcta ggtttcaa                                              28

<210> SEQ ID NO 175
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 175
cccaagacat agtaccgttg ctacccaa                                              28

<210> SEQ ID NO 176
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 176
cccaaggtct agtaacgaag caacctaa                                              28

<210> SEQ ID NO 177
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 177
cccaataagc aacaaaggtc attgccaa                                              28

<210> SEQ ID NO 178
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 178
cccaactgag tgagaagtca gaacctaa                                              28

<210> SEQ ID NO 179
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
```

<223> OTHER INFORMATION: 5' amino modifier C6

<400> SEQUENCE: 179
cccaacttcg agtgaaacaa gaacctaa                                          28

<210> SEQ ID NO 180
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 180
cccaaagcgt tcatggttct gtcataaa                                          28

<210> SEQ ID NO 181
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 181
cccaagaggt ctaggctttc gtctaaaa                                          28

<210> SEQ ID NO 182
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 182
cccaaagcca ttagtcgtgt cgttacaa                                          28

<210> SEQ ID NO 183
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 183
cccaaggtct tacgtaggtt gaagccaa                                          28

<210> SEQ ID NO 184
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 184

```
cccaagagct tagcgaactt agaaccaa                                           28

<210> SEQ ID NO 185
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 185
cccaatggaa ccctagggtt gagttcaa                                           28

<210> SEQ ID NO 186
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 186
cccaagaaca cttgagcaga cgtttcaa                                           28

<210> SEQ ID NO 187
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 187
cccaatcgaa ggaaagcatg actctaaa                                           28

<210> SEQ ID NO 188
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 188
cccaacttag tgagagtgct actcagaa                                           28

<210> SEQ ID NO 189
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 189
cccaaacttg ttgaagtgct tcacagaa                                           28

<210> SEQ ID NO 190
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 190
cccaagtgct aacactgttc tccatgaa                                         28

<210> SEQ ID NO 191
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 191
cccaaccctt agacctgaac atcgtgaa                                         28

<210> SEQ ID NO 192
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 192
cccaacttaa agggtagacc tagtcgaa                                         28

<210> SEQ ID NO 193
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 193
cccaaggcat agacctgtcg ttcttaaa                                         28

<210> SEQ ID NO 194
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 194
cccaaagcgt ttctagggta gtaaccaa                                         28

<210> SEQ ID NO 195
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      probe
<220> FEATURE:
<223> OTHER INFORMATION: 5' amino modifier C6

<400> SEQUENCE: 195
cccaagcaaa ctttccaaga cgttgtaa                                          28

<210> SEQ ID NO 196
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 196
cccaatctgg taactgcttt cgaaccaa                                          28

<210> SEQ ID NO 197
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 197
cccaatcagg agagcaagta ctagtcaa                                          28

<210> SEQ ID NO 198
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 198
cccaaacatt gtgtcgttaa cgcttcaa                                          28

<210> SEQ ID NO 199
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 199
cccaagaggt acttaggcat aaccgtaa                                          28

<210> SEQ ID NO 200
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6
```

<400> SEQUENCE: 200
cccaaaaacg gtttggcaaa ctgaccaa                                        28

<210> SEQ ID NO 201
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 201
cccaacataa ggcaagggta ctgtccaa                                        28

<210> SEQ ID NO 202
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 202
cccaaatgac gacaggagta gtgtccaa                                        28

<210> SEQ ID NO 203
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 203
cccaagacct ttgcgtttac aggactaa                                        28

<210> SEQ ID NO 204
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 204
cccaagtcta gagtcaacac agcactaa                                        28

<210> SEQ ID NO 205
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 205
cccaagagag cttaaccaga ctgtccaa                                        28

```
<210> SEQ ID NO 206
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 206
cccaagacca tactgcacat taggctaa                                            28

<210> SEQ ID NO 207
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 207
cccaagccaa ctacgtcata gtggtcaa                                            28

<210> SEQ ID NO 208
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 208
cccaatgtcg aacgtaccaa gaccataa                                            28

<210> SEQ ID NO 209
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 209
cccaacgtgt aggaagttcg tactcaaa                                            28

<210> SEQ ID NO 210
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 210
cccaaaaacc gtaagccttc atggtgaa                                            28

<210> SEQ ID NO 211
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 211
cccaatcgga aacgcaagtt catgttaa                                            28

<210> SEQ ID NO 212
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 212
cccaatcggt aactagaaag cacagtaa                                            28

<210> SEQ ID NO 213
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 213
cccaagtcga agtaggctaa agtccaaa                                            28

<210> SEQ ID NO 214
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 214
cccaaacggt agtaccttgt cgtcataa                                            28

<210> SEQ ID NO 215
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 215
cccaacattt ggaagttgca tcctgtaa                                            28

<210> SEQ ID NO 216
<211> LENGTH: 28
<212> TYPE: DNA
<213> ORGANISM: Artificial Sequence
<220> FEATURE:
<223> OTHER INFORMATION: Description of Artificial Sequence: Synthetic
```

```
     probe
<220> FEATURE:
<223> OTHER INFORMATION: 5' amino modifier C6

<400> SEQUENCE: 216
cccaacgaag tgttggtcaa gtccacaa                                             28

<210> SEQ ID NO 217
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 217
cccaatcaag gaaaggacta gttcgcaa                                             28

<210> SEQ ID NO 218
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 218
cccaacgaaa cttacaacgt aggactaa                                             28

<210> SEQ ID NO 219
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 219
cccaaggcat gcttagtctg aactttaa                                             28

<210> SEQ ID NO 220
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 220
cccaagaacc gttcccatgt agctttaa                                             28

<210> SEQ ID NO 221
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6
```

<400> SEQUENCE: 221
cccaaggcat aaagtgttct ctcgaaaa    28

<210> SEQ ID NO 222
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 222
cccaaggcta cccttaaaga ggacataa    28

<210> SEQ ID NO 223
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 223
cccaagtcct agacttcggt tcgtaaaa    28

<210> SEQ ID NO 224
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 224
cccaaggaac cttgtacaac acgactaa    28

<210> SEQ ID NO 225
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 225
cccaacacgt tgtagagaca gagactaa    28

<210> SEQ ID NO 226
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 226
cccaatccaa gcacaaggta ggtttcaa    28

<210> SEQ ID NO 227
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 227
cccaaagcca tactagttgt tgtcgaaa                                       28

<210> SEQ ID NO 228
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 228
cccaacgagt accatagtga aggactaa                                       28

<210> SEQ ID NO 229
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 229
cccaacattt gccaagggta gagactaa                                       28

<210> SEQ ID NO 230
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 230
cccaacgact gtttccgtaa agctttaa                                       28

<210> SEQ ID NO 231
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 231
cccaaggagt acgagacatc aagcttaa                                       28

<210> SEQ ID NO 232
<211> LENGTH: 28
<212> TYPE: DNA

```
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 232
cccaatggac tgtctggagt aacgtcaa                                        28

<210> SEQ ID NO 233
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 233
cccaaaccgt tacaggttta gtgtcgaa                                        28

<210> SEQ ID NO 234
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 234
cccaatgaca aagagtacga actgctaa                                        28

<210> SEQ ID NO 235
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 235
cccaatcaca agtgacaaag tacgctaa                                        28

<210> SEQ ID NO 236
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 236
cccaactgta aagagttgct agctctaa                                        28

<210> SEQ ID NO 237
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
```

```
<220> FEATURE:
<223> OTHER INFORMATION: 5' amino modifier C6

<400> SEQUENCE: 237
cccaatggga acactgtgaa gtcgacaa                                              28

<210> SEQ ID NO 238
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 238
cccaaattgc gtttggtcaa ctggacaa                                              28

<210> SEQ ID NO 239
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 239
cccaacgaag gttcaggtta gtccacaa                                              28

<210> SEQ ID NO 240
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 240
cccaaatgct gtgttaacct ttagccaa                                              28

<210> SEQ ID NO 241
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 241
cccaaccact tgtagtacta ggttcgaa                                              28

<210> SEQ ID NO 242
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 242
```

-continued cccaacccat agaggtttca cgttgtaa                              28

<210> SEQ ID NO 243
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 243
cccaactagg aaagagttca acgcataa                              28

<210> SEQ ID NO 244
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 244
cccaatccga agaaaggtct acaggtaa                              28

<210> SEQ ID NO 245
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 245
cccaatggaa acccttaaga actgctaa                              28

<210> SEQ ID NO 246
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 246
cccaagcaac ataaccttga ctcaggaa                              28

<210> SEQ ID NO 247
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 247
cccaatagaa ccacagactt tagcagaa                              28

<210> SEQ ID NO 248
<211> LENGTH: 28
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' amino modifier C6

<400> SEQUENCE: 248
cccaatcaca agaggttcgt acgaaaaa                                        28

<210> SEQ ID NO 249
<211> LENGTH: 28
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' amino modifier C6

<400> SEQUENCE: 249
cccaaagctt tgtctccagt acgaaaaa                                        28

<210> SEQ ID NO 250
<211> LENGTH: 28
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' amino modifier C6

<400> SEQUENCE: 250
cccaatcgga aggtgttcag taaaccaa                                        28

<210> SEQ ID NO 251
<211> LENGTH: 28
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' amino modifier C6

<400> SEQUENCE: 251
cccaaagtgc attccaagaa acgactaa                                        28

<210> SEQ ID NO 252
<211> LENGTH: 28
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' amino modifier C6

<400> SEQUENCE: 252
cccaagacgt aaccatcgaa ctcgttaa                                        28

<210> SEQ ID NO 253
<211> LENGTH: 28
<212> TYPE: DNA
<213> ORGANISM: Artificial Sequence

```
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 253
cccaaccgta gaacgttctt tgcttaaa                                              28

<210> SEQ ID NO 254
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 254
cccaagagct caagggttct agaaccaa                                              28

<210> SEQ ID NO 255
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 255
cccaatcggt agttacgagt aaagccaa                                              28

<210> SEQ ID NO 256
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 256
cccaagacaa ctagctcttg gactccaa                                              28

<210> SEQ ID NO 257
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 257
cccaatgacg aaggacactt agacctaa                                              28

<210> SEQ ID NO 258
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
```

```
<223> OTHER INFORMATION: 5' amino modifier C6

<400> SEQUENCE: 258
cccaaccgta gaacatttga agccataa                                              28

<210> SEQ ID NO 259
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 259
cccaaccact cgaacatggt aacgtcaa                                              28

<210> SEQ ID NO 260
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 260
cccaatcgaa ccgtaaccat ttcaggaa                                              28

<210> SEQ ID NO 261
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 261
cccaactagt ggttggaaca tgcactaa                                              28

<210> SEQ ID NO 262
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 262
cccaagtgct tactgtccat cggaaaaa                                              28

<210> SEQ ID NO 263
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 263
```
cccaatgagt ctgcatctct ttcaagaa                                        28

<210> SEQ ID NO 264
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 264
cccaatagga caaagacgtc ttaccgaa                                        28

<210> SEQ ID NO 265
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 265
cccaatcata ggctaaggga agacctaa                                        28

<210> SEQ ID NO 266
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 266
cccaacagag gtaaagtcca gtggtcaa                                        28

<210> SEQ ID NO 267
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 267
cccaagacca ctacaacgtt gcatgtaa                                        28

<210> SEQ ID NO 268
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 268
cccaatagac cacaagcatc gttaggaa                                        28

<210> SEQ ID NO 269

```
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 269
cccaagtcac tcacctaagt tcggtaaa                                           28

<210> SEQ ID NO 270
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 270
cccaagcttt caagtaccac acgagtaa                                           28

<210> SEQ ID NO 271
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 271
cccaagtcac atcctctagg gttcgaaa                                           28

<210> SEQ ID NO 272
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 272
cccaaaaacg ttcatttggt ctgacgaa                                           28

<210> SEQ ID NO 273
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 273
cccaactgtc cattcggaac gtgaaaaa                                           28

<210> SEQ ID NO 274
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      probe
<220> FEATURE:
<223> OTHER INFORMATION: 5' amino modifier C6

<400> SEQUENCE: 274
cccaaagttc tttcttcagc aagggtaa                                            28

<210> SEQ ID NO 275
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 275
cccaatagtc ctgtcgttag aaccgtaa                                            28

<210> SEQ ID NO 276
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 276
cccaacgtac atcccttaga aacgtgaa                                            28

<210> SEQ ID NO 277
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 277
cccaacggtt cagcacttta catttgaa                                            28

<210> SEQ ID NO 278
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 278
cccaatgcgt aaactcgttg tcctacaa                                            28

<210> SEQ ID NO 279
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6
```

-continued

<400> SEQUENCE: 279
cccaatcggt aaacctgttt cgcttaaa                                              28

<210> SEQ ID NO 280
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 280
cccaagtgca agcacaggtg acatttaa                                              28

<210> SEQ ID NO 281
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 281
cccaagggta cagacgagta actctgaa                                              28

<210> SEQ ID NO 282
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 282
cccaaaccct agtagttcta ctcgtgaa                                              28

<210> SEQ ID NO 283
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 283
cccaagtaac ccttccgtag gacagtaa                                              28

<210> SEQ ID NO 284
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 284
cccaatttag tcactctggt caaccgaa                                              28

<210> SEQ ID NO 285
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 285
cccaagtaca caacctctgg taacggaa                                       28

<210> SEQ ID NO 286
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 286
cccaacacaa gttcaggtag gagtgcaa                                       28

<210> SEQ ID NO 287
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 287
cccaactaaa ggtgtttacg cttccaaa                                       28

<210> SEQ ID NO 288
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 288
cccaactgaa gttggtctac ctgaggaa                                       28

<210> SEQ ID NO 289
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 289
cccaatgtcg taagttcctc aactgcaa                                       28

<210> SEQ ID NO 290
<211> LENGTH: 28

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 290
cccaaacctg agacctgtgt ttcgtaaa                                           28

<210> SEQ ID NO 291
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 291
cccaataggc tagctcaacc ataaagaa                                           28

<210> SEQ ID NO 292
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 292
cccaagttga caacgctacc ctagacaa                                           28

<210> SEQ ID NO 293
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 293
cccaatcacg aagtgagctt gtcaaaaa                                           28

<210> SEQ ID NO 294
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 294
cccaatgaaa ccgtaactca cttggcaa                                           28

<210> SEQ ID NO 295
<211> LENGTH: 28
<212> TYPE: DNA
<213> ORGANISM: Artificial Sequence
<220> FEATURE:
<223> OTHER INFORMATION: Description of Artificial Sequence: Synthetic
```

```
      probe
<220> FEATURE:
<223> OTHER INFORMATION: 5' amino modifier C6

<400> SEQUENCE: 295
cccaacttag cacaaagtgt agaagcaa                                      28

<210> SEQ ID NO 296
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 296
cccaatgcgt agaaccatgt acaaagaa                                      28

<210> SEQ ID NO 297
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 297
cccaagagtt gcttcggtac tcaaagaa                                      28

<210> SEQ ID NO 298
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 298
cccaagcgta gttcggaaac actaagaa                                      28

<210> SEQ ID NO 299
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 299
cccaaaagag tcttaccgta ctaccgaa                                      28

<210> SEQ ID NO 300
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6
```

<400> SEQUENCE: 300
cccaaaaacg gtaggtctct gactccaa            28

<210> SEQ ID NO 301
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 301
cccaaggtca gttaagccaa cccttgaa            28

<210> SEQ ID NO 302
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 302
cccaaaccag tctctcagtt tacgtgaa            28

<210> SEQ ID NO 303
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 303
cccaataaga caaggacttc catgccaa            28

<210> SEQ ID NO 304
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 304
cccaagtcga gaacatggaa gtccttaa            28

<210> SEQ ID NO 305
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 305
cccaatgcag agaaagtaca taccgtaa            28

```
<210> SEQ ID NO 306
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 306
cccaagtgca cttaaggaca acaggtaa                                              28

<210> SEQ ID NO 307
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 307
cccaaacctg tcttaaggca tacggtaa                                              28

<210> SEQ ID NO 308
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 308
cccaagtctc taagtaggca tgctgtaa                                              28

<210> SEQ ID NO 309
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 309
cccaacgtct gacattggag agaactaa                                              28

<210> SEQ ID NO 310
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 310
cccaaaaagc tcacgtcttg gtcttaaa                                              28

<210> SEQ ID NO 311
<211> LENGTH: 28
<212> TYPE: DNA
```

<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 311
cccaagggta acagacactt tagcgtaa                                          28

<210> SEQ ID NO 312
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 312
cccaatgacc tacgagtgga gagtacaa                                          28

<210> SEQ ID NO 313
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 313
cccaaagctt gcgaaaccta actaagaa                                          28

<210> SEQ ID NO 314
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 314
cccaatgtcg acagaccata cctaagaa                                          28

<210> SEQ ID NO 315
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 315
cccaaggtca acaagccata cgttccaa                                          28

<210> SEQ ID NO 316
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

```
<220> FEATURE:
<223> OTHER INFORMATION: 5' amino modifier C6

<400> SEQUENCE: 316
cccaactggt tactacgaac aggagtaa                                          28

<210> SEQ ID NO 317
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 317
cccaatagag acgttactcc taaccgaa                                          28

<210> SEQ ID NO 318
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 318
cccaaagaca gttgacacct tagcctaa                                          28

<210> SEQ ID NO 319
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 319
cccaaatcga gagttacacc ttaccgaa                                          28

<210> SEQ ID NO 320
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 320
cccaaacagg tttccaagaa ctagggaa                                          28

<210> SEQ ID NO 321
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 321
```
cccaagacag gtaggtcttg ctagtcaa                                            28

<210> SEQ ID NO 322
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 322
cccaaggagt ctcaaccgtt aaccagaa                                            28

<210> SEQ ID NO 323
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 323
cccaagaaac gtacgcttct ccattgaa                                            28

<210> SEQ ID NO 324
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 324
cccaacttag gaagcactac gtacccaa                                            28

<210> SEQ ID NO 325
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 325
cccaagtaag ctacgttcct gtacccaa                                            28

<210> SEQ ID NO 326
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 326
cccaaccaag taagtggaca ctggtgaa                                            28

```
<210> SEQ ID NO 327
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 327
cccaactgtt tacagaggtc agcagtaa                                      28

<210> SEQ ID NO 328
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 328
cccaacacgt cttaaagcag agaactaa                                      28

<210> SEQ ID NO 329
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 329
cccaagagga ctgtcctact tccatgaa                                      28

<210> SEQ ID NO 330
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 330
cccaagaaca tctccactgg tcacgtaa                                      28

<210> SEQ ID NO 331
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 331
cccaatgaag caacaagtgg tactccaa                                      28

<210> SEQ ID NO 332
<211> LENGTH: 28
<212> TYPE: DNA
<213> ORGANISM: Artificial Sequence
```

-continued

<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 332
cccaatccgt aacagtagga gaacgtaa                                              28

<210> SEQ ID NO 333
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 333
cccaaaccgt aggaactacc attctgaa                                              28

<210> SEQ ID NO 334
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 334
cccaaccagt tcgttcaaac agactgaa                                              28

<210> SEQ ID NO 335
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 335
cccaagttaa acatccagag ctcacgaa                                              28

<210> SEQ ID NO 336
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 336
cccaagtcac acaacctaga gcttggaa                                              28

<210> SEQ ID NO 337
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:

<223> OTHER INFORMATION: 5' amino modifier C6

<400> SEQUENCE: 337
cccaacatgt tagggttacc ttggcaaa        28

<210> SEQ ID NO 338
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 338
cccaagtcaa aggtactcca cttccgaa        28

<210> SEQ ID NO 339
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 339
cccaagtaga acgtcaacca cttacgaa        28

<210> SEQ ID NO 340
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 340
cccaaggaga cttgtcctac tctacgaa        28

<210> SEQ ID NO 341
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 341
cccaatttcg tagtactcac ttgcgaaa        28

<210> SEQ ID NO 342
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 342

```
cccaaccttg tactaggaag gaagctaa                                            28
```

<210> SEQ ID NO 343
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 343

```
cccaagtcgt agttgtcaca ctgcacaa                                            28
```

<210> SEQ ID NO 344
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 344

```
cccaacgaag ttacgtcttt catgccaa                                            28
```

<210> SEQ ID NO 345
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 345

```
cccaaaaggc ataaggcttg tcatccaa                                            28
```

<210> SEQ ID NO 346
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 346

```
cccaagtgtc catacgcttt accgaaaa                                            28
```

<210> SEQ ID NO 347
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 347

```
cccaacggtt gacaccagtt accaagaa                                            28
```

<210> SEQ ID NO 348

```
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 348
cccaagtgtg caaccagtta ctcctgaa                                          28

<210> SEQ ID NO 349
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 349
cccaagctga cagactctct ttcatgaa                                          28

<210> SEQ ID NO 350
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 350
cccaagaaag ctgtaccctt ctctagaa                                          28

<210> SEQ ID NO 351
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 351
cccaaatgtt gctacaagac taaccgaa                                          28

<210> SEQ ID NO 352
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 352
cccaagtctg gaagtgctag tacgtcaa                                          28

<210> SEQ ID NO 353
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      probe
<220> FEATURE:
<223> OTHER INFORMATION: 5' amino modifier C6

<400> SEQUENCE: 353
cccaatcgca acttcggtac atttgtaa                                        28

<210> SEQ ID NO 354
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 354
cccaacctgt aacattgaag aagcgtaa                                        28

<210> SEQ ID NO 355
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 355
cccaaactgt tggaaagctg aacactaa                                        28

<210> SEQ ID NO 356
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 356
cccaagacgt agcttagaga gaacctaa                                        28

<210> SEQ ID NO 357
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 357
cccaacattg ttgtggaacc tcagagaa                                        28

<210> SEQ ID NO 358
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6
```

```
<400> SEQUENCE: 358
cccaagtgga ctagcttcct acactgaa                                         28

<210> SEQ ID NO 359
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 359
cccaaaggaa ctgacattca acacgtaa                                         28

<210> SEQ ID NO 360
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 360
cccaatgttc gagtccacaa ctacagaa                                         28

<210> SEQ ID NO 361
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 361
cccaagtaac tactcacaga gctaggaa                                         28

<210> SEQ ID NO 362
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 362
cccaagagga ctcaccagta ctttcgaa                                         28

<210> SEQ ID NO 363
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 363
cccaatagcg ttgtttctaa ccactgaa                                         28
```

```
<210> SEQ ID NO 364
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 364
cccaacattt gttagtagca gtcacgaa                                       28

<210> SEQ ID NO 365
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 365
cccaataaca gcaagacctt gtagccaa                                       28

<210> SEQ ID NO 366
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 366
cccaagactc tccacacgtt gaagacaa                                       28

<210> SEQ ID NO 367
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 367
cccaagaact ccatcctgtt cgacagaa                                       28

<210> SEQ ID NO 368
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 368
cccaaggttc tagttccaac taacgcaa                                       28

<210> SEQ ID NO 369
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 369
cccaaagttg cgtttgtcat agacctaa                                          28

<210> SEQ ID NO 370
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 370
cccaacgctt gaggtaaact aaacagaa                                          28

<210> SEQ ID NO 371
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 371
cccaataacg agtagagctc tagaccaa                                          28

<210> SEQ ID NO 372
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 372
cccaagtgag tcatagccat aagccaaa                                          28

<210> SEQ ID NO 373
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 373
cccaacttac gtgacttcca ttcaggaa                                          28

<210> SEQ ID NO 374
<211> LENGTH: 28
<212> TYPE: DNA
<213> ORGANISM: Artificial Sequence
<220> FEATURE:
<223> OTHER INFORMATION: Description of Artificial Sequence: Synthetic
``` probe
<220> FEATURE:
<223> OTHER INFORMATION: 5' amino modifier C6

<400> SEQUENCE: 374
cccaaatcag tgactgtctc ttcacgaa                                      28

<210> SEQ ID NO 375
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 375
cccaaaggta ctgacttcca ctcctgaa                                      28

<210> SEQ ID NO 376
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 376
cccaatcgac attacaggaa gtacggaa                                      28

<210> SEQ ID NO 377
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 377
cccaaccact ggttaaacgt aaacggaa                                      28

<210> SEQ ID NO 378
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 378
cccaagttca ttccctaagc cttggaaa                                      28

<210> SEQ ID NO 379
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

```
<400> SEQUENCE: 379
cccaagaaac tactccatgg ttagcgaa                                            28

<210> SEQ ID NO 380
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 380
cccaactaag ggttaaagct taccgtaa                                            28

<210> SEQ ID NO 381
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 381
cccaagagac ctgtcacact ttaacgaa                                            28

<210> SEQ ID NO 382
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 382
cccaatgaac aacaacatgc ttacggaa                                            28

<210> SEQ ID NO 383
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 383
cccaatcaga aagcaacatt ctagggaa                                            28

<210> SEQ ID NO 384
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 384
cccaataggc ttgactcatt aaaccgaa                                            28
```

<210> SEQ ID NO 385
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 385
cccaaactgg tttgtagtcc taccgaaa                                            28

<210> SEQ ID NO 386
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 386
cccaaacctg acagcttgtt tcttagaa                                            28

<210> SEQ ID NO 387
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 387
cccaacttgc tacatagaga gagtgcaa                                            28

<210> SEQ ID NO 388
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 388
cccaaggtaa accttccagt ctccagaa                                            28

<210> SEQ ID NO 389
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 389
cccaatacca agtacgcaaa ctgtggaa                                            28

<210> SEQ ID NO 390
<211> LENGTH: 28
<212> TYPE: DNA

```
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 390
cccaaccgta aaccttaagg tgtagcaa                                           28

<210> SEQ ID NO 391
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 391
cccaacattg tttcccaagg catagcaa                                           28

<210> SEQ ID NO 392
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 392
cccaaggtca tcctactagc attgccaa                                           28

<210> SEQ ID NO 393
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 393
cccaagttca acatcactgc tacggtaa                                           28

<210> SEQ ID NO 394
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 394
cccaattcgc atgcatttaa ggtgtcaa                                           28

<210> SEQ ID NO 395
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
```

```
<220> FEATURE:
<223> OTHER INFORMATION: 5' amino modifier C6

<400> SEQUENCE: 395
cccaacttag cactagagaa ggagtcaa                                            28

<210> SEQ ID NO 396
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 396
cccaagctca ggacagttga gtgttcaa                                            28

<210> SEQ ID NO 397
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 397
cccaagtcct agctaagagt gtgtcaaa                                            28

<210> SEQ ID NO 398
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 398
cccaagctac aagcataagt ggttcaaa                                            28

<210> SEQ ID NO 399
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 399
cccaagtcat accaaagctg agacgtaa                                            28

<210> SEQ ID NO 400
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 400
```

-continued cccaatttag catagacgag agactcaa                                              28

<210> SEQ ID NO 401
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 401
cccaatttca tgtaacgaca gtgagcaa                                              28

<210> SEQ ID NO 402
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 402
cccaatgcac ttcgtagagt aagaacaa                                              28

<210> SEQ ID NO 403
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 403
cccaaacgtt gtctctgtag tggaacaa                                              28

<210> SEQ ID NO 404
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 404
cccaaccgaa gttagcaaac ctcatgaa                                              28

<210> SEQ ID NO 405
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 405
cccaacattt agaaggactt cgaacgaa                                              28

<210> SEQ ID NO 406
<211> LENGTH: 28
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' amino modifier C6

<400> SEQUENCE: 406
cccaagttcc aacactcaga caggtcaa                                              28

<210> SEQ ID NO 407
<211> LENGTH: 28
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' amino modifier C6

<400> SEQUENCE: 407
cccaatgaca acctctcaga gtggtcaa                                              28

<210> SEQ ID NO 408
<211> LENGTH: 28
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' amino modifier C6

<400> SEQUENCE: 408
cccaagccta ggtaggttct ggaactaa                                              28

<210> SEQ ID NO 409
<211> LENGTH: 28
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' amino modifier C6

<400> SEQUENCE: 409
cccaatcgaa cacaccatgt tactggaa                                              28

<210> SEQ ID NO 410
<211> LENGTH: 28
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' amino modifier C6

<400> SEQUENCE: 410
cccaatagtc taactgttgg cttgcaaa                                              28

<210> SEQ ID NO 411
<211> LENGTH: 28
<212> TYPE: DNA
<213> ORGANISM: Artificial Sequence

```
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 411
cccaaaagct aggtaccttc ttaccgaa                                          28

<210> SEQ ID NO 412
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 412
cccaactcag agtacagaga gtttgcaa                                          28

<210> SEQ ID NO 413
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 413
cccaagacac gtcataggag tgtagcaa                                          28

<210> SEQ ID NO 414
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 414
cccaattaag cataacgaga cagtgcaa                                          28

<210> SEQ ID NO 415
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 415
cccaagtgtc cacatgaggt gaaagcaa                                          28

<210> SEQ ID NO 416
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
```

```
<223> OTHER INFORMATION: 5' amino modifier C6

<400> SEQUENCE: 416
cccaactaaa gggttgaacg ttccagaa                                            28

<210> SEQ ID NO 417
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 417
cccaaatcgc tttctttagt ggagacaa                                            28

<210> SEQ ID NO 418
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 418
cccaaaggtc ttcactttgt gcacaaaa                                            28

<210> SEQ ID NO 419
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 419
cccaaggctt aaggtgaacc atcgacaa                                            28

<210> SEQ ID NO 420
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 420
cccaactgta gagctaccaa cactagaa                                            28

<210> SEQ ID NO 421
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 421
```

```
cccaactaag ggttgttacg ttagccaa                                              28

<210> SEQ ID NO 422
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 422
cccaagtggt actcagctac atcgtcaa                                              28

<210> SEQ ID NO 423
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 423
cccaagtcca aacaccttga gagctcaa                                              28

<210> SEQ ID NO 424
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 424
cccaatcaca agcttagagt ggagacaa                                              28

<210> SEQ ID NO 425
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 425
cccaactttg actttggcaa ctagggaa                                              28

<210> SEQ ID NO 426
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 426
cccaacctca gtctaagggt agtgtcaa                                              28

<210> SEQ ID NO 427
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 427
cccaaacacc tgtccagaga gtgtacaa                                      28

<210> SEQ ID NO 428
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 428
cccaacatag ttgtgaagca tcgctaaa                                      28

<210> SEQ ID NO 429
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 429
cccaaacgtg ttgttgtacc ctaggaaa                                      28

<210> SEQ ID NO 430
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 430
cccaaacttt ggtagaaacg tagccaaa                                      28

<210> SEQ ID NO 431
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 431
cccaactcag ttgcattaaa gtgtgcaa                                      28

<210> SEQ ID NO 432
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      probe
<220> FEATURE:
<223> OTHER INFORMATION: 5' amino modifier C6

<400> SEQUENCE: 432
cccaaactac tgttctggac ttcggaaa                                          28

<210> SEQ ID NO 433
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 433
cccaaagagc attaggactg tacgacaa                                          28

<210> SEQ ID NO 434
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 434
cccaacacca tgctgagtgg taagtcaa                                          28

<210> SEQ ID NO 435
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 435
cccaactgga acacgtgtgg tagaacaa                                          28

<210> SEQ ID NO 436
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 436
cccaacctca gaactcgttg gttaccaa                                          28

<210> SEQ ID NO 437
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6
```

<400> SEQUENCE: 437
cccaatgcca taacgcttgt acttgtaa                                           28

<210> SEQ ID NO 438
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 438
cccaaaacct tgtagacaag aagcgtaa                                           28

<210> SEQ ID NO 439
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 439
cccaacacat gttagagacg acaggtaa                                           28

<210> SEQ ID NO 440
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 440
cccaaggtac tctaacttgc agtcctaa                                           28

<210> SEQ ID NO 441
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 441
cccaatgcca acctcaagaa gtgtacaa                                           28

<210> SEQ ID NO 442
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 442
cccaactaaa gttgggaacg catcacaa                                           28

<210> SEQ ID NO 443
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 443
cccaaggact actccactgt catcagaa                                          28

<210> SEQ ID NO 444
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 444
cccaagaacc gtagttcctt ccctagaa                                          28

<210> SEQ ID NO 445
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 445
cccaactttg aggtgagact cgttacaa                                          28

<210> SEQ ID NO 446
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 446
cccaatcaga gaagagttcg tcacacaa                                          28

<210> SEQ ID NO 447
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 447
cccaagtttc attcctcaga gctgacaa                                          28

<210> SEQ ID NO 448
<211> LENGTH: 28

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 448
cccaagttgt cactcctgag cactacaa                                      28

<210> SEQ ID NO 449
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 449
cccaaaaggt tcatcgcttt gaccacaa                                      28

<210> SEQ ID NO 450
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 450
cccaatgcca agacttgtgg tgttacaa                                      28

<210> SEQ ID NO 451
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 451
cccaaaggct tcggtaacac taacagaa                                      28

<210> SEQ ID NO 452
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 452
cccaacagct agcatggttt ggttacaa                                      28

<210> SEQ ID NO 453
<211> LENGTH: 28
<212> TYPE: DNA
<213> ORGANISM: Artificial Sequence
<220> FEATURE:
<223> OTHER INFORMATION: Description of Artificial Sequence: Synthetic
``` probe
<220> FEATURE:
<223> OTHER INFORMATION: 5' amino modifier C6

<400> SEQUENCE: 453
cccaagccat tagcctagtt gtccacaa                                              28

<210> SEQ ID NO 454
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 454
cccaacggta caacggttgg gtttacaa                                              28

<210> SEQ ID NO 455
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 455
cccaacacca gttggacagg acattcaa                                              28

<210> SEQ ID NO 456
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 456
cccaatctca gactggaagg gttgacaa                                              28

<210> SEQ ID NO 457
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 457
cccaagtgtg acgaacctca aacatgaa                                              28

<210> SEQ ID NO 458
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

```
<400> SEQUENCE: 458
cccaatgcgt acaggtacat aggacaaa                                            28

<210> SEQ ID NO 459
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 459
cccaacagtt aaaggacatg agctcaaa                                            28

<210> SEQ ID NO 460
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 460
cccaatccga aagggttaca gttacgaa                                            28

<210> SEQ ID NO 461
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 461
cccaacattg tgaaagtgca gttcccaa                                            28

<210> SEQ ID NO 462
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 462
cccaaaacca tgaggtcacg ttacccaa                                            28

<210> SEQ ID NO 463
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 463
cccaatcaag gagaaacgtg tacctcaa                                            28
```

<210> SEQ ID NO 464
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 464
cccaatcagg agacgactag taggtcaa                                            28

<210> SEQ ID NO 465
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 465
cccaaggact aggtcacaca tctctgaa                                            28

<210> SEQ ID NO 466
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 466
cccaacatag agaggacatc ttcgacaa                                            28

<210> SEQ ID NO 467
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 467
cccaacgaac tcatccttgt ggacacaa                                            28

<210> SEQ ID NO 468
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 468
cccaacagtt ggtgagttca tgcacaaa                                            28

<210> SEQ ID NO 469
<211> LENGTH: 28
<212> TYPE: DNA

```
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 469
cccaacatag gacaggagtg ttgcacaa                                         28

<210> SEQ ID NO 470
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 470
cccaactagt agaagactgc atggacaa                                        28

<210> SEQ ID NO 471
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 471
cccaatagag caagaacctc agttggaa                                        28

<210> SEQ ID NO 472
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 472
cccaaccatg tggagtttct gaggacaa                                        28

<210> SEQ ID NO 473
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 473
cccaatagac aggacaggtg ttcccaaa                                        28

<210> SEQ ID NO 474
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
```

```
<220> FEATURE:
<223> OTHER INFORMATION: 5' amino modifier C6

<400> SEQUENCE: 474
cccaattcgg aagccatttc tcttagaa                                          28

<210> SEQ ID NO 475
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 475
cccaatcgga acagttcctc attctgaa                                          28

<210> SEQ ID NO 476
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 476
cccaatgaag cagttccatc attctgaa                                          28

<210> SEQ ID NO 477
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 477
cccaacatgt gtcaagggta gctctcaa                                          28

<210> SEQ ID NO 478
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 478
cccaagcctt tacaccatgt ggaaccaa                                          28

<210> SEQ ID NO 479
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 479
```

```
cccaactaac tgctgaggtg aggtacaa                                            28

<210> SEQ ID NO 480
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 480
cccaactcca agtcgagtga gttgacaa                                            28

<210> SEQ ID NO 481
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 481
cccaacgagt tgagaagcta catgacaa                                            28

<210> SEQ ID NO 482
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 482
cccaatttct gagtgagcaa ccctagaa                                            28

<210> SEQ ID NO 483
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 483
cccaagagta cagctacctc tccaagaa                                            28

<210> SEQ ID NO 484
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 484
cccaagagca ctccacttgt acaaagaa                                            28
```

```
<210> SEQ ID NO 485
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 485
cccaagctac atttcttgag tcgactaa                                          28

<210> SEQ ID NO 486
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 486
cccaaaccgt aggactacaa cacttgaa                                          28

<210> SEQ ID NO 487
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 487
cccaaattcc tgttgtgacg aagtcgaa                                          28

<210> SEQ ID NO 488
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 488
cccaaagttc tgtggttcac aagtcgaa                                          28

<210> SEQ ID NO 489
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 489
cccaagtact cgagttccct ttaacgaa                                          28

<210> SEQ ID NO 490
<211> LENGTH: 28
<212> TYPE: DNA
<213> ORGANISM: Artificial Sequence
```

<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 490
cccaagctga aggttaacaa caagctaa                                      28

<210> SEQ ID NO 491
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 491
cccaatcgca tggtaaacaa acactgaa                                      28

<210> SEQ ID NO 492
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 492
cccaactggt actaaagcca aactgcaa                                      28

<210> SEQ ID NO 493
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 493
cccaacgtta agaaggtacc tagcctaa                                      28

<210> SEQ ID NO 494
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 494
cccaacagtg aaagttgtcc ttccagaa                                      28

<210> SEQ ID NO 495
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:

<223> OTHER INFORMATION: 5' amino modifier C6

<400> SEQUENCE: 495
cccaacagga gttgggtacc agtctaaa                                              28

<210> SEQ ID NO 496
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 496
cccaagaaac tgtgcaaaca ctcctgaa                                              28

<210> SEQ ID NO 497
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 497
cccaatcgta gttcgacaaa ctccagaa                                              28

<210> SEQ ID NO 498
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 498
cccaacaggt tagttcacac catccgaa                                              28

<210> SEQ ID NO 499
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 499
cccaaggttt acgtcactcc atccagaa                                              28

<210> SEQ ID NO 500
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 500
cccaagttta acctcatgct ttagcgaa                                              28

<210> SEQ ID NO 501
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 501
cccaatttgt acgttccaac ctaggcaa                                              28

<210> SEQ ID NO 502
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 502
cccaaatcgt ttgtttccag taggcaaa                                              28

<210> SEQ ID NO 503
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 503
cccaagcatc cttgtcttaa ctgcagaa                                              28

<210> SEQ ID NO 504
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 504
cccaaactgg taagtcttgg ctacccaa                                              28

<210> SEQ ID NO 505
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 505
cccaagtcca tgtgcaacac caactgaa                                              28

<210> SEQ ID NO 506

```
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 506
cccaagtcac aggactcctc aacatgaa                                            28

<210> SEQ ID NO 507
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 507
cccaagtact ctcattctgt gcagacaa                                            28

<210> SEQ ID NO 508
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 508
cccaaggttc cacactttgt cacgacaa                                            28

<210> SEQ ID NO 509
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 509
cccaaactcg tctgtccata aagtcgaa                                            28

<210> SEQ ID NO 510
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 510
cccaacaagg tgtgttctac cattcgaa                                            28

<210> SEQ ID NO 511
<211> LENGTH: 28
<212> TYPE: DNA
<213> ORGANISM: Artificial Sequence
<220> FEATURE:
```

<223> OTHER INFORMATION: Description of Artificial Sequence: Synthetic
      probe
<220> FEATURE:
<223> OTHER INFORMATION: 5' amino modifier C6

<400> SEQUENCE: 511
cccaaactcg tgttgtactt agaacgaa                                       28

<210> SEQ ID NO 512
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 512
cccaaaggca ttgtcaacaa accagtaa                                       28

<210> SEQ ID NO 513
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 513
cccaacagta gttgttaacg actgctaa                                       28

<210> SEQ ID NO 514
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 514
cccaatgctc aggtcaaaca aactagaa                                       28

<210> SEQ ID NO 515
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 515
cccaatgtcg tactttgagt aagcctaa                                       28

<210> SEQ ID NO 516
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 516
cccaaggcta gacgaacatt accatgaa                                               28

<210> SEQ ID NO 517
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 517
cccaacgagt gttctagtgt tacacgaa                                               28

<210> SEQ ID NO 518
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 518
cccaacaggt ttacgtgtgt acagctaa                                               28

<210> SEQ ID NO 519
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 519
cccaaaggtt ccttccatgt aagctcaa                                               28

<210> SEQ ID NO 520
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 520
cccaaaggct ttgctgttac ttagacaa                                               28

<210> SEQ ID NO 521
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 521
cccaacaaag taactgttcg ttgcgaaa                                               28

-continued

<210> SEQ ID NO 522
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 522
cccaaatgct tggaacttct aactcgaa                                        28

<210> SEQ ID NO 523
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 523
cccaacctga gtactgtgct ctgaaaaa                                        28

<210> SEQ ID NO 524
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 524
cccaaggact caagtcttcc ttcacgaa                                        28

<210> SEQ ID NO 525
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 525
cccaaagggt tccgttcact aacatgaa                                        28

<210> SEQ ID NO 526
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 526
cccaaccagt actgcatttc ttggagaa                                        28

<210> SEQ ID NO 527
<211> LENGTH: 28

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 527
cccaacaagc ctagttctgg ttgtacaa                                         28

<210> SEQ ID NO 528
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 528
cccaacagac ctacctttgt tgtagcaa                                         28

<210> SEQ ID NO 529
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 529
cccaagaacc cttctttgac tgcaagaa                                         28

<210> SEQ ID NO 530
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 530
cccaaagtcg tttagtcctc tgaccaaa                                         28

<210> SEQ ID NO 531
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 531
cccaaagtct cttcgttcaa ctggagaa                                         28

<210> SEQ ID NO 532
<211> LENGTH: 28
<212> TYPE: DNA
<213> ORGANISM: Artificial Sequence
<220> FEATURE:
<223> OTHER INFORMATION: Description of Artificial Sequence: Synthetic
``` probe
<220> FEATURE:
<223> OTHER INFORMATION: 5' amino modifier C6

<400> SEQUENCE: 532
cccaacgcat tcttaacaga gacagtaa                                              28

<210> SEQ ID NO 533
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 533
cccaacgagt ctcttgagag gaaactaa                                              28

<210> SEQ ID NO 534
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 534
cccaacgtag tgagtagacg tacaccaa                                              28

<210> SEQ ID NO 535
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 535
cccaaaaagc ttgttacctt ctgcagaa                                              28

<210> SEQ ID NO 536
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 536
cccaaacttt gtactggagt agccaaaa                                              28

<210> SEQ ID NO 537
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

```
<400> SEQUENCE: 537
cccaagctta cctcttaagt gcaagaaa                                           28

<210> SEQ ID NO 538
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 538
cccaagaacc tcttaaagct aagcgaaa                                           28

<210> SEQ ID NO 539
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 539
cccaagacct aaacaagctt gagtcgaa                                           28

<210> SEQ ID NO 540
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 540
cccaatttgc ataggttctt ccaacgaa                                           28

<210> SEQ ID NO 541
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 541
cccaagcaag ttgcattcct ctcatgaa                                           28

<210> SEQ ID NO 542
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 542
cccaatcggt acacgacata catgagaa                                           28
```

<210> SEQ ID NO 543
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 543
cccaaacctc tgtttctgag tcgaagaa                                        28

<210> SEQ ID NO 544
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 544
cccaaacacg tgttggctag tctaaaaa                                        28

<210> SEQ ID NO 545
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 545
cccaacggtt taagcctttc accatgaa                                        28

<210> SEQ ID NO 546
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 546
cccaacggtt catggactaa ctgaggaa                                        28

<210> SEQ ID NO 547
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 547
cccaaaccgt tcagtttcac atgggaaa                                        28

<210> SEQ ID NO 548
<211> LENGTH: 28
<212> TYPE: DNA

<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 548
cccaagacct ctccacttga ctgtagaa                                      28

<210> SEQ ID NO 549
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 549
cccaagtctt tacctcagtg tagcagaa                                      28

<210> SEQ ID NO 550
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 550
cccaaacagc tgagtccttc cataagaa                                      28

<210> SEQ ID NO 551
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 551
cccaaaactg tcattgcctt cctaggaa                                      28

<210> SEQ ID NO 552
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 552
cccaagtcca ttcattcgtt cgaaggaa                                      28

<210> SEQ ID NO 553
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

```
<220> FEATURE:
<223> OTHER INFORMATION: 5' amino modifier C6

<400> SEQUENCE: 553
cccaagtcac ctcttggtag taaggcaa                                           28

<210> SEQ ID NO 554
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 554
cccaaccatc agctttagtt ggtgacaa                                           28

<210> SEQ ID NO 555
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 555
cccaagttac ctgactccac tggacaaa                                           28

<210> SEQ ID NO 556
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 556
cccaaagttg gcatctttgt cgtcaaaa                                           28

<210> SEQ ID NO 557
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 557
cccaaacgtt gtgtctttaa catccgaa                                           28

<210> SEQ ID NO 558
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 558
```
cccaacagtt tggctttgac atcacgaa                                          28

<210> SEQ ID NO 559
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 559
cccaaacggt tgcaactca ttcttgaa                                           28

<210> SEQ ID NO 560
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 560
cccaagacga ctgtttactt cctcagaa                                          28

<210> SEQ ID NO 561
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 561
cccaaggact ccatttcgac ttcgacaa                                          28

<210> SEQ ID NO 562
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 562
cccaaatcaa gtctagacag aaggctaa                                          28

<210> SEQ ID NO 563
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 563
cccaagtcgt catcagcaag aaacctaa                                          28

```
<210> SEQ ID NO 564
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 564
cccaatcgtg tacatggaaa gcacataa                                            28

<210> SEQ ID NO 565
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 565
cccaactttg aagcatggag aacactaa                                            28

<210> SEQ ID NO 566
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 566
cccaaaagtc ctctgtttag ttagcgaa                                            28

<210> SEQ ID NO 567
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 567
cccaagtaac caaaccatgc tagtcgaa                                            28

<210> SEQ ID NO 568
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 568
cccaaggaca ttgactcacc atcagcaa                                            28

<210> SEQ ID NO 569
<211> LENGTH: 28
<212> TYPE: DNA
<213> ORGANISM: Artificial Sequence
```

-continued

<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 569
cccaatgggt actgcataca ccatagaa                                      28

<210> SEQ ID NO 570
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 570
cccaaagaac tcgtcttcat ttacggaa                                      28

<210> SEQ ID NO 571
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 571
cccaaaggtc tttgtcctag tacgagaa                                      28

<210> SEQ ID NO 572
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 572
cccaacatgg ttaaggtcaa ctcgagaa                                      28

<210> SEQ ID NO 573
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 573
cccaagcttg taacgactta ctctcgaa                                      28

<210> SEQ ID NO 574
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:

<223> OTHER INFORMATION: 5' amino modifier C6

<400> SEQUENCE: 574
cccaagacca ctctcctagc atttggaa                                              28

<210> SEQ ID NO 575
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 575
cccaagtcca ttcccattgg tagcagaa                                              28

<210> SEQ ID NO 576
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 576
cccaacactc tgtgtcgtac atagggaa                                              28

<210> SEQ ID NO 577
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 577
cccaaacttg tgtggaaacc gtacccaa                                              28

<210> SEQ ID NO 578
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 578
cccaaatgcc ttggtgtcat acaggaaa                                              28

<210> SEQ ID NO 579
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 579

```
cccaatcgga agtcagacta gaaactaa                                              28
```

<210> SEQ ID NO 580
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 580

```
cccaaccagt accagaggtg aagtctaa                                              28
```

<210> SEQ ID NO 581
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 581

```
cccaacataa agggaaactg agctctaa                                              28
```

<210> SEQ ID NO 582
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 582

```
cccaactaag aggagaactc cagttgaa                                              28
```

<210> SEQ ID NO 583
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 583

```
cccaactagg aagtttactc cactcgaa                                              28
```

<210> SEQ ID NO 584
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 584

```
cccaacaacg tctgctaaag taggtcaa                                              28
```

<210> SEQ ID NO 585

```
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 585
cccaacgtca tcaacatagt aggctaaa                                          28

<210> SEQ ID NO 586
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 586
cccaaatcgt cactagagag agaactaa                                          28

<210> SEQ ID NO 587
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 587
cccaacttgt cacatgaagg agacctaa                                          28

<210> SEQ ID NO 588
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 588
cccaaggaga ctctagaaac ttccgaaa                                          28

<210> SEQ ID NO 589
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 589
cccaagagtt acgcttctac ttccagaa                                          28

<210> SEQ ID NO 590
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      probe
<220> FEATURE:
<223> OTHER INFORMATION: 5' amino modifier C6

<400> SEQUENCE: 590
cccaaaccag tccttaaggg taggtcaa                                              28

<210> SEQ ID NO 591
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 591
cccaaaagcc tagaacatta catcggaa                                              28

<210> SEQ ID NO 592
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 592
cccaagctga aagcactcca tcattgaa                                              28

<210> SEQ ID NO 593
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 593
cccaatcagt gtgactccat ccctagaa                                              28

<210> SEQ ID NO 594
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 594
cccaagctac ttaactctgt ttcggaaa                                              28

<210> SEQ ID NO 595
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6
```

-continued

<400> SEQUENCE: 595
cccaaatgct ttcactggtc tagggaaa                                             28

<210> SEQ ID NO 596
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 596
cccaacagtt gttcgttcat gaccagaa                                             28

<210> SEQ ID NO 597
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 597
cccaatcacg aaacgactac ttagggaa                                             28

<210> SEQ ID NO 598
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 598
cccaacattg tttggttcat caagcgaa                                             28

<210> SEQ ID NO 599
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 599
cccaaattct tgtggtacaa catgcgaa                                             28

<210> SEQ ID NO 600
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 600
cccaacctga ccaacggttc atttgtaa                                             28

<210> SEQ ID NO 601
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 601
cccaagacca ttacgtcttg ccttgaaa                                         28

<210> SEQ ID NO 602
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 602
cccaagccat acctcattga gctttgaa                                         28

<210> SEQ ID NO 603
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 603
cccaaaggac tcttccgtaa cctgtcaa                                         28

<210> SEQ ID NO 604
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 604
cccaaggagt gcatttcgta acctgaaa                                         28

<210> SEQ ID NO 605
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 605
cccaatcaca agcgaaagta gtgtctaa                                         28

<210> SEQ ID NO 606
<211> LENGTH: 28

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 606
cccaatcgaa gagacgactt gagttcaa                                              28

<210> SEQ ID NO 607
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 607
cccaaatggc tttggtacaa ctgacgaa                                              28

<210> SEQ ID NO 608
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 608
cccaagagac gttggaacac ctactgaa                                              28

<210> SEQ ID NO 609
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 609
cccaagaaag ctgttcaaac ctcacgaa                                              28

<210> SEQ ID NO 610
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 610
cccaagtgag tcttcgaaac ttcggaaa                                              28

<210> SEQ ID NO 611
<211> LENGTH: 28
<212> TYPE: DNA
<213> ORGANISM: Artificial Sequence
<220> FEATURE:
<223> OTHER INFORMATION: Description of Artificial Sequence: Synthetic
``` probe
<220> FEATURE:
<223> OTHER INFORMATION: 5' amino modifier C6

<400> SEQUENCE: 611
cccaaccagt gttaacggaa cttgggaa                                            28

<210> SEQ ID NO 612
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 612
cccaacaggt gtacttggta ctacggaa                                            28

<210> SEQ ID NO 613
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 613
cccaagtacc atccttacgt agcttgaa                                            28

<210> SEQ ID NO 614
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 614
cccaagctac ttccactagg tacaggaa                                            28

<210> SEQ ID NO 615
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 615
cccaagtacc tcaacaagtc aaggctaa                                            28

<210> SEQ ID NO 616
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

```
<400> SEQUENCE: 616
cccaagtacc caagagacta agcttgaa                                      28

<210> SEQ ID NO 617
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 617
cccaatgaac caaacactga cctgtgaa                                      28

<210> SEQ ID NO 618
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 618
cccaagtgca catcgaacca acttagaa                                      28

<210> SEQ ID NO 619
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 619
cccaatgctt agcgtactac cattagaa                                      28

<210> SEQ ID NO 620
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 620
cccaagtttg acgttcaacc atcacgaa                                      28

<210> SEQ ID NO 621
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 621
cccaatttag cttgtccact cagaggaa                                      28
```

<210> SEQ ID NO 622
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 622
cccaacgcta ctttcttagt tagagcaa                                        28

<210> SEQ ID NO 623
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 623
cccaaaagcc tttccactgt tactggaa                                        28

<210> SEQ ID NO 624
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 624
cccaacctgt tacctcagac attgggaa                                        28

<210> SEQ ID NO 625
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 625
cccaacgtca tttaggtctc taagggaa                                        28

<210> SEQ ID NO 626
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 626
cccaaacgtc ttgggttaca ctactgaa                                        28

<210> SEQ ID NO 627
<211> LENGTH: 28
<212> TYPE: DNA

```
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 627
cccaatcaca gaaccagtca gctttgaa                                             28

<210> SEQ ID NO 628
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 628
cccaagtggt actctcgtaa ctccagaa                                             28

<210> SEQ ID NO 629
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 629
cccaagaact cctaccaaga ctcgtgaa                                             28

<210> SEQ ID NO 630
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 630
cccaatttga cttgaacgca taaccgaa                                             28

<210> SEQ ID NO 631
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 631
cccaattgag acctcacgag aacactaa                                             28

<210> SEQ ID NO 632
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
```

```
<220> FEATURE:
<223> OTHER INFORMATION: 5' amino modifier C6

<400> SEQUENCE: 632
cccaaacaaa gtcattgggt tcgctaaa                                28

<210> SEQ ID NO 633
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 633
cccaatcgaa caaacctaga gtgctcaa                                28

<210> SEQ ID NO 634
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 634
cccaaggtct tagctacaac ctcatgaa                                28

<210> SEQ ID NO 635
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 635
cccaagcttt gaagccttcc aactagaa                                28

<210> SEQ ID NO 636
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 636
cccaatacag gtgtcacaaa ctcacgaa                                28

<210> SEQ ID NO 637
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 637
```
cccaaccgtt cataacaagg gaacctaa                                                28

<210> SEQ ID NO 638
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 638
cccaaagtac ccaaagcatg tctggaaa                                                28

<210> SEQ ID NO 639
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 639
cccaaatgtt ctctttacgc tagggaaa                                                28

<210> SEQ ID NO 640
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 640
cccaatttga cttcagacga aagctgaa                                                28

<210> SEQ ID NO 641
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 641
cccaatacag aaacgacata cgcttgaa                                                28

<210> SEQ ID NO 642
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 642
cccaatcacc agaagaacta cctgtgaa                                                28

```
<210> SEQ ID NO 643
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 643
cccaatacga acgacaggtc atggttaa                                          28

<210> SEQ ID NO 644
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 644
cccaagaact ccaaccatgt agtcgtaa                                          28

<210> SEQ ID NO 645
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 645
cccaaattgc gttcttcagt acacgaaa                                          28

<210> SEQ ID NO 646
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 646
cccaaatctg cttcctgtag tacacgaa                                          28

<210> SEQ ID NO 647
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 647
cccaaggtca cttgcaacct agaaccaa                                          28

<210> SEQ ID NO 648
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 648
cccaaggctt agtacgacag taacccaa                                          28

<210> SEQ ID NO 649
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 649
cccaacaagt gaagtggtct gaccagaa                                          28

<210> SEQ ID NO 650
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 650
cccaacagag tagtgtgact agcctaaa                                          28

<210> SEQ ID NO 651
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 651
cccaatcaca aggagtagca actttgaa                                          28

<210> SEQ ID NO 652
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 652
cccaacctgt aagtgaaacg actggaaa                                          28

<210> SEQ ID NO 653
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
```

-continued

<223> OTHER INFORMATION: 5' amino modifier C6

<400> SEQUENCE: 653
cccaacccta gttgaggaca aactggaa                                          28

<210> SEQ ID NO 654
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 654
cccaaggcat cacacctagc aagtttaa                                          28

<210> SEQ ID NO 655
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 655
cccaagacct accctacaga gcttgtaa                                          28

<210> SEQ ID NO 656
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 656
cccaatttcg taacaagttg gactcgaa                                          28

<210> SEQ ID NO 657
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 657
cccaatcaaa gaaacaggtt gcactgaa                                          28

<210> SEQ ID NO 658
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 658
cccaacgtct tagagtcctt gaacccaa                                              28

<210> SEQ ID NO 659
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 659
cccaatgctg aaacgtttcc cttgtaaa                                              28

<210> SEQ ID NO 660
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 660
cccaacaggt ttgtttgact cagacgaa                                              28

<210> SEQ ID NO 661
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 661
cccaaccttc gacataaaga aagcgtaa                                              28

<210> SEQ ID NO 662
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 662
cccaatgaac cattagcaag caaggtaa                                              28

<210> SEQ ID NO 663
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 663
cccaatgaac cttgagcaca aactggaa                                              28

<210> SEQ ID NO 664

```
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 664
cccaaagggt tcttggacag tacctcaa                                           28

<210> SEQ ID NO 665
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 665
cccaactgta aaggagttcg taccctaa                                           28

<210> SEQ ID NO 666
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 666
cccaatcgag aaggaagtca cactgtaa                                           28

<210> SEQ ID NO 667
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 667
cccaactaaa ggaagtgtca gctgtcaa                                           28

<210> SEQ ID NO 668
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 668
cccaagcaca taaggtcaaa cgtgtgaa                                           28

<210> SEQ ID NO 669
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      probe
<220> FEATURE:
<223> OTHER INFORMATION: 5' amino modifier C6

<400> SEQUENCE: 669
cccaacgttg aaggaacatt cacaggaa                                          28

<210> SEQ ID NO 670
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 670
cccaatgtga gctgacaaac aacatgaa                                          28

<210> SEQ ID NO 671
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 671
cccaagctac tctaacacga ctggacaa                                          28

<210> SEQ ID NO 672
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 672
cccaagccta accttcaagt gcatgtaa                                          28

<210> SEQ ID NO 673
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 673
cccaagtaaa cacctctagg ttcggaaa                                          28

<210> SEQ ID NO 674
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6
```

<400> SEQUENCE: 674
cccaagtctt gactctcgac tcgaaaaa                                             28

<210> SEQ ID NO 675
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 675
cccaactgca gagtggactt gacaaaaa                                             28

<210> SEQ ID NO 676
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 676
cccaacagct ctggtgtact taagacaa                                             28

<210> SEQ ID NO 677
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 677
cccaatacga gagagacgtt tacgacaa                                             28

<210> SEQ ID NO 678
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 678
cccaagtacc ctactctcgt caaggaaa                                             28

<210> SEQ ID NO 679
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 679
cccaataacg acacaactgg ttaccgaa                                             28

<210> SEQ ID NO 680
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 680
cccaacacgt cataacggta gacctcaa                                       28

<210> SEQ ID NO 681
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 681
cccaatccca agcaacagtc agtagtaa                                       28

<210> SEQ ID NO 682
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 682
cccaataaac gaacacctgt gagctcaa                                       28

<210> SEQ ID NO 683
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 683
cccaagttac cagactcaac aacggtaa                                       28

<210> SEQ ID NO 684
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 684
cccaagttag cttgaccaac caacgtaa                                       28

<210> SEQ ID NO 685
<211> LENGTH: 28

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 685
cccaagacca tcactacagg agtcctaa                                              28

<210> SEQ ID NO 686
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 686
cccaagtact cttcttacgg tagcagaa                                              28

<210> SEQ ID NO 687
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 687
cccaatttgc catcgacaac gtgaaaaa                                              28

<210> SEQ ID NO 688
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 688
cccaaagtct cttgggtaca acgtgtaa                                              28

<210> SEQ ID NO 689
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 689
cccaatgacc ttctcgttac aacggtaa                                              28

<210> SEQ ID NO 690
<211> LENGTH: 28
<212> TYPE: DNA
<213> ORGANISM: Artificial Sequence
<220> FEATURE:
<223> OTHER INFORMATION: Description of Artificial Sequence: Synthetic
```

```
          probe
<220> FEATURE:
<223> OTHER INFORMATION: 5' amino modifier C6

<400> SEQUENCE: 690
cccaataccg ttctgttaag aagcgtaa                                         28

<210> SEQ ID NO 691
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 691
cccaaagtcc ttcctctagt tacggaaa                                         28

<210> SEQ ID NO 692
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 692
cccaagccat acaacattgg actggtaa                                         28

<210> SEQ ID NO 693
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 693
cccaacctga gaggtaagct tgacttaa                                         28

<210> SEQ ID NO 694
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 694
cccaacacct agtagtcgtt ggacagaa                                         28

<210> SEQ ID NO 695
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6
```

<400> SEQUENCE: 695
cccaagtaca ctaaaccgtt gcgaaaaa                                              28

<210> SEQ ID NO 696
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 696
cccaaccact ggtacggaaa gctttaaa                                              28

<210> SEQ ID NO 697
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 697
cccaagacca ctctttgagg agtacgaa                                              28

<210> SEQ ID NO 698
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 698
cccaagactg accttggaaa gtaggcaa                                              28

<210> SEQ ID NO 699
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 699
cccaactcac gttacgaaac agaggtaa                                              28

<210> SEQ ID NO 700
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 700
cccaagcgta acgtcattta ctttcgaa                                              28

<210> SEQ ID NO 701
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 701
cccaacgaac gtgtcatttc actttgaa                                         28

<210> SEQ ID NO 702
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 702
cccaaatctc tggtgtccat ccgaacaa                                         28

<210> SEQ ID NO 703
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 703
cccaaagctt tggagtctgt gacaacaa                                         28

<210> SEQ ID NO 704
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 704
cccaagggta ctaggcttgt gacaacaa                                         28

<210> SEQ ID NO 705
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 705
cccaatagcg aacacctagt tacgacaa                                         28

<210> SEQ ID NO 706
<211> LENGTH: 28
<212> TYPE: DNA

```
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 706
cccaatcacg agtccaagag ttacccaa                                    28

<210> SEQ ID NO 707
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 707
cccaatgaga acaaaggcta accgttaa                                    28

<210> SEQ ID NO 708
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 708
cccaactcgt catagaacac caaggtaa                                    28

<210> SEQ ID NO 709
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 709
cccaactcca tgcaagtaaa gaacgtaa                                    28

<210> SEQ ID NO 710
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 710
cccaaatgtg actaccgaaa cgctttaa                                    28

<210> SEQ ID NO 711
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
```

<220> FEATURE:
<223> OTHER INFORMATION: 5' amino modifier C6

<400> SEQUENCE: 711
cccaagacaa gttgaccaac gcatctaa                                              28

<210> SEQ ID NO 712
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 712
cccaactgca cagtttacaa cctaggaa                                              28

<210> SEQ ID NO 713
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 713
cccaagctga ctgtcttaac ccttagaa                                              28

<210> SEQ ID NO 714
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 714
cccaaggtca agtcgacaag ctaactaa                                              28

<210> SEQ ID NO 715
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 715
cccaacacgt gagttccaac cctaagaa                                              28

<210> SEQ ID NO 716
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 716
cccaagccat aaccatcagt ctgagtaa                                      28

<210> SEQ ID NO 717
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 717
cccaagtcaa cacactcagc agtagtaa                                      28

<210> SEQ ID NO 718
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 718
cccaagtacc tactcatgct tgcagtaa                                      28

<210> SEQ ID NO 719
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 719
cccaaatgta cgtaaagcac aagcctaa                                      28

<210> SEQ ID NO 720
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 720
cccaacgtgt aaaggaacta ggctacaa                                      28

<210> SEQ ID NO 721
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 721
cccaaggtca ctaactcagg aactccaa                                      28

```
<210> SEQ ID NO 722
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 722
cccaattcga agtaagcaac accatgaa                                              28

<210> SEQ ID NO 723
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 723
cccaatcgga agtgtaaact ggacacaa                                              28

<210> SEQ ID NO 724
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 724
cccaagactc acaaaccgta cttggtaa                                              28

<210> SEQ ID NO 725
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 725
cccaacattc tgcataggag acagtgaa                                              28

<210> SEQ ID NO 726
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 726
cccaaaccca tgcacattga gaactgaa                                              28

<210> SEQ ID NO 727
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 727
cccaatggtc aggactaaac taccagaa                                           28

<210> SEQ ID NO 728
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 728
cccaagcttc cagaacttta cttgggaa                                           28

<210> SEQ ID NO 729
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 729
cccaagttca actccaacgt caggacaa                                           28

<210> SEQ ID NO 730
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 730
cccaagttac taccatacga ctcgtgaa                                           28

<210> SEQ ID NO 731
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 731
cccaacagac atgcacttaa ctcaggaa                                           28

<210> SEQ ID NO 732
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
```

```
<223> OTHER INFORMATION: 5' amino modifier C6

<400> SEQUENCE: 732
cccaacttga acctagaaag ggtagcaa                                         28

<210> SEQ ID NO 733
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 733
cccaagtcct accttaagag acgagtaa                                         28

<210> SEQ ID NO 734
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 734
cccaacagtt agggaagctt tgcatcaa                                         28

<210> SEQ ID NO 735
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 735
cccaacgtct agctagaaga agtttcaa                                         28

<210> SEQ ID NO 736
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 736
cccaatttag tcacctctgg aaccgtaa                                         28

<210> SEQ ID NO 737
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 737
```

```
cccaacagtg aaggaacctt tcgtcaaa                                            28

<210> SEQ ID NO 738
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 738
cccaaaggct tcctttcaga cagtttaa                                            28

<210> SEQ ID NO 739
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 739
cccaaacggt tgttgagtcg aaccataa                                            28

<210> SEQ ID NO 740
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 740
cccaaacctc tgagttggct aaacagaa                                            28

<210> SEQ ID NO 741
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 741
cccaagcagt tgtaagacca agacgtaa                                            28

<210> SEQ ID NO 742
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 742
cccaagagag ctaccgtttc tttgtaaa                                            28

<210> SEQ ID NO 743
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 743
cccaaagggt tctccaagtt tacaggaa                                            28

<210> SEQ ID NO 744
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 744
cccaacgtta gtgtgttcaa gcttcaaa                                            28

<210> SEQ ID NO 745
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 745
cccaactcac tgcaaaggta aaggtcaa                                            28

<210> SEQ ID NO 746
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 746
cccaagagct cacaaggtgt taggtcaa                                            28

<210> SEQ ID NO 747
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 747
cccaactgtc tactgaagga gtttgcaa                                            28

<210> SEQ ID NO 748
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      probe
<220> FEATURE:
<223> OTHER INFORMATION: 5' amino modifier C6

<400> SEQUENCE: 748
cccaaagctt cctttactga ctagtgaa                                              28

<210> SEQ ID NO 749
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 749
cccaactgct acccttgagt aaagtcaa                                              28

<210> SEQ ID NO 750
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 750
cccaagctca ttcccttgaa cagagtaa                                              28

<210> SEQ ID NO 751
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 751
cccaagagac tgtgcacaac ccttagaa                                              28

<210> SEQ ID NO 752
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 752
cccaacggtt aacctcaagt gctaaaaa                                              28

<210> SEQ ID NO 753
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6
```

-continued

<400> SEQUENCE: 753
cccaaaccct tgggtaagct agagacaa                                              28

<210> SEQ ID NO 754
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 754
cccaaattgc tcacgttctc atggacaa                                              28

<210> SEQ ID NO 755
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 755
cccaacccta ggaagccatc agtttaaa                                              28

<210> SEQ ID NO 756
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 756
cccaaaccgt ttgaaccttc tggtcaaa                                              28

<210> SEQ ID NO 757
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 757
cccaatccga aggagaactt tgaccaaa                                              28

<210> SEQ ID NO 758
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 758
cccaattgag tctgaagcaa ccaagtaa                                              28

<210> SEQ ID NO 759
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 759
cccaactgtt tagagtgaca ttgcctaa                                        28

<210> SEQ ID NO 760
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 760
cccaatactg ttaaggctac aacgctaa                                        28

<210> SEQ ID NO 761
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 761
cccaaatcgg ttcgttcact actcagaa                                        28

<210> SEQ ID NO 762
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 762
cccaaccaag gttggcttag tagtccaa                                        28

<210> SEQ ID NO 763
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 763
cccaaggcta cagactttcc catttgaa                                        28

<210> SEQ ID NO 764
<211> LENGTH: 28

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 764
cccaagaacc tcacgtgtgc ttgttaaa                                          28

<210> SEQ ID NO 765
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 765
cccaagacat ccactcttgt ttgacgaa                                          28

<210> SEQ ID NO 766
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 766
cccaaggtac acacctttgc cttacgaa                                          28

<210> SEQ ID NO 767
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 767
cccaacgagt tggagtaaca tacgacaa                                          28

<210> SEQ ID NO 768
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 768
cccaaacggt tgtggtaaca tcctagaa                                          28

<210> SEQ ID NO 769
<211> LENGTH: 28
<212> TYPE: DNA
<213> ORGANISM: Artificial Sequence
<220> FEATURE:
<223> OTHER INFORMATION: Description of Artificial Sequence: Synthetic
```

```
        probe
<220> FEATURE:
<223> OTHER INFORMATION: 5' amino modifier C6

<400> SEQUENCE: 769
cccaagacct tgactggaga aacggtaa                                              28

<210> SEQ ID NO 770
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 770
cccaagctca ctaccattgt cattggaa                                              28

<210> SEQ ID NO 771
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 771
cccaatccgt tacgtgaagg gtaaacaa                                              28

<210> SEQ ID NO 772
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 772
cccaatacag actgcacact caggtaaa                                              28

<210> SEQ ID NO 773
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 773
cccaatttac gtagtccaac ttgcgaaa                                              28

<210> SEQ ID NO 774
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6
```

<400> SEQUENCE: 774
cccaagacct tactacctga agcagtaa                28

<210> SEQ ID NO 775
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 775
cccaacattg tttctctgac aagctgaa                28

<210> SEQ ID NO 776
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 776
cccaacagca gtttagccaa gaagtcaa                28

<210> SEQ ID NO 777
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 777
cccaagacct tggactctct ctaacgaa                28

<210> SEQ ID NO 778
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 778
cccaagtact ttcttccagt cagagcaa                28

<210> SEQ ID NO 779
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 779
cccaatcaga caaccttgtt catcggaa                28

<210> SEQ ID NO 780
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 780
cccaatcacc tgttgcattc atagggaa                                          28

<210> SEQ ID NO 781
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 781
cccaatttgc agtgaacacc aacagtaa                                          28

<210> SEQ ID NO 782
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 782
cccaagtctg cagtaacaca ccaagtaa                                          28

<210> SEQ ID NO 783
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 783
cccaatgtct cagtctccac attaggaa                                          28

<210> SEQ ID NO 784
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 784
cccaagtaca ccatttcgca tttcggaa                                          28

<210> SEQ ID NO 785
<211> LENGTH: 28
<212> TYPE: DNA

```
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 785
cccaagctac cactttagaa gtaggcaa                                             28

<210> SEQ ID NO 786
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 786
cccaatcaca aggttaccac aggagtaa                                             28

<210> SEQ ID NO 787
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 787
cccaacacca tggacacttc taagggaa                                             28

<210> SEQ ID NO 788
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 788
cccaacctga aagagtttct tgcgtaaa                                             28

<210> SEQ ID NO 789
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 789
cccaagagac gtgtcatctc atccagaa                                             28

<210> SEQ ID NO 790
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
```

```
<220> FEATURE:
<223> OTHER INFORMATION: 5' amino modifier C6

<400> SEQUENCE: 790
cccaatagcg tagacaactt caaagcaa                                            28

<210> SEQ ID NO 791
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 791
cccaaagttc tctcgttcat agctgaaa                                            28

<210> SEQ ID NO 792
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 792
cccaaattgg tcttctgcat aaagcgaa                                            28

<210> SEQ ID NO 793
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 793
cccaatcgaa ggagtagtct acctgtaa                                            28

<210> SEQ ID NO 794
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 794
cccaatcagg actacggaaa gttcccaa                                            28

<210> SEQ ID NO 795
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 795
```
cccaaccgta acatccatga gacgtcaa                                       28

<210> SEQ ID NO 796
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 796
cccaatgcga aagaggtacc gtttacaa                                       28

<210> SEQ ID NO 797
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 797
cccaagacac atccaactgg tgactcaa                                       28

<210> SEQ ID NO 798
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 798
cccaagacca tccttcaaga gacgtcaa                                       28

<210> SEQ ID NO 799
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 799
cccaagctct caagtctaaa cagtgcaa                                       28

<210> SEQ ID NO 800
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 800
cccaacaaag tagaaactcg tagctgaa                                       28

```
<210> SEQ ID NO 801
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 801
cccaaccaga gtgtgaacac tagggtaa                                          28

<210> SEQ ID NO 802
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 802
cccaacctca tgaagactcc aagggtaa                                          28

<210> SEQ ID NO 803
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 803
cccaaacctg tggacactac accttgaa                                          28

<210> SEQ ID NO 804
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 804
cccaaagttc agagttctct ccactgaa                                          28

<210> SEQ ID NO 805
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 805
cccaagctac tttcaactga cagtggaa                                          28

<210> SEQ ID NO 806
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 806
cccaagccat cttctactga acggtaaa                                            28

<210> SEQ ID NO 807
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 807
cccaatgttt cagtccattg aacgctaa                                            28

<210> SEQ ID NO 808
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 808
cccaaattgc ttctcacgtc attaggaa                                            28

<210> SEQ ID NO 809
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 809
cccaatggga actctgaaac atccgaaa                                            28

<210> SEQ ID NO 810
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 810
cccaatcgta gagtcaaacc acaagtaa                                            28

<210> SEQ ID NO 811
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
```

<223> OTHER INFORMATION: 5' amino modifier C6

<400> SEQUENCE: 811
cccaacaggt gtcgtgtgaa acagtcaa                                            28

<210> SEQ ID NO 812
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 812
cccaaggtca ttaagccttc gactccaa                                            28

<210> SEQ ID NO 813
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 813
cccaacttga agtgaaggca accatgaa                                            28

<210> SEQ ID NO 814
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 814
cccaacaact aggagtgctc tggttaaa                                            28

<210> SEQ ID NO 815
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 815
cccaagacca tagcatccaa gtcgtcaa                                            28

<210> SEQ ID NO 816
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 816

```
cccaatcgag aaacacctgt acaagtaa                                          28

<210> SEQ ID NO 817
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 817
cccaacagtc tttaagcaga aggactaa                                          28

<210> SEQ ID NO 818
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 818
cccaacgtca actacacaga aggtctaa                                          28

<210> SEQ ID NO 819
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 819
cccaagtcga caacagcatt aggtctaa                                          28

<210> SEQ ID NO 820
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 820
cccaattggt cagaactttc cttgcaaa                                          28

<210> SEQ ID NO 821
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 821
cccaacctag gtcaagttta ggttgcaa                                          28

<210> SEQ ID NO 822
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 822
cccaagtcat ctgcatccac actaggaa                                            28

<210> SEQ ID NO 823
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 823
cccaaatcgc ttgaaccata ccatggaa                                            28

<210> SEQ ID NO 824
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 824
cccaaatctg aactgaggaa caagctaa                                            28

<210> SEQ ID NO 825
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 825
cccaacgtga gcatcaggaa catttgaa                                            28

<210> SEQ ID NO 826
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 826
cccaatccct agttccagtc atgaggaa                                            28

<210> SEQ ID NO 827
<211> LENGTH: 28
<212> TYPE: DNA
<213> ORGANISM: Artificial Sequence
<220> FEATURE:
```

<223> OTHER INFORMATION: Description of Artificial Sequence: Synthetic
      probe
<220> FEATURE:
<223> OTHER INFORMATION: 5' amino modifier C6

<400> SEQUENCE: 827
cccaactcct agtcctgtag tccagaaa                                       28

<210> SEQ ID NO 828
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 828
cccaagagtc aactccatga aagcctaa                                       28

<210> SEQ ID NO 829
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 829
cccaaggtag tctcagagaa cacctgaa                                       28

<210> SEQ ID NO 830
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 830
cccaagctgt aggacataag aaccgtaa                                       28

<210> SEQ ID NO 831
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 831
cccaagtcca actgaaacag agctgtaa                                       28

<210> SEQ ID NO 832
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 832
cccaagtgca actacaggac agtgtgaa                                              28

<210> SEQ ID NO 833
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 833
cccaatgaaa cagacaagta gcgttcaa                                              28

<210> SEQ ID NO 834
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 834
cccaaaaact gtagctttcc cttggaaa                                              28

<210> SEQ ID NO 835
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 835
cccaatccgt agagcagtga gtttacaa                                              28

<210> SEQ ID NO 836
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 836
cccaaggttc atgcatcctc ttcaagaa                                              28

<210> SEQ ID NO 837
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 837
cccaaacctt tgtggagtca agcatgaa                                              28

<210> SEQ ID NO 838
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 838
cccaaacctt tgtgagcaga gcatttaa                                    28

<210> SEQ ID NO 839
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 839
cccaaactgt ttcccttaga gcagtcaa                                    28

<210> SEQ ID NO 840
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 840
cccaagctgt aggagttaca tctctgaa                                    28

<210> SEQ ID NO 841
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 841
cccaagtgga cactccagaa ctctgtaa                                    28

<210> SEQ ID NO 842
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 842
cccaacgtca tctgacagaa cagactaa                                    28

<210> SEQ ID NO 843
<211> LENGTH: 28

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 843
cccaagtcca acgaagcatg acacttaa                                          28

<210> SEQ ID NO 844
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 844
cccaaagcct aaagcctttg ggttacaa                                          28

<210> SEQ ID NO 845
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 845
cccaaccgtt caaacgacta agagtcaa                                          28

<210> SEQ ID NO 846
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 846
cccaatcgga acacctttgg tttccaaa                                          28

<210> SEQ ID NO 847
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 847
cccaatgacc atcatgtttg gcttcaaa                                          28

<210> SEQ ID NO 848
<211> LENGTH: 28
<212> TYPE: DNA
<213> ORGANISM: Artificial Sequence
<220> FEATURE:
<223> OTHER INFORMATION: Description of Artificial Sequence: Synthetic
```

```
probe
<220> FEATURE:
<223> OTHER INFORMATION: 5' amino modifier C6

<400> SEQUENCE: 848
cccaagacca tgagctctct tgttcaaa                                              28

<210> SEQ ID NO 849
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 849
cccaactagg tgaagtgaca gcatccaa                                              28

<210> SEQ ID NO 850
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 850
cccaacaagt taggagactg actgcaaa                                              28

<210> SEQ ID NO 851
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 851
cccaatcagc acacgagttc tagtaaaa                                              28

<210> SEQ ID NO 852
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 852
cccaaacgtc acctaggttg ggttacaa                                              28

<210> SEQ ID NO 853
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6
```

```
<400> SEQUENCE: 853
cccaaacctt gtctcttagc catggaaa                                          28

<210> SEQ ID NO 854
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 854
cccaaacctt gttactgtgc tagagcaa                                          28

<210> SEQ ID NO 855
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 855
cccaaacaga gtgcttccaa cttctgaa                                          28

<210> SEQ ID NO 856
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 856
cccaatcgtt cacgaagtag ggttacaa                                          28

<210> SEQ ID NO 857
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 857
cccaaaaaca tgttccgtag ttgccaaa                                          28

<210> SEQ ID NO 858
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 858
cccaatgacc acaacatagc atgtcgaa                                          28
```

```
<210> SEQ ID NO 859
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 859
cccaagcata aacactctgg acaggtaa                                            28

<210> SEQ ID NO 860
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 860
cccaagctaa caaccatcga gagtctaa                                            28

<210> SEQ ID NO 861
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 861
cccaagtgaa actcacacga gactctaa                                            28

<210> SEQ ID NO 862
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 862
cccaagtaac aaacccatga gctgtgaa                                            28

<210> SEQ ID NO 863
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 863
cccaagtcga catcacagtc aaggtgaa                                            28

<210> SEQ ID NO 864
<211> LENGTH: 28
<212> TYPE: DNA
```

```
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 864
cccaagaact ctctctgcac attgtgaa                                            28

<210> SEQ ID NO 865
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 865
cccaactgca cacatggttt ctttgaaa                                            28

<210> SEQ ID NO 866
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 866
cccaataaag cactttgaga gtaccgaa                                            28

<210> SEQ ID NO 867
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 867
cccaaatcgc ttgtttaacc tactggaa                                            28

<210> SEQ ID NO 868
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 868
cccaacgttg agtttaagct accagaaa                                            28

<210> SEQ ID NO 869
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
```

-continued

```
<220> FEATURE:
<223> OTHER INFORMATION: 5' amino modifier C6

<400> SEQUENCE: 869
cccaagtttc actacacgac ttcgagaa                                              28

<210> SEQ ID NO 870
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 870
cccaatggag acagtcttcc ctttgaaa                                              28

<210> SEQ ID NO 871
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 871
cccaagtttc actgcacttc aaggtgaa                                              28

<210> SEQ ID NO 872
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 872
cccaaccagt ctggttctac tacacgaa                                              28

<210> SEQ ID NO 873
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 873
cccaaattct cgttctcaga gtcaggaa                                              28

<210> SEQ ID NO 874
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 874
```
cccaagttac caacacctga gaagctaa                                              28

<210> SEQ ID NO 875
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 875
cccaaactac tgtcaaagga gtaggcaa                                              28

<210> SEQ ID NO 876
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 876
cccaagttcc caagacctac aagctgaa                                              28

<210> SEQ ID NO 877
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 877
cccaatttag cctaacagca acaggtaa                                              28

<210> SEQ ID NO 878
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 878
cccaaatctg ttctctgcaa agtcgtaa                                              28

<210> SEQ ID NO 879
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 879
cccaaagtcc ttgtctcaaa ctcaggaa                                              28

<210> SEQ ID NO 880
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 880
cccaaatctt gtgtgtcgaa gcaactaa                                          28

<210> SEQ ID NO 881
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 881
cccaagtgca actggagaca gactttaa                                          28

<210> SEQ ID NO 882
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 882
cccaaactgt cttgttcgaa cagcataa                                          28

<210> SEQ ID NO 883
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 883
cccaatttgt acatcgcttc atcggaaa                                          28

<210> SEQ ID NO 884
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 884
cccaatacag aaggagtacc tgacctaa                                          28

<210> SEQ ID NO 885
<211> LENGTH: 28
<212> TYPE: DNA
<213> ORGANISM: Artificial Sequence

```
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 885
cccaatcgca aagaagtacc agtttcaa                                              28

<210> SEQ ID NO 886
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 886
cccaactggt agacatgcat agaagcaa                                              28

<210> SEQ ID NO 887
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 887
cccaagagaa ctaccgttgt gaaggcaa                                              28

<210> SEQ ID NO 888
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 888
cccaatttcg agagtcacat caacagaa                                              28

<210> SEQ ID NO 889
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 889
cccaacggta aggctacctc tttgtaaa                                              28

<210> SEQ ID NO 890
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
```

<223> OTHER INFORMATION: 5' amino modifier C6

<400> SEQUENCE: 890
cccaactacg ctactaaagt aaaggcaa                    28

<210> SEQ ID NO 891
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 891
cccaacgtga gttcgttaac taccagaa                    28

<210> SEQ ID NO 892
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 892
cccaatggtc tagcattcaa ctaccgaa                    28

<210> SEQ ID NO 893
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 893
cccaatgttt cagacctgac tacctgaa                    28

<210> SEQ ID NO 894
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 894
cccaataaca gaacccatgc tcaggtaa                    28

<210> SEQ ID NO 895
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 895

```
cccaaacacg ttgcactttta ctttggaa                                28
```

<210> SEQ ID NO 896
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 896

```
cccaatgctg acgtacacaa acaagtaa                                 28
```

<210> SEQ ID NO 897
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 897

```
cccaaagctg ttgctgttaa accgtaaa                                 28
```

<210> SEQ ID NO 898
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 898

```
cccaacatgt tgtggtagct accgaaaa                                 28
```

<210> SEQ ID NO 899
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 899

```
cccaaatctc tgtggtagca taacggaa                                 28
```

<210> SEQ ID NO 900
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 900

```
cccaagagct ctcgtgttac taaagtaa                                 28
```

<210> SEQ ID NO 901

```
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 901
cccaaagcct tggttgtcag tcttaaaa                                        28

<210> SEQ ID NO 902
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 902
cccaagtacc tctactctga ctcaggaa                                        28

<210> SEQ ID NO 903
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 903
cccaaggcat acaactctga cctgtcaa                                        28

<210> SEQ ID NO 904
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 904
cccaaccagt aaaccagtga cttgccaa                                        28

<210> SEQ ID NO 905
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 905
cccaagactc cttggttcaa cggtaaaa                                        28

<210> SEQ ID NO 906
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      probe
<220> FEATURE:
<223> OTHER INFORMATION: 5' amino modifier C6

<400> SEQUENCE: 906
cccaacttag gtaggtagca cactgaaa                                         28

<210> SEQ ID NO 907
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 907
cccaaagtcc agagcacatt tcatagaa                                         28

<210> SEQ ID NO 908
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 908
cccaaggcta catgtcacct aaccagaa                                         28

<210> SEQ ID NO 909
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 909
cccaatgtcc atgactttcc taacggaa                                         28

<210> SEQ ID NO 910
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 910
cccaagcaca tggttccaca taaacgaa                                         28

<210> SEQ ID NO 911
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6
```

<400> SEQUENCE: 911
cccaagccat gttgcacact acaaagaa                                      28

<210> SEQ ID NO 912
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 912
cccaaacgca tccaaagtta gggtacaa                                      28

<210> SEQ ID NO 913
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 913
cccaaccact cgtagtctac taggagaa                                      28

<210> SEQ ID NO 914
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 914
cccaaactgt gttgtctcac tagaggaa                                      28

<210> SEQ ID NO 915
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 915
cccaagtact cctactcgta catggcaa                                      28

<210> SEQ ID NO 916
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 916
cccaataaca cgaaagcttg tgcatcaa                                      28

```
<210> SEQ ID NO 917
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 917
cccaatttct agaactgtgc ttgcacaa                                           28

<210> SEQ ID NO 918
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 918
cccaaggtgt acctttgacc agtgagaa                                           28

<210> SEQ ID NO 919
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 919
cccaagttac ctcttgccat acgagaaa                                           28

<210> SEQ ID NO 920
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 920
cccaagaacg ttctgctcat agcaaaaa                                           28

<210> SEQ ID NO 921
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 921
cccaaacgct tcttcattgt aacaggaa                                           28

<210> SEQ ID NO 922
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 922
cccaagagtc tcgactcctc tactagaa                                          28

<210> SEQ ID NO 923
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 923
cccaagagta cagaacctca ctttcgaa                                          28

<210> SEQ ID NO 924
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 924
cccaagtact gctgacacaa ctaacgaa                                          28

<210> SEQ ID NO 925
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 925
cccaaagcct ttggtagtca gacagtaa                                          28

<210> SEQ ID NO 926
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 926
cccaaaggct actcagaaca actttgaa                                          28

<210> SEQ ID NO 927
<211> LENGTH: 28
<212> TYPE: DNA
<213> ORGANISM: Artificial Sequence
<220> FEATURE:
<223> OTHER INFORMATION: Description of Artificial Sequence: Synthetic
```

```
       probe
<220> FEATURE:
<223> OTHER INFORMATION: 5' amino modifier C6

<400> SEQUENCE: 927
cccaagtacc tcactcaagc atcaggaa                                          28

<210> SEQ ID NO 928
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 928
cccaaatagt ctcagtgtgc tagtgcaa                                          28

<210> SEQ ID NO 929
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 929
cccaagtcca ctttctgcac taagggaa                                          28

<210> SEQ ID NO 930
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 930
cccaacagtg cttgcaaaca tcaaagaa                                          28

<210> SEQ ID NO 931
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 931
cccaaacttg tctctctgag tacaggaa                                          28

<210> SEQ ID NO 932
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6
```

<400> SEQUENCE: 932
cccaaagttc tccacaagtg tcagagaa                                              28

<210> SEQ ID NO 933
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 933
cccaagtctt cacactcaga acgtgaaa                                              28

<210> SEQ ID NO 934
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 934
cccaatccga agttgcgtag actaaaaa                                              28

<210> SEQ ID NO 935
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 935
cccaagaaac atcgtacaca gtctcgaa                                              28

<210> SEQ ID NO 936
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 936
cccaagaacc atcacctgtc agcatgaa                                              28

<210> SEQ ID NO 937
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 937
cccaacgaca tacctaaagc atggtgaa                                              28

<210> SEQ ID NO 938
<211> LENGTH: 28
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' amino modifier C6

<400> SEQUENCE: 938
cccaaggtca cagcactttc cactagaa                                          28

<210> SEQ ID NO 939
<211> LENGTH: 28
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' amino modifier C6

<400> SEQUENCE: 939
cccaacgagt tacacgtttg cctaaaaa                                          28

<210> SEQ ID NO 940
<211> LENGTH: 28
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' amino modifier C6

<400> SEQUENCE: 940
cccaagtacg ctagtctctc acatagaa                                          28

<210> SEQ ID NO 941
<211> LENGTH: 28
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' amino modifier C6

<400> SEQUENCE: 941
cccaaagtgt ctgaccatac ttaccgaa                                          28

<210> SEQ ID NO 942
<211> LENGTH: 28
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' amino modifier C6

<400> SEQUENCE: 942
cccaacgttc cataccaagg acatagaa                                          28

<210> SEQ ID NO 943
<211> LENGTH: 28
<212> TYPE: DNA

-continued

<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 943
cccaaggact tcgacttcct actaagaa                                          28

<210> SEQ ID NO 944
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 944
cccaatgacg ttgtaaacct ctcacgaa                                          28

<210> SEQ ID NO 945
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 945
cccaagcact gtgtaaacaa ccttcgaa                                          28

<210> SEQ ID NO 946
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 946
cccaacatgt agagaaactc tcgagaaa                                          28

<210> SEQ ID NO 947
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 947
cccaacagct tcctcatagt cttaggaa                                          28

<210> SEQ ID NO 948
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

```
<220> FEATURE:
<223> OTHER INFORMATION: 5' amino modifier C6

<400> SEQUENCE: 948
cccaagtcct acacacagtc atacggaa                                           28

<210> SEQ ID NO 949
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 949
cccaagtcca tacatccgaa ctgtgcaa                                           28

<210> SEQ ID NO 950
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 950
cccaagaact tccacttagc atgtgcaa                                           28

<210> SEQ ID NO 951
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 951
cccaaggttc tacatcacgt acgcaaaa                                           28

<210> SEQ ID NO 952
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 952
cccaagagtg ctaccttcgt acagaaaa                                           28

<210> SEQ ID NO 953
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 953
```
cccaaataag tcctgaagga acgcataa                                      28

<210> SEQ ID NO 954
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 954
cccaagtgca acgagacctt tgacaaaa                                      28

<210> SEQ ID NO 955
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 955
cccaagcact gttgaaaccc tttcgaaa                                      28

<210> SEQ ID NO 956
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 956
cccaaactcg tcacctttgg gtaaacaa                                      28

<210> SEQ ID NO 957
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 957
cccaaagcct tcttggtcat agacagaa                                      28

<210> SEQ ID NO 958
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 958
cccaacaacg gtactttgtt ggtagcaa                                      28

```
-continued

<210> SEQ ID NO 959
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 959
cccaacattc tggtgttacg aactggaa                                              28

<210> SEQ ID NO 960
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 960
cccaatgaaa ccatccatgt cagagcaa                                              28

<210> SEQ ID NO 961
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' amino modifier C6

<400> SEQUENCE: 961
cccaaaactg accattgtgg tgtgcaaa                                              28
```

METHODS AND SYSTEMS FOR DIGITALLY COUNTING FEATURES ON ARRAYS

CROSS-REFERENCE

This application claims the benefit of U.S. Provisional Application No. 61/887,853, filed Oct. 7, 2013, which application is incorporated herein by reference.

SEQUENCE LISTING

The instant application contains a Sequence Listing which has been submitted electronically in ASCII format and is hereby incorporated by reference in its entirety. Said ASCII copy, created on Nov. 5, 2014, is named 41977-711.201_SL.txt and is 255,804 bytes in size.

BACKGROUND OF THE INVENTION

Array technologies have been widely used in biomedical studies for the detection of biomolecules and profiling of gene expression levels, etc. Arrays are typically comprised of immobilized probes which can bind to or hybridize with target molecules in a sample. Detection of binding or hybridization events is often achieved through the use of optical labels (e.g. fluorophores) and scanning or imaging techniques (e.g. fluorescence scanning or imaging). A feature on an array is a small region of immobilized probes that are specific for a given target molecule, e.g. probes that hybridize to specific DNA or RNA sequences. Identifying the pattern of labeled features on a hybridized array thus provides information about specific molecules, e.g. DNA or RNA molecules in the sample, which in turn can provide valuable data in biomedical studies. Two important engineering requirements for providing high quality, quantitative data for biomedical investigations are (i) to correctly image the hybridized arrays, and (ii) to correctly analyze the images to extract quantitative data. Existing optical imaging systems typically image one region of an array at a time, which can be a slow process if a number of different regions need to be imaged. In addition, current methods of image analysis typically determine a signal intensity level (i.e. an analog quantity) for each array feature. Intensity level measurements are often subject to a variety of instrumental drift and analysis errors, therefore improved methods for determining whether or not target molecules are bound to a given array feature, and improved methods for transforming that data into quantitative measures of the number of target molecules present in a sample, are of great importance to expanding the use of array technologies in biomedical applications.

SUMMARY OF THE INVENTION

The methods, systems, and platforms of the present disclosure provide means for digital counting of labeled features on arrays, and thereby enable quantitative determination of the number of target molecules present in a sample through the use of stochastic labeling techniques.

In some embodiments, an array reader system comprising an output unit for calculating an absolute number of target molecules in a sample is described, wherein the array reader system is configured to read an array comprising a plurality of labeled and non-labeled features. In some embodiments, the array reader system may further comprise an optical imaging system. In some embodiments, the calculation of absolute number of target molecules in a sample is based on transforming optical image data produced by the optical imaging system into a count of the number of labeled and non-labeled features on an array. In some embodiments, the output unit comprises a digital processor and executable software, wherein the executable software comprises computer code for transforming optical image data into a count of the number of labeled and non-labeled features. In some embodiments, the array comprises a microarray, microscope slide, or microwell plate.

In some embodiments of the disclosed array reader system, the optical imaging system has a magnification of less than 1, equal to 1, or greater than 1. In some embodiments, the optical imaging system comprises a fluorescence imaging system. In some embodiments, the optical imaging system comprises a phosphorescence imaging system. In some embodiments, the optical imaging system comprises an imaging system that operates in a transmitted light, reflected light, or scattered light imaging mode, or combinations thereof. In some embodiments, the optical imaging system comprises one or more image sensors, wherein the one or more image sensors have a resolution of at least 320×240 pixels. In some embodiments, the one or more image sensors are CCD image sensors, while in some embodiments, the one or more image sensors are CMOS image sensors. In some embodiments, the one or more image sensors comprise one or more circuit boards. In some embodiments, the optical imaging system further comprises one or more components selected from the group including, but not limited to, a microscope objective, a camera lens, a finite-conjugate lens, an infinite-conjugate lens, a plano-convex lens, a double convex lens, a plano-concave lens, a double concave lens, an achromatic cemented doublet, or a bandpass filter. In some embodiments, the optical imaging system comprises a fluorescence imaging system that is designed for use with fluorescein, Cy3, Cy5, or phycoerythrin fluorophores. In some embodiments, the optical imaging system further comprises an illumination system including at least one light source, wherein the at least one light source is an LED or LED assembly. In some embodiments, the at least one light source is electronically synchronized with the image sensor, the at least one light source being turned on when the image sensor is acquiring an image and turned off when the image sensor is not acquiring an image.

In some embodiments of the disclosed array reader system, the illumination system is an off-axis illumination system that satisfies the Scheimpflug condition. In some embodiments, the illumination system is an off-axis illumination system does not satisfy the Scheimpflug condition. In some embodiments, the illumination system is an off-axis illumination subsystem comprising a Kohler illumination system. In some embodiments, the illumination system is an off-axis illumination system comprising an Abbe illumination system. In some embodiments, the illumination system is an epi-illumination system comprising a Kohler illumination system. In some embodiments, the illumination system is an epi-illumination system comprising an Abbe illumination system. In some embodiments, the illumination system is a trans-illumination system comprising a Kohler illumination system. In some embodiments, the illumination system is a trans-illumination system comprising an Abbe illumination system.

In some embodiments of the disclosed array reader system, the optical imaging system further comprises a translation stage, wherein the translation stage is a single-axis translation stage, a dual-axis translation stage, or a multi-axis translation stage.

In some embodiments of the disclosed array reader system, the optical imaging system and output unit are combined within a single, stand-alone instrument. In some embodiments, the optical imaging system and output unit are configured as separate instrument modules.

In some embodiments of the disclosed array reader system, the executable software automatically locates features of the array within the acquired image. In some embodiments, the executable software also performs local background correction by (i) centering a predefined analysis window on each array feature within an image, (ii) calculating an intensity value statistic for signal and background pixels according to a predefined pattern of pixels within the feature, and (iii) utilizing the signal and background intensity value statistics to calculate a background corrected signal intensity value for each feature.

In some embodiments of the disclosed array reader system, the executable software performs a k-means clustering analysis of the background corrected signal intensity values for the complete set of array features, thereby determining a dynamic signal intensity threshold for discrimination between labeled and non-labeled features of the array. In some embodiments, the executable software also performs a k-medoids clustering analysis of the background corrected signal intensity values for the complete set of array features, thereby determining a dynamic signal intensity threshold for discrimination between labeled and non-labeled features of the array. In some embodiments, the executable software also performs a mixture model statistical analysis of the background corrected signal intensity values for the complete set of array features, thereby determining a dynamic signal intensity threshold for discrimination between labeled and non-labeled features of the array. In some embodiments, the executable software also performs an empirical analysis based on sorting of background corrected signal intensity values for the complete set of array features, thereby determining a dynamic signal intensity threshold for discrimination between labeled and non-labeled features of the array. In some embodiments, the executable software also performs an empirical analysis based on sorting of pairwise differences in background corrected signal intensity values for the complete set of array features, thereby determining a dynamic signal intensity threshold for discrimination between labeled and non-labeled features of the array. In some embodiments, the executable software module also performs one or more statistical analyses of the background corrected signal intensity values for the complete set of array features, thereby determining a dynamic signal intensity threshold for discrimination between labeled and non-labeled features of the array, and wherein the one or more statistical analyses are selected from the list including, but not limited to, k-means clustering, k-medoids clustering, mixture model statistical analysis, or an empirical analysis.

In some embodiments of the disclosed array reader system, the executable software calculates the absolute number of target molecules in a sample based on the number of labeled and non-labeled features detected and the predictions of the Poisson distribution. In some embodiments, the executable software also calculates a confidence interval for the number of target molecules.

Also disclosed herein is a digital imaging platform comprising: (a) an optical instrument configured to generate an image of one or more regions of an array, wherein the array comprises a plurality of features comprising oligonucleotide probes, and wherein the oligonucleotide probes are complementary to a set of labels; and (b) a digital processor, wherein the digital processor is configured to perform image analysis comprising: (i) transforming background corrected signal intensities for a plurality of features to produce binary output data that determines the number of labeled and non-labeled features in the one or more regions of the array; and (ii) calculating a number of target molecules present in a sample based on the number of labeled and non-labeled features detected within the one or more regions of the array. In some embodiments, the image analysis further comprises automatically locating the features of the array within the image. In some embodiments, the image analysis further comprises correcting a signal intensity for each feature for a local background intensity. In some embodiments, the image analysis further comprises performing one or more statistical analyses of the corrected signal intensities for a plurality of features to define one or more dynamic signal intensity thresholds for the one or more regions of the array, where the statistical analyses are selected from the list including, but not limited to, k-means clustering, k-medoids clustering, mixture model statistical analysis, or an empirical analysis. In some embodiments, the calculation of the number of target molecules present in a sample is based on both the number of labeled and non-labeled features detected within the one or more regions of the array and on the predictions of the Poisson distribution.

Disclosed herein is an imaging platform comprising: (a) an optical instrument configured to generate an image of one or more regions of an array, wherein the array comprises a plurality of features, and wherein the plurality of features comprise a set of oligonucleotide probes, and wherein the oligonucleotide probes are complementary to a set of labels; and (b) a processor configured to perform image analysis, wherein the image analysis comprises: (i) reading the image generated by the optical instrument; (ii) locating the features of the array within the image; (iii) measuring a signal intensity for each feature; (iv) measuring a local background intensity for each feature; (v) calculating a local background corrected signal intensity for each feature using the signal intensity and local background intensities; (vi) analyzing the local background corrected signal intensities for the complete set of features to determine a dynamic signal intensity threshold for discriminating between labeled and non-labeled features; and (vii) calculating a number of target molecules present in a sample based on the number of labeled and non-labeled features detected and the predictions of the Poisson distribution. In some embodiments, the image generated by the optical instrument is a fluorescence image. In some embodiments, the image generated by the optical instrument is a phosphorescence image. In some embodiments, the image generated by the optical instrument is a transmitted light, reflected light, or scattered light image. In some embodiments, the image analysis further comprises reading an image that has been previously acquired and stored in a memory device. In some embodiments, locating the features of the array within the image comprises identifying predefined fiducial features on the array. In some embodiments, the calculation of a local background corrected signal intensity is performed by (i) centering a predefined analysis window on each feature within the image, (ii) calculating an intensity value statistic for signal and background pixels according to a predefined pattern of pixels within the feature, and (iii) utilizing the signal and background intensity value statistics to calculate a local background corrected signal intensity for each feature. In some embodiments, the intensity value statistic used for calculating a local background corrected signal intensity for each feature is selected from the list including, but not limited to, the mean, the median, or the ratio of signal to background intensities. In some embodiments, the analyzing of local background corrected signal intensities for the complete set of features to determine a dynamic signal intensity threshold comprises performing one or more statistical analyses selected from the list including, but not limited to, k-means clustering, k-medoids clustering, mixture model statistical analysis, or an empirical analysis. In some embodiments, the analyzing of local background corrected signal intensities for the complete set of features to determine a dynamic signal intensity threshold comprises fitting a model function to the intensity data by varying model parameters. In some embodiments, the analyzing of local background corrected signal intensities for the complete set of features to determine a dynamic signal intensity threshold comprises maximizing a quality metric relating to a statistical difference between intensities above the threshold and below the threshold.

Also disclosed herein is a non-transitory computer readable medium storing a program that calculates a number of labeled features on an array, wherein the array comprises a plurality of feature sets, and wherein individual features of a feature set comprise a set of oligonucleotide probes that are capable of hybridizing to a set of labels, the non-transitory computer readable medium comprising: (a) computer code that locates individual features of the array within a digital image of the array; (b) computer code that performs a local background correction of a signal intensity for each feature; (c) computer code that analyzes the corrected signal intensity data for the complete set of features and determines a corrected signal intensity threshold; and (d) computer code that transforms the corrected signal intensity for each feature into binary output data, thereby providing a count of the number of labeled features on the array. In some embodiments, the computer code for locating individual features of the array within the digital image comprises identifying predefined fiducial features on the array. In some embodiments, the computer code for performing a local background correction of signal intensity for each feature comprises a calculation utilizing a statistic for signal and background intensities selected from the list including, but not limited to, the mean, the median, or the ratio of signal to background intensities. In some embodiments, the computer code for analyzing corrected signal intensities for the complete set of features to determine a corrected signal intensity threshold comprises performing one or more statistical analyses selected from the list including, but not limited to, k-means clustering, k-medoids clustering, mixture model statistical analysis, or an empirical analysis.

Also disclosed herein is a computer implemented method for performing local background correction of array signal intensity data, the method comprising: (a) centering a predefined data analysis window on a feature within a digital image of the array; (b) calculating an intensity value statistic for signal and background pixels according to a predefined pattern of pixels within or around the array feature; and (c) utilizing the signal and background intensity value statistics to calculate a background corrected signal intensity for the array feature. In some embodiments, the computer implemented method further comprises automatically locating the array feature using a predefined set of fiducial features on the array. In some embodiments, the intensity value statistic used for calculation of a background corrected signal intensity is selected from the list including, but not limited to, the mean, the median, or the ratio of signal to background intensities.

Disclosed herein is a computer implemented method for determining a dynamic image intensity threshold for use in discriminating between labeled and non-labeled features on an array comprising a plurality of labeled and non-labeled features, the computer implemented method comprising: (a) measuring image intensity data for each feature of the array; (b) performing a local background correction on the image intensity data for each feature on the array; and (c) performing one or more statistical analyses of the background corrected image intensity data for the complete set of array features, thereby determining a dynamic image intensity threshold for discrimination between labeled and non-labeled features of the array, and wherein the one or more statistical analyses are selected from the list including, but not limited to, k-means clustering, k-medoids clustering, mixture model statistical analysis, or an empirical analysis.

Also disclosed is a mechanism comprising: (a) a closure; (b) a housing which magnetically holds the closure in a first position; and (c) a translation stage which magnetically holds the closure in a second position. In some embodiments, the mechanism further comprising a gasket positioned between the closure and the housing. In some embodiments, the gasket is attached to the closure. In some embodiments, the gasket is attached to the housing. In some embodiments, the closure and housing are substantially opaque, and the gasket creates a substantially light-tight seal between the closure and the housing in the first position. In some embodiments, one or more magnets are positioned to hold the closure onto the housing in the first position. In some embodiments, one or more magnets are positioned to hold the closure onto a first surface of the translation stage in the second position. In some embodiments, two or more pairs of mating locating features to align the closure with the translation stage in the second position. In some embodiments, two or more pairs of mating locating features to align the closure with the housing in the first position. In some embodiments, the pairs of mating locating features comprise conical pins and conical holes. In some embodiments, the housing comprises an optical instrument. In some embodiments, the translation stage includes a sample holder. In some embodiments, the sample holder is designed to hold a microscope slide, a microarray, or a microwell plate. In some embodiments, the closure is not hinged. In some embodiments, the closure is not attached to either the housing or the translation stage through the use of fasteners such as screws or clips. In some embodiments, the closure is not attached to either the housing or the translation stage through the use of an adhesive.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A depicts an isometric projection of the exemplary optical system. FIG. 1B depicts a top view of the optical system. FIG. 1C depicts a dimetric view of the optical system. FIG. 1D depicts a front view of the optical system. FIG. 1E depicts a side view of the exemplary optical system comprising a single axis stage, an imaging system, and an illumination system. FIG. 1F depicts a back view of the optical system. FIG. 1G depicts components that control the operation of the optical system.

FIG. 7A is an axonometric view of the instrument as viewed from the upper right. FIG. 7B is an axonometric view of the instrument as viewed from the right-front. FIG. 7C is a front view of the instrument. FIG. 7D is an axonometric view of the instrument as viewed from the upper left.

FIG. 18A: workflow for a single-axis system with manual sample loading. FIG. 18B: workflow for a dual-axis system with automatic sample tray loading.

DETAILED DESCRIPTION OF THE INVENTION

Figure 1A:
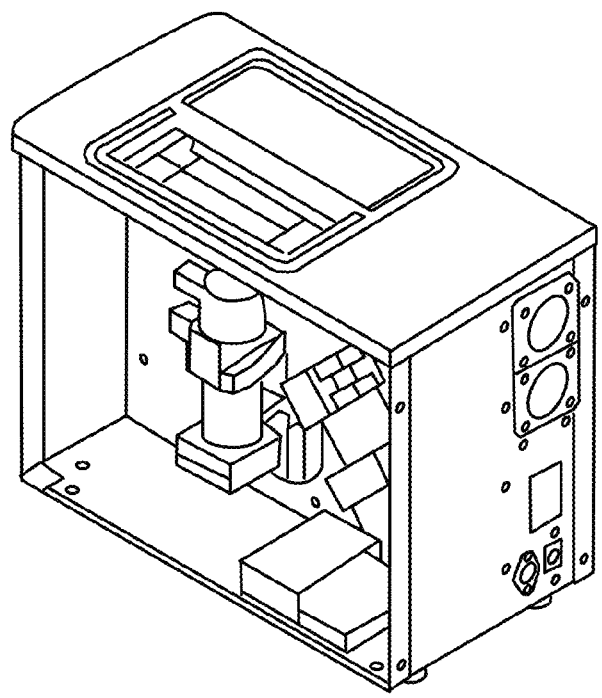
FIGS. 1A-1G show one example of an optical system, and components thereof.
Figure 1B:
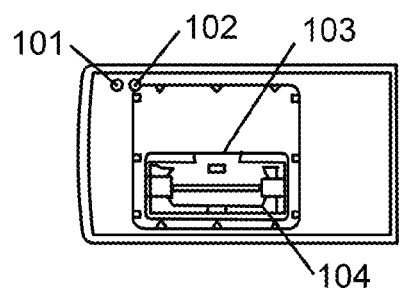
Figure 1C:
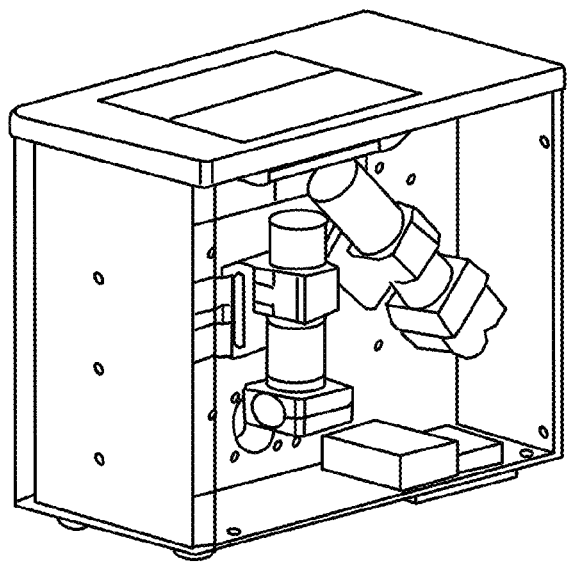
Figure 1D:
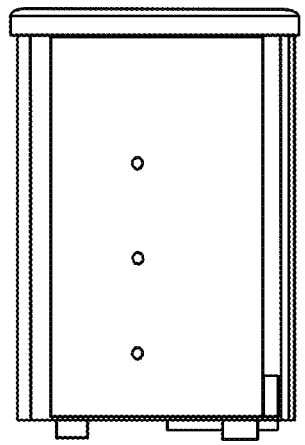
Figure 1E:
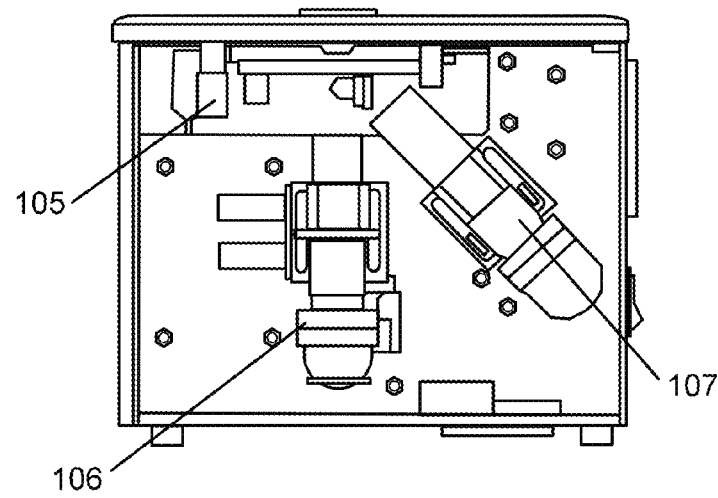
Figure 1F:
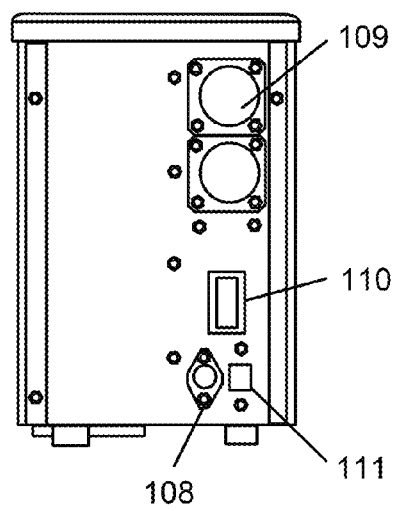
Figure 1G:
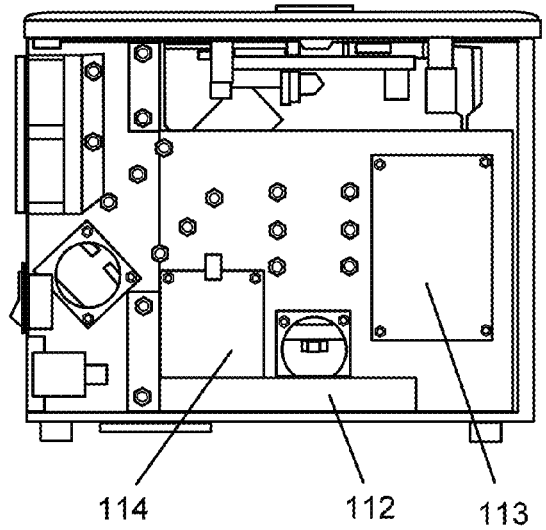

Array technologies have been widely used in biomedical studies for the detection of biomolecules and profiling of gene expression levels, etc. Arrays are typically comprised of immobilized probes which can bind to or hybridize with target molecules in a sample. Detection of binding or hybridization events is often achieved through the use of optical labels (e.g. fluorophores) and scanning or imaging techniques (e.g. fluorescence scanning or imaging). A feature on an array is a small region of immobilized probes that are specific for a given target molecule, e.g. probes that hybridize to specific DNA or RNA sequences. Identifying the pattern of labeled features on a hybridized array thus provides information about the presence of specific molecules, e.g. DNA or RNA molecules in the sample, which in turn can provide valuable data in biomedical studies. Two important engineering requirements for providing high quality, quantitative data for biomedical investigations are (i) to correctly image the hybridized arrays, and (ii) to correctly analyze the images to extract quantitative data. Existing optical imaging systems typically image one region of an array at a time, which can be a slow process if a number of different regions need to be imaged. In addition, current methods of image analysis typically determine an analog signal intensity level (i.e. a signal that can have any value between some minimum and maximum values that are determined by various instrumental and experimental parameters) for each array feature. Analog intensity level measurements are often subject to a variety of instrumental drift and analysis errors, therefore improved methods for determining whether or not target molecules are bound to a given array feature, and improved methods for transforming that data into quantitative measures of the number of target molecules present in a sample, are of great importance to expanding the use of array technologies in biomedical applications.

The advantages of the methods, systems, and platforms disclosed herein include: (i) simultaneous imaging of multiple regions of an array for higher throughput image acquisition, and (ii) improved methods for reduction of image data to a digital determination of the presence or absence of bound target molecules (or target molecule labels) for each feature of an array, thereby providing for improved quantitation in some types of array experiments, for example, those utilizing a set of stochastic labels for quantifying the number of target molecules present in a sample. The use of stochastic labeling techniques is described in U.S. Pat. No. 8,835,358 and PCT application US2011/065291, which are incorporated in their entirety herein by reference. In addition to providing a means for more quantitative detection of target molecules, the use of stochastic labeling techniques allows for mitigation of amplification bias in assays involving nucleic acid amplification.

Accordingly, disclosed herein are methods, devices, systems, and platforms for digital counting of labeled features on arrays comprising: (i) optical instruments configured to form images of one or more regions of an array, (ii) arrays comprising a plurality of features further comprising a plurality of probes, and wherein one or more regions of an array may comprise one or more sub-arrays, and wherein the arrays or sub-arrays are designed for use with sets of stochastic labels, and (iii) computer implemented methods for receiving input image data; locating array features within array images; correcting the signal intensity values associated with each feature for local background intensity values; determining dynamic signal intensity thresholds for the one or more array regions by performing statistical analyses of the corrected signal intensity data for a plurality of features; counting the number of labeled and non-labeled features on the one or more regions of the array by comparing corrected signal intensity data for the features to signal intensity thresholds; and calculating the number of target molecules in a sample, for one or more target molecule species, from the number of labeled and non-labeled features detected on the one or more regions of the array.

In some embodiments, systems are described which comprise: (i) an optical instrument (or reader) configured to form images of one or more regions of an array, (ii) a digital processor configured to perform executable instructions and store data in memory devices, and (iii) computer code for performing image analysis in order to transform image data into a digital count of the number of labeled and non-labeled features on the one or more regions of the array. In some embodiments, the computer code further comprises performing a calculation of the number of target molecules in a sample, for one or more target molecule species, from the number of labeled and non-labeled features detected on the one or more regions of the array.

In some embodiments, platforms are described which comprise: (i) arrays designed for use in stochastic labeling experiments, wherein the arrays comprise a plurality of features further comprising a plurality of probes, and wherein one or more regions of an array may comprise one or more sub-arrays, and wherein the arrays or sub-arrays are designed for use with sets of stochastic labels, (ii) an optical instrument (or reader) configured to form images of one or more regions of an array, (iii) a digital processor configured to perform executable instructions and store data in memory devices, and (iv) computer code for performing image analysis in order to transform image data into a digital count of the number of labeled and non-labeled features on the one or more regions of the array. In some embodiments, the computer code further comprises performing a calculation of the number of target molecules in a sample, for one or more target molecule species, from the number of labeled and non-labeled features detected on the one or more regions of the array.

In some embodiments, software applications (or computer code products) are described that determine the number of labeled features on an array, wherein the software application includes code for performing one or more of the following computer implemented methods: (i) receiving input image data, (ii) locating array features within array images, (iii) correcting the signal intensity values associated with each feature for local background intensity values, (iv) determining dynamic signal intensity thresholds for the one or more array regions by performing statistical analyses of the corrected signal intensity data for a plurality of features, (v) counting the number of labeled and non-labeled features on the one or more regions of the array by comparing corrected signal intensity data for the features to signal intensity thresholds, and (vi) calculating the number of target molecules in a sample, for one or more target molecule species, from the number of labeled and non-labeled features detected on the one or more regions of the array.

In some embodiments, computer implemented methods are described for performing local background correction of array signal intensity data, the methods comprising: (i) centering a predefined data analysis window on each array feature within a digital image of the array, (ii) calculating mean or median intensity values for signal and background pixels according to a predefined pattern of pixels within or around each array feature, and (iii) subtracting the mean or median background intensity from the mean or median signal intensity to determine a background corrected signal intensity value for each array feature.

In some embodiments, computer implemented methods are described for determining dynamic image intensity thresholds from the corrected image intensity data for a plurality of features on an array, the methods comprising: (i) collecting image intensity data for each feature of the array, (ii) optionally performing a local background correction on the image intensity data for each feature on the array; and (iii) performing one or more statistical analyses of the background corrected image intensity data for the complete set of array features, thereby determining a dynamic image intensity threshold for discrimination between labeled and non-labeled features of the array. In some embodiments, the one or more statistical analyses are selected from the list including, but not limited to, k-means clustering, k-medoids clustering, mixture model statistical analysis, or empirical analyses based on sorting of image intensity values or pairwise differences in image intensity values. As used herein, the term "dynamic intensity threshold" refers to a parameter that is determined based on an analysis of data derived from the experiment in progress. The use of a dynamic image intensity threshold for discrimination between labeled and non-labeled features of an array helps to minimize or eliminate errors in data processing that may arise from instrumental drift or experimental procedure.

DEFINITIONS

Unless otherwise defined, all technical terms used herein have the same meaning as commonly understood by one of ordinary skill in the art in the field to which this disclosure belongs. As used in this specification and the appended claims, the singular forms "a," "an," and "the" include plural references unless the context clearly dictates otherwise. Any reference to "or" herein is intended to encompass "and/or" unless otherwise stated.

As used herein, the terms "system" and "platform" are used interchangeably. Similarly, the terms "image sensor", "imaging sensor", "sensor chip", and "camera" are used interchangeably to describe two dimensional photosensors used for imaging purposes, and the use of the terms "image intensity" and "signal intensity" are also used interchangeably in describing data analysis methods. Finally, unless otherwise stated, the terms "software", "software application", "software module", "computer program", and "computer code" are also used interchangeably.

Stochastic Labeling Methods

The use of stochastic labeling techniques is described in U.S. Pat. No. 8,835,358 and PCT application US2011/065291, which are incorporated in their entirety herein by reference.

Briefly, high-sensitivity single molecule digital counting may be achieved through the stochastic labeling of a collection of identical target molecules. Each copy of a target molecule is randomly labeled using a large, non-depleting reservoir of unique labels. The uniqueness of each labeled target molecule is determined by the statistics of random choice, and depends on the number of copies of identical target molecules in the collection compared to the diversity of labels. The size of the resulting set of labeled target molecules is determined by the stochastic nature of the labeling process, and analysis of the number of labels detected then allows calculation of the number of target molecules present in the original collection or sample. When the ratio of the number of copies of a target molecule present to the number of unique labels is low, the labeled target molecules are highly unique (i.e. there is a very low probability that more than one target molecule will have been labeled with a given label), and the digital counting efficiency is high. This stochastic methodology transforms the problem of counting molecules from one of locating and identifying identical molecules to a series of yes/no digital questions regarding detection of a set of predefined labels. In some embodiments, the labeled products are detected by means of DNA sequencing. In other embodiments, the labeled products for one or more target molecules of choice are detected with high specificity using the array readout systems described herein.

Arrays and Features

Disclosed herein are arrays designed for use in stochastic counting of one or more target molecules in a sample. Arrays provide a means of detecting the presence of labeled target molecules, wherein the labels comprise a large and diverse set of unique labels.

In many embodiments, arrays comprise a plurality of features (or spots) on the surface of a substrate, wherein each feature further comprises a plurality of attached probes. In some embodiments, the array may comprise one or more regions, each of which may comprise a plurality of features or sub-arrays. For example, an array may comprise 2, 3, 4, 5, 6, 7, 8, 9, 10 or more regions, or alternatively, an array may comprise 15, 20, 25, 30, 35, 40, 45, 50 or more regions. In some embodiments, an array may comprise 60, 70, 80, 90, 100 or more regions. In other embodiments, an array may comprise hundreds, thousands, or tens of thousands of regions.

Non-limiting examples of arrays include microtiter plates, microwell plates, 16-well microscope slides, spotted microarrays, or microarrays fabricated by in situ solid-phase synthesis. A region of an array may comprise one well of a 16-well microscope slide, one well of a glass-bottomed 96-well plate, or one well of a glass-bottomed 384-well plate. Alternatively, a region of an array may comprise more than one well, for example, in some embodiments, a region may comprise 2 adjacent wells, 4 adjacent wells; or a larger number of wells positioned in close proximity to each other. In some embodiments, the arrays may comprise high-density oligonucleotide arrays with more than 1,000 features per square millimeter, and a region on the array may comprise a selected area of the array substrate surface, for example, an area of approximately 1 mm×1 mm.

As indicated previously, in many embodiments, the set of probes attached to a set of features of an array are selected for detection of a specific set of unique labels designed for use in stochastic labeling studies. The attachment of the probes to the array substrate may be covalent or non-covalent, and permanent or temporary. A probe may be a sequence of monomers including, but not limited to, for example, deoxy-ribonucleotides, ribonucleotides, amino acids, or synthetic monomers, or they may be a sequence of oligomers, including, but not limited to, for example, oligonucleotides (e.g. DNA or RNA sequences) or peptide sequences. In some cases, a probe may be a macromolecule, including but not limited to, for example, antibodies or antibody fragments. Each feature on an array corresponds to a small area of the array substrate comprising immobilized probes having the same molecular sequence that bind to or hybridize with the same target molecule. Two or more features on the array may be identical, similar, or different. In many embodiments, arrays will include one or more fiducial marks used for alignment or orientation purposes, as well as positive and negative control features in addition to feature sets used for detection of a stochastic label set. Positive control features may comprise probes that bind to or hybridize with molecules known to be always present in a sample, or probes that bind to or hybridize with molecules spiked into a sample in a controlled fashion. Negative control features may comprise probes that are specific for molecules that are known to be absent from a sample, or they may comprise features having no probes attached to the substrate surface at all.

In many embodiments, the array substrate, also called a support, may be fabricated from a number of materials. The materials may be solid. The materials may be semi-solid. Examples of materials that may be used to fabricate array substrates include, but are not limited to, glass, fused silica, silicon, polymer, or paper.

In some embodiments, the present disclosure also describes arrays for use in stochastic labeling studies. In particular, arrays are described wherein the arrays comprise a plurality of features having immobilized probes thereon that are complementary to a set of labels designed for use in stochastic labeling experiments, and wherein there is at least one feature on the array for every label in the label set. Some embodiments include an array comprising: (a) a plurality of features, optionally organized into a plurality of sub-arrays, wherein the plurality of features comprise: (i) one or more fiducial features comprising oligonucleotide probes of a defined fiducial sequence; (ii) one or more positive control features comprising oligonucleotide probes of one or more defined positive control sequences; (iii) one or more negative control features having no oligonucleotide probes; and (iv) a plurality of label set features comprising oligonucleotide probes, wherein each individual feature comprises a unique sequence selected from a set of label sequences designed for stochastic labeling of one or more target molecules. In some embodiments, the arrays described in the present disclosure comprise oligonucleotide probe sequences comprising 25-mers, wherein the 5' terminus may optionally be labeled with a 6 carbon atom amino-modifier. In some embodiments, the arrays described in the present disclosure further comprise oligonucleotide probes comprising the set of 960 unique oligonucleotide sequences listed in Table 1. In some embodiments, the arrays described in the present disclosure comprise a set of olignucleotide probes that are 70% homologous, 80% homologous, 85% homologous, 90% homologous, or 95% homologous with the set of sequences listed in Table 1. In some embodiments, the array described in the present disclosure comprise a set of oligonucleotide probes that includes 10%, 20%, 30%, 40%, 50%, 60%, 70%, 80%, or 90% or more of the sequences listed in Table 1.

Hybridization and Detection

In many embodiments of the disclosed methods, systems, and platforms, samples may be processed prior to placing them in contact with the immobilized probes on arrays. For example, target molecules in the samples may be labeled with fluorescent dye molecules and/or stochastic labels during the sample preparation step. Prior to hybridization with oligonucleotide probes, for example, target DNA or RNA molecules may be covalently linked to fluorescent dye molecules including, but not limited to, fluorescein, Cy3, or Cy5. Alternatively, target molecules may be labeled after binding or hybridizing to probes on the array. For example, target molecules may be covalently linked to biotin prior to binding or hybridization with probes on the array. Following the binding or hybridization step, the immobilized target molecules may then be labeled with streptavidin conjugated to optical tags including, but not limited to, phycoerythrin, quantum dot nanoparticles, gold nanoparticles, or blue latex beads. There are many methods for labeling target molecules, either before or after binding or hybridization to the array, and many possible choices for suitable optical labels or tags.

Once a sample has been contacted with an array, the array (or one or more regions of the array) may comprise one or more labeled features. Each region of an array that has been contacted with a sample comprising labeled target molecules (where the target molecules are labeled either before or after contact with the array) may, for example, comprise zero, one, two, or more labeled features. Alternatively, a region of an array that has been contacted with a sample may comprise 2, 3, 4, 5, 6, 7, 8, 9, 10 or more labeled features. In some embodiments, a region of an array that has been contacted with a sample may comprise 15, 20, 25, 30, 35, 40, 45, 50, or more labeled features. In high-density arrays, a region of an array that has been contacted with a sample may comprise more than 100 labeled features, more than 1,000 labeled features, more than 10,000 labeled features, more 100,000 labeled features, or more than 1,000,000 labeled features.

Optical Instruments

The methods, systems, and platforms described herein may comprise an optical instrument used for finite-conjugate digital imaging of one or more regions of an array, wherein the instrument typically includes an illumination system, an imaging system, and a translation stage. In some embodiments, the instrument operates as a "macroscope" having a magnification of less than one. In other embodiments, the instrument operates as a "microscope" having a magnification of greater than one. In still other embodiments, the instrument operates as a "contact imager" having a magnification equal to one. The choice of magnification will typically depend on the field of view required to image the region of interest, and on the size of the image sensor.

By way of non-limiting example, if a region of an array comprises a single well of a 16-well microscope slide, or a single well of a glass-bottomed 96-well plate, the dimensions of the region to be imaged may be approximately 7 mm×7 mm, and the pitch (center-to-center distance between two adjacent regions of the array may be approximately 9 mm. In some embodiments, the optical instrument may be used to take an image of one well at a time, or an image of 2 adjacent wells simultaneously, or an image of 4 (2×2) adjacent wells simultaneously, and the required field of view, or region to be imaged, may be adjusted accordingly. Similarly, the optical instrument may form an image of 6 (3×2 or 2×3), 8 (4×2 or 2×4), 9 (3×3), 10 (5×2 or 5×2), or 12 (6×2, 4×3, 3×4, or 2×6) adjacent wells simultaneously.

By way of another non-limiting example, if a region of an array is a single well of a glass-bottomed 384-well plate, the dimensions of the region to be imaged may be approximately 3 mm×3 mm, and the pitch between two adjacent regions of the array may be approximately 4.5 mm. Again, in some embodiments, the optical instrument may be used to take an image of one well at a time, or an image of 2 adjacent wells simultaneously, or an image of 4 (2×2), 6 (3×2 or 2×3), 8 (4×2 or 2×4), 12 (4×3 or 3×4), or 16 (4×4) adjacent wells simultaneously.

In another non-limiting example, the optical instrument may be used to image high-density oligonucleotide arrays, for example arrays having more than 1,000 features per square millimeter, and a region on the array may be approximately 1 mm×1 mm in area, for example.

Imaging System

One main component of the optical instrument is an imaging system. The imaging system may include one or more lenses in addition to a CCD or CMOS camera. Typically the CCD or CMOS camera will have a resolution between a few hundred thousand and a few million pixels. A high resolution camera may have tens of millions of pixels, or more.

The imaging system may be configured to magnify the image of the array. The required magnification of the imaging system can be determined by the required field of view and by the size of the CCD or CMOS sensor. By way of a non-limiting example, if the optical instrument is used to take an image of 2 adjacent wells of a 16-well microscope slide simultaneously, the required field of view is approximately 16 mm×8 mm. If the light-sensitive area of the CCD or CMOS sensor is about 4.8 mm×3.6 mm, the instrument is a macroscope and a magnification of about 0.3 is required. In this case, only data from the central 4.8 mm×2.4 mm of the sensor would be used.

By way of non-limiting example, an appropriate imaging system with a magnification of 0.3 may be constructed using an achromatic cemented doublet lens with a focal length of 85 mm and an infinite-conjugate camera lens with a focal length of 25 mm. If a spectrally selective emission filter is used (for example, a single-band interference filter, multiband interference filter, longpass interference filter, or longpass colored glass filter), and this filter is typically located between the achromatic cemented doublet lens and the camera lens. Additional configurations of an imaging system with a magnification of 0.3 are possible. For example, the achromatic cemented doublet lens can be omitted, and a finite-conjugate camera lens can be used instead of an infinite-conjugate camera lens. In this case, the spectrally selective emission filter is preferably located on the long-conjugate side of the camera lens.

A sensor with a light-sensitive area of 4.8 mm×3.6 mm is known as a ⅓-inch format sensor. If a sensor of different size is used, the required magnification will be different. By way of a non-limiting example, if the required field of view is 16 mm×8 mm and a sensor having a light-sensitive area of 6.4 mm×4.8 mm (known as a ½-inch format sensor) is used, then the required magnification is 0.4. An appropriate imaging system with a magnification of 0.4 can be constructed using, for example, an achromatic cemented doublet lens with a focal length of 85 mm and an infinite-conjugate camera lens with a focal length of 35 mm.

As another non-limiting example, if the dimensions of a region are about 0.66 mm×0.66 mm and a sensor with a light-sensitive area of 8.8 mm×6.6 mm (known as a ⅔-inch format sensor) is used, then the instrument is a microscope and the required magnification is about 10. In this case, only data from the central 6.6 mm×6.6 mm of the sensor will be used. An appropriate imaging system with a magnification of 10 can be constructed using, for example, an infinite-conjugate microscope objective with a focal length of 20 mm and a microscope tube lens with a focal length of 200 mm, with a spectrally selective emission filter typically located between the microscope objective and the tube lens. Alternatively a finite-conjugate 10× microscope objective can be used and the microscope tube lens can be omitted. In this case the spectrally selective emission filter can be located on the long-conjugate side of the microscope objective.

An imaging system of any required magnification can be constructed using a combination of off-the-shelf and custom optical elements that does not necessarily include either a camera lens or a microscope objective. The optical elements may have various combinations of spherical, flat, aspheric, or diffractive surfaces.

Illumination System

Another main component of the optical instrument is an illumination system. The purpose of the illumination system is to illuminate the array within the field of view of the CCD or CMOS camera. To reduce sensitivity to edge effects and to misalignment, it may be desirable for the illuminated area to be slightly larger than the camera's field of view. By way of a non-limiting example, if the field of view is about 16 mm×8 mm, a reasonable illuminated area may be about 18 mm×10 mm. The types of illumination may be Abbe, Kohler, or neither Abbe nor Kohler illumination. Abbe illumination and Kohler illumination are well known and are described in, for example, Chapter 14 of *Optical System Design*, Second Edition by Robert E. Fischer et al., SPIE Press, McGraw-Hill, N.Y., 2008.

In some embodiments, the illumination system may be used for off-axis illumination. In other embodiments, the illumination system may be used for trans-illumination or epi-illumination. If the illumination system is used for off-axis illumination or trans-illumination, then the illumination system and the imaging system are separate from each other, with no shared optical components. If the illumination system is used for epi-illumination, then the illumination system and the imaging system may share a beamsplitter and possibly one or more lenses. The beamsplitter may be a plate beamsplitter or a cube beamsplitter. If the optical instrument is used for fluorescence imaging, the beamsplitter is typically a single-edge or multi-edge longpass dichroic beamsplitter.

Often the illumination system may contain a square or rectangular aperture so that the illuminated area has the same shape as the region that is imaged by the CCD or CMOS camera. In embodiments where off-axis illumination is used, the aperture may be trapezoidal in shape instead of square or rectangular. An off-axis illumination system may or may not satisfy the Scheimpflug condition. The Scheimpflug condition is described in, for example, *Modern Optical Engineering*, Second Edition by Warren J. Smith, McGraw-Hill, N.Y., 1990.

In some embodiments, the illumination system may contain one or more of the following: spherical lenses, aspheric lenses, a solid homogenizing rod with a rectangular or trapezoidal cross section, a hollow homogenizing light tunnel with a rectangular or trapezoidal cross section, a microlens array or a pair of microlens arrays, a stationary or rotating diffuser, a compound parabolic concentrator, a non-imaging optical element other than a compound parabolic concentrator (e.g., a free-form catadioptric element), an optical fiber, a fiber bundle, or a liquid light guide.

The illumination system may contain one or more light sources, selected from the group including, but not limited to, one or more LEDs, one or more lasers, a xenon arc lamp, a metal halide lamp, or an incandescent lamp, or a combination thereof. The illumination system may also contain a spectrally selective excitation filter selected from the list including, but not limited to, a single-band interference filter, a multi-band interference filter, or a shortpass interference filter. If the illumination system contains two or more light sources, they may be the same (by way of non-limiting example, two or more LEDs with peak emission wavelengths of about 525 nm for excitation of Cy3 dye, mounted as close together as possible on a circuit board) or different (by way of non-limiting example, an LED with a peak excitation wavelength of about 525 nm for excitation of Cy3 dye, and an LED with a peak excitation wavelength of about 625 nm for excitation of Cy5 dye, mounted as close together as possible on a circuit board). Two-color or multicolor LED assemblies are available from, for example, LED Engin, Inc. (San Jose, Calif.) and Innovations in Optics, Inc. (Woburn, Mass.).

In some embodiments, a light source in the illumination system may be controlled electronically. By way of a non-limiting example, a light source may be synchronized with the CCD or CMOS camera so that the light source turns on when the CCD or CMOS camera begins an exposure and turns off when the camera finishes an exposure. If the illumination system contains two or more light sources, they may optionally be controlled together or independently of each other.

In some embodiments, a light source may be left on continuously. In this case, the illumination system may contain an electronically controlled shutter, and the shutter may be synchronized with the CCD or CMOS camera so that the shutter opens when the CCD or CMOS camera begins an exposure and closes when the camera finishes an exposure.

In some embodiments, the optical instrument may contain a single illumination system. In other embodiments, the instrument may contain two or more illumination systems that are identical. In yet other embodiments, the instrument may contain two or more illumination systems that are different. By way of non-limiting examples, an optical instrument for detecting fluorescence from Cy3 and Cy5 may contain one illumination system for Cy3 excitation and another illumination system for Cy5 excitation, or it may contain a single illumination system that is used for both Cy3 and Cy5 excitation.

Translation Stage

Yet another main component of the optical instrument may be one or more translation stages. One purpose of the translation stage may be to move sample holders in and out of the field view of the imaging system. Another purpose of the translation stage system may be to move the imaging system, components of the imaging system, the illumination system, or components of the illumination system relative to the sample or relative to one another, for obtaining the best possible image.

In many embodiments of the presently disclosed systems, the translation stage may further comprise a sample holder. By way of non-limiting examples, if the optical instrument is used to take images of 16-well microscope slides, the translation stage contains a slide holder. If the optical instrument is used to take images of 96-well plates or 384-well plates, and it contains a plate holder. The slide holder, plate holder, or other array support holder may be mounted on the translation stage system in any of a variety of ways known to those skilled in the art.

The translation stage may have one or more axes of motion. By way of a non-limiting example, if the support is a 16-well microscope slide and the instrument takes images of 2 adjacent wells simultaneously, a single axis of motion may be sufficient. By way of another non-limiting example, if the support is a 96-well plate and the instrument takes images of 2 adjacent wells simultaneously, then at least 2 axes of motion would be required. Additional axes of motion for adjustment of focus and tilt may also be added. If the instrument can take an image of all of the regions on the support in a single exposure, then the translation stage may be omitted in some embodiments of the optical instrument.

Housing

The systems and devices described herein can include features for insuring that the sensors of the device detect appropriate signal. For example the systems and devices can include light excluding features. The light excluding features generally reduce unintended signal from reaching light sensitive sensors. In many embodiments, one or more of the imaging system, illumination system, translation stage, and other components of the instrument are surrounded by a housing. The housing can be opaque. The housing can, in some instances, act as a faraday cage. In some instances a single housing is sufficient to exclude light from systems. The single housing can also provide external protection of the system. Alternatively, multiple housings may individually contain one or more components of the instrument. In some instances the housings are nested housings. In various embodiments, the housing can be gas and/or liquid tight.

The housing may have an access point which can exclude light from the interior of the housing. The access point may comprise materials that absorb light in the spectrum relevant to the sensors within the housing, e.g. vantablack in the visible spectrum. The access point may comprise a closure device. The closure device may be opaque. The closure device may be, e.g., a door. The closure device may be substantially light-tight in a closed position. The closure may be light-tight in a closed position.

The closure device can be opened, e.g., for insertion and removal of a 16-well slide, 96-well plate, 384-well plate, or other array support. A sensor (for example, a photointerrupter) may be used to determine whether the closure device is open or closed. The instrument's software or electronic hardware may prevent the light source in the illumination system from turning on when the closure device is open, may prevent power from being applied to the image sensor, and/or may prevent the translation stage from moving when the closure device is open.

In some embodiments, the housing may further comprise a mechanism for automated opening and closing of the closure device, as illustrated in FIGS. 10-13. The closure device can provide access to the interior of the housing. The closure device can provide access for the array to be loaded in and out of the instrument. This operation can be performed automatically. In some instances, the closure device can exclude ambient light during imaging, while opening reliably to permit loading.

In some instances the closure device does not comprise pivoting parts. In some embodiments of the disclosed systems and platforms, the closure device is held by magnets to the housing. Magnets can hold the closure device to the housing in a closed position. Magnets can hold the closure device to a loading device, e.g. a tray, in an open position. During a transition from an open to closed position the closure device can transition from being primarily magnetically attached to a loading device to being primarily magnetically attached to the housing. During a transition from a closed to open position the closure device can transition from being primarily magnetically attached to the housing to being primarily magnetically attached to the loading device. In some instances the transition between the open and closed state is magnetically unstable, such instability causing the closure device to move from the transition state to either the more stable open or closed position.

Figure 10:
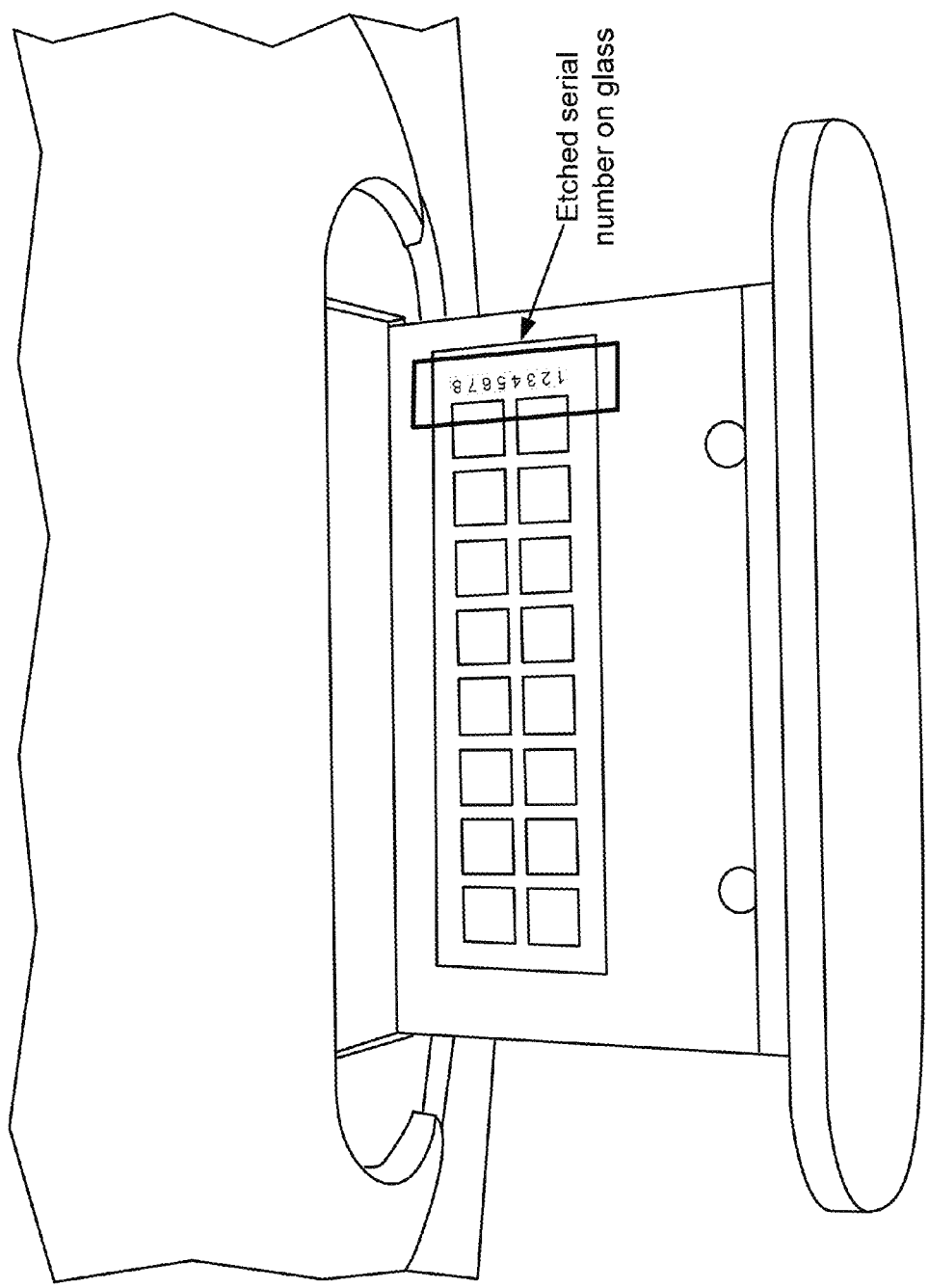
FIG. 10 shows a photograph of a system with the sample loading stage in the extended (loading) position, having pulled the door away from the front panel. A Pixel 16 array assembly is shown in the loading tray.
Figure 11A:
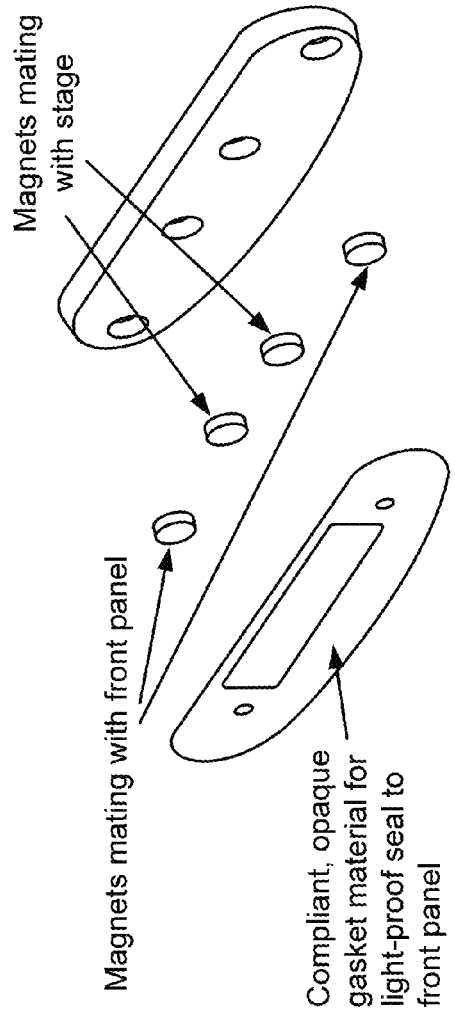
FIG. 11A shows an exploded view of a door assembly that utilizes a magnetic mechanism for positioning a door on a sample compartment stage.
Figure 11B:
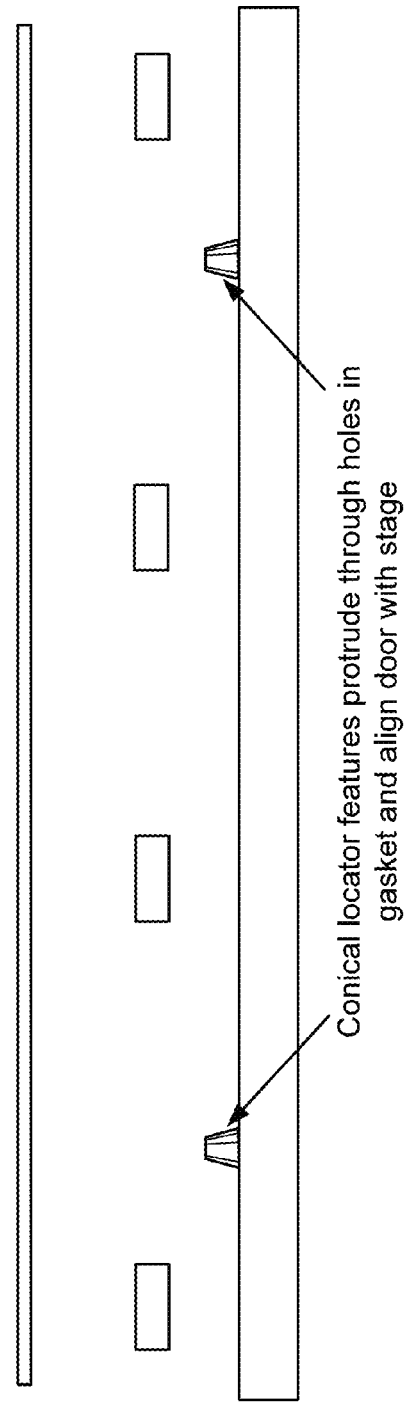
FIG. 11B shows another exploded view of the door assembly that illustrates conical locator features for ensuring proper alignment of the door with the stage.
Figure 12:
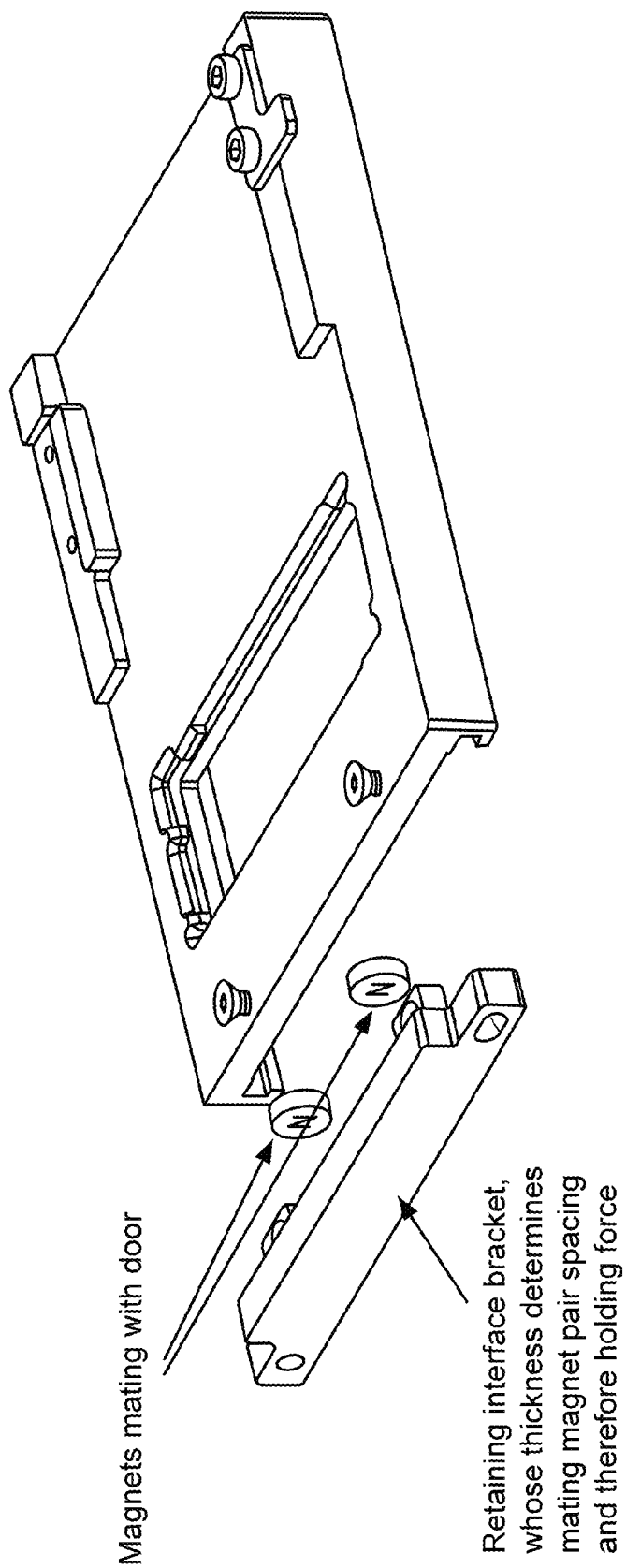
FIG. 12 depicts an exploded view of an upper stage assembly with magnets which mate with a corresponding pair of magnets on the door.
Figure 13:
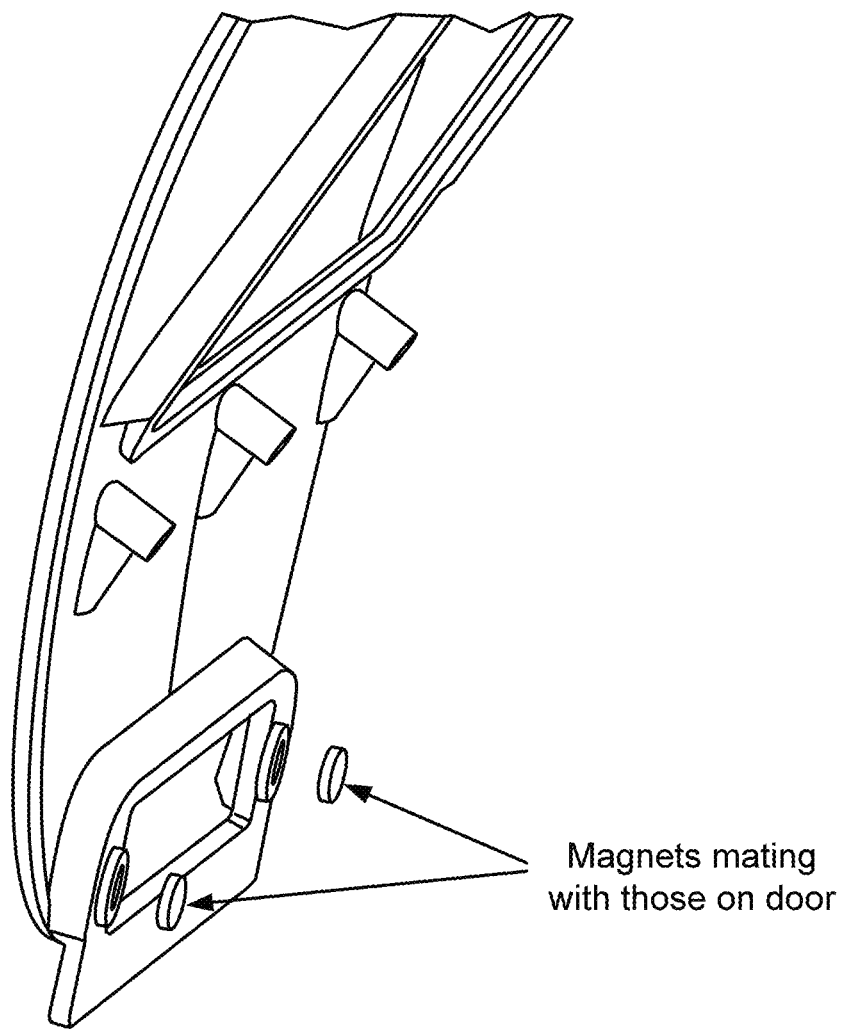
FIG. 13 shows an exploded view of a front panel assembly with magnets which mate with a corresponding pair of magnets on the door.

The closure device can comprise a self-locating function provided by conical features on the door. The thicknesses of the parts which support the magnets on each side of a mating pair, and the depth of retaining pockets within those parts, defines the spacing between magnets in each mating pair, and thus the holding forces. The design geometry is matched to the power of the motors to provide enough retaining force, without requiring high motor torque. The system is further designed such that the motor current and speed (and hence torque) can be controlled to improve the performance, and avoid creating a safety hazard. Two of the four magnet pairs are used to temporarily hold the door to the front of the sample tray, when the tray moves outward for loading an array assembly, as depicted in FIG. 10. The other two magnet pairs are used to hold the door closed against the front panel, after the tray has moved inwards (and separated the other two magnet pairs in the process). The respective allocation of magnets is shown in FIG. 11A. The mating magnets on the front of the stage are shown in FIG. 12. The locations of the mating magnets in the front panel are shown in FIG. 13. To provide for secure grip (and therefore reliable operation), rare earth magnets provide high strength (e.g. neodymium magnets). Some embodiments of the design call for disc magnets approximately 8 mm in diameter and 3 mm thick, with the magnetic field parallel to the axis. In some embodiments, it is sufficient to replace one magnet from each pair with a weaker magnet, or with a piece of magnetic material such as iron or mild steel.

In some embodiments of the systems and platforms disclosed herein, a mechanism for providing for automated door or lid closure on one or more instrument compartments is provided, wherein the mechanism comprises: (a) a closure; (b) a housing which magnetically holds the closure in a first position; and (c) a translation stage which magnetically holds the closure in a second position. In some embodiment, the mechanism further comprises a gasket positioned between the closure and the housing. In some embodiments of the mechanism, the gasket is attached to the closure. In other embodiments, the gasket is attached to the housing. In some embodiments, the closure and housing are substantially opaque, and the gasket creates a substantially light-tight seal between the closure and the housing in the first position. In some embodiments of the mechanism, one or more magnets are positioned to hold the closure onto the housing in the first position. In some embodiments of the mechanism, one or more magnets are positioned to hold the closure onto a first surface of the translation stage in the second position. In some embodiments, the mechanism further comprises two or more pairs of mating locating features to align the closure with the translation stage in the second position. In some embodiments, the mechanism further comprises two or more pairs of mating locating features to align the closure with the housing in the first position. In some embodiments of the mechanism, the pairs of mating locating features comprise conical pins and conical holes. In some embodiments, the housing comprises an optical instrument. In some embodiments, the translation stage includes a sample holder. In some embodiments, the sample holder is designed to hold a microscope slide, a microarray, or a microwell plate. In some embodiments, the closure is not hinged. In some embodiments, the closure is not attached to either the housing or the translation stage through the use of fasteners such as screws or clips. In some embodiments, the closure is not attached to either the housing or the translation stage through the use of an adhesive.

Image Data

The methods, systems, and platforms described herein for counting one or more labeled features on an array may comprise data input, or use of the same. The data input may comprise imaging information and/or images of one or more regions of arrays. The images comprise pixel data, wherein each unit of pixel data may be encoded in, by way of non-limiting examples, 4, 8, 12, 14, 16, 32, 64, 128, 256, or more bits. An image may encompass one or more regions of an array. The spatial resolution of an image may be determined by the spatial resolution of the optical instrument, but in some embodiments of the disclosed methods and systems, spatial resolution may be enhanced by digital image processing schemes based on, by way of non-limiting examples, interpolations, extrapolations, modeling, and/or transforms.

The methods, systems, and platforms described herein for counting one or more labeled features on an array may comprise acquisition and analysis of images of one, two, or more distinct regions on an array. In some embodiments, two or more regions to be imaged may overlap, partially overlap, or not overlap at all. Furthermore, two or more regions to be imaged may be adjacent, or non-adjacent.

The methods, software, systems, and platforms described herein for counting one or more labeled features on an array may comprise acquisition and analysis of images of all or a portion of an array. In some embodiments, the region of an array that is imaged may comprise at least about 1% of the total area of the array. In some embodiments, the region of the array that is imaged image may comprise at least about 2%, 3%, 4%, 5%, 6%, 7%, 8%, 9%, 10% or more of the total area of the array. In other embodiments, the region of the array to be imaged may comprise at least about 11%, 12%, 13%, 14%, 15%, 16%, 17%, 18%, 19%, 20%, 21%, 22%, 23%, 24%, 25% or more of the total area of the array. In still other embodiments, the region of the array to be imaged may comprise at least about 30%, 35%, 40%, 45%, 50%, 55%, 60%, 65%, 70% or more of the total area of the array. In some embodiments, the region of the array to be imaged may comprise at least about 75%, 80%, 85%, 90%, 92%, 95%, 97% or more of the total area of the array.

The methods, software, systems, and platforms described herein for counting one or more labeled features on an array may comprise acquisiton and analysis of images of all or a portion of the features of an array. In some embodiments, the image may encompass between 10% and 100% of the total number of features on the array. In some embodiments, the image may encompass at least 5%, at least 10%, at least 20%, at least 30%, at least 40%, at least 50%, at least 60%, at least 70%, at least 80%, at least 90%, or at least 95% of the total number of features on the array. In some embodiments, the image may encompass at most 95%, at most 90%, at most, 80%, at most 70%, at most 60%, at most 50%, at most 40%, at most 30%, at most 20%, at more 10%, or at most 5% of the total number of features on the array. The number of features encompassed by the image may fall within any range bounded by any of these values (e.g. from about 15% to about 90% of the total number of features of the array).

Image Acquisition

The methods, systems, and platforms described herein comprise software for acquiring images from an optical instrument. In some embodiments, e.g. for optical instruments comprising two or more image sensors, the image acquisition may operate in a parallel mode, i.e. where two or more images are acquired simultaneously. Alternatively, the image acquisition may operate in a serial mode, where two or more images are acquired sequentially. In general, image acquisition may be performed in a continuous fashion (i.e., wherein the image is acquired within a single exposure time period) or intermittently (i.e., wherein the image is acquired in a discontinuous fashion, e.g. using two or more separate exposure time periods, wherein in some embodiments two more more images are combined for signal averaging purposes).

In a non-limiting example, an array may comprise 16 wells where an image is formed for each well. The image acquisition module may sequentially read the 16 images. Reading the 16 images can be completed in a continuous time period; or, the system may read a first image followed by analyzing the first image, and then the procedure of image reading and image analysis repeats till the 16th image is analyzed. Alternatively, the image acquisition module may read a pair of images at once, and repeat the reading till all the 16 images are acquired. The 16 images may be read sequentially in a single time period. In some applications, a pair of images may be read, followed by immediate image analyses.

Image Analysis

In general, one of the objectives in performing image processing and analysis is to improve signal-to-noise ratios and quantitation. In an ideal array experiment, labeled features comprising bound target molecules and/or labels would produce a uniform, non-saturated signal level when imaged and non-labeled features would appear uniformly dark, with a signal level of close to zero. In reality, a variety of artifacts due to instrumental and/or assay procedural issues including, but not limited to, stray light, background fluorescence (in the case of fluorescence-based imaging), particulate contaminants, and non-specific binding of assay components, can produce images that hinder one's ability to extract quantitative signal intensity data and make definitive calls as to which features of the array are labeled. Accordingly, the methods, systems, and platforms disclosed herein may comprise software for performing a variety of image processing tasks including, but not limited to, feature location, image orientation correction, background correction, intensity measurement, data scaling, data thresholding, and data analysis functions.

Figure 14:
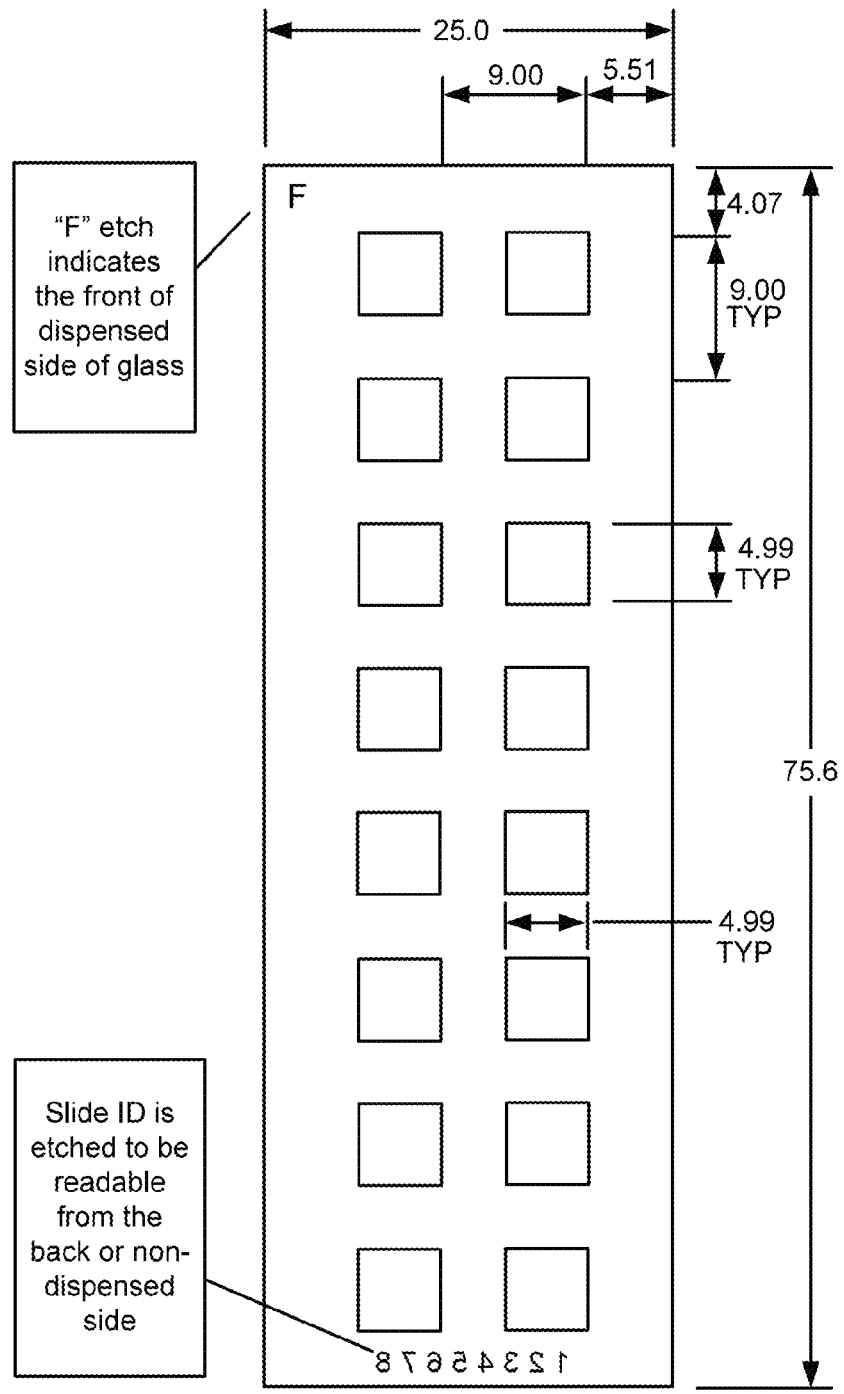
FIG. 14 shows the viewing reference orientation for array production and analysis in one embodiment of an array, showing the 16 array locations on a glass substrate. Nominal dimensions are shown (in millimeters).

Image orientation and location of features. In some embodiments, fiducial features incorporated into the design of an array are used to orient the image and locate features in an automated fashion using custom image analysis software. By way of non-limiting example, the microarray pattern shown in FIGS. 15 and 16 consists of a 32×32 array of features, where fiducial features in the top and bottom rows permit location of the array in the digital images. The fiducial features are typically arranged in an asymmetric pattern whose orientation is readily identifiable, e.g. fiducial features located in the top row of features in an array such as that depicted in FIG. 16 may comprise a distinctive pattern for which the left and right ends of the row are asymmetric, while the pattern of fiducial features in the bottom row is typically different from that in the top row. This permits easy manual and automatic identification of incorrect placement of the array, and also facilitated detection of imaging problems. In some embodiments, the image may be transformed also transformed so that the apparent orientation of the images corresponds to the orientation as viewed by a user, often referred to as the viewing reference orientation, as shown in FIG. 14 for a specific embodiment of an array designed for use with the methods, systems, and platforms disclosed herein.

Figure 19:
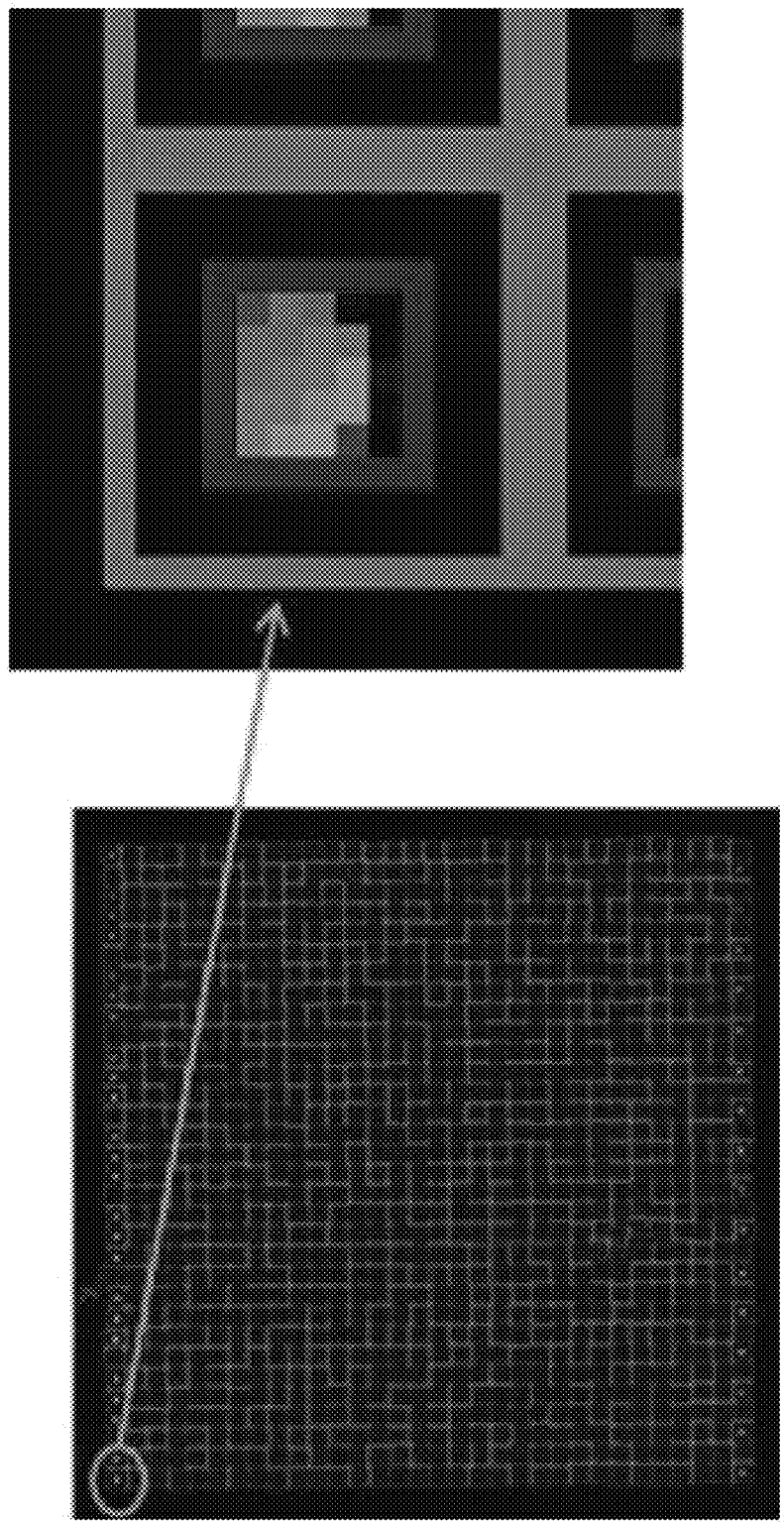
FIG. 19 depicts an analysis window comprising a 12×12 pixel area associated with each feature in the array.

Refinement of feature locations. In some embodiments, the measured location of each feature is refined so as to account for array fabrication errors, which can produce offsets of several image pixels. The locations of features obtained during the initial image orientation and feature location step may be used to subdivide the array or array region into analysis windows, for example an array may be divided into 32×32 analysis windows, wherein each analysis window comprises an image area of 12×12 pixels centered on each feature, as shown in FIG. 19. The size of the analysis window used is dependent on the size of the features on the array, and may be any size that is necessary to correctly locate and distinguish between features and background regions on the array. By way of non-limiting examples, the analysis window may be defined as a 5×5, 7×7, 9×9, 15×15, 51×51, or 101×101 pixel area that is centered on the array feature. The position of the feature within the window may be determined on the basis of the signal intensity distribution and clustering of the pixels within the analysis window. The refined location of the feature is calculated as an offset in coordinates X and Y from the site predicted by a perfect rectilinear grid. In some embodiments, distortion of the feature location results due to defects such as dust is avoided by making use of the correlation between printing artifacts between different arrays on the same substrate. Since the printing artifacts are typically consistent, the correction relative to a hypothetical rectilinear grid is also consistent. The feature location optimization results for a given feature are combined across all of the arrays being analyzed, and the median offset is used for subsequent analysis, which greatly decreases noise in the final experimental results.

Figure 20:
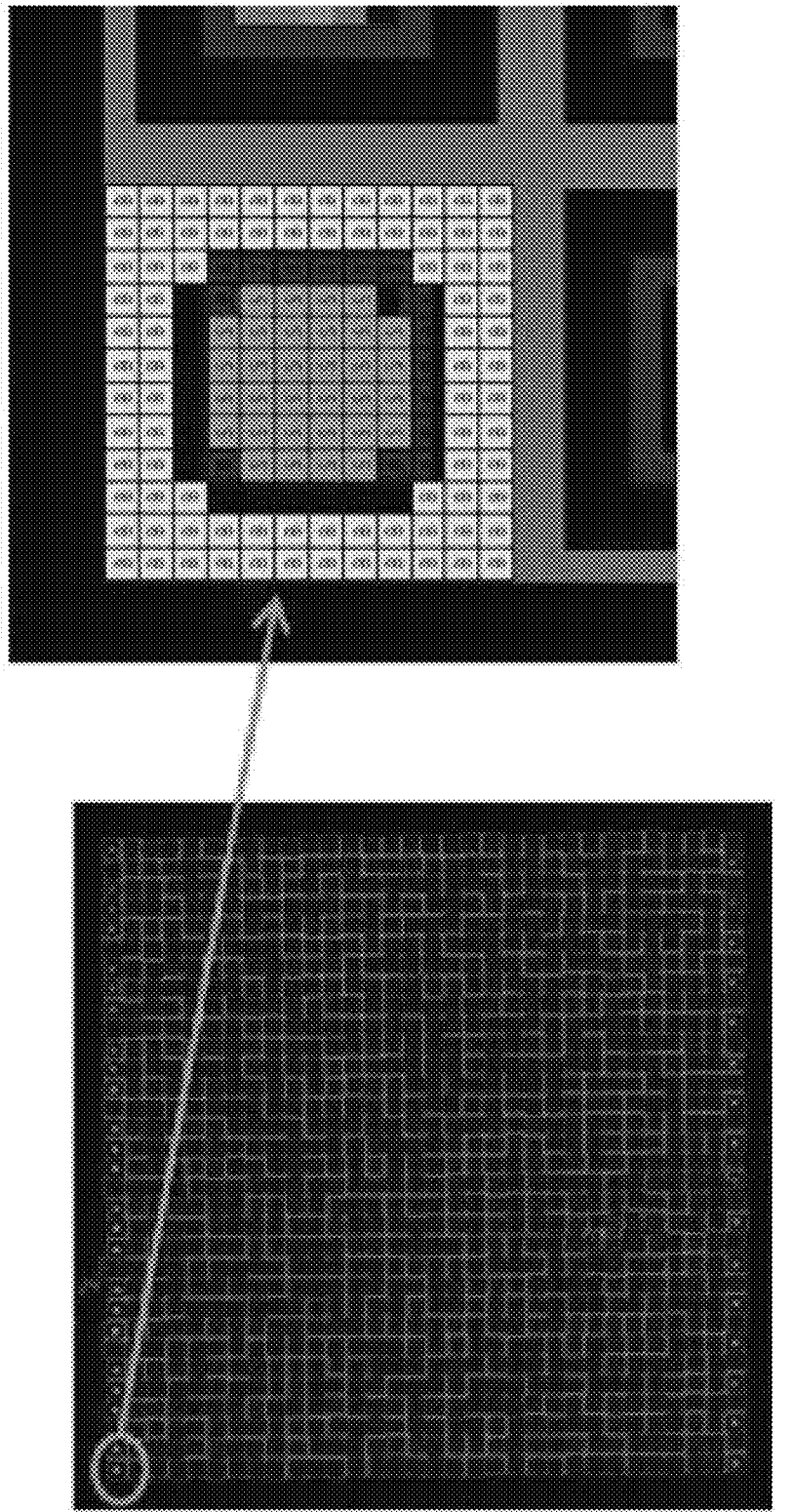
FIG. 20 depicts a map of the pixel designations within the analysis window for each feature in the array.

Local background correction. Once the feature pixel set "S" and background pixel set "B" have been defined for each location in the array (for example, see FIG. 20), the local background is removed via a calculation involving signal intensity and background intensity statistics. Examples of suitable signal and background intensity statistics for use in local background correction calculations include, but are not limited to, the mean, the median, or a ratio of signal-to-background. In some embodiments, following feature location refinement performed as described above, the pixels within the analysis window are assigned to be signal pixels, background pixels, or transitional pixels, i.e. pixels to be disregarded, in subsequent calculations of signal and background intensity statistics (see FIG. 20). In some embodiments of the disclosed methods, local background correction is performed via subtraction in logarithm space, i.e. a calculation that is closely related to a signal-to-background ratio calculation, as illustrated in a non-limiting example below:

Given the 16-bit pixel data measurements for a defined feature and background area, on next calculates a single value $\bar{S}$ for the signal pixels and a value $\bar{B}$ for the background pixels respectively. One useful statistic is the median value for each set of pixels, i.e.

$\bar{S}$=the median of the pixel values for the set of pixels "S"
$\bar{B}$=the median of the pixel values for the set of pixels "B"

Various other statistics could be used in this situation, such as the mean of the set of values, or a nominated percentile within the set. It is not necessary, and may not be optimal, to use the same statistic for both $\bar{S}$ and $\bar{B}$. For example, low data noise and strong separation between "on" and "off" data points can be obtained by using:

$\bar{S}$=the median of the pixel values for the set of pixels "S", and
$\bar{B}$=the $25^{th}$ percentile of the pixel values for the set of pixels "B".

As a further enhancement, the particular percentile used can be a pre-stored and re-configurable parameter stored in a settings file.

The background-corrected intensity statistic for each spot is:

$$I=\log_2(16\bar{S})-\log_2(16\bar{B})$$

Figure 21:
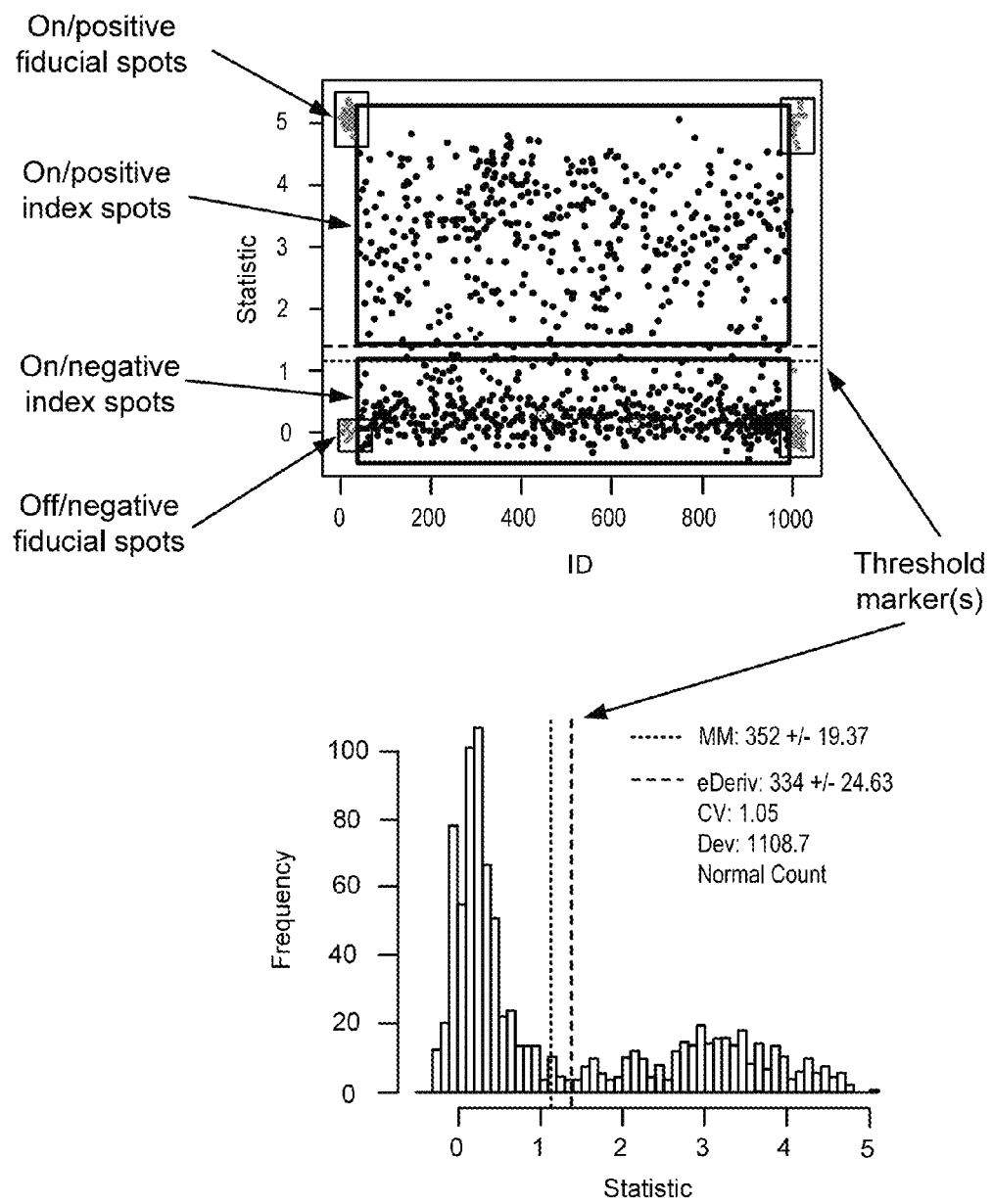
FIG. 21 depicts a scatter plot (upper) of intensity data obtained from an image of an array that illustrates the different categories of features identified by the analysis software, and a histogram (lower) of the feature intensity data. Dashed lines indicate examples of intensity thresholds determined by the software that are used to discriminate between labeled ("on") and non-labeled ("off") features.

An example of a scatter plot (intensity statistic vs feature number) and histogram of intensity data are shown in FIG. 21. In this example, the background is corrected for by performing a subtraction of logarithms, such that the intensity metric is related to a ratio of $\bar{S}$ and $\bar{B}$. In some situations, a linear subtraction (e.g. I=$\bar{S}$−$\bar{B}$) is preferable. Once the background-corrected intensity statistics have been calculated for the compete set of features, the next task is to determine which of the features are labeled (i.e. "on", or "positive") and which are non-labeled (i.e. "off" or "negative"). This is accomplished by determining a signal intensity threshold value based on a statistical analysis of the local background-corrected feature intensities, and subsequently counting how many features, k, have background-corrected signal intensities that are larger than this threshold level. The signal intensity threshold may be considered a "dynamic" signal intensity threshold in that the threshold is determined through analysis of the data from the current experiment, and thereby eliminates potential errors due to such factors as instrumental drift and variations in assay procedure.

Determination of dynamic signal intensity thresholds. In many embodiments of the methods, systems, and platforms disclosed herein, a dynamic signal intensity threshold is determined for one or more regions of an array by performing one or more statistical analyses of the background corrected signal intensity data for the complete set of features. Any of a variety of statistical (or empirical) analysis techniques may be used, including but not limited to, k-means clustering, k-medoids clustering, mixture model statistical analysis, probe reference distribution methods, or empirical analysis based on sorting of background corrected signal intensity values, sorting of pairwise differences in background corrected signal intensity values, etc. In some embodiments, analyses may utilize spatial and/or temporal information collected across multiple analysis windows, across multiple array regions, or over specified periods of time, or combinations thereof, to improve the quality of the analysis and thereby improve the quantitative aspects of the disclosed methods. In some embodiments, other sources of information, including, but not limited to, for example, locations of probes, frequently occurring artifact patterns, previously derived results, literature reports, array manufacturers' suggestions, human knowledge, and/or human guidance may also be integrated into the analysis.

Figure 22:
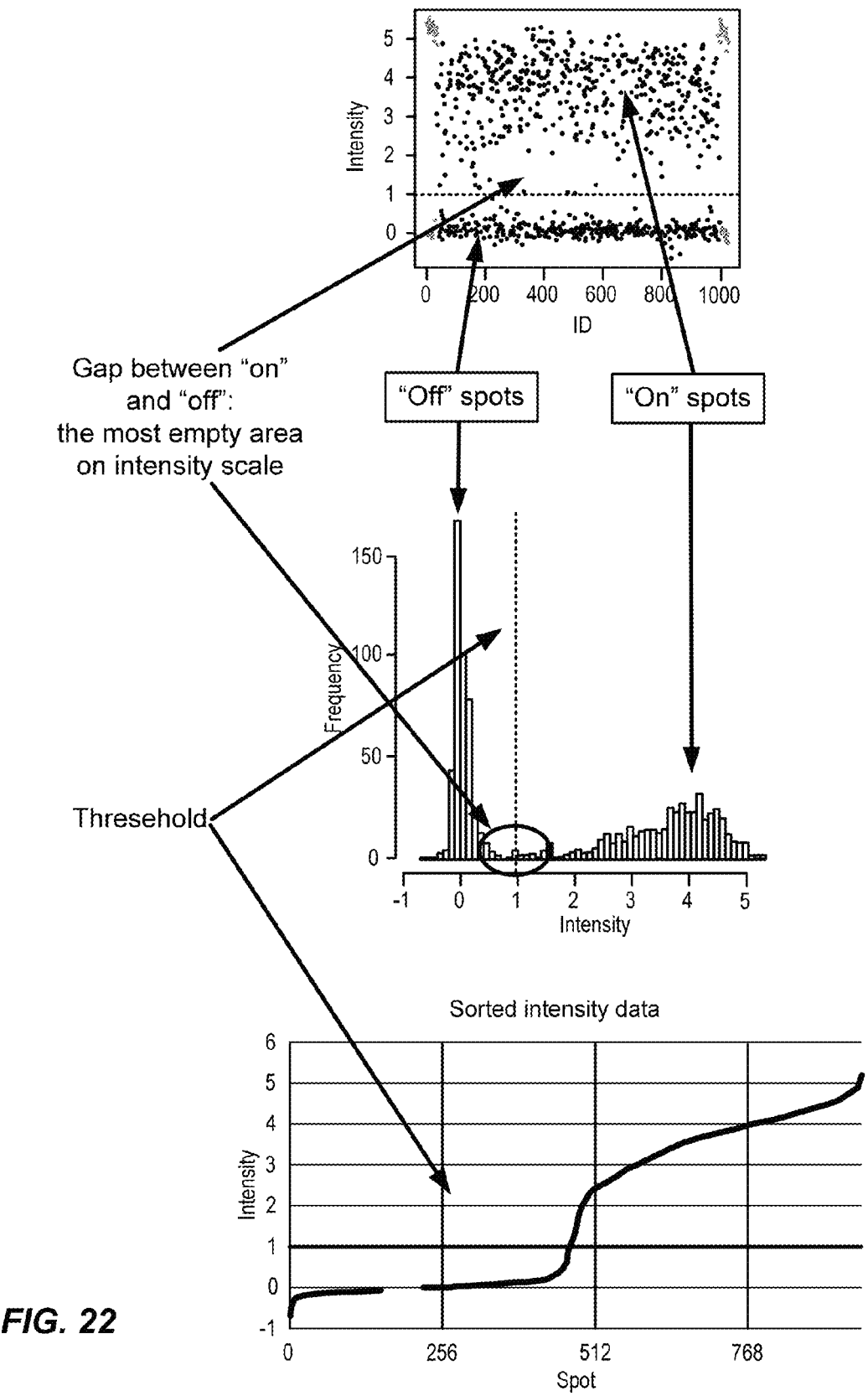
FIG. 22 depicts a scatter plot (upper) and histogram (middle) of array feature intensity data that illustrate the use of an intensity threshold (dashed lines) that discriminate between labeled ("on") and non-labeled ("off") features of an array. In one embodiment of the presently described analysis methods, the threshold is determined from the maximum slope of a plot of sorted intensity data (lower).

By way of a non-limiting example of threshold determination, in some embodiments of the disclosed methods, the background corrected signal intensity threshold may be determined using an empirical approach (e.g. the "E-Derivative" approach; see FIG. 22) wherein the background corrected signal intensity data for the complete set of array features constitutes a set $I=\{I_i\}$. The set I is sorted in increasing order to obtain a set of ordered corrected signal intensity values $z=\{z_i\}=\{Sort[y_i]\}$. Next, the differences between each sorted array value are calculated to obtain $d=\{d_1, d_2, \ldots, d_m\}$, where $d_i=z_{i+1}-z_i$. The intensity differences are then smoothed using a "window" whose width is w, to produce a smoothed, sorted array s:

$$s_j = \frac{\sum_{i=j-w}^{j+w} d_i}{2w+1}$$

The threshold is T, the point for which the slope of the smoothed, sorted data is steepest (see FIG. 21):

$T=\max(s_j)$

The number of features, k, which are "on" (or labeled) is:

$k=\Sigma_{i=1}^{m} I[I_i > T]$.

By way of another non-limiting example of threshold determination, in some embodiments the background corrected signal intensity threshold may be determined by fitting the background corrected feature intensity data to two more more assumed distributions (i.e. a "Mixture Model" approach), wherein the assumed distributions comprise normal distributions, uniform distributions, etc. The mixture model approach essentially models the underlying process that generated the data, by assuming that the positive feature intensities are generated from a positive feature distribution with higher average signal intensity, and the negative feature intensities are generated from a negative feature distribution with lower average signal intensity. This approach additionally models the variability in the feature intensities generated by each distribution, which can be useful in cases where the negative feature intensities tend to be much less variable, while the positive feature intensities tends to be much more variable. The choice of the distributions is determined by the shape of the data curve in a background corrected feature intensity histogram. The parameters of the model, e.g. the estimated average intensities for "on" and "off" features and their corresponding variance, are estimated from the data using a method such as the Expectation Maximization algorithm.

Figure 23:
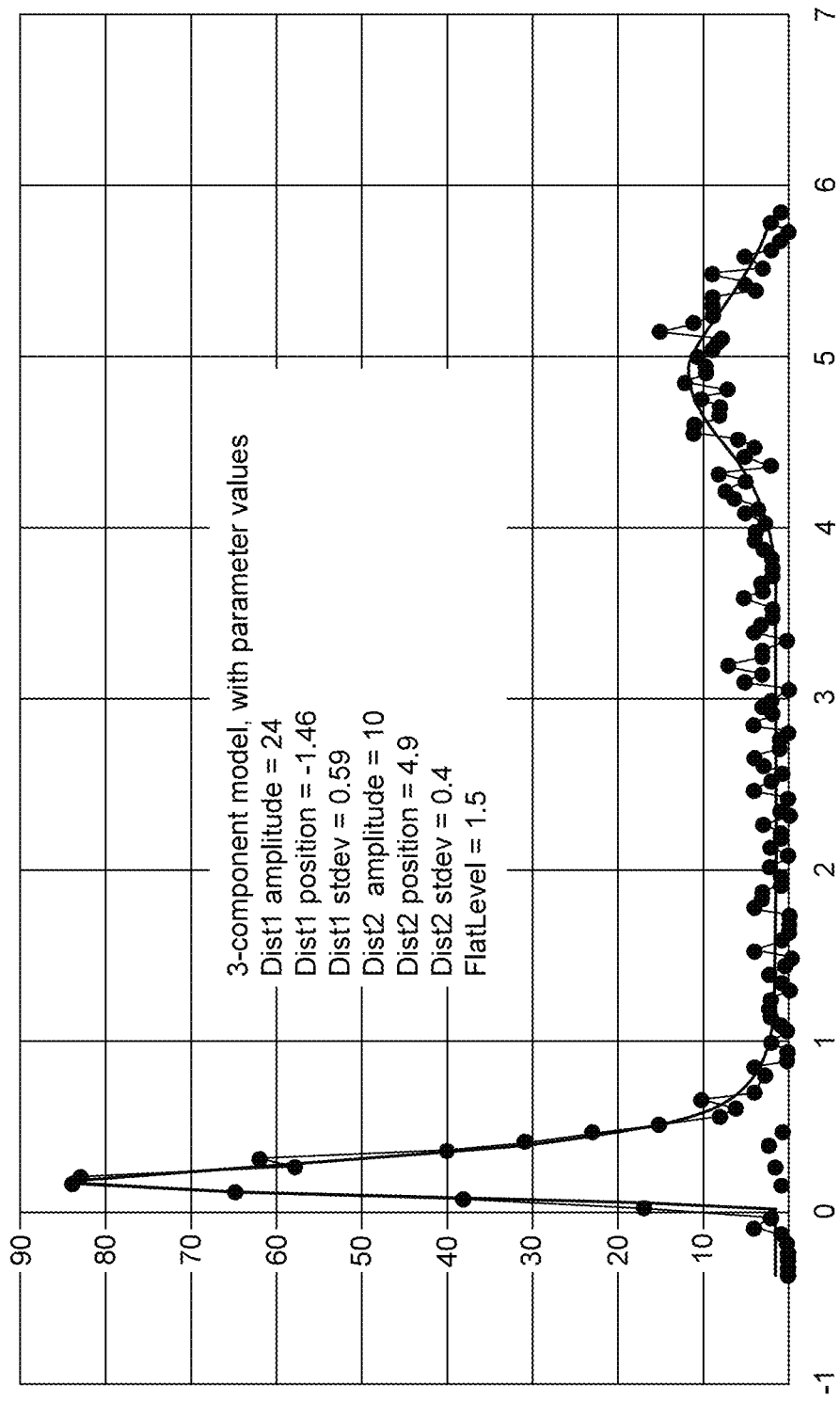
FIG. 23 depicts the results of fitting a 3-component distribution model used to determine an intensity threshold in one embodiment to a 128-*bin* feature intensity histogram.

By way of another non-limiting example of threshold determination, in some embodiments the background corrected signal intensity threshold may be determined by fitting the background corrected feature intensity data to a model function comprising three assumed distributions (i.e. a "3-Component Model" approach), wherein the assumed distributions comprise a log-normal distribution, Dist1, for the "off" spots, a normal distribution, Dist2, for the "on" spots, and a flat offset FlatLevel. Adjustable parameters for the model include: (i) the number of bins in the starting histogram, (ii) Dist1 amplitude, (iii) Dist1 position, (iv) Dist1 standard deviation, (v) Dist2 amplitude, (vi) Dist2 position, (vii) Dist2 standard deviation, and (viii) FlatLevel. An example fit to histogram data is shown in FIG. 23. One non-limiting example of a method to determine the threshold after fitting feature intensity data to such a distribution is as follows: (i) fit the 3-component distribution to the histogram data, and (ii) set the threshold T by calculating the following values: (1) the intensity $t_{low}$ where the high-intensity side of the fitted log-normal distribution component drops below 1 (or a defined parameter for comparison), (2) the intensity $t_{subflat}$ where the high-intensity side of the fitted log-normal distribution component drops below the fitted FlatLevel result, (3) the intensity $t_{subnorm}$ where the high-intensity side of the fitted log-normal distribution component drops below the value of the fitted normal distribution at that histogram bin, and (4) choosing $T=\min[t_{low}, t_{subflat}, t_{subnorm}]$. Alternative approaches for determining a threshold using a 3-component model approach will be apparent to those of skill in the art. It can be beneficial to calculate starting values of model parameters, to improve the speed and reliability of the modelling process, which can be achieved using methods such as a coarse search to identify the dominant peaks in the histogram, or based on assumptions derived from typical historical data sets.

By way of another non-limiting example of threshold determination, in some embodiments the background corrected signal intensity threshold may be determined using a "Peak Split Fiducials" approach. This approach, which copes well with low-quality data, is described as follows. An initial split of the feature intensity data into high and low intensity groups is made using the scale defined naturally by the spread between "on" (label present) and "off" (label absent) features in the fiducial rows. Then, the histogram peak (after optionally smoothing the data using standard methods such as a moving average filter) is found for each group. The threshold is then determined by examining the spread in the intensity data around the low-intensity group peak. Define upper and lower bounds of fiducial intensity: (i) $F_{off}$=[median of OFF fiducials], $F_{on}$=[median of ON fiducials], and (iii) $F_{range}=F_{on}-F_{off}$. Perform an initial split of the data based on the fiducial scale, at the level Splitvalue=$F_{off}$+ PeakSplit×$F_{range}$, where the parameter PeakSplit is a percentage of $F_{range}$. Find 2 peaks: (i) Peak4=the intensity peak for which the histogram is a maximum, for all features of intensity less than Splitvalue, (ii) Peak2=the intensity peak for which the histogram is a maximum, for all features of intensity greater than Splitvalue. Calculate the standard deviation, Stdev1, of all the features in the neighbourhood of Peak1, defined as all index features from the lowest intensity up to Peak1+PeakOffsetFraction×(Peak2−Peak1), where PeakOffsetFraction is an adjustable parameter. Set the threshold to the lesser of $T_{psf}$ and $T_{LocMin}$, which are calculated as follows: (i) $T_{psf}$=Peak1+StdevMultiple×Stdev1, where StdevMultiple is a parameter, OR $T_{LocMin}$=the intensity corresponding to the minimum of a smoothed histogram curve between Peak1 and $T_{psf}$. Similar approaches using different methods for determining the spread around either peak can also be used.

The methods and systems disclosed herein may comprise detecting one or more labeled features within one or more regions on an array. In some embodiments, detecting a labeled feature within a region may comprise comparing the background corrected signal intensity for a feature with a dynamic signal intensity threshold derived through statistical analysis of the background corrected signal intensities for the complete set of features. When the background corrected signal intensity for a given feature is above the threshold, the feature may be classified as a labeled feature. Alternatively, if the background corrected signal intensity for a given feature is below the threshold, the feature may be classified as non-labeled. Application of a background corrected signal intensity threshold to the corrected signal intensity data for the complete set of features thus constitutes a binary transformation of the data to a digital output wherein features are classified as either labeled ("on") or non-labeled ("off"). Those of skill in the art will recognize that there are many possible variations in the type and order of analysis steps that may be applied to achieve this binary transformation.

Calculation of the absolute number of target molecules in a sample. The absolute number of target molecules in a sample, wherein the target molecules have been labeled in a stochastic fashion as described previously, may be determined using arrays comprising feature sets comprising probes that are specific for the labels in the stochastic label set. Following hybridization or binding of the target molecules or labeled target molecules to the array, the array is imaged and processed as described above, and the number of target molecules, N, in the sample is determined from the number, k, of labeled features based on Poisson distribution statistics:

$$N = -m * \log\left(1 - \frac{k}{m}\right)$$

where m is the total number of features (i.e. the total number of unique labels in the set of stochastic labels).

Figure 24A:
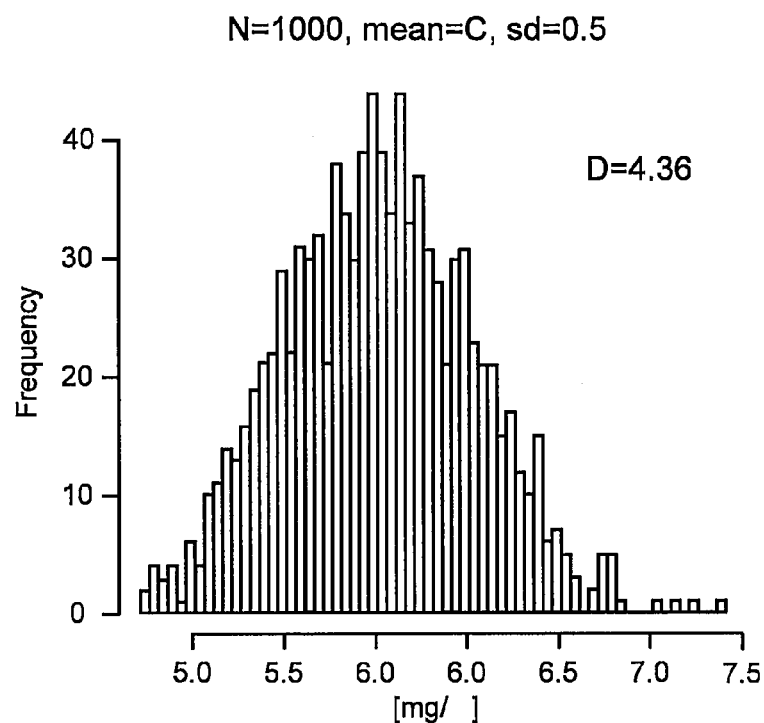
FIG. 24A illustrates deviance calculations for fitting one normal distribution to histograms of array feature intensity data.
Figure 24B:
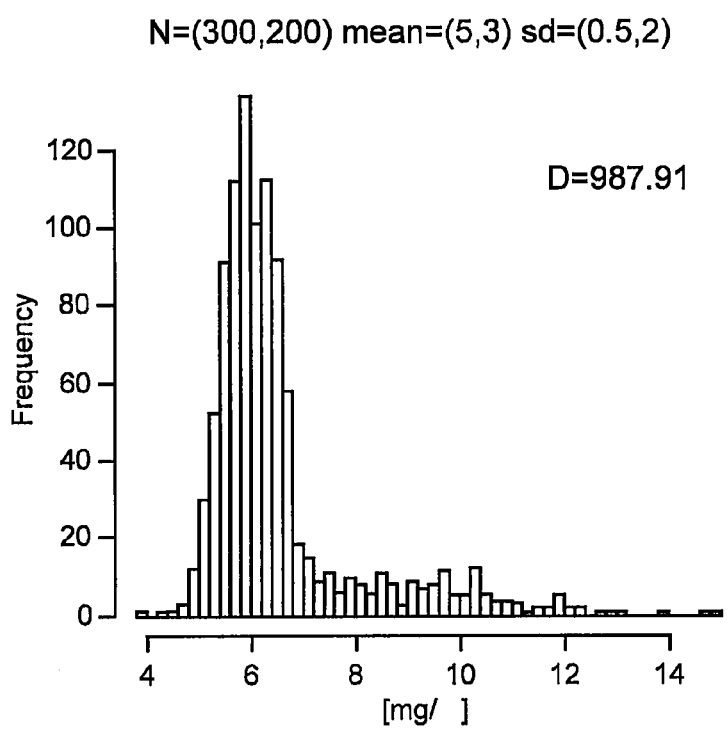
FIG. 24B illustrates the deviance calculations for fitting two normal distributions to histograms of array feature intensity data. In some embodiments, deviance measurement may be used as a quality metric.

Quality metrics. In some embodiments, it is beneficial to include a numerical measure of the quality of the data, to help to gauge the success of an experiment. In some embodiment, this quality measurement may be based on statistics from the feature-by-feature intensity data. One simple quality measurement $Q_{Sep1}$ is simply the difference between the means of the positive and negative features intensities, after background correction and scaling, i.e. $Q_{Sep1}$=(mean intensity of features having an intensity above the signal intensity threshold)−(mean intensity of features having an intensity below the threshold). In some embodiments, this metric may also incorporate the spread in the intensities of the feature distribution(s) by scaling the difference between means by the standard deviation of each distribution, e.g. $Q_{Sep2}=Q_{Sep1}$/(standard deviation of intensities for feature having intensities below the threshold intensity). Other quality measurements can be constructed based on the separation and breadth of modelled distributions which are fitted to the experimental data. In some embodiments, deviance measurement may be used for a quality metric (FIG. 24); this is a calculation based on the degree of separation between two fitted normal distributions. In some embodiments, it is preferable to empirically determine a dynamic intensity threshold by setting the threshold to a value which maximizes a quality metric.

Confidence intervals. In some embodiments of the methods disclosed herein, it is beneficial to define confidence intervals (see Dube, et al. (2008), PLoS ONE 3(8): e2876 for a more complete description) when specifying estimates of the absolute number of target molecules detected in a sample using the techniques described above. The 95% confidence interval of the estimation of N from stochastic labeling experiments can be derived from k for a single reaction employing a single set of $_m$ distinct labels. The 95% confidence interval for N ranges from $N_{low}$ to $N_{high}$, where $$N_{low} = -m \times \ln\left[1 - \left(\frac{k}{m} - 1.96\sqrt{\frac{\frac{k}{m}\left(1 - \frac{k}{m}\right)}{m}}\right)\right], \text{ and}$$

$$N_{high} = -m \times \ln\left[1 - \left(\frac{k}{m} + 1.96\sqrt{\frac{\frac{k}{m}\left(1 - \frac{k}{m}\right)}{m}}\right)\right]$$

Ratio of the number of copies of a target molecule in two samples. Frequently, researchers seek to compare the expression levels of genes in different samples, by calculating a ratio between gene expression levels in two or more samples. Using calculations such as those described above, it is possible to derive confidence intervals for such ratios where the number of target molecules in each sample are determined using the methods, systems, and platforms as disclosed herein.

Figure 25:
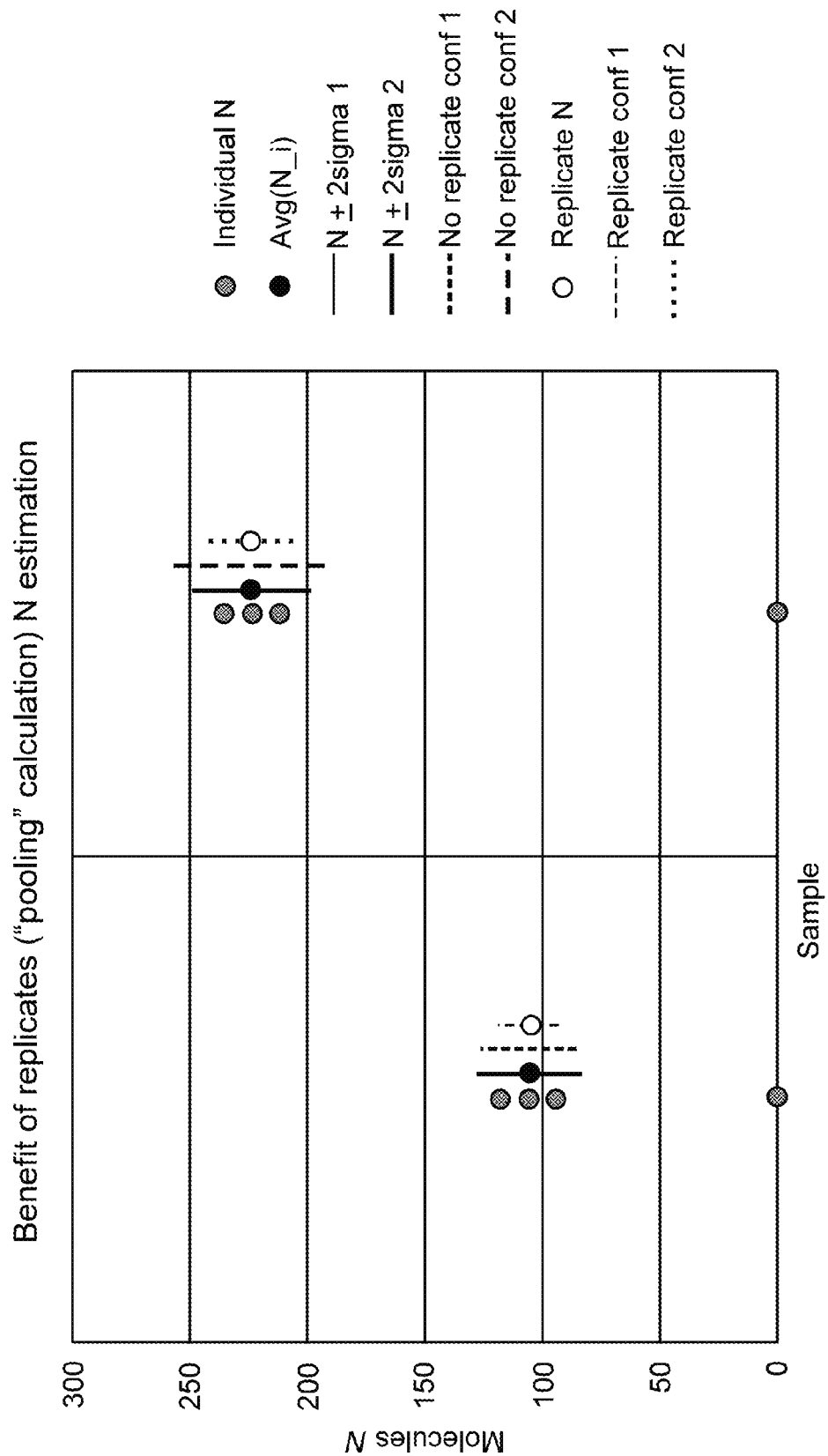
FIG. 25 depicts the uncertainties calculated for various methods of combining output data from replicate experiments.

Replicate experiments. The benefit of performing replicate experiments, and the proper calculation of associated uncertainties, is illustrated in FIG. 25. While results (blue points) from replicate experiments can simply be combined (blue error bars), calculating the uncertainty from Poisson statistics, wherein one considers the replicates as comprising a larger pool of labels, gives the smaller green error bars illustrated in the figure. The accuracy of this estimation will vary depending on the consistency between replicates, and there is a numerical simplification employed in considering the labels of replicate experiments to be a pool of diverse labels. Therefore, in some embodiments of the disclosed methods, different methods for calculating confidence intervals may be more appropriate at high ratios of k/m.

User Interface

The methods, software, systems, and platforms disclosed herein may comprise a user interface, or use of the same. The user interface may provide one or more inputs from a user. The input from the user interface may comprise instructions for counting the one or more labeled features in a real time mode. The input from the user interface may comprise instructions for counting the one or more features from one or more images. The one or more images may be archived images. The one or more images may be live captured images.

Different platform operators may have their own preferences about the timing to analyze images. One platform operator may want to run the image analyses while live capturing images. Another platform operator may run the image analyses after all the images have been collected. Or, another platform operator may run the image analyses on a set of archived images. These options can be selected via inputs to the user interface.

Digital Processing Device

The methods, software, systems, and platforms disclosed herein may comprise a digital processing device, or use of the same. The digital processing device may comprise one or more hardware central processing units (CPU) that carry out the device's functions. The digital processing device may comprise an operating system configured to perform executable instructions. The digital processing device may be connected to a computer network. The digital processing device may be connected to the Internet such that it accesses the World Wide Web. The digital processing device may be connected to a cloud computing infrastructure. The digital processing device may be connected to an intranet. The digital processing device may be connected to a data storage device.

Suitable digital processing devices may include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. In some instances, smartphones may be suitable for use in the system described herein. In some instances, select televisions, video players, and digital music players with optional computer network connectivity may be suitable for use in the system described herein. Suitable tablet computers may include those with booklet, slate, and convertible configurations, known to those of skill in the art.

The digital processing device may comprise an operating system configured to perform executable instructions. The operating system may be software, including programs and data, which manages the device's hardware and provides services for execution of applications. Suitable server operating systems may include, by way of non-limiting examples, FreeBSD, OpenBSD, NetBSD®, Linux, Apple® Mac OS X Server®, Oracle® Solaris®, Windows Server®, and Novell® NetWare®. Suitable personal computer operating systems may include, by way of non-limiting examples, Microsoft® Windows®, Apple® Mac OS X®, UNIX®, and UNIX-like operating systems such as GNU/Linux®. The operating system is provided by cloud computing. Suitable mobile smart phone operating systems may include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

The digital processing device may comprise a storage and/or memory device. The storage and/or memory device may be one or more physical apparatuses used to store data or programs on a temporary or permanent basis. The digital processing device may be a volatile memory and may require power to maintain stored information. The digital processing device may be a non-volatile memory and may retain stored information when the digital processing device is not powered. The non-volatile memory may comprise flash memory. The non-volatile memory may comprise dynamic random-access memory (DRAM). The non-volatile memory may comprise ferroelectric random access memory (FRAM). The non-volatile memory may comprise phase-change random access memory (PRAM). The storage device may include, by way of non-limiting examples, CD-ROMs, DVDs, flash memory devices, magnetic disk drives, magnetic tapes drives, optical disk drives, and cloud computing based storage. The storage and/or memory device may be a combination of devices such as those disclosed herein.

The digital processing device may comprise a display. The display may be used to send visual information to a user. The display may be a cathode ray tube (CRT). The display may be a liquid crystal display (LCD). The display may be a thin film transistor liquid crystal display (TFT-LCD). The display may be an organic light emitting diode (OLED) display. The OLED display may be a passive-matrix OLED (PMOLED) or active-matrix OLED (AMOLED) display. The display may be a plasma display. The display may be a video projector. The display may be a combination of devices such as those disclosed herein.

The digital processing device may comprise an input device to receive information from a user. The input device may be a keyboard. The input device may be a pointing device including, by way of non-limiting examples, a mouse, trackball, track pad, joystick, game controller, or stylus. The input device may be a touch screen or a multi-touch screen. The input device may be a microphone to capture voice or other sound input. The input device may be a video camera to capture motion or visual input. The input device may be a combination of devices such as those disclosed herein.

Non-Transitory Computer Readable Storage Medium

The methods, software, systems, and platforms disclosed herein may comprise one or more non-transitory computer readable storage media encoded with a program including instructions executable by the operating system of an optionally networked digital processing device. A computer readable storage medium may be a tangible component of a digital processing device. A computer readable storage medium may be optionally removable from a digital processing device. A computer readable storage medium may include, by way of non-limiting examples, CD-ROMs, DVDs, flash memory devices, solid state memory, magnetic disk drives, magnetic tape drives, optical disk drives, cloud computing systems and services, and the like. The program and instructions may be permanently, substantially permanently, semi-permanently, or non-transitorily encoded on the media.

Computer Programs (General)

The methods, software, systems, and platforms disclosed herein may comprise at least one computer processor, or use of the same. The computer processor may comprise a computer program. A computer program may include a sequence of instructions, executable in the digital processing device's CPU, written to perform a specified task. Computer readable instructions may be implemented as program modules, such as functions, features, Application Programming Interfaces (APIs), data structures, and the like, that perform particular tasks or implement particular abstract data types. A computer program may be written in various versions of various languages.

The functionality of the computer readable instructions may be combined or distributed as desired in various environments. A computer program may comprise one sequence of instructions. A computer program may comprise a plurality of sequences of instructions. A computer program may be provided from one location. A computer program may be provided from a plurality of locations. A computer program may include one or more software modules. A computer program may include, in part or in whole, one or more web applications, one or more mobile applications, one or more standalone applications, one or more web browser plug-ins, extensions, add-ins, or add-ons, or combinations thereof.

Web Applications

A computer program may include a web application. In light of the disclosure provided herein, those of skill in the art will recognize that a web application may utilize one or more software frameworks and one or more database systems. A web application may be created upon a software framework such as Microsoft®.NET or Ruby on Rails (RoR). A web application may utilize one or more database systems including, by way of non-limiting examples, relational, non-relational, feature oriented, associative, and XML database systems. Suitable relational database systems may include, by way of non-limiting examples, Microsoft® SQL Server, mySQL™, and Oracle®. Those of skill in the art will also recognize that a web application may be written in one or more versions of one or more languages. A web application may be written in one or more markup languages, presentation definition languages, client-side scripting languages, server-side coding languages, database query languages, or combinations thereof. A web application may be written to some extent in a markup language such as Hypertext Markup Language (HTML), Extensible Hypertext Markup Language (XHTML), or eXtensible Markup Language (XML). A web application may be written to some extent in a presentation definition language such as Cascading Style Sheets (CSS). A web application may be written to some extent in a client-side scripting language such as Asynchronous Javascript and XML (AJAX), Flash® Actionscript, Javascript, or Silverlight®. A web application may be written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. A web application may be written to some extent in a database query language such as Structured Query Language (SQL). A web application may integrate enterprise server products such as IBM Lotus Domino. A web application may include a media player element. A media player element may utilize one or more of many suitable multimedia technologies including, by way of non-limiting examples, Adobe® Flash®, HTML 5, Apple® QuickTime®, Microsoft® Silverlight®, Java™, and Unity Mobile Applications A computer program may include a mobile application provided to a mobile digital processing device. The mobile application may be provided to a mobile digital processing device at the time it is manufactured. The mobile application may be provided to a mobile digital processing device via the computer network described herein.

A mobile application may be created by techniques known to those of skill in the art using hardware, languages, and development environments known to the art. Those of skill in the art will recognize that mobile applications may be written in several languages. Suitable programming languages include, by way of non-limiting examples, C, C++, C#, Featureive-C, Java™, Javascript, Pascal, Feature Pascal, Python™, Ruby, VB.NET, WML, and XHTML/HTML with or without CSS, or combinations thereof.

Suitable mobile application development environments may be available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments may be available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums may be available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Applications

A computer program may include a standalone application, which may be a program that may be run as an independent computer process, not an add-on to an existing process, e.g., not a plug-in. Those of skill in the art will recognize that standalone applications may be often compiled. A compiler may be a computer program(s) that transforms source code written in a programming language into binary feature code such as assembly language or machine code. Suitable compiled programming languages include, by way of non-limiting examples, C, C++, Featureive-C, COBOL, Delphi, Eiffel, Java™, Lisp, Python™, Visual Basic, and VB .NET, or combinations thereof. Compilation may be often performed, at least in part, to create an executable program. A computer program may include one or more executable complied applications.

Web Browser Plug-Ins

A computer program may include a web browser plug-in. In computing, a plug-in may be one or more software components that add specific functionality to a larger software application. Makers of software applications may support plug-ins to enable third-party developers to create abilities which extend an application, to support easily adding new features, and to reduce the size of an application. When supported, plug-ins may enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. The toolbar may comprise one or more web browser extensions, add-ins, or add-ons. The toolbar may comprise one or more explorer bars, tool bands, or desk bands.

In view of the disclosure provided herein, those of skill in the art will recognize that several plug-in frameworks may be available that enable development of plug-ins in various programming languages, including, by way of non-limiting examples, C++, Delphi, Java™, PHP, Python™, and VB .NET, or combinations thereof.

Web browsers (also called Internet browsers) may be software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. The web browser may be a mobile web browser. Mobile web browsers (also called mircrobrowsers, mini-browsers, and wireless browsers) may be designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules (General)

The methods, software, systems, and platforms disclosed herein may comprise one or more softwares, servers, and database modules, or use of the same. In view of the disclosure provided herein, software modules may be created by techniques known to those of skill in the art using machines, software, and languages known to the art. The software modules disclosed herein may be implemented in a multitude of ways. A software module may comprise a file, a section of code, a programming feature, a programming structure, or combinations thereof. A software module may comprise a plurality of files, a plurality of sections of code, a plurality of programming features, a plurality of programming structures, or combinations thereof. The one or more software modules may comprise, by way of non-limiting examples, a web application, a mobile application, and a standalone application. Software modules may be in one computer program or application. Software modules may be in more than one computer program or application. Software modules may be hosted on one machine. Software modules may be hosted on more than one machine. Software modules may be hosted on cloud computing platforms. Software modules may be hosted on one or more machines in one location. Software modules may be hosted on one or more machines in more than one location.

Databases

The methods, software, systems, and platforms disclosed herein may comprise one or more databases, or use of the same. In view of the disclosure provided herein, those of skill in the art will recognize that many databases may be suitable for storage and retrieval of imaging information. Suitable databases may include, by way of non-limiting examples, relational databases, non-relational databases, feature oriented databases, feature databases, entity-relationship model databases, associative databases, and XML databases. A database may be internet-based. A database may be web-based. A database may be cloud computing-based. A database may be based on one or more local computer storage devices.

EXAMPLES

The following illustrative examples are representative of specific embodiments of the methods, systems, and platforms described herein, but are not meant to be limiting in any way.

Example 1

Optical Instrument

FIG. 1 shows one embodiment of the optical instrument. This embodiment was used for simultaneously imaging 2 adjacent wells of a 16-well microscope slide. Each well contained 1024 (32×32) features, also called spots, which may be labeled with fluorescence. A spot diameter was approximately 80 microns. Center-to-center distance between adjacent spots was 161 microns. The purpose of the instrument was to determine the brightness of each spot. FIG. 1E shows the translation stage system 105, imaging system 106, and illumination system 107. The translation stage system contained a single-axis translation stage which was constructed from a Misumi model SSELBW9-170 recirculating ball slide driven by a Haydon Kerk 26000-series linear actuator. A holder for a 16-well microscope slide was mounted on the translation stage. The linear actuator was controlled by a Peter Norberg Consulting model BC2D20-0700 motion controller. FIG. 1G shows a USB hub 112, custom circuit board 113, and a motion controller 114. The motion controller and the CCD camera were USB devices. The USB hub allowed communication between a computer and the instrument to take place over a single USB cable. The custom circuit board contained a Luxdrive model 3021-D-E-1000 LED driver. The custom circuit board contained a logic chip to synchronize the LED with the CCD camera (turn the LED on when the CCD camera starts an exposure and off when the CCD camera finishes an exposure) and to prevent the LED from turning on when the instrument's door is open.

Example 2

Imaging System

Figure 2:
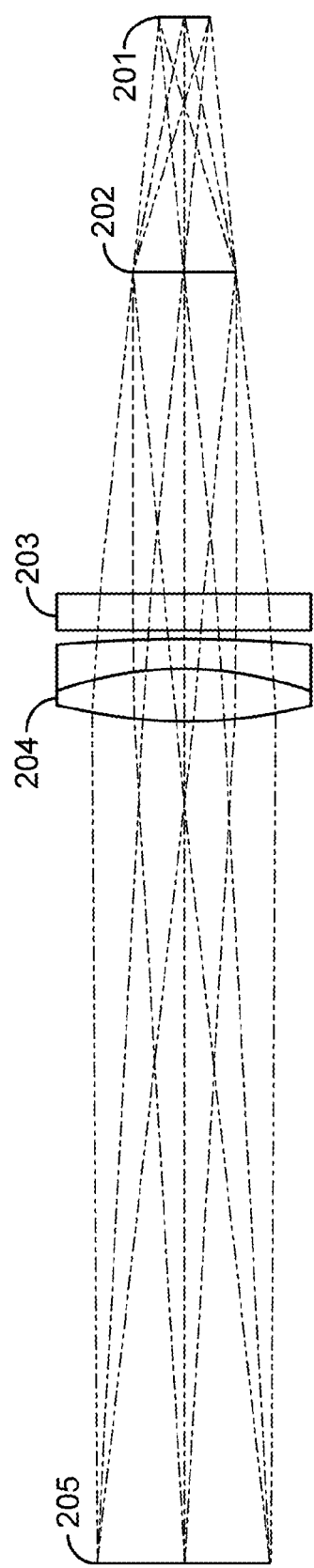
FIG. 2 shows an exemplary layout of lenses in an imaging system.

An embodiment of an imaging system is illustrated in FIG. 2. Light emitted by dye molecules on a surface of the support 205 was collimated by an achromatic cemented doublet lens 204, filtered by a bandpass filter 203, and focused by a camera lens 202 onto the sensor 201 of a CCD camera. Lens 204 (Edmund Optics model 47640) had a focal length of 85 mm and a diameter of 25 mm. Filter 203 (Semrock model FF01-593/40-25) was an emission bandpass filter for use with cy3 or phycoerythrin dye. Lens 202 (Fujinon model HF25HA-1B) has a focal length of 25 mm. Lens 202 was a multi-element lens, but it is shown in FIG. 2 as an infinitesimally thin single-element lens because the design details of the multi-element lens were proprietary to Fujinon. The adjustable aperture stop of lens 202 was set to 2.8. The CCD camera (Point Grey Research model CMLN-13S2M-CS) had 1296×964 pixels and a pixel size of 3.75 microns. In this embodiment only the central 1280×640 pixels were used. The camera's plastic housing was removed and the camera's circuit board was cooled by a small fan. Lenses 204 and 202 formed a finite-conjugate imaging system with a magnification of 0.3.

Example 3

Illumination System

Figure 3:
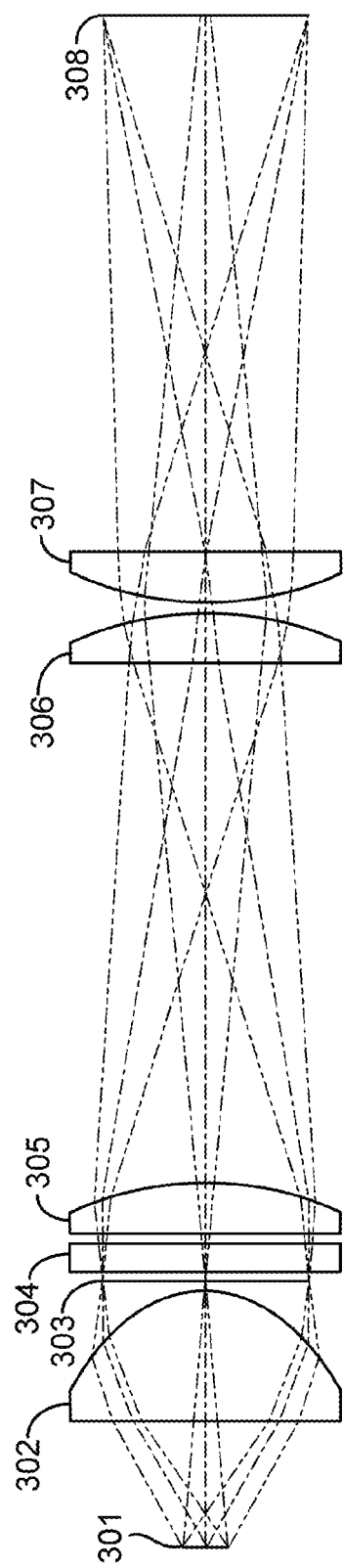
FIG. 3 shows an exemplary layout of lenses in an illumination system.

An embodiment of an illumination system is illustrated in FIG. 3. Light emitted by light source 301 was collimated by lens 302 and then passed through aperture 303, bandpass filter 304, and lenses 305, 306, and 307, before reaching sample 308. Light source 301 (LedEngin model LZ4-40G100) was an LED with a peak emission wavelength of approximately 525 nm. Lens 302 (Thorlabs model ACL2520-A) was an aspheric lens with a diameter of 25 mm and a focal length of 20 mm. Aperture 303 (Fotofab custom part) was a rectangular hole (19 mm×7.5 mm) in a 25-mm-diameter steel disk. Filter 304 (Semrock model FF01-531/40-25) was an excitation bandpass filter for use with cy3 or phycoerythrin dye. Lenses 305, 306, and 307 were plano-convex lenses with diameters of 25 mm and focal lengths of 60 mm. Lenses 301 and 302 formed a finite-conjugate imaging system with a magnification of 3 and imaged light source 301 onto the pupils of lenses 306 and 307. Lenses 306 and 307 formed a finite-conjugate imaging system with a magnification of 1 and imaged aperture 303 onto sample 308. The illumination system was tilted at 45 degrees with respect to sample 308. The illuminated area was approximately 19 mm×10.6 mm, where 10.6 mm (=7.5 mm/cosine (45 degrees)).

Example 4

Reference Probe Preparation

The purpose of this experiment was to illustrate the use of an ad hoc method to count the number of hybridizations taking place on an array. This example used probes that the specific DNA sequences attached to an array. The 32×32 feature arrays used in this experiment contain 960 different measure spots along with 32 positive control probes and 32 negative control probes (see FIGS. 15 and 16). The 32 positive control probes were used to ensure actual binding can occur by using stock oligonucleotide, while the 32 negative control probes contained empty spots with no probes at all. In the image analysis step, we considered a probe to have intensity above the set intensity threshold, then we referred to the probe as a positive probe, while if the probe intensity was below the set intensity threshold, we referred to the probe as a negative feature. Positive probes were assumed to measure whether there was a significant amount of corresponding complementary oligonucleotide in the sample, while negative features represented absent oligonucleotides. The positive probes were otherwise referred to as labels, meaning we can count up to 960 unique labels or barcodes, to measure 960 copies of oligonucleotides in the sample, which can then be further generalized to predict the actual amount of oligonucleotides in the original sample. Depending on the experiment, out of the M total labels, or 960 total labels, we could calculate the total number of copies, N, of the oligonucleotides in the sample, by predicting N from the actual observed unique barcodes or number of positive probes, k.

Example 5

Threshold Computation

The purpose of this experiment was to demonstrate one method to compute a threshold for discriminating between labeled and non-labeled features on an array.

I. Set $I_{LL}$, intensity lower limit, $I_{UL}$, intensity upper limit, and w, window size.

II. Obtain a set of feasible threshold intensities, $y=\{y_i: I_{LL} < I_i < I_{UL}\}$ III. Sort y in increasing order to obtain y*.

IV. Calculate $d=\{d_1, d_2, d_i, \ldots, d_m\}$, where $d_i = y_{i+1}^* - y_i^*$.

V. Calculate a gap statistic for each of the observed intensities:

$$x_j = \frac{\sum_{i=j-w}^{j+w} d_i}{2w+1}$$

VI. Identify the threshold c, such that $c = \max(x_j)$

VII. Count the number of spots, k, above the threshold c, where $k = \sum_{i=1}^{m} I[y_i > c]$.

VIII. Given a number of simulations desired, nsim, perform the following procedure nsim times: Randomly select m values with replacement from $y=\{y_1, y_2, \ldots, y_m\}$ to obtain $y_{sim}$. Then repeat Step I-VII with $y_{sim}$ to obtain a final count.

IX. Calculate $\hat{\sigma}_k$ the standard deviation of the nsim simulated counts.

X. Calculate the 95% CI for the count as:

$[k-1.96\hat{\sigma}_k, k+1.96\hat{\sigma}_k]$.

Note that in order to obtain the true estimate of the molecule count in the sample, we needed to transform by:

$$N = -m * \log\left(1 - \frac{k}{m}\right)$$

and similarly, for the 95% CI upper and lower values, where m is the total number of features on the array.

Example 6

Detection of Kan Genes

Figure 4A:
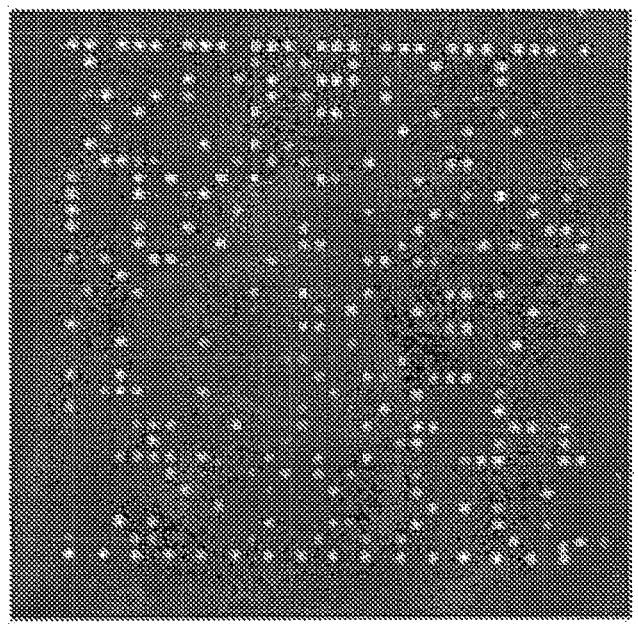
FIG. 4A shows an array image acquired from the optical instrument.
Figure 4B:
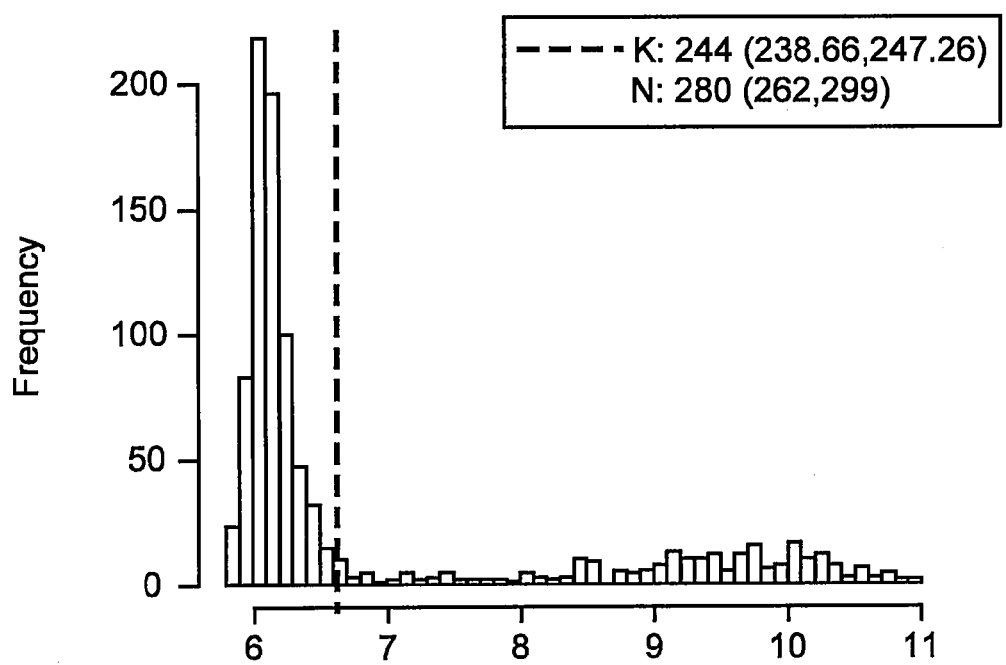
FIG. 4B shows a histogram of intensities for individual features.

The purpose of this experiment was to determine the count of kan genes in a sample. The sample containing the kan genes was hybridized to an array. FIG. 4A displays a region of the array acquired from the imaging system. The bright intensity at a spot was correlated with a higher probability of a gene being present at the spot. The image analysis software examined the statistics of the intensity distribution, such as deviance, skewness, kurtosis, and median. These statistics provided guidance for the software to automatically choose the best method to detect the presence of kan genes. In this example, a mixture model algorithm was used to determine the intensity threshold to be 6.6, which optimally divided the intensity distribution into "on" and "off" domains, as shown in FIG. 4B.

Example 7

Titration Experiment

Figure 5:
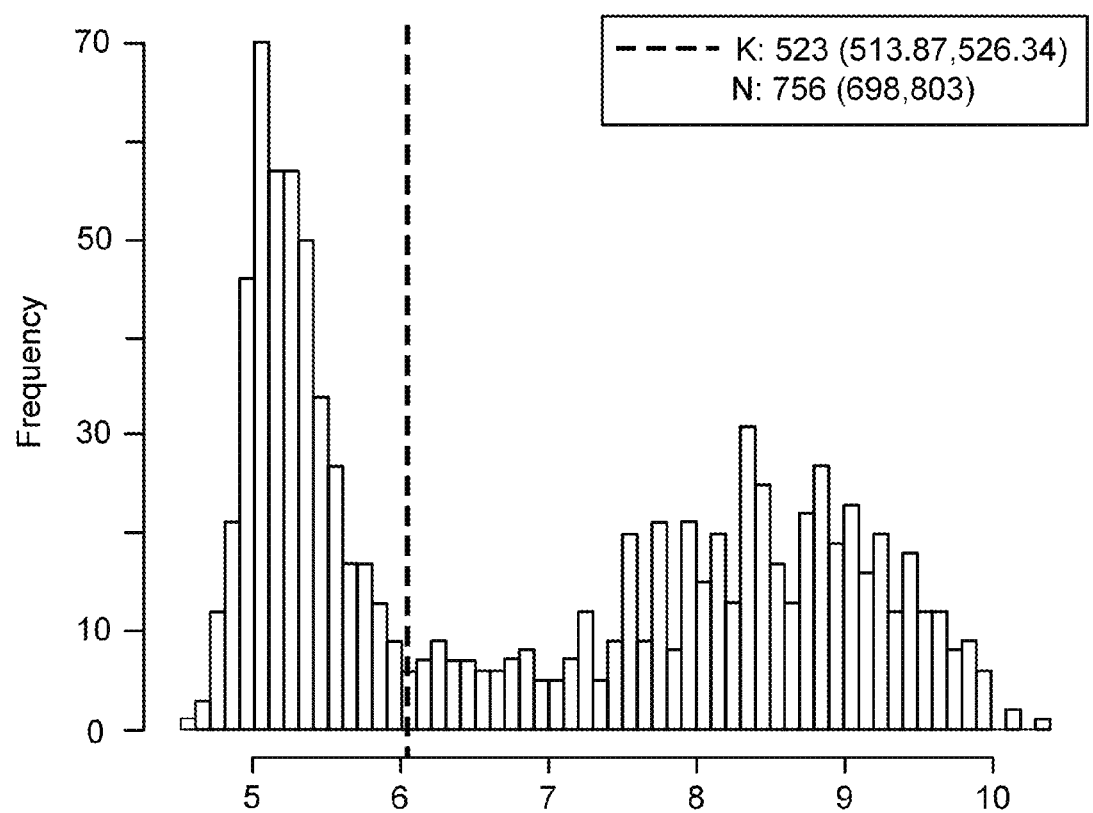
FIG. 5 shows a feature intensity distribution observed for hybridization of array probes with labeled target molecules in atitration experiment.

The purpose of this experiment was to detect the presence of molecular hybridization in a titration experiment. After obtaining the intensity measurements of a region, the intensity distribution was computed and is shown in FIG. 5. A person with ordinary skill can identify two modes in the distribution; however, it was very difficult to determine the precise value of the threshold. The invented software automated the task of determining the signal intensity threshold, and determined that an intensity value of 6.02 provides the optimal threshold for distinguishing between labeled and non-labeled features.

Example 8

Background Adjustment

Figure 6A:
FIG. 6A shows a noisy array image.

The purpose of this experiment was to demonstrate use of one background subtraction method to process images. FIG. 6A shows an acquired image with pronounced artifacts. A systematic background subtraction was performed to reduce noise. We defined an analysis window centered on a spot. The software then calculated the mean spot intensity, $\bar{S}$, spot standard deviation $\sigma_S$, number of spot pixels $n_S$, background mean $\bar{B}$, background standard deviation $\sigma_B$, and number of background pixels $n_B$. Then, the software calculated the log 2 background subtracted intensity statistic for each spot:

$$I = \frac{\log_2(16\bar{S}) - \log_2(16\bar{B})}{\sqrt{\frac{\tau_S^2}{n_S} + \frac{\tau_B^2}{n_B}}}$$

-continued where $$\tau_S = \log_2(16(\sigma_S + \overline{S})) - \log_2(16\sigma_S)$$

$$\tau_B = \log_2(16(\sigma_B + \overline{B})) - \log_2(16\sigma_B)$$

Figure 6B:
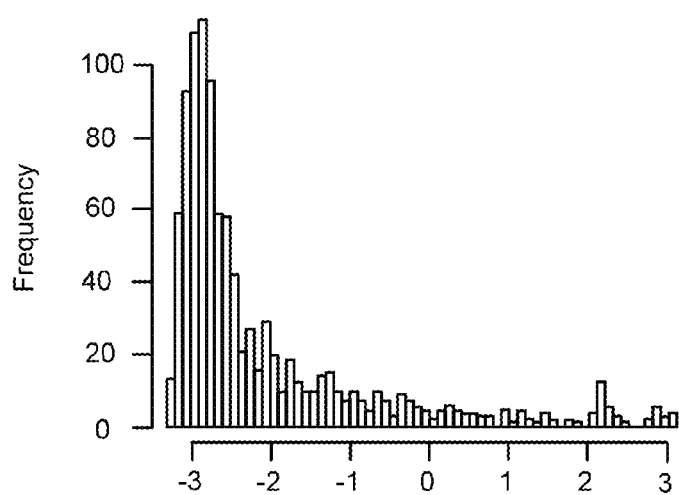
FIG. 6B shows the intensity distribution before background adjustment.
Figure 6C:
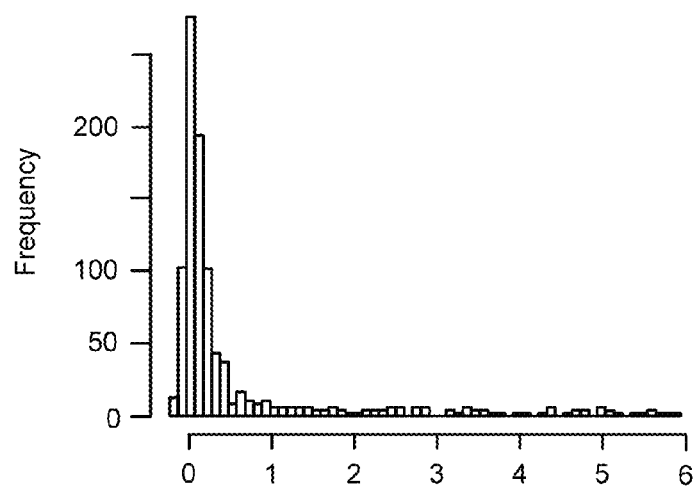
FIG. 6C shows the intensity distribution after background adjustment.
Figure 7A:
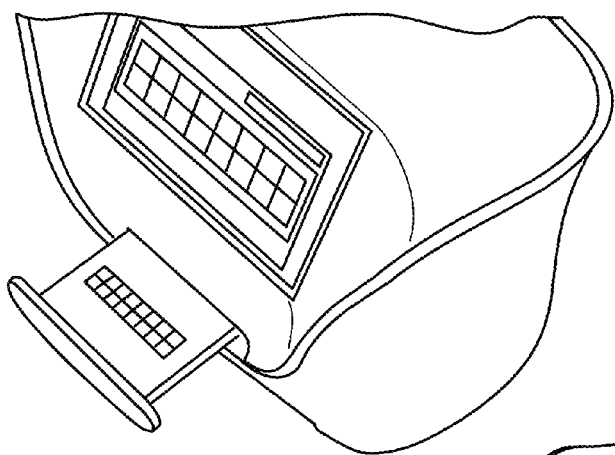
FIGS. 7A-7D show external views of instrument designed for digital counting of features on arrays.
Figure 7B:
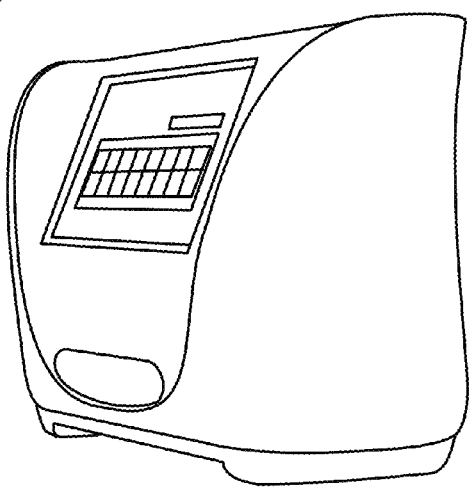
Figure 7C:
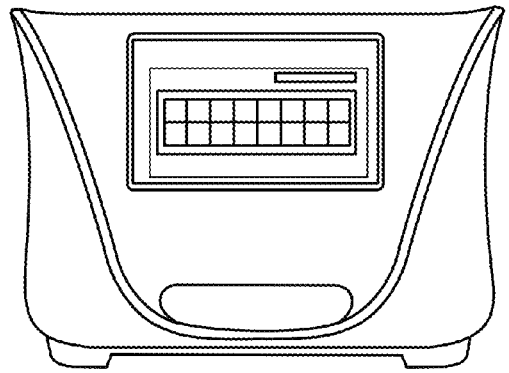
Figure 7D:
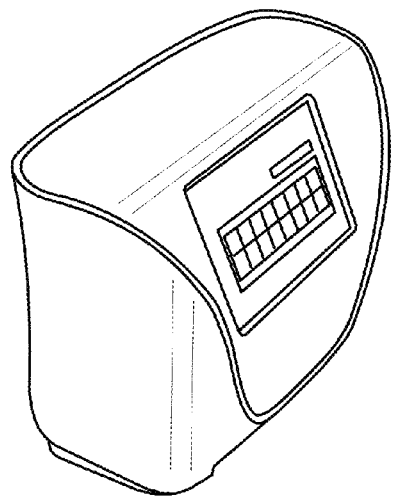
Figure 8:
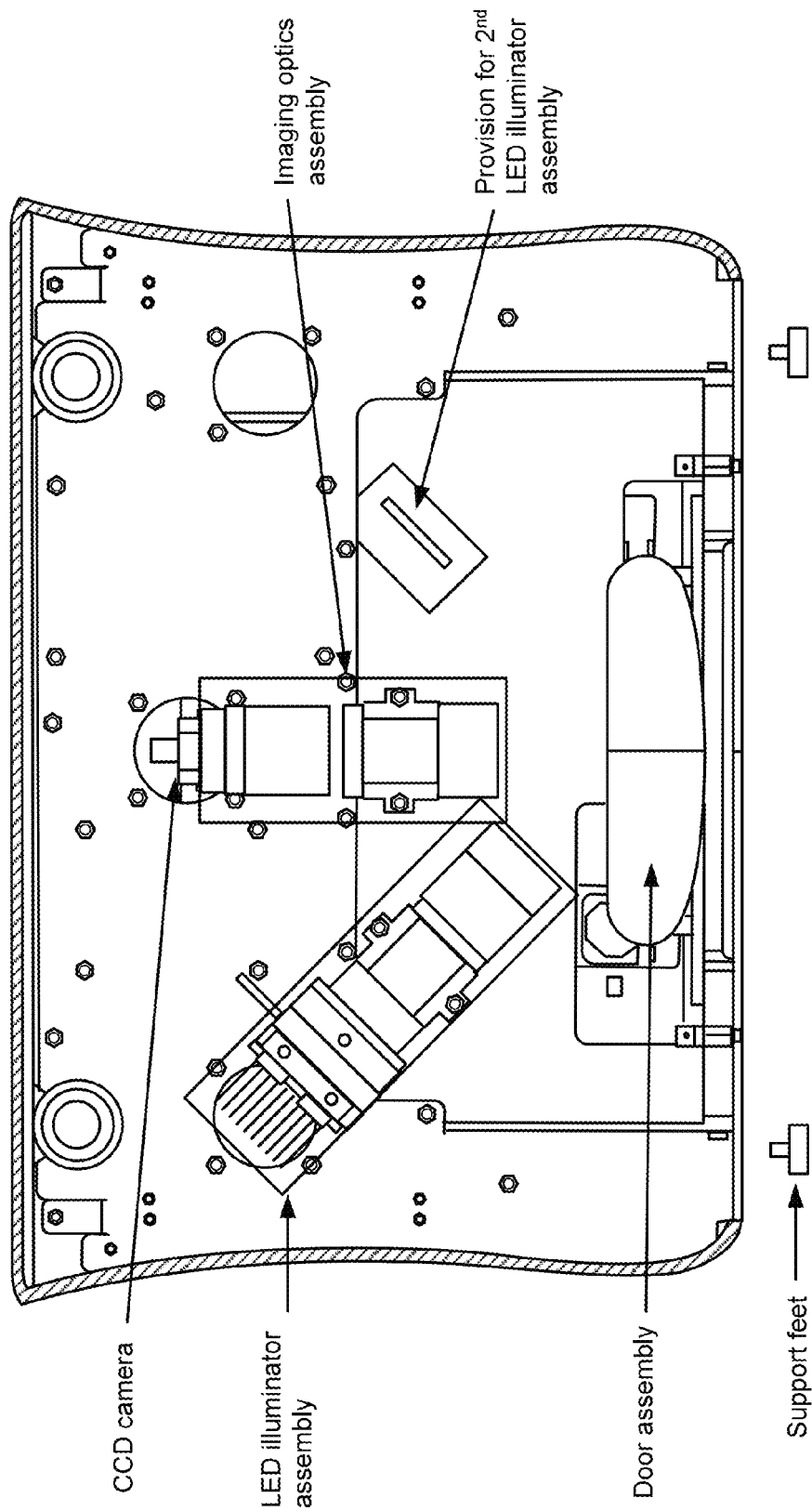
FIG. 8 shows an internal view (front view; 3D CAD model) of an instrument designed for digital counting of features on arrays.
Figure 9:
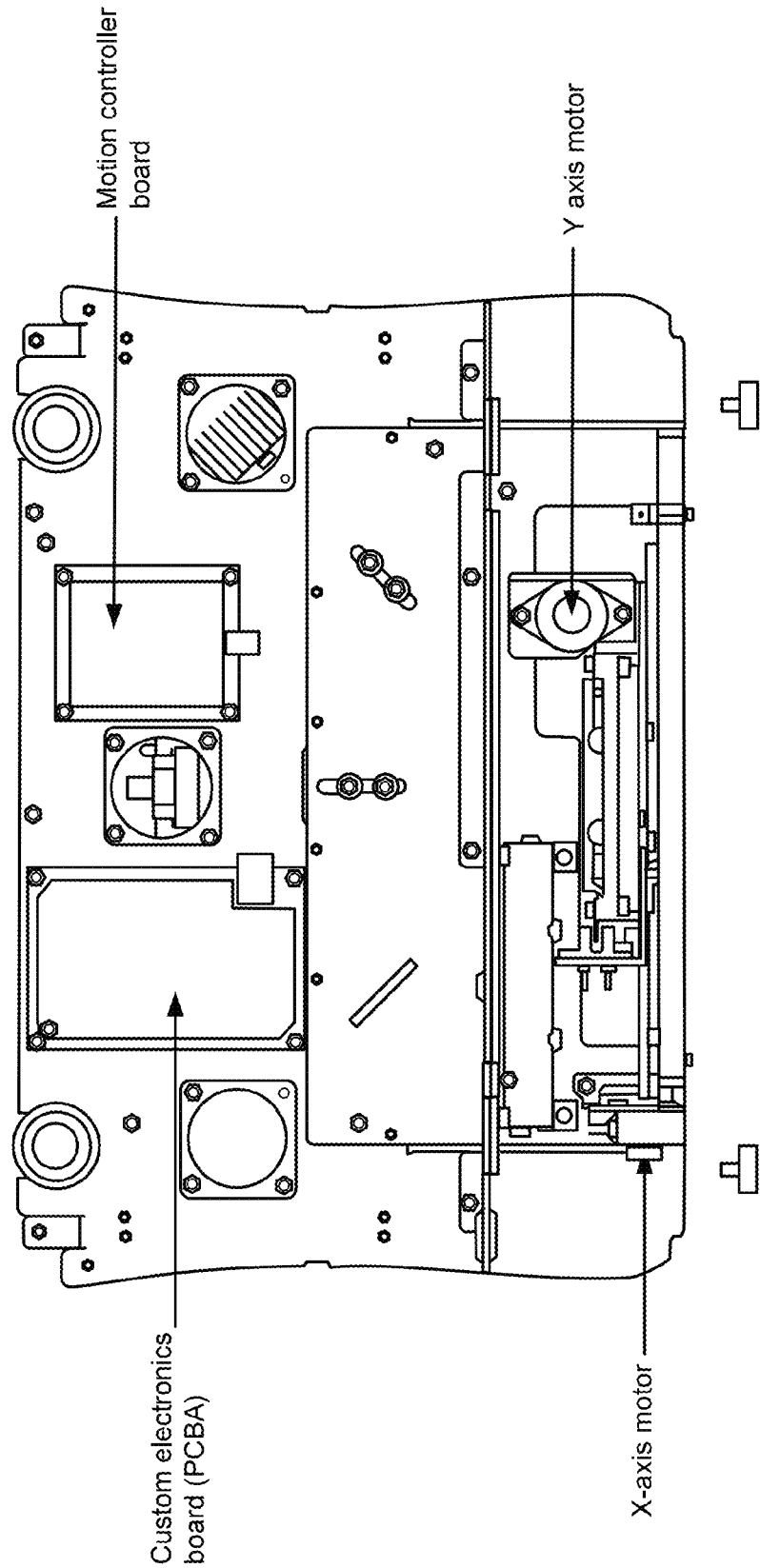
FIG. 9 depicts an internal view (rear view; 3D CAD model) of an instrument designed for digital counting of features on arrays.

FIGS. 6B and 6C show the intensity distributions before and after background adjustment, respectively, demonstrating that background correction enhances the ability of the software to correctly evaluate the presence of the labeled features on the array.

Example 9

Alternative Background Correction

The purpose of this experiment was an alternative way to adjust background. We defined an analysis window centered on a spot. The software then calculated the median spot intensity $\tilde{S}$ and median local background intensity $\tilde{B}$. Then, the software calculated the log 2 background subtracted intensity statistic for each spot:

$$I = \log_2(16\tilde{S}) - \log_2(16\tilde{B}).$$

Example 10

Pixel 16 Cartridge and Custom Microarray

This example illustrated one embodiment of an array for use with the disclosed methods, systems, and platforms in performing stochastic labeling experiment.

Figure 15:
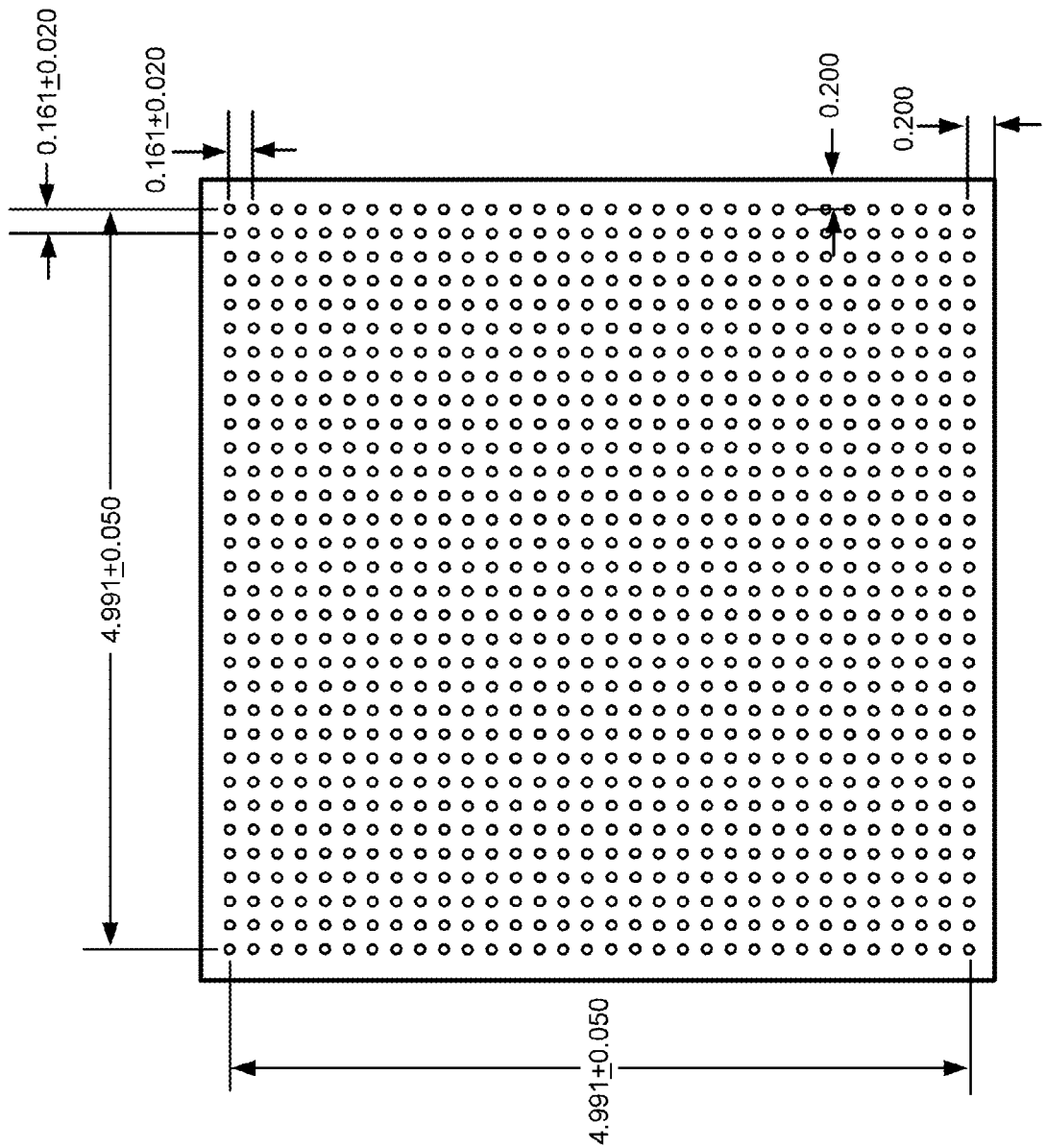
FIG. 15 shows the layout of features on one embodiment of an array. Nominal dimensions are shown (in millimeters).
Figure 16:
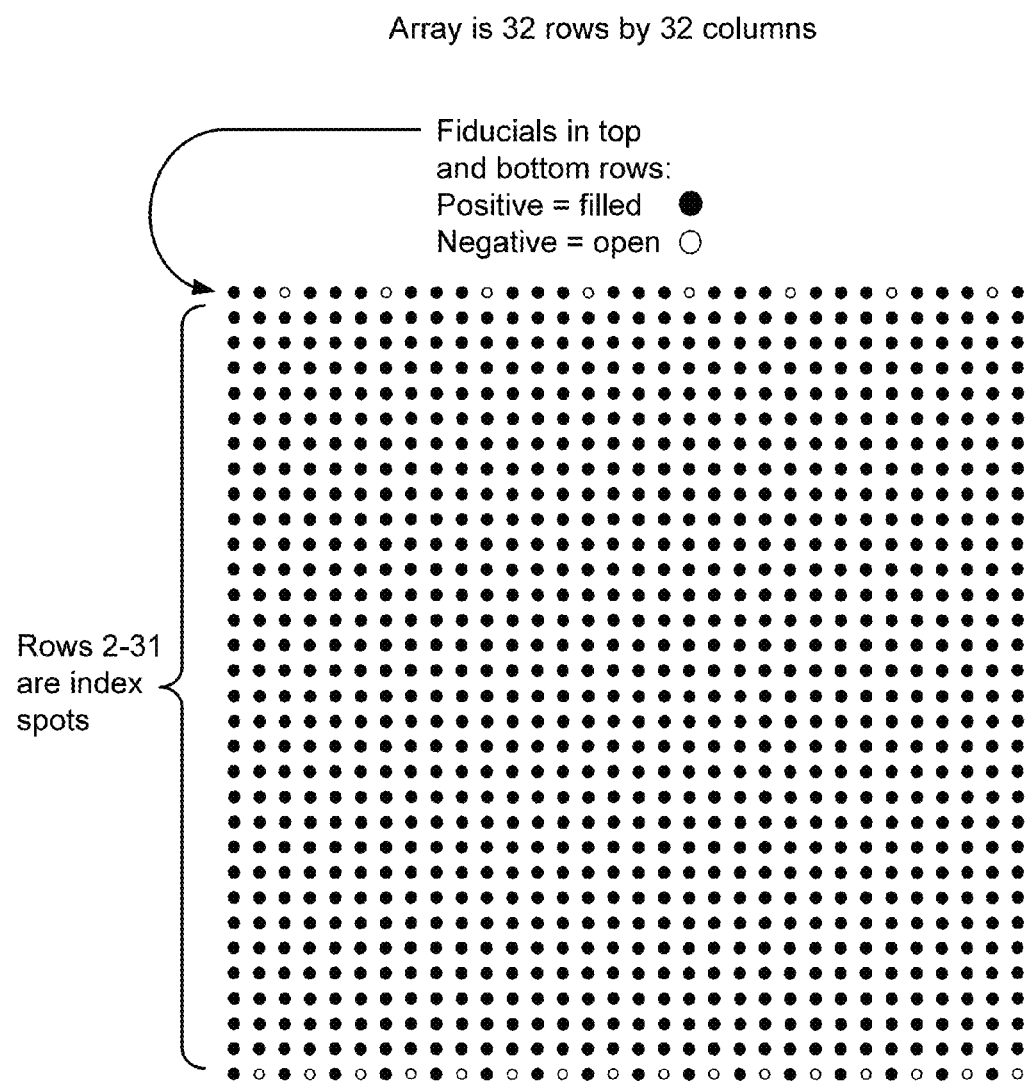
FIG. 16 shows the layout of an array designed for digital counting of target molecules in a sample, including the positions of positive controls (fiducials), negative controls, and index spots.
Figure 17A:
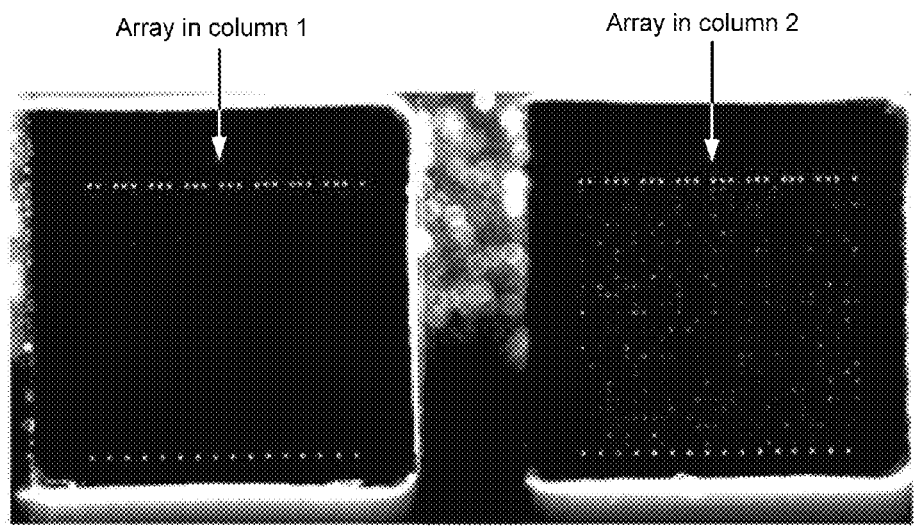
FIG. 17A shows an example of an array image after transformation to the reference orientation.
Figure 17B:
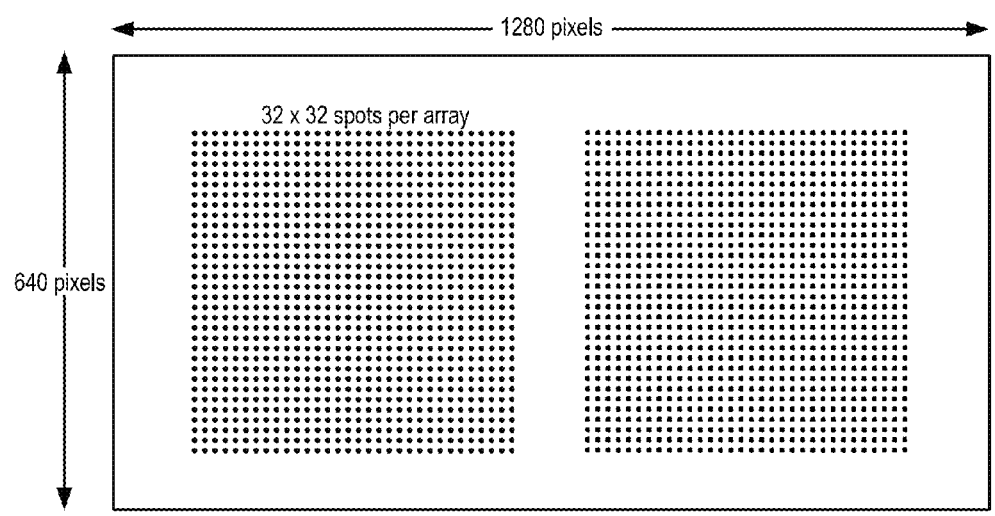
FIG. 17B shows the image size (in pixels) and a schematic of feature positions for the two-array image.
Figure 18A:
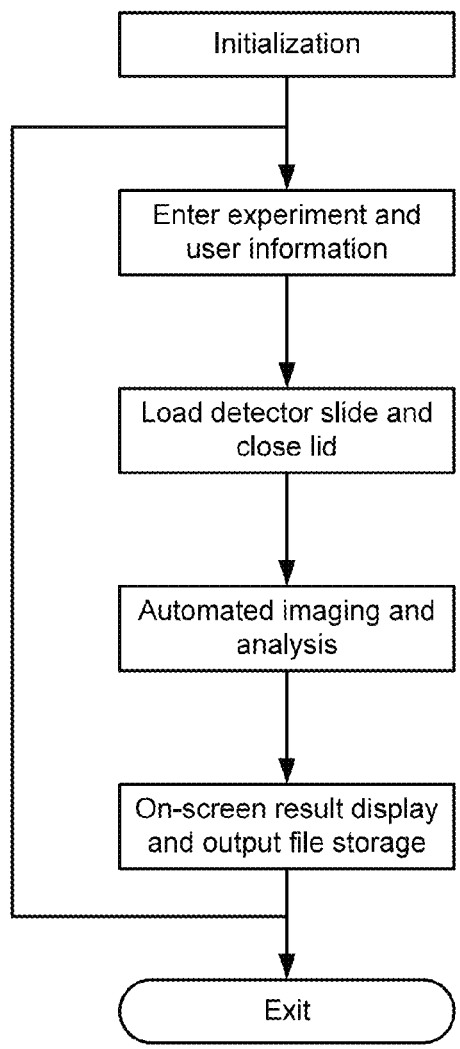
FIGS. 18A-B depict software workflows for performing an experiment on an instrument designed for digital counting of features on arrays.
Figure 18B:
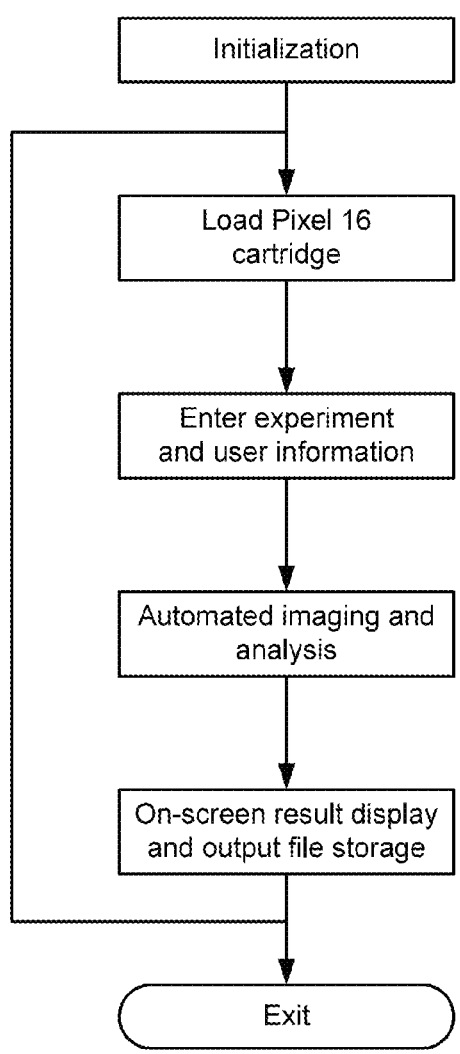

The Pixel 16 cartridge consists of (i) an epoxysilane functionalized glass slide serving as an array substrate, (ii) 16 copies of the custom microarray described in FIGS. 14-16, printed on the functionalized surface of the slide, and (iii) a polymer well frame affixed to the printed side of the slide which serves to define 16 wells which are fluidically separate and in register with the array pattern. The well frame is affixed to the slide following array printing using a die-cut double-sided adhesive.

Custom DNA microarray layout. The microarray pattern consists of a 32×32 array of spots as shown in FIGS. 15 and 16. Fiducial spots in the top and bottom rows permit location of the array in the scanned images. Also, the fiducial spots are arranged in an asymmetric pattern whose orientation is readily identifiable: the top row has a distinctive pattern whose ends are distinct, and the bottom row is different from the top row. This permits easy manual and automatic identification of incorrect placement of the Pixel 16, and also facilitates detection of imaging problems. The remaining 960 spots are each associated with one of the unique probe sequences listed in Table 1.

Oligonucleotide sequences and solution components. Oligonucleotide solutions are provided for preparation of printing solutions in 96-well microplates. Concentration as supplied is 100 µM in H2O. Dilution prior to printing is performed using the Tecan GenMate. Dilution is 880 µL of stock oligo+1320 µL of buffer. The dilution buffer used is 250 mM sodium phosphate with 0.00833% sarcosyl. Buffer is filtered using a 0.2 µm filter. Three sets of plates are prepared in each probe preparation operation. Tips are discarded after each source plate. The final dispensed solution is 40 µM DNA in 150 mM sodium phosphate with 0.005% sarcosyl. The fiducial oligo is supplied at 500 µM in H2O. The fiducial oligonucleotide sequence is: 5'-/5AmMC6/TCC TGA ACG GTA GCATCT TGA CGA C-3' (SEQ ID NO: 1), 25 bases, 5' Amino Modifier C6, standard desalting; supplied at 500 µM in H$_2$O. The fiducial is diluted by mixing 176 µL of fiducial, 704 µL of water, and 1320 µL of buffer. The final fiducial mixture is 40 µM in 150 mM sodium phosphate with 0.005% sarcosyl.

Table of oligonucleotide sequences. The oligonucleotide sequences for the 960 probe sequences (i.e. the sequences that are complementary to the set of stochastic labeling sequences used in molecular counting experiments) are listed in Table 1.

TABLE 1

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P1 | 85652789A01 | | AJ_1 | /5AmMC6/CCC AAA GGG TAC CAG AGC TTA AGG TCA A | 106534039 | 8795 | 61.7 |
| AJ_P1 | 85652790A02 | | AJ_2 | /5AmMC6/CCC AAA GCG TTA AGG TTT CTT GTC ACA A | 106534040 | 8727 | 59.7 |
| AJ_P1 | 85652791A03 | | AJ_3 | /5AmMC6/CCC AAG TCG TAC GAA CTC ACC ACA TGA A | 106534041 | 8675 | 61.8 |
| AJ_P1 | 85652792A04 | | AJ_4 | /5AmMC6/CCC AAA CTT GTT CCC TTG AGA CCA GTA A | 106534042 | 8672 | 60.3 |
| AJ_P1 | 85652793A05 | | AJ_5 | /5AmMC6/CCC AAG ACT TCT ACC CTA GGT TCC AGA A | 106534043 | 8657 | 60.7 |
| AJ_P1 | 85652794A06 | | AJ_6 | /5AmMC6/CCC AAC CAG ACT TGG GTA CGT GAA ACA A | 106534044 | 8755 | 62.3 |
| AJ_P1 | 85652795A07 | | AJ_7 | /5AmMC6/CCC AAC GAC TGG TTC TGA AGT GGA ACA A | 106534045 | 8786 | 62.3 |
| AJ_P1 | 85652796A08 | | AJ_8 | /5AmMC6/CCC AAT TTA GCT TCG TGA GTC AGA CCA A | 106534046 | 8712 | 60.4 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P1 | 85652797A09 | AJ_9 | /5AmMC6/CCC AAC TCG AAG AGT GGT CAG TCT TTA A | 106534047 | 8752 | 59.8 |
| AJ_P1 | 85652798A10 | AJ_10 | /5AmMC6/CCC AAT CGC AAG GAG ACA TAG TCT TTA A | 106534048 | 8745 | 58.4 |
| AJ_P1 | 85652799A11 | AJ_11 | /5AmMC6/CCC AAG TCC TAG TGA GAG CAA CGT TTA A | 106534049 | 8761 | 60 |
| AJ_P1 | 85652800A12 | AJ_12 | /5AmMC6/CCC AAG GAA CCT ACT GTC CTT GTC AGA A | 106534050 | 8697 | 61.4 |
| AJ_P1 | 85652801B01 | AJ_13 | /5AmMC6/CCC AAA CTA GAA GAC GAG TTC GAG TCA A | 106534051 | 8779 | 59.7 |
| AJ_P1 | 85652802B02 | AJ_14 | /5AmMC6/CCC AAG GAC ATA CTC AAC GTA GCT CAA A | 106534052 | 8699 | 60 |
| AJ_P1 | 85652803B03 | AJ_15 | /5AmMC6/CCC AAG GCA TTT GCA ACC TCA CAT GAA A | 106534053 | 8690 | 61.9 |
| AJ_P1 | 85652804B04 | AJ_16 | /5AmMC6/CCC AAG TAC CCA TCC ACT GTC GAG TAA A | 106534054 | 8666 | 61.3 |
| AJ_P1 | 85652805B05 | AJ_17 | /5AmMC6/CCC AAA GCG TTT GTG TAA CAG ACC ATA A | 106534055 | 8745 | 59.4 |
| AJ_P1 | 85652806B06 | AJ_18 | /5AmMC6/CCC AAA TGG TCT GGT TCG ACA GTC ACA A | 106534056 | 8737 | 62.3 |
| AJ_P1 | 85652807B07 | AJ_19 | /5AmMC6/CCC AAG AGG TAC AAC GAC TCT AGG GTA A | 106534057 | 8795 | 60.6 |
| AJ_P1 | 85652808B08 | AJ_20 | /5AmMC6/CCC AAG AAC TTC TAC TTG CTT CGT GAA A | 106534058 | 8687 | 58.9 |
| AJ_P1 | 85652809B09 | AJ_21 | /5AmMC6/CCC AAG CAC TTT CTG TTA ACT AGC TGA A | 106534059 | 8687 | 58.8 |
| AJ_P1 | 85652810B10 | AJ_22 | /5AmMC6/CCC AAG AAC CTC TCT CTA GTG CTA GTA A | 106534060 | 8672 | 58.6 |
| AJ_P1 | 85652811B11 | AJ_23 | /5AmMC6/CCC AAG CCT TTA AGC CTA AAG TCC TGA A | 106534061 | 8681 | 60.4 |
| AJ_P1 | 85652812B12 | AJ_24 | /5AmMC6/CCC AAT CTG GTA GCT CAA CAT CCT TGA A | 106534062 | 8672 | 60.3 |
| AJ_P1 | 85652813C01 | AJ_25 | /5AmMC6/CCC AAA GGA CTC CAT GGA GAA GTG TCA A | 106534063 | 8795 | 61.8 |
| AJ_P1 | 85652814C02 | AJ_26 | /5AmMC6/CCC AAG AAC CCT TTC TGG AAG CTT CCA A | 106534064 | 8657 | 62.4 |
| AJ_P1 | 85652815C03 | AJ_27 | /5AmMC6/CCC AAA TTC GCT TCC TAG TAG TGG ACA A | 106534065 | 8712 | 60.1 |
| AJ_P1 | 85652816C04 | AJ_28 | /5AmMC6/CCC AAC CGT ACG AAG ACC TAG TTT CTA A | 106534066 | 8681 | 59.4 |
| AJ_P1 | 85652817C05 | AJ_29 | /5AmMC6/CCC AAT CAC GAA GAG AGT CAC TGT TTA A | 106534067 | 8745 | 58.4 |
| AJ_P1 | 85652818C06 | AJ_30 | /5AmMC6/CCC AAG AAA CAT AAA CTC GAG TTG CGA A | 106534068 | 8763 | 59.3 |
| AJ_P1 | 85652819C07 | AJ_31 | /5AmMC6/CCC AAC CAG TTA CGT GAG TGT TGC TAA A | 106534069 | 8752 | 60.7 |
| AJ_P1 | 85652820C08 | AJ_32 | /5AmMC6/CCC AAA CTC GTG ACT CCT GTT TCA GAA A | 106534070 | 8672 | 60.5 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P1 | 85652821C09 | AJ_33 | /5AmMC6/CCC AAC GGT TGA AGA GAC TCC TGA AAA A | 106534071 | 8779 | 60.6 |
| AJ_P1 | 85652822C10 | AJ_34 | /5AmMC6/CCC AAA TTG CTC TGG TCA CAT CGA AAA A | 106534072 | 8705 | 59.8 |
| AJ_P1 | 85652823C11 | AJ_35 | /5AmMC6/CCC AAC AGG ACT TGT GCT ACG TGT TAA A | 106534073 | 8752 | 60.7 |
| AJ_P1 | 85652824C12 | AJ_36 | /5AmMC6/CCC AAA TTT CGT GTG TCA ACC ATG CCA A | 106534074 | 8672 | 61.9 |
| AJ_P1 | 85652825D01 | AJ_37 | /5AmMC6/CCC AAC GTG AAG GCT TAA CAA CAT TGA A | 106534075 | 8754 | 59.7 |
| AJ_P1 | 85652826D02 | AJ_38 | /5AmMC6/CCC AAT GAA CAC AAC TAC GAA GCT GTA A | 106534076 | 8723 | 59 |
| AJ_P1 | 85652827D03 | AJ_39 | /5AmMC6/CCC AAA CTT CCG TTG TTA CTA GTC GAA A | 106534077 | 8687 | 58.7 |
| AJ_P1 | 85652828D04 | AJ_40 | /5AmMC6/CCC AAG GAG TAC AAG CTT CCT AGG GTA A | 106534078 | 8786 | 61 |
| AJ_P1 | 85652829D05 | AJ_41 | /5AmMC6/CCC AAG TGC TAA ACT GCT CTT TAC GTA A | 106534079 | 8687 | 58.8 |
| AJ_P1 | 85652830D06 | AJ_42 | /5AmMC6/CCC AAA GAA ACT GCA TCT CCT TTG GAA A | 106534080 | 8705 | 59.5 |
| AJ_P1 | 85652831D07 | AJ_43 | /5AmMC6/CCC AAG GAC TAA GTT CCA CTC ACC TGA A | 106534081 | 8666 | 61.4 |
| AJ_P1 | 85652832D08 | AJ_44 | /5AmMC6/CCC AAA GTT GTC TGG TTC ACT CGA GAA A | 106534082 | 8752 | 60.5 |
| AJ_P1 | 85652833D09 | AJ_45 | /5AmMC6/CCC AAC GTT CTA AGT TTG CTT CGA AGA A | 106534083 | 8727 | 59.2 |
| AJ_P1 | 85652834D10 | AJ_46 | /5AmMC6/CCC AAC TAA AGG TTG TGC ATC CAA GCA A | 106534084 | 8730 | 61.5 |
| AJ_P1 | 85652835D11 | AJ_47 | /5AmMC6/CCC AAA GGC TTC ACG ACA TGT CAT TTA A | 106534085 | 8696 | 59.4 |
| AJ_P1 | 85652836D12 | AJ_48 | /5AmMC6/CCC AAC TGC TAG GTT CCT ACA CAA GTA A | 106534086 | 8681 | 59.7 |
| AJ_P1 | 85652837E01 | AJ_49 | /5AmMC6/CCC AAA TCA GTA GCT ACA CCA CAG GTA A | 106534087 | 8699 | 59.8 |
| AJ_P1 | 85652838E02 | AJ_50 | /5AmMC6/CCC AAG ACT GCA AGC TCA CTA CAT TGA A | 106534088 | 8690 | 60.6 |
| AJ_P1 | 85652839E03 | AJ_51 | /5AmMC6/CCC AAG CTA CTC CTC TAA GAG CAT AGA A | 106534089 | 8690 | 58.9 |
| AJ_P1 | 85652840E04 | AJ_52 | /5AmMC6/CCC AAT GGA ACG CTA AGG TGT AAA CCA A | 106534090 | 8779 | 60.9 |
| AJ_P1 | 85652841E05 | AJ_53 | /5AmMC6/CCC AAG AAA CTA ACC TTG GCT TGC CAA A | 106534091 | 8690 | 61.5 |
| AJ_P1 | 85652842E06 | AJ_54 | /5AmMC6/CCC AAC CAT TAG ACC TTG TGT TGC CAA A | 106534092 | 8672 | 61.3 |
| AJ_P1 | 85652843E07 | AJ_55 | /5AmMC6/CCC AAG GTC TGA CAG TAG GTG TTC CAA A | 106534093 | 8777 | 61.7 |
| AJ_P1 | 85652844E08 | AJ_56 | /5AmMC6/CCC AAT TTC GCA AGC CTT GGT ACA TAA A | 106534094 | 8696 | 59.7 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P1 | 85652845E09 | AJ_57 | /5AmMC6/CCC AAG TTT CTA GCC TAC CAC TAC GGA A | 106534095 | 8657 | 61.2 |
| AJ_P1 | 85652846E10 | AJ_58 | /5AmMC6/CCC AAA TAG ACC TAA CGG AAG CTG TGA A | 106534096 | 8779 | 60.1 |
| AJ_P1 | 85652847E11 | AJ_59 | /5AmMC6/CCC AAG GAG TCA TCC ATG CAT CTT TGA A | 106534097 | 8712 | 60.7 |
| AJ_P1 | 85652848E12 | AJ_60 | /5AmMC6/CCC AAC CGT ACT AGC TTG GGT TAA ACA A | 106534098 | 8721 | 60.5 |
| AJ_P1 | 85652849F01 | AJ_61 | /5AmMC6/CCC AAA AAG GCT AGC CTT CTG ACT TTA A | 106534099 | 8696 | 59 |
| AJ_P1 | 85652850F02 | AJ_62 | /5AmMC6/CCC AAA GAG CTC TGC ACT ACA AGT TTA A | 106534100 | 8705 | 58.8 |
| AJ_P1 | 85652851F03 | AJ_63 | /5AmMC6/CCC AAC AGC TAA CGG TAG TAA AGG TCA A | 106534101 | 8779 | 60 |
| AJ_P1 | 85652852F04 | AJ_64 | /5AmMC6/CCC AAA GCT TTC CGT TTC AAA GTG ACA A | 106534102 | 8696 | 60 |
| AJ_P1 | 85652853F05 | AJ_65 | /5AmMC6/CCC AAG TCC ATG CTT CCA GTG ACA AAA A | 106534103 | 8690 | 61.3 |
| AJ_P1 | 85652854F06 | AJ_66 | /5AmMC6/CCC AAG TAG CTT TGC TCT ACT CGT AAA A | 106534104 | 8687 | 58.4 |
| AJ_P1 | 85652855F07 | AJ_67 | /5AmMC6/CCC AAC TTC GAA CTA AGG AGT AGA GCA A | 106534105 | 8779 | 59.7 |
| AJ_P1 | 85652856F08 | AJ_68 | /5AmMC6/CCC AAT TCA GTC CTA GAG GAG AGA CTA A | 106534106 | 8770 | 58.5 |
| AJ_P1 | 85652857F09 | AJ_69 | /5AmMC6/CCC AAT AGG TCT GTC TTA CCC AAC GTA A | 106534107 | 8672 | 59.6 |
| AJ_P1 | 85652858F10 | AJ_70 | /5AmMC6/CCC AAC GTG AGG AAA GTT CTG CTA ACA A | 106534108 | 8770 | 60.7 |
| AJ_P1 | 85652859F11 | AJ_71 | /5AmMC6/CCC AAG TTG GCA ACT TGC TCT CTA AGA A | 106534109 | 8712 | 60.7 |
| AJ_P1 | 85652860F12 | AJ_72 | /5AmMC6/CCC AAG ACA TCT CTC TCA GAG CTA GAA A | 106534110 | 8690 | 59 |
| AJ_P1 | 85652861G01 | AJ_73 | /5AmMC6/CCC AAT TTC GCA TGT CTC ATC AGG ACA A | 106534111 | 8672 | 60.9 |
| AJ_P1 | 85652862G02 | AJ_74 | /5AmMC6/CCC AAA GCC TTC CTT GGT ACT GAA AGA A | 106534112 | 8721 | 60.6 |
| AJ_P1 | 85652863G03 | AJ_75 | /5AmMC6/CCC AAA CTT GCC TTG CGT ACT GTA AAA A | 106534113 | 8696 | 59.9 |
| AJ_P1 | 85652864G04 | AJ_76 | /5AmMC6/CCC AAC ACT TTG TAC GGT AGA GAC GTA A | 106534114 | 8761 | 59.7 |
| AJ_P1 | 85652865G05 | AJ_77 | /5AmMC6/CCC AAG TTT CCA TCA ACC GAA GCT TGA A | 106534115 | 8681 | 61.2 |
| AJ_P1 | 85652866G06 | AJ_78 | /5AmMC6/CCC AAG CAT TAC CAA ACT GGA ACC TGA A | 106534116 | 8699 | 61 |
| AJ_P1 | 85652867G07 | AJ_79 | /5AmMC6/CCC AAC CGT ACA ACT TGT TCG TTT GAA A | 106534117 | 8687 | 59.7 |
| AJ_P1 | 85652868G08 | AJ_80 | /5AmMC6/CCC AAC AGC TAG TAG CAC ACC ATT TGA A | 106534118 | 8690 | 60.7 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P1 | 85652869G09 | | AJ_81 | /5AmMC6/CCC AAC CTC ACG AAA GCA TCA TTG TGA A | 106534119 | 8690 | 61.2 |
| AJ_P1 | 85652870G10 | | AJ_82 | /5AmMC6/CCC AAA CAA AGT GAG GTC ATC TCG ACA A | 106534120 | 8739 | 60.5 |
| AJ_P1 | 85652871G11 | | AJ_83 | /5AmMC6/CCC AAG AAA CCT TCT TGT AGG ACT CGA A | 106534121 | 8721 | 59.9 |
| AJ_P1 | 85652872G12 | | AJ_84 | /5AmMC6/CCC AAA AGC CTA AGC TCT GTC AGT TTA A | 106534122 | 8696 | 58.9 |
| AJ_P1 | 85652873H01 | | AJ_85 | /5AmMC6/CCC AAA CGT TCC CTT CAT GTC GAA AGA A | 106534123 | 8681 | 60.9 |
| AJ_P1 | 85652874H02 | | AJ_86 | /5AmMC6/CCC AAG TAG CAC TGA CAC CAA GCA TTA A | 106534124 | 8699 | 60.7 |
| AJ_P1 | 85652875H03 | | AJ_87 | /5AmMC6/CCC AAG TTT GAC TCC AAG CCT ACG TCA A | 106534125 | 8657 | 62.2 |
| AJ_P1 | 85652876H04 | | AJ_88 | /5AmMC6/CCC AAA CCG TTG GTG AAG CCT TAA AGA A | 106534126 | 8770 | 61.2 |
| AJ_P1 | 85652877H05 | | AJ_89 | /5AmMC6/CCC AAG CCT ACA CCT TCA GTG AAC AGA A | 106534127 | 8675 | 61.9 |
| AJ_P1 | 85652878H06 | | AJ_90 | /5AmMC6/CCC AAC AGC TCA AGC AGT TAG TAA ACA A | 106534128 | 8723 | 59.2 |
| AJ_P1 | 85652879H07 | | AJ_91 | /5AmMC6/CCC AAT ACG CAA GCA TGT AGG TTT ACA A | 106534129 | 8745 | 59.3 |
| AJ_P1 | 85652880H08 | | AJ_92 | /5AmMC6/CCC AAC ACG AGT CGT TAG TTG TTT CAA A | 106534130 | 8727 | 59.3 |
| AJ_P1 | 85652881H09 | | AJ_93 | /5AmMC6/CCC AAT TCG GAA GAC CTA CTA ACC TGA A | 106534131 | 8690 | 59.6 |
| AJ_P1 | 85652882H10 | | AJ_94 | /5AmMC6/CCC AAA GGT CTC TAC GAA AGG AAC ATA A | 106534132 | 8763 | 58.2 |
| AJ_P1 | 85652883H11 | | AJ_95 | /5AmMC6/CCC AAG TGC TAG ACG TCT GTG TCA AAA A | 106534133 | 8761 | 60.6 |
| AJ_P1 | 85652884H12 | | AJ_96 | /5AmMC6/CCC AAA CCA GTG GAC TTC TCT CCT AGA A | 106534134 | 8657 | 61 |
| AJ_P2 | 85652886A01 | | AJ_97 | /5AmMC6/CCC AAC ATG TAG GAG ACG TAG TTC CCA A | 106534135 | 8746 | 61.3 |
| AJ_P2 | 85652887A02 | | AJ_98 | /5AmMC6/CCC AAG AAC TCT CTG GTT AGG CTT GAA A | 106534136 | 8752 | 60.2 |
| AJ_P2 | 85652888A03 | | AJ_99 | /5AmMC6/CCC AAG GAC ATC CAC ATC GTC TGA CAA A | 106534137 | 8675 | 62.1 |
| AJ_P2 | 85652889A04 | | AJ_100 | /5AmMC6/CCC AAA CTT GTT GGG TTC AGC TAA CAA A | 106534138 | 8736 | 59.8 |
| AJ_P2 | 85652890A05 | | AJ_101 | /5AmMC6/CCC AAC ACG TGT CCT GTC ATG TCA AAA A | 106534139 | 8681 | 61.2 |
| AJ_P2 | 85652891A06 | | AJ_102 | /5AmMC6/CCC AAT CGG AAA CCA ACG TTA GCT TTA A | 106534140 | 8705 | 59.4 |
| AJ_P2 | 85652892A07 | | AJ_103 | /5AmMC6/CCC AAG GAC TTA GGT ACC TGT TCG GAA A | 106534141 | 8777 | 61.4 |
| AJ_P2 | 85652893A08 | | AJ_104 | /5AmMC6/CCC AAG ACT TAA CAA CCT GTG ACG AGA A | 106534142 | 8739 | 60.1 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P2 | 85652894A09 | AJ_105 | /5AmMC6/CCC AAG TTA ACA TGC AGA CGA ACG GTA A | 106534143 | 8779 | 60.7 |
| AJ_P2 | 85652895A10 | AJ_106 | /5AmMC6/CCC AAG CGT ACA ACT CTT GTC AGT TTA A | 106534144 | 8687 | 58.9 |
| AJ_P2 | 85652896A11 | AJ_107 | /5AmMC6/CCC AAG TAA CAC CTT CTG AGC AGT GGA A | 106534145 | 8746 | 61.9 |
| AJ_P2 | 85652897A12 | AJ_108 | /5AmMC6/CCC AAG ACC TAC CTC TCA GGA ACA GTA A | 106534146 | 8675 | 60.7 |
| AJ_P2 | 85652898B01 | AJ_109 | /5AmMC6/CCC AAA CCT GAC CTT AGG AAG AGC ATA A | 106534147 | 8739 | 59.9 |
| AJ_P2 | 85652899B02 | AJ_110 | /5AmMC6/CCC AAC AAA GTT TGT CTC AGT TAG CGA A | 106534148 | 8736 | 59.3 |
| AJ_P2 | 85652900B03 | AJ_111 | /5AmMC6/CCC AAC GGT AGC ATT GTT CCT GTA GAA A | 106534149 | 8752 | 60.5 |
| AJ_P2 | 85652901B04 | AJ_112 | /5AmMC6/CCC AAC TAG GTT TGT TCT AGA CAG CTA A | 106534150 | 8727 | 58 |
| AJ_P2 | 85652902B05 | AJ_113 | /5AmMC6/CCC AAG TCT CTA CGT TCC ATC GAA AGA A | 106534151 | 8681 | 59.8 |
| AJ_P2 | 85652903B06 | AJ_114 | /5AmMC6/CCC AAA CCT TCG TTC TTG AGT ACA GCA A | 106534152 | 8672 | 60.7 |
| AJ_P2 | 85652904B07 | AJ_115 | /5AmMC6/CCC AAG AAC ACT CCT CAT GTG ACT GCA A | 106534153 | 8666 | 62.2 |
| AJ_P2 | 85652905B08 | AJ_116 | /5AmMC6/CCC AAA CGC TTG GTA ACA AAG ACA GTA A | 106534154 | 8763 | 59.3 |
| AJ_P2 | 85652906B09 | AJ_117 | /5AmMC6/CCC AAC CCT AGA GTA GTA CTA CGG TTA A | 106534155 | 8721 | 58.4 |
| AJ_P2 | 85652907B10 | AJ_118 | /5AmMC6/CCC AAC CTG AGG TAG TGA CTG AAA CAA A | 106534156 | 8779 | 60.3 |
| AJ_P2 | 85652908B11 | AJ_119 | /5AmMC6/CCC AAG CTA CGA ACT TGG TTG TTT CAA A | 106534157 | 8727 | 59.7 |
| AJ_P2 | 85652909B12 | AJ_120 | /5AmMC6/CCC AAG CAA GTC CTA GGT TGT GTT CAA A | 106534158 | 8752 | 60.8 |
| AJ_P2 | 85652910C01 | AJ_121 | /5AmMC6/CCC AAC TCC ATG TCA AGG AAG GGT ACA A | 106534159 | 8755 | 61.9 |
| AJ_P2 | 85652911C02 | AJ_122 | /5AmMC6/CCC AAT CCG AAC ACG AAG TAC AAG TTA A | 106534160 | 8723 | 58.7 |
| AJ_P2 | 85652912C03 | AJ_123 | /5AmMC6/CCC AAC ACG TTG ACA TTG TTG GCT TAA A | 106534161 | 8727 | 60.1 |
| AJ_P2 | 85652913C04 | AJ_124 | /5AmMC6/CCC AAC CTC TAG GAA CGT AGT ACA CCA A | 106534162 | 8675 | 60.9 |
| AJ_P2 | 85652914C05 | AJ_125 | /5AmMC6/CCC AAT AGG ACA CCA CAG TTC ATC GAA A | 106534163 | 8699 | 60.3 |
| AJ_P2 | 85652915C06 | AJ_126 | /5AmMC6/CCC AAA TGT CGT TCG GTT AGC TCA AAA A | 106534164 | 8736 | 59.7 |
| AJ_P2 | 85652916C07 | AJ_127 | /5AmMC6/CCC AAA TCG GTT GTG TCT AGC TCA AAA A | 106534165 | 8736 | 59.4 |
| AJ_P2 | 85652917C08 | AJ_128 | /5AmMC6/CCC AAT AAG AAC GAA ACG TAC CTT GCA A | 106534166 | 8723 | 59.3 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P2 | 85652918C09 | AJ_129 | /5AmMC6/CCC AAT CGC AAG AAC CGT TAG TCA AAA A | 106534167 | 8723 | 59.7 |
| AJ_P2 | 85652919C10 | AJ_130 | /5AmMC6/CCC AAG TCA CAC GTC TCC ACA GGT TTA A | 106534168 | 8657 | 61.9 |
| AJ_P2 | 85652920C11 | AJ_131 | /5AmMC6/CCC AAG AGC TTA CAT CGT TCT AGG GTA A | 106534169 | 8752 | 59.4 |
| AJ_P2 | 85652921C12 | AJ_132 | /5AmMC6/CCC AAG ACC TTC TCC TTG ACA GAG GTA A | 106534170 | 8697 | 61 |
| AJ_P2 | 85652922D01 | AJ_133 | /5AmMC6/CCC AAA AGG CTT AGC TCT CTT TAC TGA A | 106534171 | 8687 | 58.6 |
| AJ_P2 | 85652923D02 | AJ_134 | /5AmMC6/CCC AAG TCG TAA CAG AGG TGT CCA CAA A | 106534172 | 8755 | 61.9 |
| AJ_P2 | 85652924D03 | AJ_135 | /5AmMC6/CCC AAA CTA CTG CAA GTG GTA GGT TCA A | 106534173 | 8761 | 60.5 |
| AJ_P2 | 85652925D04 | AJ_136 | /5AmMC6/CCC AAT TTC GGA ACC AGT ACC ATG GGA A | 106534174 | 8746 | 62.3 |
| AJ_P2 | 85652926D05 | AJ_137 | /5AmMC6/CCC AAT CGA GAA GCA ACT TCC TTG TAA A | 106534175 | 8705 | 59.1 |
| AJ_P2 | 85652927D06 | AJ_138 | /5AmMC6/CCC AAT GGA GAC TTC CGT ACT GTT GAA A | 106534176 | 8752 | 60.3 |
| AJ_P2 | 85652928D07 | AJ_139 | /5AmMC6/CCC AAA CAT GCG TTT CGT AGT CTT CAA A | 106534177 | 8687 | 59.6 |
| AJ_P2 | 85652929D08 | AJ_140 | /5AmMC6/CCC AAG AAC CTC AGC TCT TTC GAA AGA A | 106534178 | 8690 | 60.4 |
| AJ_P2 | 85652930D09 | AJ_141 | /5AmMC6/CCC AAG TCC TTA AGC TGT TCG AGA GTA A | 106534179 | 8752 | 59.7 |
| AJ_P2 | 85652931D10 | AJ_142 | /5AmMC6/CCC AAT CTC GAA ACT CTT GTG TGA CCA A | 106534180 | 8672 | 60.5 |
| AJ_P2 | 85652932D11 | AJ_143 | /5AmMC6/CCC AAC CAT TAG AGG AAC TAA GAG CTA A | 106534181 | 8763 | 57.7 |
| AJ_P2 | 85652933D12 | AJ_144 | /5AmMC6/CCC AAC CCT AGA GTG AGT CAG GAA CTA A | 106534182 | 8755 | 60.7 |
| AJ_P2 | 85652934E01 | AJ_145 | /5AmMC6/CCC AAT GAA CCA TAA GAG CAA CGG TTA A | 106534183 | 8763 | 59.1 |
| AJ_P2 | 85652935E02 | AJ_146 | /5AmMC6/CCC AAG AAC CTT CCC TTA GTC GTT GAA A | 106534184 | 8672 | 60.3 |
| AJ_P2 | 85652936E03 | AJ_147 | /5AmMC6/CCC AAG TGG TCA GTA ACC CTT TCC GAA A | 106534185 | 8697 | 62.1 |
| AJ_P2 | 85652937E04 | AJ_148 | /5AmMC6/CCC AAA GCA TGT ACG TCT CCT ACT AGA A | 106534186 | 8681 | 59.3 |
| AJ_P2 | 85652938E05 | AJ_149 | /5AmMC6/CCC AAG GAC TTC ACC TAC GTT CGA ACA A | 106534187 | 8666 | 61.9 |
| AJ_P2 | 85652939E06 | AJ_150 | /5AmMC6/CCC AAC GAA CTT TAC CTT GTC CAT GGA A | 106534188 | 8672 | 60.7 |
| AJ_P2 | 85652940E07 | AJ_151 | /5AmMC6/CCC AAC AGG TTC TTA CGC AAC ACA TGA A | 106534189 | 8690 | 61.1 |
| AJ_P2 | 85652941E08 | AJ_152 | /5AmMC6/CCC AAC TTG TTA GGG TAG CTG ACT CAA A | 106534190 | 8752 | 60.1 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P2 | 85652942E09 | | AJ_153 | /5AmMC6/CCC AAC TGG AGA AGA GAC TAC CTG TTA A | 106534191 | 8770 | 59.2 |
| AJ_P2 | 85652943E10 | | AJ_154 | /5AmMC6/CCC AAC TAA GGT TTG GTC AGT CCT GAA A | 106534192 | 8752 | 60.3 |
| AJ_P2 | 85652944E11 | | AJ_155 | /5AmMC6/CCC AAG CAC ACT AGC CTT TCT GAA AGA A | 106534193 | 8690 | 60.7 |
| AJ_P2 | 85652945E12 | | AJ_156 | /5AmMC6/CCC AAG TCC TGA CGA GAG TTT GGT ACA A | 106534194 | 8777 | 61.6 |
| AJ_P2 | 85652946F01 | | AJ_157 | /5AmMC6/CCC AAT CCC AAG AGT CTC TGG TTG ACA A | 106534195 | 8697 | 61.8 |
| AJ_P2 | 85652947F02 | | AJ_158 | /5AmMC6/CCC AAG GCA TTC AGC ATT CAT TCT TGA A | 106534196 | 8687 | 59.8 |
| AJ_P2 | 85652948F03 | | AJ_159 | /5AmMC6/CCC AAG TTT GAC TAC CAA GCA ACT GCA A | 106534197 | 8690 | 61.3 |
| AJ_P2 | 85652949F04 | | AJ_160 | /5AmMC6/CCC AAC CTT AAG CTA AGT GTG AGA CGA A | 106534198 | 8770 | 60 |
| AJ_P2 | 85652950F05 | | AJ_161 | /5AmMC6/CCC AAC TTA CAG CTA GTT TGA AGT GCA A | 106534199 | 8736 | 59.2 |
| AJ_P2 | 85652951F06 | | AJ_162 | /5AmMC6/CCC AAC TAG TCT CTT AGA GTT TGG CAA A | 106534200 | 8727 | 58.3 |
| AJ_P2 | 85652952F07 | | AJ_163 | /5AmMC6/CCC AAT AAA GCT CTA GGA GAA CAC GTA A | 106534201 | 8763 | 58 |
| AJ_P2 | 85652953F08 | | AJ_164 | /5AmMC6/CCC AAA GCG TAG TAG TGA CTA ACG ACA A | 106534202 | 8779 | 59.8 |
| AJ_P2 | 85652954F09 | | AJ_165 | /5AmMC6/CCC AAG ACG TAA ACG CTT CCT TCT AGA A | 106534203 | 8681 | 59.9 |
| AJ_P2 | 85652955F10 | | AJ_166 | /5AmMC6/CCC AAA GCT GTA GTA CCC TTT CCT AGA A | 106534204 | 8672 | 59.5 |
| AJ_P2 | 85652956F11 | | AJ_167 | /5AmMC6/CCC AAC TCG TAC AGC ATA CCT AGA AGA A | 106534205 | 8699 | 59.3 |
| AJ_P2 | 85652957F12 | | AJ_168 | /5AmMC6/CCC AAT CGC TAC ATA GCA ACT GAA AGA A | 106534206 | 8723 | 58.9 |
| AJ_P2 | 85652958G01 | | AJ_169 | /5AmMC6/CCC AAC TTG GCA ACG TGT GTA GTA CAA A | 106534207 | 8761 | 61 |
| AJ_P2 | 85652959G02 | | AJ_170 | /5AmMC6/CCC AAA CCT GTT ACG CTT GTG CTA AAA A | 106534208 | 8696 | 59.9 |
| AJ_P2 | 85652960G03 | | AJ_171 | /5AmMC6/CCC AAA GCT TGG TTG TAA CTT TAC CGA A | 106534209 | 8727 | 59.4 |
| AJ_P2 | 85652961G04 | | AJ_172 | /5AmMC6/CCC AAG AGA CCT TAG CAA CAA CCT TGA A | 106534210 | 8699 | 60.5 |
| AJ_P2 | 85652962G05 | | AJ_173 | /5AmMC6/CCC AAT ACC GAA GAG TGC TAG GTT TCA A | 106534211 | 8761 | 60.1 |
| AJ_P2 | 85652963G06 | | AJ_174 | /5AmMC6/CCC AAG ACA TAG TAC CGT TGC TAC CCA A | 106534212 | 8666 | 61.6 |
| AJ_P2 | 85652964G07 | | AJ_175 | /5AmMC6/CCC AAG GTC TAG TAA CGA AGC AAC CTA A | 106534213 | 8739 | 59.7 |
| AJ_P2 | 85652965G08 | | AJ_176 | /5AmMC6/CCC AAT AAG CAA CAA AGG TCA TTG CCA A | 106534214 | 8723 | 60.1 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P2 | 85652966G09 | AJ_177 | /5AmMC6/CCC AAC TGA GTG AGA AGT CAG AAC CTA A | 106534215 | 8779 | 59.5 |
| AJ_P2 | 85652967G10 | AJ_178 | /5AmMC6/CCC AAC TTC GAG TGA AAC AAG AAC CTA A | 106534216 | 8723 | 58.8 |
| AJ_P2 | 85652968G11 | AJ_179 | /5AmMC6/CCC AAA GCG TTC ATG GTT CTG TCA TAA A | 106534217 | 8727 | 59.4 |
| AJ_P2 | 85652969G12 | AJ_180 | /5AmMC6/CCC AAG AGG TCT AGG CTT TCG TCT AAA A | 106534218 | 8752 | 59.7 |
| AJ_P2 | 85652970H01 | AJ_181 | /5AmMC6/CCC AAA GCC ATT AGT CGT GTC GTT ACA A | 106534219 | 8712 | 60.7 |
| AJ_P2 | 85652971H02 | AJ_182 | /5AmMC6/CCC AAG GTC TTA CGT AGG TTG AAG CCA A | 106534220 | 8777 | 61.9 |
| AJ_P2 | 85652972H03 | AJ_183 | /5AmMC6/CCC AAG AGC TTA GCG AAC TTA GAA CCA A | 106534221 | 8739 | 60.2 |
| AJ_P2 | 85652973H04 | AJ_184 | /5AmMC6/CCC AAT GGA ACC CTA GGG TTG AGT TCA A | 106534222 | 8777 | 61.9 |
| AJ_P2 | 85652974H05 | AJ_185 | /5AmMC6/CCC AAG AAC ACT TGA GCA GAC GTT TCA A | 106534223 | 8730 | 61 |
| AJ_P2 | 85652975H06 | AJ_186 | /5AmMC6/CCC AAT CGA AGG AAA GCA TGA CTC TAA A | 106534224 | 8763 | 58.8 |
| AJ_P2 | 85652976H07 | AJ_187 | /5AmMC6/CCC AAC TTA GTG AGA GTG CTA CTC AGA A | 106534225 | 8761 | 59.3 |
| AJ_P2 | 85652977H08 | AJ_188 | /5AmMC6/CCC AAA CTT GTT GAA GTG CTT CAC AGA A | 106534226 | 8736 | 59.7 |
| AJ_P2 | 85652978H09 | AJ_189 | /5AmMC6/CCC AAG TGC TAA CAC TGT TCT CCA TGA A | 106534227 | 8672 | 60.5 |
| AJ_P2 | 85652979H10 | AJ_190 | /5AmMC6/CCC AAC CCT TAG ACC TGA ACA TCG TGA A | 106534228 | 8666 | 61.7 |
| AJ_P2 | 85652980H11 | AJ_191 | /5AmMC6/CCC AAC TTA AAG GGT AGA CCT AGT CGA A | 106534229 | 8770 | 59.2 |
| AJ_P2 | 85652981H12 | AJ_192 | /5AmMC6/CCC AAG GCA TAG ACC TGT CGT TCT TAA A | 106534230 | 8712 | 60.1 |
| AJ_P3 | 85652983A01 | AJ_193 | /5AmMC6/CCC AAA GCG TTT CTA GGG TAG TAA CCA A | 106534231 | 8761 | 60.1 |
| AJ_P3 | 85652984A02 | AJ_194 | /5AmMC6/CCC AAG CAA ACT TTC CAA GAC GTT GTA A | 106534232 | 8705 | 59.7 |
| AJ_P3 | 85652985A03 | AJ_195 | /5AmMC6/CCC AAT CTG GTA ACT GCT TTC GAA CCA A | 106534233 | 8672 | 60.8 |
| AJ_P3 | 85652986A04 | AJ_196 | /5AmMC6/CCC AAT CAG GAG AGC AAG TAC TAG TCA A | 106534234 | 8779 | 59.4 |
| AJ_P3 | 85652987A05 | AJ_197 | /5AmMC6/CCC AAA CAT TGT GTC GTT AAC GCT TCA A | 106534235 | 8687 | 59.9 |
| AJ_P3 | 85652988A06 | AJ_198 | /5AmMC6/CCC AAG AGG TAC TTA GGC ATA ACC GTA A | 106534236 | 8770 | 59.5 |
| AJ_P3 | 85652989A07 | AJ_199 | /5AmMC6/CCC AAA AAC GGT TTG GCA AAC TGA CCA A | 106534237 | 8739 | 62.2 |
| AJ_P3 | 85652990A08 | AJ_200 | /5AmMC6/CCC AAC ATA AGG CAA GGG TAC TGT CCA A | 106534238 | 8755 | 62.1 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P3 | 85652991A09 | | AJ_201 | /5AmMC6/CCC AAA TGA CGA CAG GAG TAG TGT CCA A | 106534239 | 8795 | 61.6 |
| AJ_P3 | 85652992A10 | | AJ_202 | /5AmMC6/CCC AAG ACC TTT GCG TTT ACA GGA CTA A | 106534240 | 8712 | 60.4 |
| AJ_P3 | 85652993A11 | | AJ_203 | /5AmMC6/CCC AAG TCT AGA GTC AAC ACA GCA CTA A | 106534241 | 8699 | 59.6 |
| AJ_P3 | 85652994A12 | | AJ_204 | /5AmMC6/CCC AAG AGA GCT TAA CCA GAC TGT CCA A | 106534242 | 8715 | 61.5 |
| AJ_P3 | 85652995B01 | | AJ_205 | /5AmMC6/CCC AAG ACC ATA CTG CAC ATT AGG CTA A | 106534243 | 8690 | 60.1 |
| AJ_P3 | 85652996B02 | | AJ_206 | /5AmMC6/CCC AAG CCA ACT ACG TCA TAG TGG TCA A | 106534244 | 8706 | 61.8 |
| AJ_P3 | 85652997B03 | | AJ_207 | /5AmMC6/CCC AAT GTC GAA CGT ACC AAG ACC ATA A | 106534245 | 8699 | 60.2 |
| AJ_P3 | 85652998B04 | | AJ_208 | /5AmMC6/CCC AAC GTG TAG GAA GTT CGT ACT CAA A | 106534246 | 8761 | 60 |
| AJ_P3 | 85652999B05 | | AJ_209 | /5AmMC6/CCC AAA AAC CGT AAG CCT TCA TGG TGA A | 106534247 | 8730 | 61.3 |
| AJ_P3 | 85653000B06 | | AJ_210 | /5AmMC6/CCC AAT CGG AAA CGC AAG TTC ATG TTA A | 106534248 | 8745 | 59.7 |
| AJ_P3 | 85653001B07 | | AJ_211 | /5AmMC6/CCC AAT CGG TAA CTA GAA AGC ACA GTA A | 106534249 | 8763 | 58.3 |
| AJ_P3 | 85653002B08 | | AJ_212 | /5AmMC6/CCC AAG TCG AAG TAG GCT AAA GTC CAA A | 106534250 | 8779 | 60.1 |
| AJ_P3 | 85653003B09 | | AJ_213 | /5AmMC6/CCC AAA CGG TAG TAC CTT GTC GTC ATA A | 106534251 | 8712 | 59.8 |
| AJ_P3 | 85653004B10 | | AJ_214 | /5AmMC6/CCC AAC ATT TGG AAG TTG CAT CCT GTA A | 106534252 | 8727 | 59.6 |
| AJ_P3 | 85653005B11 | | AJ_215 | /5AmMC6/CCC AAC GAA GTG TTG GTC AAG TCC ACA A | 106534253 | 8746 | 62.6 |
| AJ_P3 | 85653006B12 | | AJ_216 | /5AmMC6/CCC AAT CAA GGA AAG GAC TAG TTC GCA A | 106534254 | 8779 | 60.5 |
| AJ_P3 | 85653007C01 | | AJ_217 | /5AmMC6/CCC AAC GAA ACT TAC AAC GTA GGA CTA A | 106534255 | 8723 | 58.3 |
| AJ_P3 | 85653008C02 | | AJ_218 | /5AmMC6/CCC AAG GCA TGC TTA GTC TGA ACT TTA A | 106534256 | 8727 | 59 |
| AJ_P3 | 85653009C03 | | AJ_219 | /5AmMC6/CCC AAG AAC CGT TCC CAT GTA GCT TTA A | 106534257 | 8672 | 60.5 |
| AJ_P3 | 85653010C04 | | AJ_220 | /5AmMC6/CCC AAG GCA TAA AGT GTT CTC TCG AAA A | 106534258 | 8745 | 59.1 |
| AJ_P3 | 85653011C05 | | AJ_221 | /5AmMC6/CCC AAG GCT ACC CTT AAA GAG GAC ATA A | 106534259 | 8739 | 59.6 |
| AJ_P3 | 85653012C06 | | AJ_222 | /5AmMC6/CCC AAG TCC TAG ACT TCG GTT CGT AAA A | 106534260 | 8712 | 59.8 |
| AJ_P3 | 85653013C07 | | AJ_223 | /5AmMC6/CCC AAG GAA CCT TGT ACA ACA CGA CTA A | 106534261 | 8699 | 60.2 |
| AJ_P3 | 85653014C08 | | AJ_224 | /5AmMC6/CCC AAC ACG TTG TAG AGA CAG AGA CTA A | 106534262 | 8779 | 59.3 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P3 | 85653015C09 | AJ_225 | /5AmMC6/CCC AAT CCA AGC ACA AGG TAG GTT TCA A | 106534263 | 8730 | 61 |
| AJ_P3 | 85653016C10 | AJ_226 | /5AmMC6/CCC AAA GCC ATA CTA GTT GTT GTC GAA A | 106534264 | 8736 | 59 |
| AJ_P3 | 85653017C11 | AJ_227 | /5AmMC6/CCC AAC GAG TAC CAT AGT GAA GGA CTA A | 106534265 | 8779 | 59.2 |
| AJ_P3 | 85653018C12 | AJ_228 | /5AmMC6/CCC AAC ATT TGC CAA GGG TAG AGA CTA A | 106534266 | 8770 | 60.3 |
| AJ_P3 | 85653019D01 | AJ_229 | /5AmMC6/CCC AAC GAC TGT TTC CGT AAA GCT TTA A | 106534267 | 8687 | 59.3 |
| AJ_P3 | 85653020D02 | AJ_230 | /5AmMC6/CCC AAG GAG TAC GAG ACA TCA AGC TTA A | 106534268 | 8779 | 59.7 |
| AJ_P3 | 85653021D03 | AJ_231 | /5AmMC6/CCC AAT GGA CTG TCT GGA GTA ACG TCA A | 106534269 | 8777 | 61.6 |
| AJ_P3 | 85653022D04 | AJ_232 | /5AmMC6/CCC AAA CCG TTA CAG GTT TAG TGT CGA A | 106534270 | 8752 | 60.5 |
| AJ_P3 | 85653023D05 | AJ_233 | /5AmMC6/CCC AAT GAC AAA GAG TAC GAA CTG CTA A | 106534271 | 8763 | 58.6 |
| AJ_P3 | 85653024D06 | AJ_234 | /5AmMC6/CCC AAT CAC AAG TGA CAA AGT ACG CTA A | 106534272 | 8723 | 59 |
| AJ_P3 | 85653025D07 | AJ_235 | /5AmMC6/CCC AAC TGT AAA GAG TTG CTA GCT CTA A | 106534273 | 8736 | 58.1 |
| AJ_P3 | 85653026D08 | AJ_236 | /5AmMC6/CCC AAT GGG AAC ACT GTG AAG TCG ACA A | 106534274 | 8795 | 62.3 |
| AJ_P3 | 85653027D09 | AJ_237 | /5AmMC6/CCC AAA TTG CGT TTG GTC AAC TGG ACA A | 106534275 | 8752 | 61.9 |
| AJ_P3 | 85653028D10 | AJ_238 | /5AmMC6/CCC AAC GAA GGT TCA GGT TAG TCC ACA A | 106534276 | 8746 | 62 |
| AJ_P3 | 85653029D11 | AJ_239 | /5AmMC6/CCC AAA TGC TGT GTT AAC CTT TAG CCA A | 106534277 | 8687 | 59.7 |
| AJ_P3 | 85653030D12 | AJ_240 | /5AmMC6/CCC AAC CAC TTG TAG TAC TAG GTT CGA A | 106534278 | 8712 | 59.5 |
| AJ_P3 | 85653031E01 | AJ_241 | /5AmMC6/CCC AAC CCA TAG AGG TTT CAC GTT GTA A | 106534279 | 8712 | 60.3 |
| AJ_P3 | 85653032E02 | AJ_242 | /5AmMC6/CCC AAC TAG GAA AGA GTT CAA CGC ATA A | 106534280 | 8763 | 58.7 |
| AJ_P3 | 85653033E03 | AJ_243 | /5AmMC6/CCC AAT CCG AAG AAA GGT CTA CAG GTA A | 106534281 | 8779 | 59.6 |
| AJ_P3 | 85653034E04 | AJ_244 | /5AmMC6/CCC AAT GGA AAC CCT TAA GAA CTG CTA A | 106534282 | 8714 | 58.9 |
| AJ_P3 | 85653035E05 | AJ_245 | /5AmMC6/CCC AAG CAA CAT AAC CTT GAC TCA GGA A | 106534283 | 8699 | 60.5 |
| AJ_P3 | 85653036E06 | AJ_246 | /5AmMC6/CCC AAT AGA ACC ACA GAC TTT AGC AGA A | 106534284 | 8723 | 58.4 |
| AJ_P3 | 85653037E07 | AJ_247 | /5AmMC6/CCC AAT CAC AAG AGG TTC GTA CGA AAA A | 106534285 | 8763 | 59.1 |
| AJ_P3 | 85653038E08 | AJ_248 | /5AmMC6/CCC AAA GCT TTG TCT CCA GTA CGA AAA A | 106534286 | 8705 | 59.3 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P3 | 85653039E09 | AJ_249 | /5AmMC6/CCC AAT CGG AAG GTG TTC AGT AAA CCA A | 106534287 | 8770 | 60.7 |
| AJ_P3 | 85653040E10 | AJ_250 | /5AmMC6/CCC AAA GTG CAT TCC AAG AAA CGA CTA A | 106534288 | 8723 | 59.4 |
| AJ_P3 | 85653041E11 | AJ_251 | /5AmMC6/CCC AAG ACG TAA CCA TCG AAC TCG TTA A | 106534289 | 8690 | 60.1 |
| AJ_P3 | 85653042E12 | AJ_252 | /5AmMC6/CCC AAC CGT AGA ACG TTC TTT GCT AAA | 106534290 | 8687 | 59.3 |
| AJ_P3 | 85653043F01 | AJ_253 | /5AmMC6/CCC AAG AGC TCA AGG GTT CTA GAA CCA A | 106534291 | 8755 | 61.6 |
| AJ_P3 | 85653044F02 | AJ_254 | /5AmMC6/CCC AAT CGG TAG TTA CGA GTA AAG CCA A | 106534292 | 8770 | 60 |
| AJ_P3 | 85653045F03 | AJ_255 | /5AmMC6/CCC AAG ACA ACT AGC TCT TGG ACT CCA A | 106534293 | 8666 | 61.5 |
| AJ_P3 | 85653046F04 | AJ_256 | /5AmMC6/CCC AAT GAC GAA GGA CAC TTA GAC CTA A | 106534294 | 8739 | 59.5 |
| AJ_P3 | 85653047F05 | AJ_257 | /5AmMC6/CCC AAC CGT AGA ACA TTT GAA GCC ATA A | 106534295 | 8714 | 59.1 |
| AJ_P3 | 85653048F06 | AJ_258 | /5AmMC6/CCC AAC CAC TCG AAC ATG GTA ACG TCA A | 106534296 | 8675 | 62.2 |
| AJ_P3 | 85653049F07 | AJ_259 | /5AmMC6/CCC AAT CGA ACC GTA ACC ATT TCA GGA A | 106534297 | 8690 | 60.7 |
| AJ_P3 | 85653050F08 | AJ_260 | /5AmMC6/CCC AAC TAG TGG TTG GAA CAT GCA CTA A | 106534298 | 8761 | 60.5 |
| AJ_P3 | 85653051F09 | AJ_261 | /5AmMC6/CCC AAG TGC TTA CTG TCC ATC GGA AAA A | 106534299 | 8721 | 60.8 |
| AJ_P3 | 85653052F10 | AJ_262 | /5AmMC6/CCC AAT GAG TCT GCA TCT CTT TCA AGA A | 106534300 | 8687 | 58.8 |
| AJ_P3 | 85653053F11 | AJ_263 | /5AmMC6/CCC AAT AGG ACA AAG ACG TCT TAC CGA A | 106534301 | 8739 | 59.8 |
| AJ_P3 | 85653054F12 | AJ_264 | /5AmMC6/CCC AAT CAT AGG CTA AGG GAA GAC CTA A | 106534302 | 8779 | 59.3 |
| AJ_P3 | 85653055G01 | AJ_265 | /5AmMC6/CCC AAC AGA GGT AAA GTC CAG TGG TCA A | 106534303 | 8795 | 61.7 |
| AJ_P3 | 85653056G02 | AJ_266 | /5AmMC6/CCC AAG ACC ACT ACA ACG TTG CAT GTA A | 106534304 | 8690 | 60.7 |
| AJ_P3 | 85653057G03 | AJ_267 | /5AmMC6/CCC AAT AGA CCA CAA GCA TCG TTA GGA A | 106534305 | 8739 | 60.2 |
| AJ_P3 | 85653058G04 | AJ_268 | /5AmMC6/CCC AAG TCA CTC ACC TAA GTT CGG TAA A | 106534306 | 8681 | 59.8 |
| AJ_P3 | 85653059G05 | AJ_269 | /5AmMC6/CCC AAG CTT TCA AGT ACC ACA CGA GTA A | 106534307 | 8690 | 60.3 |
| AJ_P3 | 85653060G06 | AJ_270 | /5AmMC6/CCC AAG TCA CAT CCT CTA GGG TTC GAA A | 106534308 | 8697 | 61.4 |
| AJ_P3 | 85653061G07 | AJ_271 | /5AmMC6/CCC AAA AAC GTT CAT TTG GTC TGA CGA A | 106534309 | 8736 | 59.8 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P3 | 85653062G08 | AJ_272 | /5AmMC6/CCC AAC TGT CCA TTC GGA ACG TGA AAA A | 106534310 | 8730 | 61.2 |
| AJ_P3 | 85653063G09 | AJ_273 | /5AmMC6/CCC AAA GTT CTT TCT TCA GCA AGG GTA A | 106534311 | 8727 | 59.1 |
| AJ_P3 | 85653064G10 | AJ_274 | /5AmMC6/CCC AAT AGT CCT GTC GTT AGA ACC GTA A | 106534312 | 8712 | 59.5 |
| AJ_P3 | 85653065G11 | AJ_275 | /5AmMC6/CCC AAC GTA CAT CCC TTA GAA ACG TGA A | 106534313 | 8690 | 60.2 |
| AJ_P3 | 85653066G12 | AJ_276 | /5AmMC6/CCC AAC GGT TCA GCA CTT TAC ATT TGA A | 106534314 | 8687 | 59.7 |
| AJ_P3 | 85653067H01 | AJ_277 | /5AmMC6/CCC AAT GCG TAA ACT CGT TGT CCT ACA A | 106534315 | 8672 | 60.7 |
| AJ_P3 | 85653068H02 | AJ_278 | /5AmMC6/CCC AAT CGG TAA ACC TGT TTC GCT TAA A | 106534316 | 8687 | 59.4 |
| AJ_P3 | 85653069H03 | AJ_279 | /5AmMC6/CCC AAG TGC AAG CAC AGG TGA CAT TTA A | 106534317 | 8770 | 61.4 |
| AJ_P3 | 85653070H04 | AJ_280 | /5AmMC6/CCC AAG GGT ACA GAC GAG TAA CTC TGA A | 106534318 | 8795 | 60.9 |
| AJ_P3 | 85653071H05 | AJ_281 | /5AmMC6/CCC AAA CCC TAG TAG TTC TAC TCG TGA A | 106534319 | 8672 | 59.1 |
| AJ_P3 | 85653072H06 | AJ_282 | /5AmMC6/CCC AAG TAA CCC TTC CGT AGG ACA GTA A | 106534320 | 8706 | 61 |
| AJ_P3 | 85653073H07 | AJ_283 | /5AmMC6/CCC AAT TTA GTC ACT CTG GTC AAC CGA A | 106534321 | 8672 | 60.3 |
| AJ_P3 | 85653074H08 | AJ_284 | /5AmMC6/CCC AAG TAC ACA ACC TCT GGT AAC GGA A | 106534322 | 8715 | 61.6 |
| AJ_P3 | 85653075H09 | AJ_285 | /5AmMC6/CCC AAC ACA AGT TCA GGT AGG AGT GCA A | 106534323 | 8795 | 62.2 |
| AJ_P3 | 85653076H10 | AJ_286 | /5AmMC6/CCC AAC TAA AGG TGT TTA CGC TTC CAA A | 106534324 | 8696 | 59.4 |
| AJ_P3 | 85653077H11 | AJ_287 | /5AmMC6/CCC AAC TGA AGT TGG TCT ACC TGA GGA A | 106534325 | 8777 | 61.4 |
| AJ_P3 | 85653078H12 | AJ_288 | /5AmMC6/CCC AAT GTC GTA AGT TCC TCA ACT GCA A | 106534326 | 8672 | 60.8 |
| AJ_P4 | 85653080A01 | AJ_289 | /5AmMC6/CCC AAA CCT GAG ACC TGT GTT TCG TAA A | 106534327 | 8712 | 60.5 |
| AJ_P4 | 85653081A02 | AJ_290 | /5AmMC6/CCC AAT AGG CTA GCT CAA CCA TAA AGA A | 106534328 | 8723 | 58.4 |
| AJ_P4 | 85653082A03 | AJ_291 | /5AmMC6/CCC AAG TTG ACA ACG CTA CCC TAG ACA A | 106534329 | 8675 | 61.8 |
| AJ_P4 | 85653083A04 | AJ_292 | /5AmMC6/CCC AAT CAC GAA GTG AGC TTG TCA AAA A | 106534330 | 8754 | 59.7 |
| AJ_P4 | 85653084A05 | AJ_293 | /5AmMC6/CCC AAT GAA ACC GTA ACT CAC TTG GCA A | 106534331 | 8690 | 61.2 |
| AJ_P4 | 85653085A06 | AJ_294 | /5AmMC6/CCC AAC TTA GCA CAA AGT GTA GAA GCA A | 106534332 | 8763 | 59.2 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P4 | 85653086A07 | AJ_295 | /5AmMC6/CCC AAT GCG TAG AAC CAT GTA CAA AGA A | 106534333 | 8763 | 59.1 |
| AJ_P4 | 85653087A08 | AJ_296 | /5AmMC6/CCC AAG AGT TGC TTC GGT ACT CAA AGA A | 106534334 | 8761 | 60.4 |
| AJ_P4 | 85653088A09 | AJ_297 | /5AmMC6/CCC AAG CGT AGT TCG GAA ACA CTA AGA A | 106534335 | 8779 | 60.3 |
| AJ_P4 | 85653089A10 | AJ_298 | /5AmMC6/CCC AAA AGA GTC TTA CCG TAC TAC CGA A | 106534336 | 8690 | 59.4 |
| AJ_P4 | 85653090A11 | AJ_299 | /5AmMC6/CCC AAA AAC GGT AGG TCT CTG ACT CCA A | 106534337 | 8706 | 61.7 |
| AJ_P4 | 85653091A12 | AJ_300 | /5AmMC6/CCC AAG GTC AGT TAA GCC AAC CCT TGA A | 106534338 | 8706 | 62.4 |
| AJ_P4 | 85653092B01 | AJ_301 | /5AmMC6/CCC AAA CCA GTC TCT CAG TTT ACG TGA A | 106534339 | 8672 | 60.1 |
| AJ_P4 | 85653093B02 | AJ_302 | /5AmMC6/CCC AAT AAG ACA AGG ACT TCC ATG CCA A | 106534340 | 8699 | 60.7 |
| AJ_P4 | 85653094B03 | AJ_303 | /5AmMC6/CCC AAG TCG AGA ACA TGG AAG TCC TTA A | 106534341 | 8770 | 59.9 |
| AJ_P4 | 85653095B04 | AJ_304 | /5AmMC6/CCC AAT GCA GAG AAA GTA CAT ACC GTA A | 106534342 | 8763 | 58.4 |
| AJ_P4 | 85653096B05 | AJ_305 | /5AmMC6/CCC AAG TGC ACT TAA GGA CAA CAG GTA A | 106534343 | 8779 | 60.5 |
| AJ_P4 | 85653097B06 | AJ_306 | /5AmMC6/CCC AAA CCT GTC TTA AGG CAT ACG GTA A | 106534344 | 8721 | 60.2 |
| AJ_P4 | 85653098B07 | AJ_307 | /5AmMC6/CCC AAG TCT CTA AGT AGG CAT GCT GTA A | 106534345 | 8752 | 59.6 |
| AJ_P4 | 85653099B08 | AJ_308 | /5AmMC6/CCC AAC GTC TGA CAT TGG AGA GAA CTA A | 106534346 | 8770 | 59.8 |
| AJ_P4 | 85653100B09 | AJ_309 | /5AmMC6/CCC AAA AAG CTC ACG TCT TGG TCT TAA A | 106534347 | 8696 | 59.3 |
| AJ_P4 | 85653101B10 | AJ_310 | /5AmMC6/CCC AAG GGT AAC AGA CAC TTT AGC GTA A | 106534348 | 8770 | 60 |
| AJ_P4 | 85653102B11 | AJ_311 | /5AmMC6/CCC AAT GAC CTA CGA GTG GAG AGT ACA A | 106534349 | 8795 | 60.9 |
| AJ_P4 | 85653103B12 | AJ_312 | /5AmMC6/CCC AAA GCT TGC GAA ACC TAA CTA AGA A | 106534350 | 8723 | 59.2 |
| AJ_P4 | 85653104C01 | AJ_313 | /5AmMC6/CCC AAT GTC GAC AGA CCA TAC CTA AGA A | 106534351 | 8699 | 59.6 |
| AJ_P4 | 85653105C02 | AJ_314 | /5AmMC6/CCC AAG GTC AAC AAG CCA TAC GTT CCA A | 106534352 | 8675 | 62.6 |
| AJ_P4 | 85653106C03 | AJ_315 | /5AmMC6/CCC AAC TGG TTA CTA CGA ACA GGA GTA A | 106534353 | 8770 | 59.5 |
| AJ_P4 | 85653107C04 | AJ_316 | /5AmMC6/CCC AAT AGA GAC GTT ACT CCT AAC CGA A | 106534354 | 8690 | 59.1 |
| AJ_P4 | 85653108C05 | AJ_317 | /5AmMC6/CCC AAA GAC AGT TGA CAC CTT AGC CTA A | 106534355 | 8690 | 60.1 |
| AJ_P4 | 85653109C06 | AJ_318 | /5AmMC6/CCC AAA TCG AGA GTT ACA CCT TAC CGA A | 106534356 | 8690 | 59.8 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P4 | 85653110C07 | AJ_319 | /5AmMC6/CCC AAA CAG GTT CCC AAG AAC TAG GGA A | 106534357 | 8779 | 60.4 |
| AJ_P4 | 85653111C08 | AJ_320 | /5AmMC6/CCC AAG ACA GGT AGG TCT TGC TAG TCA A | 106534358 | 8777 | 61.2 |
| AJ_P4 | 85653112C09 | AJ_321 | /5AmMC6/CCC AAG GAG TCT CAA CCG TTA ACC AGA A | 106534359 | 8715 | 61.7 |
| AJ_P4 | 85653113C10 | AJ_322 | /5AmMC6/CCC AAG AAA CGT ACG CTT CTC CAT TGA A | 106534360 | 8681 | 60.7 |
| AJ_P4 | 85653114C11 | AJ_323 | /5AmMC6/CCC AAC TTA GGA AGC ACT ACG TAC CCA A | 106534361 | 8675 | 61.5 |
| AJ_P4 | 85653115C12 | AJ_324 | /5AmMC6/CCC AAG TAA GCT ACG TTC CTG TAC CCA A | 106586457 | 8657 | 61.5 |
| AJ_P4 | 85653116D01 | AJ_325 | /5AmMC6/CCC AAC CAA GTA AGT GGA CAC TGG TGA A | 106534363 | 8795 | 62.1 |
| AJ_P4 | 85653117D02 | AJ_326 | /5AmMC6/CCC AAC TGT TTA CAG AGG TCA GCA GTA A | 106534364 | 8761 | 60 |
| AJ_P4 | 85653118D03 | AJ_327 | /5AmMC6/CCC AAC ACG TCT TAA AGC AGA GAA CTA A | 106534365 | 8723 | 58.6 |
| AJ_P4 | 85653119D04 | AJ_328 | /5AmMC6/CCC AAG AGG ACT GTC CTA CTT CCA TGA A | 106534366 | 8697 | 61.1 |
| AJ_P4 | 85653120D05 | AJ_329 | /5AmMC6/CCC AAG AAC ATC TCC ACT GGT CAC GTA A | 106534367 | 8666 | 61.6 |
| AJ_P4 | 85653121D06 | AJ_330 | /5AmMC6/CCC AAT GAA GCA ACA AGT GGT ACT CCA A | 106534368 | 8739 | 60.9 |
| AJ_P4 | 85653122D07 | AJ_331 | /5AmMC6/CCC AAT CCG TAA CAG TAG GAG AAC GTA A | 106534369 | 8779 | 59.5 |
| AJ_P4 | 85653123D08 | AJ_332 | /5AmMC6/CCC AAA CCG TAG GAA CTA CCA TTC TGA A | 106534370 | 8690 | 60 |
| AJ_P4 | 85653124D09 | AJ_333 | /5AmMC6/CCC AAC CAG TTC GTT CAA ACA GAC TGA A | 106534371 | 8690 | 60.8 |
| AJ_P4 | 85653125D10 | AJ_334 | /5AmMC6/CCC AAG TTA AAC ATC CAG AGC TCA CGA A | 106534372 | 8699 | 60.4 |
| AJ_P4 | 85653126D11 | AJ_335 | /5AmMC6/CCC AAG TCA CAC AAC CTA GAG CTT GGA A | 106534373 | 8715 | 61.9 |
| AJ_P4 | 85653127D12 | AJ_336 | /5AmMC6/CCC AAC ATG TTA GGG TTA CCT TGG CAA A | 106534374 | 8752 | 61 |
| AJ_P4 | 85653128E01 | AJ_337 | /5AmMC6/CCC AAG TCA AAG GTA CTC CAC TTC CGA A | 106534375 | 8666 | 61.7 |
| AJ_P4 | 85653129E02 | AJ_338 | /5AmMC6/CCC AAG TAG AAC GTC AAC CAC TTA CGA A | 106534376 | 8699 | 60 |
| AJ_P4 | 85653130E03 | AJ_339 | /5AmMC6/CCC AAG GAG ACT TGT CCT ACT CTA CGA A | 106534377 | 8697 | 60.5 |
| AJ_P4 | 85653131E04 | AJ_340 | /5AmMC6/CCC AAT TTC GTA GTA CTC ACT TGC GAA A | 106534378 | 8687 | 58.9 |
| AJ_P4 | 85653132E05 | AJ_341 | /5AmMC6/CCC AAC CTT GTA CTA GGA AGG AAG CTA A | 106534379 | 8770 | 59.5 |
| AJ_P4 | 85653133E06 | AJ_342 | /5AmMC6/CCC AAG TCG TAG TTG TCA CAC TGC ACA A | 106534380 | 8697 | 62.3 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P4 | 85653134E07 | AJ_343 | /5AmMC6/CCC AAC GAA GTT ACG TCT TTC ATG CCA A | 106534381 | 8672 | 61 |
| AJ_P4 | 85653135E08 | AJ_344 | /5AmMC6/CCC AAA AGG CAT AAG GCT TGT CAT CCA A | 106534382 | 8730 | 61.3 |
| AJ_P4 | 85653136E09 | AJ_345 | /5AmMC6/CCC AAG TGT CCA TAC GCT TTA CCG AAA A | 106534383 | 8681 | 60.8 |
| AJ_P4 | 85653137E10 | AJ_346 | /5AmMC6/CCC AAC GGT TGA CAC CAG TTA CCA AGA A | 106534384 | 8715 | 62.3 |
| AJ_P4 | 85653138E11 | AJ_347 | /5AmMC6/CCC AAG TGT GCA ACC AGT TAC TCC TGA A | 106534385 | 8697 | 62.2 |
| AJ_P4 | 85653139E12 | AJ_348 | /5AmMC6/CCC AAG CTG ACA GAC TCT CTT TCA TGA A | 106534386 | 8672 | 60.1 |
| AJ_P4 | 85653140F01 | AJ_349 | /5AmMC6/CCC AAG AAA GCT GTA CCC TTC TCT AGA A | 106534387 | 8681 | 59.4 |
| AJ_P4 | 85653141F02 | AJ_350 | /5AmMC6/CCC AAA TGT TGC TAC AAG ACT AAC CGA A | 106534388 | 8714 | 59 |
| AJ_P4 | 85653142F03 | AJ_351 | /5AmMC6/CCC AAG TCT GGA AGT GCT AGT ACG TCA A | 106534389 | 8777 | 61.4 |
| AJ_P4 | 85653143F04 | AJ_352 | /5AmMC6/CCC AAT CGC AAC TTC GGT ACA TTT GTA A | 106534390 | 8687 | 59.4 |
| AJ_P4 | 85653144F05 | AJ_353 | /5AmMC6/CCC AAC CTG TAA CAT TGA AGA AGC GTA A | 106534391 | 8754 | 59 |
| AJ_P4 | 85653145F06 | AJ_354 | /5AmMC6/CCC AAA CTG TTG GAA AGC TGA ACA CTA A | 106534392 | 8754 | 59.4 |
| AJ_P4 | 85653146F07 | AJ_355 | /5AmMC6/CCC AAG ACG TAG CTT AGA GAG AAC CTA A | 106534393 | 8779 | 58.9 |
| AJ_P4 | 85653147F08 | AJ_356 | /5AmMC6/CCC AAC ATT GTT GTG GAA CCT CAG AGA A | 106534394 | 8761 | 60.7 |
| AJ_P4 | 85653148F09 | AJ_357 | /5AmMC6/CCC AAG TGG ACT AGC TTC CTA CAC TGA A | 106534395 | 8697 | 61.2 |
| AJ_P4 | 85653149F10 | AJ_358 | /5AmMC6/CCC AAA GGA ACT GAC ATT CAA CAC GTA A | 106534396 | 8723 | 59.2 |
| AJ_P4 | 85653150F11 | AJ_359 | /5AmMC6/CCC AAT GTT CGA GTC CAC AAC TAC AGA A | 106534397 | 8690 | 60.2 |
| AJ_P4 | 85653151F12 | AJ_360 | /5AmMC6/CCC AAG TAA CTA CTC ACA GAG CTA GGA A | 106534398 | 8739 | 59 |
| AJ_P4 | 85653152G01 | AJ_361 | /5AmMC6/CCC AAG AGG ACT CAC CAG TAC TTT CGA A | 106534399 | 8706 | 61.2 |
| AJ_P4 | 85653153G02 | AJ_362 | /5AmMC6/CCC AAT AGC GTT GTT TCT AAC CAC TGA A | 106534400 | 8687 | 59 |
| AJ_P4 | 85653154G03 | AJ_363 | /5AmMC6/CCC AAC ATT GTT TAG TAG CAG TCA CGA A | 106534401 | 8736 | 59 |
| AJ_P4 | 85653155G04 | AJ_364 | /5AmMC6/CCC AAT AAC AGC AAG ACC TTG TAG CCA A | 106534402 | 8699 | 60.8 |
| AJ_P4 | 85653156G05 | AJ_365 | /5AmMC6/CCC AAG ACT CTC CAC ACG TTG AAG ACA A | 106534403 | 8675 | 61.9 |
| AJ_P4 | 85653157G06 | AJ_366 | /5AmMC6/CCC AAG AAC TCC ATC CTG TTC GAC AGA A | 106534404 | 8666 | 61.7 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P4 | 85653158G07 | AJ_367 | /5AmMC6/CCC AAG GTT CTA GTT CCA ACT AAC GCA A | 106534405 | 8681 | 60.4 |
| AJ_P4 | 85653159G08 | AJ_368 | /5AmMC6/CCC AAA GTT GCG TTT GTC ATA GAC CTA A | 106534406 | 8727 | 59 |
| AJ_P4 | 85653160G09 | AJ_369 | /5AmMC6/CCC AAC GCT TGA GGT AAA CTA AAC AGA A | 106534407 | 8763 | 59 |
| AJ_P4 | 85653161G10 | AJ_370 | /5AmMC6/CCC AAT AAC GAG TAG AGC TCT AGA CCA A | 106534408 | 8739 | 59 |
| AJ_P4 | 85653162G11 | AJ_371 | /5AmMC6/CCC AAG TGA GTC ATA GCC ATA AGC CAA A | 106534409 | 8739 | 60.5 |
| AJ_P4 | 85653163G12 | AJ_372 | /5AmMC6/CCC AAC TTA CGT GAC TTC CAT TCA GGA A | 106534410 | 8672 | 60.3 |
| AJ_P4 | 85653164H01 | AJ_373 | /5AmMC6/CCC AAA TCA GTG ACT GTC TCT TCA CGA A | 106534411 | 8672 | 60.1 |
| AJ_P4 | 85653165H02 | AJ_374 | /5AmMC6/CCC AAA GGT ACT GAC TTC CAC TCC TGA A | 106534412 | 8657 | 61.4 |
| AJ_P4 | 85653166H03 | AJ_375 | /5AmMC6/CCC AAT CGA CAT TAC AGG AAG TAC GGA A | 106534413 | 8779 | 59.9 |
| AJ_P4 | 85653167H04 | AJ_376 | /5AmMC6/CCC AAC CAC TGG TTA AAC GTA AAC GGA A | 106534414 | 8739 | 60.9 |
| AJ_P4 | 85653168H05 | AJ_377 | /5AmMC6/CCC AAG TTC ATT CCC TAA GCC TTG GAA A | 106534415 | 8672 | 60.7 |
| AJ_P4 | 85653169H06 | AJ_378 | /5AmMC6/CCC AAG AAA CTA CTC CAT GGT TAG CGA A | 106534416 | 8730 | 60.1 |
| AJ_P4 | 85653170H07 | AJ_379 | /5AmMC6/CCC AAC TAA GGG TTA AAG CTT ACC GTA A | 106534417 | 8745 | 58.4 |
| AJ_P4 | 85653171H08 | AJ_380 | /5AmMC6/CCC AAG AGA CCT GTC ACA CTT TAA CGA A | 106534418 | 8690 | 60.1 |
| AJ_P4 | 85653172H09 | AJ_381 | /5AmMC6/CCC AAT GAA CAA CAA CAT GCT TAC GGA A | 106534419 | 8723 | 59.8 |
| AJ_P4 | 85653173H10 | AJ_382 | /5AmMC6/CCC AAT CAG AAA GCA ACA TTC TAG GGA A | 106534420 | 8763 | 58.9 |
| AJ_P4 | 85653174H11 | AJ_383 | /5AmMC6/CCC AAT AGG CTT GAC TCA TTA AAC CGA A | 106534421 | 8705 | 58.8 |
| AJ_P4 | 85653175H12 | AJ_384 | /5AmMC6/CCC AAA CTG GTT TGT AGT CCT ACC GAA A | 106534422 | 8712 | 60.3 |
| AJ_P5 | 85653177A01 | AJ_385 | /5AmMC6/CCC AAA CCT GAC AGC TTG TTT CTT AGA A | 106534423 | 8687 | 59 |
| AJ_P5 | 85653178A02 | AJ_386 | /5AmMC6/CCC AAC TTG CTA CAT AGA GAG AGT GCA A | 106534424 | 8770 | 59.9 |
| AJ_P5 | 85653179A03 | AJ_387 | /5AmMC6/CCC AAG GTA AAC CTT CCA GTC TCC AGA A | 106534425 | 8666 | 61.5 |
| AJ_P5 | 85653180A04 | AJ_388 | /5AmMC6/CCC AAT ACC AAG TAC GCA AAC TGT GGA A | 106534426 | 8739 | 60.8 |
| AJ_P5 | 85653181A05 | AJ_389 | /5AmMC6/CCC AAC CGT AAA CCT TAA GGT GTA GCA A | 106534427 | 8730 | 60.5 |
| AJ_P5 | 85653182A06 | AJ_390 | /5AmMC6/CCC AAC ATT GTT TCC CAA GGC ATA GCA A | 106534428 | 8681 | 61.6 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P5 | 85653183A07 | AJ_391 | /5AmMC6/CCC AAG GTC ATC CTA CTA GCA TTG CCA A | 106534429 | 8657 | 61.9 |
| AJ_P5 | 85653184A08 | AJ_392 | /5AmMC6/CCC AAG TTC AAC ATC ACT GCT ACG GTA A | 106534430 | 8681 | 60.4 |
| AJ_P5 | 85653185A09 | AJ_393 | /5AmMC6/CCC AAT TCG CAT GCA TTT AAG GTG TCA A | 106534431 | 8727 | 60.1 |
| AJ_P5 | 85653186A10 | AJ_394 | /5AmMC6/CCC AAC TTA GCA CTA GAG AAG GAG TCA A | 106534432 | 8779 | 59.4 |
| AJ_P5 | 85653187A11 | AJ_395 | /5AmMC6/CCC AAG CTC AGG ACA GTT GAG TGT TCA A | 106534433 | 8777 | 62.2 |
| AJ_P5 | 85653188A12 | AJ_396 | /5AmMC6/CCC AAG TCC TAG CTA AGA GTG TGT CAA A | 106534434 | 8761 | 59.7 |
| AJ_P5 | 85653189B01 | AJ_397 | /5AmMC6/CCC AAG CTA CAA GCA TAA GTG GTT CAA A | 106534435 | 8754 | 59.3 |
| AJ_P5 | 85653190B02 | AJ_398 | /5AmMC6/CCC AAG TCA TAC CAA AGC TGA GAC GTA A | 106534436 | 8739 | 60 |
| AJ_P5 | 85653191B03 | AJ_399 | /5AmMC6/CCC AAT TTA GCA TAG ACG AGA GAC TCA A | 106534437 | 8754 | 58 |
| AJ_P5 | 85653192B04 | AJ_400 | /5AmMC6/CCC AAT TTC ATG TAA CGA CAG TGA GCA A | 106534438 | 8745 | 59.4 |
| AJ_P5 | 85653193B05 | AJ_401 | /5AmMC6/CCC AAT GCA CTT CGT AGA GTA AGA ACA A | 106534439 | 8754 | 58.6 |
| AJ_P5 | 85653194B06 | AJ_402 | /5AmMC6/CCC AAA CGT TGT CTC TGT AGT GGA ACA A | 106534440 | 8752 | 60.5 |
| AJ_P5 | 85653195B07 | AJ_403 | /5AmMC6/CCC AAC CGA AGT TAG CAA ACC TCA TGA A | 106534441 | 8699 | 60.8 |
| AJ_P5 | 85653196B08 | AJ_404 | /5AmMC6/CCC AAC ATT TAG AAG GAC TTC GAA CGA A | 106534442 | 8754 | 58.8 |
| AJ_P5 | 85653197B09 | AJ_405 | /5AmMC6/CCC AAG TTC CAA CAC TCA GAC AGG TCA A | 106534443 | 8675 | 62 |
| AJ_P5 | 85653198B10 | AJ_406 | /5AmMC6/CCC AAT GAC AAC CTC TCA GAG TGG TCA A | 106534444 | 8706 | 61.7 |
| AJ_P5 | 85653199B11 | AJ_407 | /5AmMC6/CCC AAG CCT AGG TAG GTT CTG GAA CTA A | 106534445 | 8777 | 61 |
| AJ_P5 | 85653200B12 | AJ_408 | /5AmMC6/CCC AAT CGA ACA CAC CAT GTT ACT GGA A | 106534446 | 8690 | 60.6 |
| AJ_P5 | 85653201C01 | AJ_409 | /5AmMC6/CCC AAT AGT CTA ACT GTT GGC TTG CAA A | 106534447 | 8727 | 59.3 |
| AJ_P5 | 85653202C02 | AJ_410 | /5AmMC6/CCC AAA AGC TAG GTA CCT TCT TAC CGA A | 106534448 | 8681 | 59.8 |
| AJ_P5 | 85653203C03 | AJ_411 | /5AmMC6/CCC AAC TCA GAG TAC AGA GAG TTT GCA A | 106534449 | 8770 | 60 |
| AJ_P5 | 85653204C04 | AJ_412 | /5AmMC6/CCC AAG ACA CGT CAT AGG AGT GTA GCA A | 106534450 | 8795 | 61.4 |
| AJ_P5 | 85653205C05 | AJ_413 | /5AmMC6/CCC AAT TAA GCA TAA CGA GAC AGT GCA A | 106534451 | 8763 | 59.2 |
| AJ_P5 | 85653206C06 | AJ_414 | /5AmMC6/CCC AAG TGT CCA CAT GAG GTG AAA GCA A | 106534452 | 8795 | 62.6 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P5 | 85653207C07 | AJ_415 | /5AmMC6/CCC AAC TAA AGG GTT GAA CGT TCC AGA A | 106534453 | 8770 | 60.6 |
| AJ_P5 | 85653208C08 | AJ_416 | /5AmMC6/CCC AAA TCG CTT TCT TTA GTG GAG ACA A | 106534454 | 8727 | 59.1 |
| AJ_P5 | 85653209C09 | AJ_417 | /5AmMC6/CCC AAA GGT CTT CAC TTT GTG CAC AAA A | 106534455 | 8696 | 60.1 |
| AJ_P5 | 85653210C10 | AJ_418 | /5AmMC6/CCC AAG GCT TAA GGT GAA CCA TCG ACA A | 106534456 | 8755 | 62.3 |
| AJ_P5 | 85653211C11 | AJ_419 | /5AmMC6/CCC AAC TGT AGA GCT ACC AAC ACT AGA A | 106534457 | 8699 | 59.3 |
| AJ_P5 | 85653212C12 | AJ_420 | /5AmMC6/CCC AAC TAA GGG TTG TTA CGT TAG CCA A | 106534458 | 8752 | 60.5 |
| AJ_P5 | 85653213D01 | AJ_421 | /5AmMC6/CCC AAG TGG TAC TCA GCT ACA TCG TCA A | 106534459 | 8697 | 61.4 |
| AJ_P5 | 85653214D02 | AJ_422 | /5AmMC6/CCC AAG TCC AAA CAC CTT GAG AGC TCA A | 106534460 | 8675 | 62.3 |
| AJ_P5 | 85653215D03 | AJ_423 | /5AmMC6/CCC AAT CAC AAG CTT AGA GTG GAG ACA A | 106534461 | 8779 | 60.1 |
| AJ_P5 | 85653216D04 | AJ_424 | /5AmMC6/CCC AAC TTT GAC TTT GGC AAC TAG GGA A | 106534462 | 8752 | 60.9 |
| AJ_P5 | 85653217D05 | AJ_425 | /5AmMC6/CCC AAC CTC AGT CTA AGG GTA GTG TCA A | 106534463 | 8737 | 61 |
| AJ_P5 | 85653218D06 | AJ_426 | /5AmMC6/CCC AAA CAC CTG TCC AGA GAG TGT ACA A | 106534464 | 8715 | 61.6 |
| AJ_P5 | 85653219D07 | AJ_427 | /5AmMC6/CCC AAC ATA GTT GTG AAG CAT CGC TAA A | 106534465 | 8745 | 59.2 |
| AJ_P5 | 85653220D08 | AJ_428 | /5AmMC6/CCC AAA CGT GTT GTT GTA CCC TAG GAA A | 106534466 | 8752 | 60.6 |
| AJ_P5 | 85653221D09 | AJ_429 | /5AmMC6/CCC AAA CTT TGG TAG AAA CGT AGC CAA A | 106534467 | 8754 | 59.4 |
| AJ_P5 | 85653222D10 | AJ_430 | /5AmMC6/CCC AAC TCA GTT GCA TTA AAG TGT GCA A | 106534468 | 8736 | 59.9 |
| AJ_P5 | 85653223D11 | AJ_431 | /5AmMC6/CCC AAA CTA CTG TTC TGG ACT TCG GAA A | 106534469 | 8712 | 60.2 |
| AJ_P5 | 85653224D12 | AJ_432 | /5AmMC6/CCC AAA GAG CAT TAG GAC TGT ACG ACA A | 106534470 | 8779 | 60 |
| AJ_P5 | 85653225E01 | AJ_433 | /5AmMC6/CCC AAC ACC ATG CTG AGT GGT AAG TCA A | 106534471 | 8746 | 62.3 |
| AJ_P5 | 85653226E02 | AJ_434 | /5AmMC6/CCC AAC TGG AAC ACG TGT GGT AGA ACA A | 106534472 | 8795 | 62.2 |
| AJ_P5 | 85653227E03 | AJ_435 | /5AmMC6/CCC AAC CTC AGA ACT CGT TGG TTA CCA A | 106534473 | 8657 | 62 |
| AJ_P5 | 85653228E04 | AJ_436 | /5AmMC6/CCC AAT GCC ATA ACG CTT GTA CTT GTA A | 106534474 | 8687 | 59.3 |
| AJ_P5 | 85653229E05 | AJ_437 | /5AmMC6/CCC AAA ACC TTG TAG ACA AGA AGC GTA A | 106534475 | 8763 | 59 |
| AJ_P5 | 85653230E06 | AJ_438 | /5AmMC6/CCC AAC ACA TGT TAG AGA CGA CAG GTA A | 106534476 | 8779 | 59.8 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P5 | 85653231E07 | AJ_439 | /5AmMC6/CCC AAG GTA CTC TAA CTT GCA GTC CTA A | 106534477 | 8672 | 59.4 |
| AJ_P5 | 85653232E08 | AJ_440 | /5AmMC6/CCC AAT GCC AAC CTC AAG AAG TGT ACA A | 106534478 | 8699 | 60.9 |
| AJ_P5 | 85653233E09 | AJ_441 | /5AmMC6/CCC AAC TAA AGT TGG GAA CGC ATC ACA A | 106534479 | 8739 | 61.2 |
| AJ_P5 | 85653234E10 | AJ_442 | /5AmMC6/CCC AAG GAC TAC TCC ACT GTC ATC AGA A | 106534480 | 8666 | 61 |
| AJ_P5 | 85653235E11 | AJ_443 | /5AmMC6/CCC AAG AAC CGT AGT TCC TTC CCT AGA A | 106534481 | 8657 | 61 |
| AJ_P5 | 85653236E12 | AJ_444 | /5AmMC6/CCC AAC TTT GAG GTG AGA CTC GTT ACA A | 106534482 | 8752 | 60.1 |
| AJ_P5 | 85653237F01 | AJ_445 | /5AmMC6/CCC AAT CAG AGA AGA GTT CGT CAC ACA A | 106534483 | 8739 | 60.1 |
| AJ_P5 | 85653238F02 | AJ_446 | /5AmMC6/CCC AAG TTT CAT TCC TCA GAG CTG ACA A | 106534484 | 8672 | 60.5 |
| AJ_P5 | 85653239F03 | AJ_447 | /5AmMC6/CCC AAG TTG TCA CTC CTG AGC ACT ACA A | 106534485 | 8657 | 61.8 |
| AJ_P5 | 85653240F04 | AJ_448 | /5AmMC6/CCC AAA AGG TTC ATC GCT TTG ACC ACA A | 106534486 | 8681 | 61.5 |
| AJ_P5 | 85653241F05 | AJ_449 | /5AmMC6/CCC AAT GCC AAG ACT TGT GGT GTT ACA A | 106534487 | 8752 | 61.2 |
| AJ_P5 | 85653242F06 | AJ_450 | /5AmMC6/CCC AAA GGC TTC GGT AAC ACT AAC AGA A | 106534488 | 8739 | 60.4 |
| AJ_P5 | 85653243F07 | AJ_451 | /5AmMC6/CCC AAC AGC TAG CAT GGT TTG GTT ACA A | 106534489 | 8752 | 61.1 |
| AJ_P5 | 85653244F08 | AJ_452 | /5AmMC6/CCC AAG CCA TTA GCC TAG TTG TCC ACA A | 106534490 | 8657 | 62.2 |
| AJ_P5 | 85653245F09 | AJ_453 | /5AmMC6/CCC AAC GGT ACA ACG GTT GGG TTT ACA A | 106534491 | 8777 | 62.7 |
| AJ_P5 | 85653246F10 | AJ_454 | /5AmMC6/CCC AAC ACC AGT TGG ACA GGA CAT TCA A | 106534492 | 8715 | 62.5 |
| AJ_P5 | 85653247F11 | AJ_455 | /5AmMC6/CCC AAT CTC AGA CTG GAA GGG TTG ACA A | 106534493 | 8786 | 61.8 |
| AJ_P5 | 85653248F12 | AJ_456 | /5AmMC6/CCC AAG TGT GAC GAA CCT CAA ACA TGA A | 106534494 | 8739 | 60.9 |
| AJ_P5 | 85653249G01 | AJ_457 | /5AmMC6/CCC AAT GCG TAC AGG TAC ATA GGA CAA A | 106534495 | 8779 | 60.1 |
| AJ_P5 | 85653250G02 | AJ_458 | /5AmMC6/CCC AAC AGT TAA AGG ACA TGA GCT CAA A | 106534496 | 8763 | 59.1 |
| AJ_P5 | 85653251G03 | AJ_459 | /5AmMC6/CCC AAT CCG AAA GGG TTA CAG TTA CGA A | 106534497 | 8770 | 60.3 |
| AJ_P5 | 85653252G04 | AJ_460 | /5AmMC6/CCC AAC ATT GTG AAA GTG CAG TTC CCA A | 106534498 | 8721 | 61.6 |
| AJ_P5 | 85653253G05 | AJ_461 | /5AmMC6/CCC AAA ACC ATG AGG TCA CGT TAC CCA A | 106534499 | 8675 | 62.5 |
| AJ_P5 | 85653254G06 | AJ_462 | /5AmMC6/CCC AAT CAA GGA GAA ACG TGT ACC TCA A | 106534500 | 8739 | 60.3 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P5 | 85653255G07 | AJ_463 | /5AmMC6/CCC AAT CAG GAG ACG ACT AGT AGG TCA A | 106534501 | 8795 | 60.6 |
| AJ_P5 | 85653256G08 | AJ_464 | /5AmMC6/CCC AAG GAC TAG GTC ACA CAT CTC TGA A | 106534502 | 8706 | 61 |
| AJ_P5 | 85653257G09 | AJ_465 | /5AmMC6/CCC AAC ATA GAG AGG ACA TCT TCG ACA A | 106534503 | 8739 | 59.5 |
| AJ_P5 | 85653258G10 | AJ_466 | /5AmMC6/CCC AAC GAA CTC ATC CTT GTG GAC ACA A | 106534504 | 8666 | 62.3 |
| AJ_P5 | 85653259G11 | AJ_467 | /5AmMC6/CCC AAC AGT TGG TGA GTT CAT GCA CAA A | 106534505 | 8761 | 61.5 |
| AJ_P5 | 85653260G12 | AJ_468 | /5AmMC6/CCC AAC ATA GGA CAG GAG TGT TGC ACA A | 106534506 | 8795 | 62.3 |
| AJ_P5 | 85653261H01 | AJ_469 | /5AmMC6/CCC AAC TAG TAG AAG ACT GCA TGG ACA A | 106534507 | 8779 | 59.8 |
| AJ_P5 | 85653262H02 | AJ_470 | /5AmMC6/CCC AAT AGA GCA AGA ACC TCA GTT GGA A | 106534508 | 8779 | 60.2 |
| AJ_P5 | 85653263H03 | AJ_471 | /5AmMC6/CCC AAC CAT GTG GAG TTT CTG AGG ACA A | 106534509 | 8777 | 62.1 |
| AJ_P5 | 85653264H04 | AJ_472 | /5AmMC6/CCC AAT AGA CAG GAC AGG TGT TCC CAA A | 106534510 | 8755 | 61.9 |
| AJ_P5 | 85653265H05 | AJ_473 | /5AmMC6/CCC AAT TCG GAA GCC ATT TCT CTT AGA A | 106534511 | 8687 | 58.8 |
| AJ_P5 | 85653266H06 | AJ_474 | /5AmMC6/CCC AAT CGG AAC AGT TCC TCA TTC TGA A | 106534512 | 8672 | 60.3 |
| AJ_P5 | 85653267H07 | AJ_475 | /5AmMC6/CCC AAT GAA GCA GTT CCA TCA TTC TGA A | 106534513 | 8696 | 59.2 |
| AJ_P5 | 85653268H08 | AJ_476 | /5AmMC6/CCC AAC ATG TGT CAA GGG TAG CTC TCA A | 106534514 | 8737 | 61.9 |
| AJ_P5 | 85653269H09 | AJ_477 | /5AmMC6/CCC AAG CCT TTA CAC CAT GTG GAA CCA A | 106534515 | 8666 | 62.8 |
| AJ_P5 | 85653270H10 | AJ_478 | /5AmMC6/CCC AAC TAA CTG CTG AGG TGA GGT ACA A | 106534516 | 8786 | 61.5 |
| AJ_P5 | 85653271H11 | AJ_479 | /5AmMC6/CCC AAC TCC AAG TCG AGT GAG TTG ACA A | 106534517 | 8746 | 61.9 |
| AJ_P5 | 85653272H12 | AJ_480 | /5AmMC6/CCC AAC GAG TTG AGA AGC TAC ATG ACA A | 106534518 | 8779 | 60.3 |
| AJ_P6 | 85653274A01 | AJ_481 | /5AmMC6/CCC AAT TTC TGA GTG AGC AAC CCT AGA A | 106534519 | 8721 | 60.2 |
| AJ_P6 | 85653275A02 | AJ_482 | /5AmMC6/CCC AAG AGT ACA GCT ACC TCT CCA AGA A | 106534520 | 8675 | 60.8 |
| AJ_P6 | 85653276A03 | AJ_483 | /5AmMC6/CCC AAG AGC ACT CCA CTT GTA CAA AGA A | 106534521 | 8699 | 60.4 |
| AJ_P6 | 85653277A04 | AJ_484 | /5AmMC6/CCC AAG CTA CAT TTC TTG AGT CGA CTA A | 106534522 | 8687 | 58.3 |
| AJ_P6 | 85653278A05 | AJ_485 | /5AmMC6/CCC AAA CCG TAG GAC TAC AAC ACT TGA A | 106534523 | 8699 | 60.2 |
| AJ_P6 | 85653279A06 | AJ_486 | /5AmMC6/CCC AAA TTC CTG TTG TGA CGA AGT CGA A | 106534524 | 8752 | 60.8 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P6 | 85653280A07 | AJ_487 | /5AmMC6/CCC AAA GTT CTG TGG TTC ACA AGT CGA A | 106534525 | 8752 | 60.8 |
| AJ_P6 | 85653281A08 | AJ_488 | /5AmMC6/CCC AAG TAC TCG AGT TCC CTT TAA CGA A | 106534526 | 8672 | 59.8 |
| AJ_P6 | 85653282A09 | AJ_489 | /5AmMC6/CCC AAG CTG AAG GTT AAC AAC AAG CTA A | 106534527 | 8763 | 59.3 |
| AJ_P6 | 85653283A10 | AJ_490 | /5AmMC6/CCC AAT CGC ATG GTA AAC AAA CAC TGA A | 106534528 | 8723 | 59.8 |
| AJ_P6 | 85653284A11 | AJ_491 | /5AmMC6/CCC AAC TGG TAC TAA AGC CAA ACT GCA A | 106534529 | 8699 | 61 |
| AJ_P6 | 85653285A12 | AJ_492 | /5AmMC6/CCC AAC GTT AAG AAG GTA CCT AGC CTA A | 106534530 | 8730 | 59.4 |
| AJ_P6 | 85653286B01 | AJ_493 | /5AmMC6/CCC AAC AGT GAA AGT TGT CCT TCC AGA A | 106534531 | 8721 | 60.6 |
| AJ_P6 | 85653287B02 | AJ_494 | /5AmMC6/CCC AAC AGG AGT TGG GTA CCA GTC TAA A | 106534532 | 8786 | 61.4 |
| AJ_P6 | 85653288B03 | AJ_495 | /5AmMC6/CCC AAG AAA CTG TGC AAA CAC TCC TGA A | 106534533 | 8699 | 61.1 |
| AJ_P6 | 85653289B04 | AJ_496 | /5AmMC6/CCC AAT CGT AGT TCG ACA AAC TCC AGA A | 106534534 | 8690 | 60.1 |
| AJ_P6 | 85653290B05 | AJ_497 | /5AmMC6/CCC AAC AGG TTA GTT CAC ACC ATC CGA A | 106534535 | 8666 | 62.1 |
| AJ_P6 | 85653291B06 | AJ_498 | /5AmMC6/CCC AAG GTT TAC GTC ACT CCA TCC AGA A | 106534536 | 8657 | 61.7 |
| AJ_P6 | 85653292B07 | AJ_499 | /5AmMC6/CCC AAG TTT AAC CTC ATG CTT TAG CGA A | 106534537 | 8687 | 59.3 |
| AJ_P6 | 85653293B08 | AJ_500 | /5AmMC6/CCC AAT TTG TAC GTT CCA ACC TAG GCA A | 106534538 | 8672 | 60.9 |
| AJ_P6 | 85653294B09 | AJ_501 | /5AmMC6/CCC AAA TCG TTT GTT TCC AGT AGG CAA A | 106534539 | 8727 | 59.8 |
| AJ_P6 | 85653295B10 | AJ_502 | /5AmMC6/CCC AAG CAT CCT TGT CTT AAC TGC AGA A | 106586458 | 8672 | 60.7 |
| AJ_P6 | 85653296B11 | AJ_503 | /5AmMC6/CCC AAA CTG GTA AGT CTT GGC TAC CCA A | 106534541 | 8697 | 62 |
| AJ_P6 | 85653297B12 | AJ_504 | /5AmMC6/CCC AAG TCC ATG TGC AAC ACC AAC TGA A | 106534542 | 8675 | 63 |
| AJ_P6 | 85653298C01 | AJ_505 | /5AmMC6/CCC AAG TCA CAG GAC TCC TCA ACA TGA A | 106534543 | 8675 | 61.7 |
| AJ_P6 | 85653299C02 | AJ_506 | /5AmMC6/CCC AAG TAC TCT CAT TCT GTG CAG ACA A | 106577185 | 8672 | 60.1 |
| AJ_P6 | 85653300C03 | AJ_507 | /5AmMC6/CCC AAG GTT CCA CAC TTT GTC ACG ACA A | 106577186 | 8657 | 62.6 |
| AJ_P6 | 85653301C04 | AJ_508 | /5AmMC6/CCC AAA CTC GTC TGT CCA TAA AGT CGA A | 106586459 | 8681 | 60.1 |
| AJ_P6 | 85653302C05 | AJ_509 | /5AmMC6/CCC AAC AAG GTG TGT TCT ACC ATT CGA A | 106577187 | 8712 | 60.6 |
| AJ_P6 | 85653303C06 | AJ_510 | /5AmMC6/CCC AAA CTC GTG TTG TAC TTA GAA CGA A | 106577188 | 8736 | 58.6 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P6 | 85653304C07 | AJ_511 | /5AmMC6/CCC AAA GGC ATT GTC AAC AAA CCA GTA A | 106534549 | 8723 | 59.9 |
| AJ_P6 | 85653305C08 | AJ_512 | /5AmMC6/CCC AAC AGT AGT TGT TAA CGA CTG CTA A | 106577189 | 8736 | 58.5 |
| AJ_P6 | 85653306C09 | AJ_513 | /5AmMC6/CCC AAT GCT CAG GTC AAA CAA ACT AGA A | 106534551 | 8723 | 59.1 |
| AJ_P6 | 85653307C10 | AJ_514 | /5AmMC6/CCC AAT GTC GTA CTT TGA GTA AGC CTA A | 106586460 | 8727 | 58.3 |
| AJ_P6 | 85653308C11 | AJ_515 | /5AmMC6/CCC AAG GCT AGA CGA ACA TTA CCA TGA A | 106534553 | 8739 | 60.2 |
| AJ_P6 | 85653309C12 | AJ_516 | /5AmMC6/CCC AAC GAG TGT TCT AGT GTT ACA CGA A | 106586461 | 8752 | 60 |
| AJ_P6 | 85653310D01 | AJ_517 | /5AmMC6/CCC AAC AGG TTT ACG TGT GTA CAG CTA A | 106534555 | 8752 | 60.3 |
| AJ_P6 | 85653311D02 | AJ_518 | /5AmMC6/CCC AAA GGT TCC TTC CAT GTA AGC TCA A | 106534556 | 8672 | 60.6 |
| AJ_P6 | 85653312D03 | AJ_519 | /5AmMC6/CCC AAA GGC TTT GCT GTT ACT TAG ACA A | 106534557 | 8727 | 59.3 |
| AJ_P6 | 85653313D04 | AJ_520 | /5AmMC6/CCC AAC AAA GTA ACT GTT CGT TGC GAA A | 106534558 | 8745 | 59.9 |
| AJ_P6 | 85653314D05 | AJ_521 | /5AmMC6/CCC AAA TGC TTG GAA CTT CTA ACT CGA A | 106534559 | 8696 | 59.1 |
| AJ_P6 | 85653315D06 | AJ_522 | /5AmMC6/CCC AAC CTG AGT ACT GTG CTC TGA AAA A | 106534560 | 8721 | 60.4 |
| AJ_P6 | 85653316D07 | AJ_523 | /5AmMC6/CCC AAG GAC TCA AGT CTT CCT TCA CGA A | 106534561 | 8657 | 61.6 |
| AJ_P6 | 85653317D08 | AJ_524 | /5AmMC6/CCC AAA GGG TTC CGT TCA CTA ACA TGA A | 106534562 | 8721 | 60.7 |
| AJ_P6 | 85653318D09 | AJ_525 | /5AmMC6/CCC AAC CAG TAC TGC ATT TCT TGG AGA A | 106534563 | 8712 | 60.5 |
| AJ_P6 | 85653319D10 | AJ_526 | /5AmMC6/CCC AAC AAG CCT AGT TCT GGT TGT ACA A | 106534564 | 8712 | 60.5 |
| AJ_P6 | 85653320D11 | AJ_527 | /5AmMC6/CCC AAC AGA CCT ACC TTT GTT GTA GCA A | 106534565 | 8672 | 60.5 |
| AJ_P6 | 85653321D12 | AJ_528 | /5AmMC6/CCC AAG AAC CCT TCT TTG ACT GCA AGA A | 106534566 | 8681 | 60.9 |
| AJ_P6 | 85653322E01 | AJ_529 | /5AmMC6/CCC AAA GTC GTT TAG TCC TCT GAC CAA A | 106534567 | 8672 | 60.2 |
| AJ_P6 | 85653323E02 | AJ_530 | /5AmMC6/CCC AAA GTC TCT TCG TTC AAC TGG AGA A | 106534568 | 8712 | 60.2 |
| AJ_P6 | 85653324E03 | AJ_531 | /5AmMC6/CCC AAC GCA TTC TTA ACA GAG ACA GTA A | 106534569 | 8714 | 58.6 |
| AJ_P6 | 85653325E04 | AJ_532 | /5AmMC6/CCC AAC GAG TCT CTT GAG AGG AAA CTA A | 106534570 | 8770 | 59.4 |
| AJ_P6 | 85653326E05 | AJ_533 | /5AmMC6/CCC AAC GTA GTG AGT AGA CGT ACA CCA A | 106534571 | 8755 | 61 |
| AJ_P6 | 85653327E06 | AJ_534 | /5AmMC6/CCC AAA AAG CTT GTT ACC TTC TGC AGA A | 106534572 | 8696 | 59.6 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P6 | 85653328E07 | AJ_535 | /5AmMC6/CCC AAA CTT TGT ACT GGA GTA GCC AAA A | 106534573 | 8745 | 59.1 |
| AJ_P6 | 85653329E08 | AJ_536 | /5AmMC6/CCC AAG CTT ACC TCT TAA GTG CAA GAA A | 106534574 | 8705 | 58.9 |
| AJ_P6 | 85653330E09 | AJ_537 | /5AmMC6/CCC AAG AAC CTC TTA AAG CTA AGC GAA A | 106534575 | 8723 | 58.9 |
| AJ_P6 | 85653331E10 | AJ_538 | /5AmMC6/CCC AAG ACC TAA ACA AGC TTG AGT CGA A | 106534576 | 8739 | 60.4 |
| AJ_P6 | 85653332E11 | AJ_539 | /5AmMC6/CCC AAT TTG CAT AGG TTC TTC CAA CGA A | 106534577 | 8687 | 59.5 |
| AJ_P6 | 85653333E12 | AJ_540 | /5AmMC6/CCC AAG CAA GTT GCA TTC CTC TCA TGA A | 106534578 | 8672 | 61.1 |
| AJ_P6 | 85653334F01 | AJ_541 | /5AmMC6/CCC AAT CGG TAC ACG ACA TAC ATG AGA A | 106534579 | 8739 | 59.9 |
| AJ_P6 | 85653335F02 | AJ_542 | /5AmMC6/CCC AAA CCT CTG TTT CTG AGT CGA AGA A | 106534580 | 8712 | 60.2 |
| AJ_P6 | 85653336F03 | AJ_543 | /5AmMC6/CCC AAA CAC GTG TTG GCT AGT CTA AAA A | 106534581 | 8745 | 59.3 |
| AJ_P6 | 85653337F04 | AJ_544 | /5AmMC6/CCC AAC GGT TTA AGC CTT TCA CCA TGA A | 106534582 | 8672 | 61.3 |
| AJ_P6 | 85653338F05 | AJ_545 | /5AmMC6/CCC AAC GGT TCA TGG ACT AAC TGA GGA A | 106534583 | 8786 | 61.7 |
| AJ_P6 | 85653339F06 | AJ_546 | /5AmMC6/CCC AAA CCG TTC AGT TTC ACA TGG GAA A | 106534584 | 8721 | 61.4 |
| AJ_P6 | 85653340F07 | AJ_547 | /5AmMC6/CCC AAG ACC TCT CCA CTT GAC TGT AGA A | 106534585 | 8657 | 61 |
| AJ_P6 | 85653341F08 | AJ_548 | /5AmMC6/CCC AAG TCT TTA CCT CAG TGT AGC AGA A | 106534586 | 8712 | 59.7 |
| AJ_P6 | 85653342F09 | AJ_549 | /5AmMC6/CCC AAA CAG CTG AGT CCT TCC ATA AGA A | 106534587 | 8690 | 60.2 |
| AJ_P6 | 85653343F10 | AJ_550 | /5AmMC6/CCC AAA ACT GTC ATT GCC TTC CTA GGA A | 106534588 | 8672 | 60.6 |
| AJ_P6 | 85653344F11 | AJ_551 | /5AmMC6/CCC AAG TCC ATT CAT TCG TTC GAA GGA A | 106534589 | 8712 | 60.6 |
| AJ_P6 | 85653345F12 | AJ_552 | /5AmMC6/CCC AAG TCA CCT CTT GGT AGT AAG GCA A | 106534590 | 8737 | 61.6 |
| AJ_P6 | 85653346G01 | AJ_553 | /5AmMC6/CCC AAC CAT CAG CTT TAG TTG GTG ACA A | 106534591 | 8712 | 60.9 |
| AJ_P6 | 85653347G02 | AJ_554 | /5AmMC6/CCC AAG TTA CCT GAC TCC ACT GGA CAA A | 106534592 | 8666 | 61.7 |
| AJ_P6 | 85653348G03 | AJ_555 | /5AmMC6/CCC AAA GTT GGC ATC TTT GTC GTC AAA A | 106534593 | 8727 | 60.1 |
| AJ_P6 | 85653349G04 | AJ_556 | /5AmMC6/CCC AAA CGT TGT GTC TTT AAC ATC CGA A | 106534594 | 8687 | 59.4 |
| AJ_P6 | 85653350G05 | AJ_557 | /5AmMC6/CCC AAC AGT TTG CTT TTG ACA TCA CGA A | 106534595 | 8712 | 61.5 |
| AJ_P6 | 85653351G06 | AJ_558 | /5AmMC6/CCC AAA CGG TTT GCA ACT CAT TCT TGA A | 106534596 | 8687 | 60.1 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P6 | 85653352G07 | AJ_559 | /5AmMC6/CCC AAG ACG ACT GTT TAC TTC CTC AGA A | | 106534597 | 8672 | 59.8 |
| AJ_P6 | 85653353G08 | AJ_560 | /5AmMC6/CCC AAG GAC TCC ATT TCG ACT TCG ACA A | | 106534598 | 8657 | 61.9 |
| AJ_P6 | 85653354G09 | AJ_561 | /5AmMC6/CCC AAA TCA AGT CTA GAC AGA AGG CTA A | | 106534599 | 8763 | 58 |
| AJ_P6 | 85653355G10 | AJ_562 | /5AmMC6/CCC AAG TCG TCA TCA GCA AGA AAC CTA A | | 106534600 | 8699 | 60.4 |
| AJ_P6 | 85653356G11 | AJ_563 | /5AmMC6/CCC AAT CGT GTA CAT GGA AAG CAC ATA A | | 106534601 | 8754 | 59.1 |
| AJ_P6 | 85653357G12 | AJ_564 | /5AmMC6/CCC AAC TTT GAA GCA TGG AGA ACA CTA A | | 106534602 | 8754 | 59.1 |
| AJ_P6 | 85653358H01 | AJ_565 | /5AmMC6/CCC AAA AGT CCT CTG TTT AGT TAG CGA A | | 106534603 | 8727 | 58.6 |
| AJ_P6 | 85653359H02 | AJ_566 | /5AmMC6/CCC AAG TAA CCA AAC CAT GCT AGT CGA A | | 106534604 | 8699 | 60.5 |
| AJ_P6 | 85653360H03 | AJ_567 | /5AmMC6/CCC AAG GAC ATT GAC TCA CCA TCA GCA A | | 106534605 | 8675 | 62.4 |
| AJ_P6 | 85653361H04 | AJ_568 | /5AmMC6/CCC AAT GGG TAC TGC ATA CAC CAT AGA A | | 106534606 | 8730 | 60 |
| AJ_P6 | 85653362H05 | AJ_569 | /5AmMC6/CCC AAA GAA CTC GTC TTC ATT TAC GGA A | | 106534607 | 8696 | 58.8 |
| AJ_P6 | 85653363H06 | AJ_570 | /5AmMC6/CCC AAA GGT CTT TGT CCT AGT ACG AGA A | | 106534608 | 8752 | 59.5 |
| AJ_P6 | 85653364H07 | AJ_571 | /5AmMC6/CCC AAC ATG GTT AAG GTC AAC TCG AGA A | | 106534609 | 8770 | 60.3 |
| AJ_P6 | 85653365H08 | AJ_572 | /5AmMC6/CCC AAG CTT GTA ACG ACT TAC TCT CGA A | | 106534610 | 8672 | 59.9 |
| AJ_P6 | 85653366H09 | AJ_573 | /5AmMC6/CCC AAG ACC ACT CTC CTA GCA TTT GGA A | | 106534611 | 8657 | 61.7 |
| AJ_P6 | 85653367H10 | AJ_574 | /5AmMC6/CCC AAG TCC ATT CCC ATT GGT AGC AGA A | | 106534612 | 8697 | 62.2 |
| AJ_P6 | 85653368H11 | AJ_575 | /5AmMC6/CCC AAC ACT CTG TGT CGT ACA TAG GGA A | | 106534613 | 8737 | 61.3 |
| AJ_P6 | 85653369H12 | AJ_576 | /5AmMC6/CCC AAA CTT GTG TGG AAA CCG TAC CCA A | | 106534614 | 8706 | 62.8 |
| AJ_P7 | 85653371A01 | AJ_577 | /5AmMC6/CCC AAA TGC CTT GGT GTC ATA CAG GAA A | | 106534711 | 8761 | 61 |
| AJ_P7 | 85653372A02 | AJ_578 | /5AmMC6/CCC AAT CGG AAG TCA GAC TAG AAA CTA A | | 106534712 | 8763 | 57.8 |
| AJ_P7 | 85653373A03 | AJ_579 | /5AmMC6/CCC AAC CAG TAC CAG AGG TGA AGT CTA A | | 106534713 | 8755 | 61 |
| AJ_P7 | 85653374A04 | AJ_580 | /5AmMC6/CCC AAC ATA AAG GGA AAC TGA GCT CTA A | | 106534714 | 8763 | 58.4 |
| AJ_P7 | 85653375A05 | AJ_581 | /5AmMC6/CCC AAC TAA GAG GAG AAC TCC AGT TGA A | | 106534715 | 8779 | 59.6 |
| AJ_P7 | 85653376A06 | AJ_582 | /5AmMC6/CCC AAC TAG GAA GTT TAC TCC ACT CGA A | | 106534716 | 8681 | 59.5 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P7 | 85653377A07 | AJ_583 | /5AmMC6/CCC AAC AAC GTC TGC TAA AGT AGG TCA A | 106534717 | 8730 | 60.3 |
| AJ_P7 | 85653378A08 | AJ_584 | /5AmMC6/CCC AAC GTC ATC AAC ATA GTA GGC TAA A | 106534718 | 8714 | 58.4 |
| AJ_P7 | 85653379A09 | AJ_585 | /5AmMC6/CCC AAA TCG TCA CTA GAG AGA GAA CTA A | 106534719 | 8763 | 57.3 |
| AJ_P7 | 85653380A10 | AJ_586 | /5AmMC6/CCC AAC TTG TCA CAT GAA GGA GAC CTA A | 106534720 | 8730 | 60 |
| AJ_P7 | 85653381A11 | AJ_587 | /5AmMC6/CCC AAG GAG ACT CTA GAA ACT TCC GAA A | 106534721 | 8739 | 59.5 |
| AJ_P7 | 85653382A12 | AJ_588 | /5AmMC6/CCC AAG AGT TAC GCT TCT ACT TCC AGA A | 106534722 | 8672 | 59.7 |
| AJ_P7 | 85653383B01 | AJ_589 | /5AmMC6/CCC AAA CCA GTC CTT AAG GGT AGG TCA A | 106534723 | 8746 | 61.5 |
| AJ_P7 | 85653384B02 | AJ_590 | /5AmMC6/CCC AAA AGC CTA GAA CAT TAC ATC GGA A | 106534724 | 8723 | 58.8 |
| AJ_P7 | 85653385B03 | AJ_591 | /5AmMC6/CCC AAG CTG AAA GCA CTC CAT CAT TGA A | 106534725 | 8690 | 61.1 |
| AJ_P7 | 85653386B04 | AJ_592 | /5AmMC6/CCC AAT CAG TGT GAC TCC ATC CCT AGA A | 106534726 | 8657 | 61.1 |
| AJ_P7 | 85653387B05 | AJ_593 | /5AmMC6/CCC AAG CTA CTT AAC TCT GTT TCG GAA A | 106534727 | 8687 | 58.6 |
| AJ_P7 | 85653388B06 | AJ_594 | /5AmMC6/CCC AAA TGC TTT CAC TGG TCT AGG GAA A | 106534728 | 8752 | 60.6 |
| AJ_P7 | 85653389B07 | AJ_595 | /5AmMC6/CCC AAC AGT TGT TCG TTC ATG ACC AGA A | 106534729 | 8712 | 60.9 |
| AJ_P7 | 85653390B08 | AJ_596 | /5AmMC6/CCC AAT CAC GAA ACG ACT ACT TAG GGA A | 106534730 | 8739 | 59.8 |
| AJ_P7 | 85653391B09 | AJ_597 | /5AmMC6/CCC AAC ATT GTT TGG TTC ATC AAG CGA A | 106534731 | 8727 | 60.1 |
| AJ_P7 | 85653392B10 | AJ_598 | /5AmMC6/CCC AAA TTC TTG TGG TAC AAC ATG CGA A | 106534732 | 8736 | 59.8 |
| AJ_P7 | 85653393B11 | AJ_599 | /5AmMC6/CCC AAC CTG ACC AAC GGT TCA TTT GTA A | 106534733 | 8672 | 61 |
| AJ_P7 | 85653394B12 | AJ_600 | /5AmMC6/CCC AAG ACC ATT ACG TCT TGC CTT GAA A | 106534734 | 8672 | 60.8 |
| AJ_P7 | 85653395C01 | AJ_601 | /5AmMC6/CCC AAG CCA TAC CTC ATT GAG CTT TGA A | 106534735 | 8672 | 60.8 |
| AJ_P7 | 85653396C02 | AJ_602 | /5AmMC6/CCC AAA GGA CTC TTC CGT AAC CTG TCA A | 106534736 | 8657 | 61.7 |
| AJ_P7 | 85653397C03 | AJ_603 | /5AmMC6/CCC AAG GAG TGC ATT TCG TAA CCT GAA A | 106534737 | 8761 | 60.8 |
| AJ_P7 | 85653398C04 | AJ_604 | /5AmMC6/CCC AAT CAC AAG CGA AAG TAG TGT CTA A | 106534738 | 8754 | 58.6 |
| AJ_P7 | 85653399C05 | AJ_605 | /5AmMC6/CCC AAT CGA AGA GAC GAC TTG AGT TCA A | 106534739 | 8770 | 60.1 |
| AJ_P7 | 85653400C06 | AJ_606 | /5AmMC6/CCC AAA TGG CTT TGG TAC AAC TGA CGA A | 106534740 | 8761 | 61.2 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P7 | 85653401C07 | AJ_607 | /5AmMC6/CCC AAG AGA CGT TGG AAC ACC TAC TGA A | 106534741 | 8755 | 61.6 |
| AJ_P7 | 85653402C08 | AJ_608 | /5AmMC6/CCC AAG AAA GCT GTT CAA ACC TCA CGA A | 106534742 | 8699 | 61.1 |
| AJ_P7 | 85653403C09 | AJ_609 | /5AmMC6/CCC AAG TGA GTC TTC GAA ACT TCG GAA A | 106534743 | 8761 | 60.4 |
| AJ_P7 | 85653404C10 | AJ_610 | /5AmMC6/CCC AAC CAG TGT TAA CGG AAC TTG GGA A | 106534744 | 8786 | 62.4 |
| AJ_P7 | 85653405C11 | AJ_611 | /5AmMC6/CCC AAC AGG TGT ACT TGG TAC TAC GGA A | 106534745 | 8777 | 61.3 |
| AJ_P7 | 85653406C12 | AJ_612 | /5AmMC6/CCC AAG TAC CAT CCT TAC GTA GCT TGA A | 106534746 | 8672 | 59.8 |
| AJ_P7 | 85653407D01 | AJ_613 | /5AmMC6/CCC AAG CTA CTT CCA CTA GGT ACA GGA A | 106534747 | 8706 | 60.9 |
| AJ_P7 | 85653408D02 | AJ_614 | /5AmMC6/CCC AAG TAC CTC AAC AAG TCA AGG CTA A | 106534748 | 8699 | 60.1 |
| AJ_P7 | 85653409D03 | AJ_615 | /5AmMC6/CCC AAG TAC CCA AGA GAC TAA GCT TGA A | 106534749 | 8739 | 59.8 |
| AJ_P7 | 85653410D04 | AJ_616 | /5AmMC6/CCC AAT GAA CCA AAC ACT GAC CTG TGA A | 106534750 | 8699 | 61 |
| AJ_P7 | 85653411D05 | AJ_617 | /5AmMC6/CCC AAG TGC ACA TCG AAC CAA CTT AGA A | 106534751 | 8699 | 60.8 |
| AJ_P7 | 85653412D06 | AJ_618 | /5AmMC6/CCC AAT GCT TAG CGT ACT ACC ATT AGA A | 106534752 | 8696 | 58.2 |
| AJ_P7 | 85653413D07 | AJ_619 | /5AmMC6/CCC AAG TTT GAC GTT CAA CCA TCA CGA A | 106534753 | 8681 | 61.2 |
| AJ_P7 | 85653414D08 | AJ_620 | /5AmMC6/CCC AAT TTA GCT TGT CCA CTC AGA GGA A | 106534754 | 8712 | 60.2 |
| AJ_P7 | 85653415D09 | AJ_621 | /5AmMC6/CCC AAC GCT ACT TTC TTA GTT AGA GCA A | 106534755 | 8687 | 58.4 |
| AJ_P7 | 85653416D10 | AJ_622 | /5AmMC6/CCC AAA AGC CTT TCC ACT GTT ACT GGA A | 106534756 | 8672 | 60.9 |
| AJ_P7 | 85653417D11 | AJ_623 | /5AmMC6/CCC AAC CTG TTA CCT CAG ACA TTG GGA A | 106534757 | 8697 | 61.9 |
| AJ_P7 | 85653418D12 | AJ_624 | /5AmMC6/CCC AAC GTC ATT TAG GTC TCT AAG GGA A | 106534758 | 8752 | 59.6 |
| AJ_P7 | 85653419E01 | AJ_625 | /5AmMC6/CCC AAA CGT CTT GGG TTA CAC TAC TGA A | 106534759 | 8712 | 60.2 |
| AJ_P7 | 85653420E02 | AJ_626 | /5AmMC6/CCC AAT CAC AGA ACC AGT CAG CTT TGA A | 106534760 | 8690 | 60.8 |
| AJ_P7 | 85653421E03 | AJ_627 | /5AmMC6/CCC AAG TGG TAC TCT CGT AAC TCC AGA A | 106534761 | 8697 | 60.9 |
| AJ_P7 | 85653422E04 | AJ_628 | /5AmMC6/CCC AAG AAC TCC TAC CAA GAC TCG TGA A | 106534762 | 8675 | 61.2 |
| AJ_P7 | 85653423E05 | AJ_629 | /5AmMC6/CCC AAT TTG ACT TGA ACG CAT AAC CGA A | 106534763 | 8705 | 59.7 |
| AJ_P7 | 85653424E06 | AJ_630 | /5AmMC6/CCC AAT TGA GAC CTC ACG AGA ACA CTA A | 106534764 | 8699 | 59.8 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P7 | 85653425E07 | | AJ_631 | /5AmMC6/CCC AAA CAA AGT CAT TGG GTT CGC TAA A | 106534765 | 8745 | 59.8 |
| AJ_P7 | 85653426E08 | | AJ_632 | /5AmMC6/CCC AAT CGA ACA AAC CTA GAG TGC TCA A | 106534766 | 8699 | 60.4 |
| AJ_P7 | 85653427E09 | | AJ_633 | /5AmMC6/CCC AAG GTC TTA GCT ACA ACC TCA TGA A | 106534767 | 8681 | 59.8 |
| AJ_P7 | 85653428E10 | | AJ_634 | /5AmMC6/CCC AAG CTT TGA AGC CTT CCA ACT AGA A | 106534768 | 8681 | 60.7 |
| AJ_P7 | 85653429E11 | | AJ_635 | /5AmMC6/CCC AAT ACA GGT GTC ACA AAC TCA CGA A | 106534769 | 8699 | 60.5 |
| AJ_P7 | 85653430E12 | | AJ_636 | /5AmMC6/CCC AAC CGT TCA TAA CAA GGG AAC CTA A | 106534770 | 8699 | 60.4 |
| AJ_P7 | 85653431F01 | | AJ_637 | /5AmMC6/CCC AAA GTA CCC AAA GCA TGT CTG GAA A | 106534771 | 8739 | 61 |
| AJ_P7 | 85653432F02 | | AJ_638 | /5AmMC6/CCC AAA TGT TCT CTT TAC GCT AGG GAA A | 106534772 | 8727 | 58.8 |
| AJ_P7 | 85653433F03 | | AJ_639 | /5AmMC6/CCC AAT TTG ACT TCA GAC GAA AGC TGA A | 106534773 | 8745 | 59.3 |
| AJ_P7 | 85653434F04 | | AJ_640 | /5AmMC6/CCC AAT ACA GAA ACG ACA TAC GCT TGA A | 106534774 | 8723 | 59 |
| AJ_P7 | 85653435F05 | | AJ_641 | /5AmMC6/CCC AAT CAC CAG AAG AAC TAC CTG TGA A | 106534775 | 8699 | 60 |
| AJ_P7 | 85653436F06 | | AJ_642 | /5AmMC6/CCC AAT ACG AAC GAC AGG TCA TGG TTA A | 106534776 | 8770 | 60.2 |
| AJ_P7 | 85653437F07 | | AJ_643 | /5AmMC6/CCC AAG AAC TCC AAC CAT GTA GTC GTA A | 106534777 | 8690 | 59.9 |
| AJ_P7 | 85653438F08 | | AJ_644 | /5AmMC6/CCC AAA TTG CGT TCT TCA GTA CAC GAA A | 106534778 | 8696 | 59.6 |
| AJ_P7 | 85653439F09 | | AJ_645 | /5AmMC6/CCC AAA TCT GCT TCC TGT AGT ACA CGA A | 106534779 | 8672 | 60 |
| AJ_P7 | 85653440F10 | | AJ_646 | /5AmMC6/CCC AAG GTC ACT TGC AAC CTA GAA CCA A | 106534780 | 8675 | 62.3 |
| AJ_P7 | 85653441F11 | | AJ_647 | /5AmMC6/CCC AAG GCT TAG TAC GAC AGT AAC CCA A | 106534781 | 8715 | 61.5 |
| AJ_P7 | 85653442F12 | | AJ_648 | /5AmMC6/CCC AAC AAG TGA AGT GGT CTG ACC AGA A | 106534782 | 8795 | 62 |
| AJ_P7 | 85653443G01 | | AJ_649 | /5AmMC6/CCC AAC AGA GTA GTG TGA CTA GCC TAA A | 106534783 | 8770 | 59.3 |
| AJ_P7 | 85653444G02 | | AJ_650 | /5AmMC6/CCC AAT CAC AAG GAG TAG CAA CTT TGA A | 106534784 | 8754 | 59.1 |
| AJ_P7 | 85653445G03 | | AJ_651 | /5AmMC6/CCC AAC CTG TAA GTG AAA CGA CTG GAA A | 106534785 | 8779 | 60.5 |
| AJ_P7 | 85653446G04 | | AJ_652 | /5AmMC6/CCC AAC CCT AGT TGA GGA CAA ACT GGA A | 106534786 | 8755 | 61.8 |
| AJ_P7 | 85653447G05 | | AJ_653 | /5AmMC6/CCC AAG GCA TCA CAC CTA GCA AGT TTA A | 106534787 | 8690 | 60.8 |
| AJ_P7 | 85653448G06 | | AJ_654 | /5AmMC6/CCC AAG ACC TAC CCT ACA GAG CTT GTA A | 106534788 | 8666 | 60.9 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P7 | 85653449G07 | AJ_655 | /5AmMC6/CCC AAT TTC GTA ACA AGT TGG ACT CGA A | 106534789 | 8736 | 59.1 |
| AJ_P7 | 85653450G08 | AJ_656 | /5AmMC6/CCC AAT CAA AGA AAC AGG TTG CAC TGA A | 106534790 | 8763 | 59.8 |
| AJ_P7 | 85653451G09 | AJ_657 | /5AmMC6/CCC AAC GTC TTA GAG TCC TTG AAC CCA A | 106534791 | 8657 | 61.7 |
| AJ_P7 | 85653452G10 | AJ_658 | /5AmMC6/CCC AAT GCT GAA ACG TTT CCC TTG TAA A | 106534792 | 8687 | 59.8 |
| AJ_P7 | 85653453G11 | AJ_659 | /5AmMC6/CCC AAC AGG TTT GTT TGA CTC AGA CGA A | 106534793 | 8752 | 60.8 |
| AJ_P7 | 85653454G12 | AJ_660 | /5AmMC6/CCC AAC CTT CGA CAT AAA GAA AGC GTA A | 106534794 | 8723 | 59 |
| AJ_P7 | 85653455H01 | AJ_661 | /5AmMC6/CCC AAT GAA CCA TTA GCA AGC AAG GTA A | 106534795 | 8763 | 59.4 |
| AJ_P7 | 85653456H02 | AJ_662 | /5AmMC6/CCC AAT GAA CCT TGA GCA CAA ACT GGA A | 106534796 | 8739 | 61.3 |
| AJ_P7 | 85653457H03 | AJ_663 | /5AmMC6/CCC AAA GGG TTC TTG GAC AGT ACC TCA A | 106534797 | 8737 | 61.8 |
| AJ_P7 | 85653458H04 | AJ_664 | /5AmMC6/CCC AAC TGT AAA GGA GTT CGT ACC CTA A | 106534798 | 8721 | 59.5 |
| AJ_P7 | 85653459H05 | AJ_665 | /5AmMC6/CCC AAT CGA GAA GGA AGT CAC ACT GTA A | 106534799 | 8779 | 59.8 |
| AJ_P7 | 85653460H06 | AJ_666 | /5AmMC6/CCC AAC TAA AGG AAG TGT CAG CTG TCA A | 106534800 | 8770 | 60.4 |
| AJ_P7 | 85653461H07 | AJ_667 | /5AmMC6/CCC AAG CAC ATA GGG TCA AAC GTG TGA A | 106534801 | 8779 | 61.1 |
| AJ_P7 | 85653462H08 | AJ_668 | /5AmMC6/CCC AAC GTT GAA GGA ACA TTC ACA GGA A | 106534802 | 8779 | 61 |
| AJ_P7 | 85653463H09 | AJ_669 | /5AmMC6/CCC AAT GTG AGC TGA CAA ACA ACA TGA A | 106534803 | 8763 | 59.8 |
| AJ_P7 | 85653464H10 | AJ_670 | /5AmMC6/CCC AAG CTA CTC TAA CAC GAC TGG ACA A | 106534804 | 8675 | 61.4 |
| AJ_P7 | 85653465H11 | AJ_671 | /5AmMC6/CCC AAG CCT AAC CTT CAA GTG CAT GTA A | 106534805 | 8681 | 60.8 |
| AJ_P7 | 85653466H12 | AJ_672 | /5AmMC6/CCC AAG TAA ACA CCT CTA GGT TCG GAA A | 106534806 | 8730 | 59.9 |
| AJ_P8 | 85653468A01 | AJ_673 | /5AmMC6/CCC AAG TCT TGA CTC TCG ACT CGA AAA A | 106534807 | 8681 | 60 |
| AJ_P8 | 85653469A02 | AJ_674 | /5AmMC6/CCC AAC TGC AGA GTG GAC TTG ACA AAA A | 106534808 | 8779 | 61.1 |
| AJ_P8 | 85653470A03 | AJ_675 | /5AmMC6/CCC AAC AGC TCT GGT GTA CTT AAG ACA A | 106534809 | 8721 | 60 |
| AJ_P8 | 85653471A04 | AJ_676 | /5AmMC6/CCC AAT ACG AGA GAG ACG TTT ACG ACA A | 106534810 | 8779 | 59.6 |
| AJ_P8 | 85653472A05 | AJ_677 | /5AmMC6/CCC AAG TAC CCT ACT CTC GTC AAG GAA A | 106534811 | 8666 | 60.9 |
| AJ_P8 | 85653473A06 | AJ_678 | /5AmMC6/CCC AAT AAC GAC ACA ACT GGT TAC CGA A | 106534812 | 8699 | 60.5 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P8 | 85653474A07 | AJ_679 | /5AmMC6/CCC AAC ACG TCA TAA CGG TAG ACC TCA A | 106534813 | 8675 | 61.5 |
| AJ_P8 | 85653475A08 | AJ_680 | /5AmMC6/CCC AAT CCC AAG CAA CAG TCA GTA GTA A | 106534814 | 8699 | 60.2 |
| AJ_P8 | 85653476A09 | AJ_681 | /5AmMC6/CCC AAT AAA CGA ACA CCT GTG AGC TCA A | 106534815 | 8699 | 60.8 |
| AJ_P8 | 85653477A10 | AJ_682 | /5AmMC6/CCC AAG TTA CCA GAC TCA ACA ACG GTA A | 106534816 | 8699 | 60.2 |
| AJ_P8 | 85653478A11 | AJ_683 | /5AmMC6/CCC AAG TTA GCT TGA CCA ACC AAC GTA A | 106534817 | 8690 | 60.8 |
| AJ_P8 | 85653479A12 | AJ_684 | /5AmMC6/CCC AAG ACC ATC ACT ACA GGA GTC CTA A | 106534818 | 8675 | 60.7 |
| AJ_P8 | 85653480B01 | AJ_685 | /5AmMC6/CCC AAG TAC TCT TCT TAC GGT AGC AGA A | 106534819 | 8712 | 59.3 |
| AJ_P8 | 85653481B02 | AJ_686 | /5AmMC6/CCC AAT TTG CCA TCG ACA ACG TGA AAA A | 106534820 | 8714 | 60.4 |
| AJ_P8 | 85653482B03 | AJ_687 | /5AmMC6/CCC AAA GTC TCT TGG GTA CAA CGT GTA A | 106534821 | 8752 | 60.2 |
| AJ_P8 | 85653483B04 | AJ_688 | /5AmMC6/CCC AAT GAC CTT CTC GTT ACA ACG GTA A | 106534822 | 8672 | 60.2 |
| AJ_P8 | 85653484B05 | AJ_689 | /5AmMC6/CCC AAT ACC GTT CTG TTA AGA AGC GTA A | 106534823 | 8736 | 58.6 |
| AJ_P8 | 85653485B06 | AJ_690 | /5AmMC6/CCC AAA GTC CTT CCT CTA GTT ACG GAA A | 106534824 | 8672 | 59.6 |
| AJ_P8 | 85653486B07 | AJ_691 | /5AmMC6/CCC AAG CCA TAC AAC ATT GGA CTG GTA A | 106534825 | 8730 | 60.6 |
| AJ_P8 | 85653487B08 | AJ_692 | /5AmMC6/CCC AAC CTG AGA GGT AAG CTT GAC TTA A | 106534826 | 8761 | 59.8 |
| AJ_P8 | 85653488B09 | AJ_693 | /5AmMC6/CCC AAC ACC TAG TAG TCG TTG GAC AGA A | 106534827 | 8746 | 61.2 |
| AJ_P8 | 85653489B10 | AJ_694 | /5AmMC6/CCC AAG TAC ACT AAA CCG TTG CGA AAA A | 106534828 | 8723 | 59.6 |
| AJ_P8 | 85653490B11 | AJ_695 | /5AmMC6/CCC AAC CAC TGG TAC GGA AAG CTT TAA A | 106534829 | 8730 | 60.8 |
| AJ_P8 | 85653491B12 | AJ_696 | /5AmMC6/CCC AAG ACC ACT CTT TGA GGA GTA CGA A | 106534830 | 8746 | 61.2 |
| AJ_P8 | 85653492C01 | AJ_697 | /5AmMC6/CCC AAG ACT GAC CTT GGA AAG TAG GCA A | 106534831 | 8795 | 62 |
| AJ_P8 | 85653493C02 | AJ_698 | /5AmMC6/CCC AAC TCA CGT TAC GAA ACA GAG GTA A | 106534832 | 8739 | 60 |
| AJ_P8 | 85653494C03 | AJ_699 | /5AmMC6/CCC AAG CGT AAC GTC ATT TAC TTT CGA A | 106534833 | 8687 | 59.2 |
| AJ_P8 | 85653495C04 | AJ_700 | /5AmMC6/CCC AAC GAA CGT GTC ATT TCA CTT TGA A | 106534834 | 8687 | 59.7 |
| AJ_P8 | 85653496C05 | AJ_701 | /5AmMC6/CCC AAA TCT CTG GTG TCC ATC CGA ACA A | 106534835 | 8657 | 62.1 |
| AJ_P8 | 85653497C06 | AJ_702 | /5AmMC6/CCC AAA GCT TTG GAG TCT GTG ACA ACA A | 106534836 | 8761 | 61.1 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P8 | 85653498C07 | AJ_703 | /5AmMC6/CCC AAG GGT ACT AGG CTT GTG ACA ACA A | 106534837 | 8786 | 61.9 |
| AJ_P8 | 85653499C08 | AJ_704 | /5AmMC6/CCC AAT AGC GAA CAC CTA GTT ACG ACA A | 106534838 | 8699 | 60 |
| AJ_P8 | 85653500C09 | AJ_705 | /5AmMC6/CCC AAT CAC GAG TCC AAG AGT TAC CCA A | 106534839 | 8675 | 61.7 |
| AJ_P8 | 85653501C10 | AJ_706 | /5AmMC6/CCC AAT GAG AAC AAA GGC TAA CCG TTA A | 106534840 | 8763 | 59.1 |
| AJ_P8 | 85653502C11 | AJ_707 | /5AmMC6/CCC AAC TCG TCA TAG AAC ACC AAG GTA A | 106534841 | 8699 | 59.9 |
| AJ_P8 | 85653503C12 | AJ_708 | /5AmMC6/CCC AAC TCC ATG CAA GTA AAG AAC GTA A | 106534842 | 8723 | 59 |
| AJ_P8 | 85653504D01 | AJ_709 | /5AmMC6/CCC AAA TGT GAC TAC CGA AAC GCT TTA A | 106534843 | 8705 | 59.3 |
| AJ_P8 | 85653505D02 | AJ_710 | /5AmMC6/CCC AAG ACA AGT TGA CCA ACG CAT CTA A | 106534844 | 8699 | 60.8 |
| AJ_P8 | 85653506D03 | AJ_711 | /5AmMC6/CCC AAC TGC ACA GTT TAC AAC CTA GGA A | 106534845 | 8690 | 60.5 |
| AJ_P8 | 85653507D04 | AJ_712 | /5AmMC6/CCC AAG CTG ACT GTC TTA ACC CTT AGA A | 106534846 | 8672 | 59.8 |
| AJ_P8 | 85653508D05 | AJ_713 | /5AmMC6/CCC AAG GTC AAG TCG ACA AGC TAA CTA A | 106534847 | 8739 | 60 |
| AJ_P8 | 85653509D06 | AJ_714 | /5AmMC6/CCC AAC ACG TGA GTT CCA ACC CTA AGA A | 106534848 | 8675 | 62 |
| AJ_P8 | 85653510D07 | AJ_715 | /5AmMC6/CCC AAG CCA TAA CCA TCA GTC TGA GTA A | 106534849 | 8690 | 59.9 |
| AJ_P8 | 85653511D08 | AJ_716 | /5AmMC6/CCC AAG TCA ACA CAC TCA GCA GTA GTA A | 106534850 | 8699 | 60 |
| AJ_P8 | 85653512D09 | AJ_717 | /5AmMC6/CCC AAG TAC CTA CTC ATG CTT GCA GTA A | 106534851 | 8672 | 60 |
| AJ_P8 | 85653513D10 | AJ_718 | /5AmMC6/CCC AAA TGT ACG TAA AGC ACA AGC CTA A | 106534852 | 8723 | 59.2 |
| AJ_P8 | 85653514D11 | AJ_719 | /5AmMC6/CCC AAC GTG TAA AGG AAC TAG GCT ACA A | 106534853 | 8779 | 60 |
| AJ_P8 | 85653515D12 | AJ_720 | /5AmMC6/CCC AAG GTC ACT AAC TCA GGA ACT CCA A | 106534854 | 8675 | 61.4 |
| AJ_P8 | 85653516E01 | AJ_721 | /5AmMC6/CCC AAT TCG AAG TAA GCA ACA CCA TGA A | 106534855 | 8723 | 59.4 |
| AJ_P8 | 85653517E02 | AJ_722 | /5AmMC6/CCC AAT CGG AAG TGT AAA CTG GAC ACA A | 106534856 | 8779 | 60.6 |
| AJ_P8 | 85653518E03 | AJ_723 | /5AmMC6/CCC AAG ACT CAC AAA CCG TAC TTG GTA A | 106534857 | 8690 | 60.2 |
| AJ_P8 | 85653519E04 | AJ_724 | /5AmMC6/CCC AAC ATT CTG CAT AGG AGA CAG TGA A | 106534858 | 8770 | 60.2 |
| AJ_P8 | 85653520E05 | AJ_725 | /5AmMC6/CCC AAA CCC ATG CAC ATT GAG AAC TGA A | 106534859 | 8699 | 61.3 |
| AJ_P8 | 85653521E06 | AJ_726 | /5AmMC6/CCC AAT GGT CAG GAC TAA ACT ACC AGA A | 106534860 | 8739 | 59.7 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P8 | 85653522E07 | AJ_727 | /5AmMC6/CCC AAG CTT CCA GAA CTT TAC TTG GGA A | 106534861 | 8712 | 60.6 |
| AJ_P8 | 85653523E08 | AJ_728 | /5AmMC6/CCC AAG TTC AAC TCC AAC GTC AGG ACA A | 106534862 | 8675 | 62.3 |
| AJ_P8 | 85653524E09 | AJ_729 | /5AmMC6/CCC AAG TTA CTA CCA TAC GAC TCG TGA A | 106534863 | 8681 | 59.4 |
| AJ_P8 | 85653525E10 | AJ_730 | /5AmMC6/CCC AAC AGA CAT GCA CTT AAC TCA GGA A | 106534864 | 8699 | 60.5 |
| AJ_P8 | 85653526E11 | AJ_731 | /5AmMC6/CCC AAC TTG AAC CTA GAA AGG GTA GCA A | 106534865 | 8779 | 60.2 |
| AJ_P8 | 85653527E12 | AJ_732 | /5AmMC6/CCC AAG TCC TAC CTT AAG AGA CGA GTA A | 106534866 | 8730 | 58.8 |
| AJ_P8 | 85653528F01 | AJ_733 | /5AmMC6/CCC AAC AGT TAG GGA AGC TTT GCA TCA A | 106534867 | 8761 | 61.1 |
| AJ_P8 | 85653529F02 | AJ_734 | /5AmMC6/CCC AAC GTC TAG CTA GAA GAA GTT TCA A | 106534868 | 8745 | 58.2 |
| AJ_P8 | 85653530F03 | AJ_735 | /5AmMC6/CCC AAT TTA GTC ACC TCT GGA ACC GTA A | 106534869 | 8672 | 60 |
| AJ_P8 | 85653531F04 | AJ_736 | /5AmMC6/CCC AAC AGT GAA GGA ACC TTT CGT CAA A | 106534870 | 8730 | 60.9 |
| AJ_P8 | 85653532F05 | AJ_737 | /5AmMC6/CCC AAA GGC TTC CTT TCA GAC AGT TTA A | 106534871 | 8687 | 59.1 |
| AJ_P8 | 85653533F06 | AJ_738 | /5AmMC6/CCC AAA CGG TTG TTG AGT CGA ACC ATA A | 106534872 | 8761 | 60.9 |
| AJ_P8 | 85653534F07 | AJ_739 | /5AmMC6/CCC AAA CCT CTG AGT TGG CTA AAC AGA A | 106534873 | 8730 | 60.5 |
| AJ_P8 | 85653535F08 | AJ_740 | /5AmMC6/CCC AAG CAG TTG TAA GAC CAA GAC GTA A | 106534874 | 8779 | 60.3 |
| AJ_P8 | 85653536F09 | AJ_741 | /5AmMC6/CCC AAG AGA GCT ACC GTT TCT TTG TAA A | 106534875 | 8727 | 58.6 |
| AJ_P8 | 85653537F10 | AJ_742 | /5AmMC6/CCC AAA GGG TTC TCC AAG TTT ACA GGA A | 106534876 | 8761 | 60.4 |
| AJ_P8 | 85653538F11 | AJ_743 | /5AmMC6/CCC AAC GTT AGT GTG TTC AAG CTT CAA A | 106534877 | 8727 | 59.6 |
| AJ_P8 | 85653539F12 | AJ_744 | /5AmMC6/CCC AAC TCA CTG CAA AGG TAA AGG TCA A | 106534878 | 8739 | 60.8 |
| AJ_P8 | 85653540G01 | AJ_745 | /5AmMC6/CCC AAG AGC TCA CAA GGT GTT AGG TCA A | 106534879 | 8786 | 61.9 |
| AJ_P8 | 85653541G02 | AJ_746 | /5AmMC6/CCC AAC TGT CTA CTG AAG GAG TTT GCA A | 106534880 | 8752 | 60.4 |
| AJ_P8 | 85653542G03 | AJ_747 | /5AmMC6/CCC AAA GCT TCC TTT ACT GAC TAG TGA A | 106534881 | 8687 | 58.3 |
| AJ_P8 | 85653543G04 | AJ_748 | /5AmMC6/CCC AAC TGC TAC CCT TGA GTA AAG TCA A | 106534882 | 8681 | 60.1 |
| AJ_P8 | 85653544G05 | AJ_749 | /5AmMC6/CCC AAG CTC ATT CCC TTG AAC AGA GTA A | 106534883 | 8681 | 60.2 |
| AJ_P8 | 85653545G06 | AJ_750 | /5AmMC6/CCC AAG AGA CTG TGC ACA ACC CTT AGA A | 106534884 | 8715 | 61.9 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P8 | 85653546G07 | AJ_751 | /5AmMC6/CCC AAC GGT TAA CCT CAA GTG CTA AAA A | 106534885 | 8714 | 59.4 |
| AJ_P8 | 85653547G08 | AJ_752 | /5AmMC6/CCC AAA CCC TTG GGT AAG CTA GAG ACA A | 106534886 | 8755 | 61.7 |
| AJ_P8 | 85653548G09 | AJ_753 | /5AmMC6/CCC AAA TTG CTC ACG TTC TCA TGG ACA A | 106534887 | 8672 | 61.2 |
| AJ_P8 | 85653549G10 | AJ_754 | /5AmMC6/CCC AAC CCT AGG AAG CCA TCA GTT TAA A | 106534888 | 8690 | 60.3 |
| AJ_P8 | 85653550G11 | AJ_755 | /5AmMC6/CCC AAA CCG TTT GAA CCT TCT GGT CAA A | 106534889 | 8672 | 61.3 |
| AJ_P8 | 85653551G12 | AJ_756 | /5AmMC6/CCC AAT CCG AAG GAG AAC TTT GAC CAA A | 106534890 | 8739 | 60.7 |
| AJ_P8 | 85653552H01 | AJ_757 | /5AmMC6/CCC AAT TGA GTC TGA AGC AAC CAA GTA A | 106534891 | 8754 | 59.1 |
| AJ_P8 | 85653553H02 | AJ_758 | /5AmMC6/CCC AAC TGT TTA GAG TGA CAT TGC CTA A | 106534892 | 8727 | 58.7 |
| AJ_P8 | 85653554H03 | AJ_759 | /5AmMC6/CCC AAT ACT GTT AAG GCT ACA ACG CTA A | 106534893 | 8705 | 58.5 |
| AJ_P8 | 85653555H04 | AJ_760 | /5AmMC6/CCC AAA TCG TTT CGT TCA CTA CTC AGA A | 106534894 | 8672 | 60.1 |
| AJ_P8 | 85653556H05 | AJ_761 | /5AmMC6/CCC AAC CAA GGT TGG CTT AGT AGT CCA A | 106534895 | 8737 | 62 |
| AJ_P8 | 85653557H06 | AJ_762 | /5AmMC6/CCC AAG GCT ACA GAC TTT CCC ATT TGA A | 106534896 | 8672 | 60.6 |
| AJ_P8 | 85653558H07 | AJ_763 | /5AmMC6/CCC AAG AAC CTC ACG TGT GCT TGT TAA A | 106534897 | 8712 | 61 |
| AJ_P8 | 85653559H08 | AJ_764 | /5AmMC6/CCC AAG ACA TCC ACT CTT GTT TGA CGA A | 106534898 | 8672 | 60.5 |
| AJ_P8 | 85653560H09 | AJ_765 | /5AmMC6/CCC AAG GTA CAC ACC TTT GCC TTA CGA A | 106534899 | 8657 | 62.2 |
| AJ_P8 | 85653561H10 | AJ_766 | /5AmMC6/CCC AAC GAG TTG GAG TAA CAT ACG ACA A | 106534900 | 8779 | 60.1 |
| AJ_P8 | 85653562H11 | AJ_767 | /5AmMC6/CCC AAA CGG TTG TGG TAA CAT CCT AGA A | 106534901 | 8761 | 60.3 |
| AJ_P8 | 85653563H12 | AJ_768 | /5AmMC6/CCC AAG ACC TTG ACT GGA GAA ACG GTA A | 106586462 | 8795 | 61.7 |
| AJ_P9 | 85653565A01 | AJ_769 | /5AmMC6/CCC AAG CTC ACT ACC ATT GTC ATT GGA A | 106534903 | 8672 | 60.6 |
| AJ_P9 | 85653566A02 | AJ_770 | /5AmMC6/CCC AAT CCG TTA CGT GAA GGG TAA ACA A | 106534904 | 8770 | 60.6 |
| AJ_P9 | 85653567A03 | AJ_771 | /5AmMC6/CCC AAT ACA GAC TGC ACA CTC AGG TAA A | 106534905 | 8699 | 60.1 |
| AJ_P9 | 85653568A04 | AJ_772 | /5AmMC6/CCC AAT TTA CGT AGT CCA ACT TGC GAA A | 106534906 | 8696 | 59.3 |
| AJ_P9 | 85653569A05 | AJ_773 | /5AmMC6/CCC AAG ACC TTA CTA CCT GAA GCA GTA A | 106534907 | 8690 | 59.4 |
| AJ_P9 | 85653570A06 | AJ_774 | /5AmMC6/CCC AAC ATT GTT TCT CTG ACA AGC TGA A | 106534908 | 8687 | 59.4 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P9 | 85653571A07 | AJ_775 | /5AmMC6/CCC AAC AGC AGT TTA GCC AAG AAG TCA A | 106534909 | 8739 | 61 |
| AJ_P9 | 85653572A08 | AJ_776 | /5AmMC6/CCC AAG ACC TTG GAC TCT CTC TAA CGA A | 106534910 | 8657 | 60.9 |
| AJ_P9 | 85653573A09 | AJ_777 | /5AmMC6/CCC AAG TAC TTT CTT CCA GTC AGA GCA A | 106534911 | 8672 | 60.1 |
| AJ_P9 | 85653574A10 | AJ_778 | /5AmMC6/CCC AAT CAG ACA ACC TTG TTC ATC GGA A | 106534912 | 8681 | 60.7 |
| AJ_P9 | 85653575A11 | AJ_779 | /5AmMC6/CCC AAT CAC CTG TTG CAT TCA TAG GGA A | 106534913 | 8712 | 60.7 |
| AJ_P9 | 85653576A12 | AJ_780 | /5AmMC6/CCC AAT TTG CAG TGA ACA CCA ACA GTA A | 106534914 | 8714 | 59.8 |
| AJ_P9 | 85653577B01 | AJ_781 | /5AmMC6/CCC AAG TCT GCA GTA ACA CAC CAA GTA A | 106534915 | 8699 | 60.4 |
| AJ_P9 | 85653578B02 | AJ_782 | /5AmMC6/CCC AAT GTC TCA GTC TCC ACA TTA GGA A | 106534916 | 8672 | 59.7 |
| AJ_P9 | 85653579B03 | AJ_783 | /5AmMC6/CCC AAG TAC ACC ATT TCG CAT TTC GGA A | 106534917 | 8672 | 61.2 |
| AJ_P9 | 85653580B04 | AJ_784 | /5AmMC6/CCC AAG CTA CCA CTT TAG AAG TAG GCA A | 106534918 | 8730 | 60 |
| AJ_P9 | 85653581B05 | AJ_785 | /5AmMC6/CCC AAT CAC AAG GTT ACC ACA GGA GTA A | 106534919 | 8739 | 60 |
| AJ_P9 | 85653582B06 | AJ_786 | /5AmMC6/CCC AAC ACC ATG GAC ACT TCT AAG GGA A | 106534920 | 8715 | 61.9 |
| AJ_P9 | 85653583B07 | AJ_787 | /5AmMC6/CCC AAC CTG AAA GAG TTT CTT GCG TAA A | 106534921 | 8736 | 59.3 |
| AJ_P9 | 85653584B08 | AJ_788 | /5AmMC6/CCC AAG AGA CGT GTC ATC TCA TCC AGA A | 106534922 | 8706 | 61.3 |
| AJ_P9 | 85653585B09 | AJ_789 | /5AmMC6/CCC AAT AGC GTA GAC AAC TTC AAA GCA A | 106534923 | 8723 | 59.2 |
| AJ_P9 | 85653586B10 | AJ_790 | /5AmMC6/CCC AAA GTT CTC TCG TTC ATA GCT GAA A | 106534924 | 8687 | 58.6 |
| AJ_P9 | 85653587B11 | AJ_791 | /5AmMC6/CCC AAA TTG GTC TTC TGC ATA AAG CGA A | 106534925 | 8736 | 59.7 |
| AJ_P9 | 85653588B12 | AJ_792 | /5AmMC6/CCC AAT CGA AGG AGT AGT CTA CCT GTA A | 106534926 | 8761 | 58.8 |
| AJ_P9 | 85653589C01 | AJ_793 | /5AmMC6/CCC AAT CAG GAC TAC GGA AAG TTC CCA A | 106534927 | 8715 | 61.8 |
| AJ_P9 | 85653590C02 | AJ_794 | /5AmMC6/CCC AAC CGT AAC ATC CAT GAG ACG TCA A | 106534928 | 8675 | 62 |
| AJ_P9 | 85653591C03 | AJ_795 | /5AmMC6/CCC AAT GCG AAA GAG GTA CCG TTT ACA A | 106534929 | 8770 | 60.8 |
| AJ_P9 | 85653592C04 | AJ_796 | /5AmMC6/CCC AAG ACA CAT CCA ACT GGT GAC TCA A | 106534930 | 8675 | 62.1 |
| AJ_P9 | 85653593C05 | AJ_797 | /5AmMC6/CCC AAG ACC ATC CTT CAA GAG ACG TCA A | 106534931 | 8675 | 61.7 |
| AJ_P9 | 85653594C06 | AJ_798 | /5AmMC6/CCC AAG CTC TCA AGT CTA AAC AGT GCA A | 106534932 | 8690 | 60.6 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P9 | 85653595C07 | AJ_799 | /5AmMC6/CCC AAC AAA GTA GAA ACT CGT AGC TGA A | 106534933 | 8763 | 58.6 |
| AJ_P9 | 85653596C08 | AJ_800 | /5AmMC6/CCC AAC CAG AGT GTG AAC ACT AGG GTA A | 106534934 | 8795 | 61.3 |
| AJ_P9 | 85653597C09 | AJ_801 | /5AmMC6/CCC AAC CTC ATG AAG ACT CCA AGG GTA A | 106534935 | 8715 | 61.5 |
| AJ_P9 | 85653598C10 | AJ_802 | /5AmMC6/CCC AAA CCT GTG GAC ACT ACA CCT TGA A | 106534936 | 8666 | 62.1 |
| AJ_P9 | 85653599C11 | AJ_803 | /5AmMC6/CCC AAA GTT CAG AGT TCT CTC CAC TGA A | 106534937 | 8672 | 59.9 |
| AJ_P9 | 85653600C12 | AJ_804 | /5AmMC6/CCC AAG CTA CTT TCA ACT GAC AGT GGA A | 106534938 | 8721 | 60.4 |
| AJ_P9 | 85653601D01 | AJ_805 | /5AmMC6/CCC AAG CCA TCT TCT ACT GAA CGG TAA A | 106534939 | 8681 | 60.1 |
| AJ_P9 | 85653602D02 | AJ_806 | /5AmMC6/CCC AAT GTT TCA GTC CAT TGA ACG CTA A | 106534940 | 8687 | 59.4 |
| AJ_P9 | 85653603D03 | AJ_807 | /5AmMC6/CCC AAA TTG CTT CTC ACG TCA TTA GGA A | 106534941 | 8687 | 59.1 |
| AJ_P9 | 85653604D04 | AJ_808 | /5AmMC6/CCC AAT GGG AAC TCT GAA ACA TCC GAA A | 106534942 | 8739 | 60.8 |
| AJ_P9 | 85653605D05 | AJ_809 | /5AmMC6/CCC AAT CGT AGA GTC AAA CCA CAA GTA A | 106534943 | 8723 | 58.4 |
| AJ_P9 | 85653606D06 | AJ_810 | /5AmMC6/CCC AAC AGG TGT CGT GTG AAA CAG TCA A | 106534944 | 8786 | 62.5 |
| AJ_P9 | 85653607D07 | AJ_811 | /5AmMC6/CCC AAG GTC ATT AAG CCT TCG ACT CCA A | 106534945 | 8657 | 62 |
| AJ_P9 | 85653608D08 | AJ_812 | /5AmMC6/CCC AAC TTG AAG TGA AGG CAA CCA TGA A | 106534946 | 8779 | 61.3 |
| AJ_P9 | 85653609D09 | AJ_813 | /5AmMC6/CCC AAC AAC TAG GAG TGC TCT GGT TAA A | 106534947 | 8761 | 60.1 |
| AJ_P9 | 85653610D10 | AJ_814 | /5AmMC6/CCC AAG ACC ATA GCA TCC AAG TCG TCA A | 106534948 | 8675 | 61.9 |
| AJ_P9 | 85653611D11 | AJ_815 | /5AmMC6/CCC AAT CGA GAA ACA CCT GTA CAA GTA A | 106534949 | 8723 | 58.4 |
| AJ_P9 | 85653612D12 | AJ_816 | /5AmMC6/CCC AAC AGT CTT TAA GCA GAA GGA CTA A | 106534950 | 8754 | 58.3 |
| AJ_P9 | 85653613E01 | AJ_817 | /5AmMC6/CCC AAC GTC AAC TAC ACA GAA GGT CTA A | 106534951 | 8699 | 59.8 |
| AJ_P9 | 85653614E02 | AJ_818 | /5AmMC6/CCC AAG TCG ACA ACA GCA TTA GGT CTA A | 106534952 | 8730 | 60 |
| AJ_P9 | 85653615E03 | AJ_819 | /5AmMC6/CCC AAT TGG TCA GAA CTT TCC TTG CAA A | 106534953 | 8687 | 59.9 |
| AJ_P9 | 85653616E04 | AJ_820 | /5AmMC6/CCC AAC CTA GGT CAA GTT TAG GTT GCA A | 106534954 | 8752 | 60.5 |
| AJ_P9 | 85653617E05 | AJ_821 | /5AmMC6/CCC AAG TCA TCT GCA TCC ACA CTA GGA A | 106534955 | 8666 | 61.6 |
| AJ_P9 | 85653618E06 | AJ_822 | /5AmMC6/CCC AAA TCG CTT GAA CCA TAC CAT GGA A | 106534956 | 8690 | 61 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P9 | 85653619E07 | AJ_823 | /5AmMC6/CCC AAA TCT GAA CTG AGG AAC AAG CTA A | 106534957 | 8763 | 58.8 |
| AJ_P9 | 85653620E08 | AJ_824 | /5AmMC6/CCC AAC GTG AGC ATC AGG AAC ATT TGA A | 106534958 | 8770 | 61.2 |
| AJ_P9 | 85653621E09 | AJ_825 | /5AmMC6/CCC AAT CCC TAG TTC CAG TCA TGA GGA A | 106534959 | 8697 | 61.2 |
| AJ_P9 | 85653622E10 | AJ_826 | /5AmMC6/CCC AAC TCC TAG TCC TGT AGT CCA GAA A | 106534960 | 8657 | 60.7 |
| AJ_P9 | 85653623E11 | AJ_827 | /5AmMC6/CCC AAG AGT CAA CTC CAT GAA AGC CTA A | 106534961 | 8699 | 60.2 |
| AJ_P9 | 85653624E12 | AJ_828 | /5AmMC6/CCC AAG GTA GTC TCA GAG AAC ACC TGA A | 106534962 | 8755 | 61 |
| AJ_P9 | 85653625F01 | AJ_829 | /5AmMC6/CCC AAG CTG TAG GAC ATA AGA ACC GTA A | 106534963 | 8779 | 59.8 |
| AJ_P9 | 85653626F02 | AJ_830 | /5AmMC6/CCC AAG TCC AAC TGA AAC AGA GCT GTA A | 106534964 | 8739 | 60.4 |
| AJ_P9 | 85653627F03 | AJ_831 | /5AmMC6/CCC AAG TGC AAC TAC AGG ACA GTG TGA A | 106534965 | 8795 | 62.1 |
| AJ_P9 | 85653628F04 | AJ_832 | /5AmMC6/CCC AAT GAA ACA GAC AAG TAG CGT TCA A | 106534966 | 8763 | 59.3 |
| AJ_P9 | 85653629F05 | AJ_833 | /5AmMC6/CCC AAA AAC TGT AGC TTT CCC TTG GAA A | 106534967 | 8696 | 59.5 |
| AJ_P9 | 85653630F06 | AJ_834 | /5AmMC6/CCC AAT CCG TAG AGC AGT GAG TTT ACA A | 106534968 | 8761 | 60 |
| AJ_P9 | 85653631F07 | AJ_835 | /5AmMC6/CCC AAG GTT CAT GCA TCC TCT TCA AGA A | 106534969 | 8672 | 60.6 |
| AJ_P9 | 85653632F08 | AJ_836 | /5AmMC6/CCC AAA CCT TTG TGG AGT CAA GCA TGA A | 106534970 | 8761 | 61.3 |
| AJ_P9 | 85653633F09 | AJ_837 | /5AmMC6/CCC AAA CCT TTG TGA GCA GAG CAT TTA A | 106534971 | 8736 | 59.7 |
| AJ_P9 | 85653634F10 | AJ_838 | /5AmMC6/CCC AAA CTG TTT CCC TTA GAG CAG TCA A | 106534972 | 8672 | 60.5 |
| AJ_P9 | 85653635F11 | AJ_839 | /5AmMC6/CCC AAG CTG TAG GAG TTA CAT CTC TGA A | 106534973 | 8752 | 59.4 |
| AJ_P9 | 85653636F12 | AJ_840 | /5AmMC6/CCC AAG TGG ACA CTC CAG AAC TCT GTA A | 106534974 | 8706 | 61.3 |
| AJ_P9 | 85653637G01 | AJ_841 | /5AmMC6/CCC AAC GTC ATC TGA CAG AAC AGA CTA A | 106534975 | 8699 | 59.8 |
| AJ_P9 | 85653638G02 | AJ_842 | /5AmMC6/CCC AAG TCC AAC GAA GCA TGA CAC TTA A | 106534976 | 8699 | 60.8 |
| AJ_P9 | 85653639G03 | AJ_843 | /5AmMC6/CCC AAA GCC TAA AGC CTT TGG GTT ACA A | 106534977 | 8721 | 61.2 |
| AJ_P9 | 85653640G04 | AJ_844 | /5AmMC6/CCC AAC CGT TCA AAC GAC TAA GAG TCA A | 106534978 | 8699 | 60.4 |
| AJ_P9 | 85653641G05 | AJ_845 | /5AmMC6/CCC AAT CGG AAC ACC TTT GGT TTC CAA A | 106534979 | 8672 | 61.5 |
| AJ_P9 | 85653642G06 | AJ_846 | /5AmMC6/CCC AAT GAC CAT CAT GTT TGG CTT CAA A | 106534980 | 8687 | 60 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P9 | 85653643 | G07 | AJ_847 | /5AmMC6/CCC AAG ACC ATG AGC TCT CTT GTT CAA A | 106534981 | 8672 | 60.5 |
| AJ_P9 | 85653644 | G08 | AJ_848 | /5AmMC6/CCC AAC TAG GTG AAG TGA CAG CAT CCA A | 106534982 | 8755 | 61.9 |
| AJ_P9 | 85653645 | G09 | AJ_849 | /5AmMC6/CCC AAC AAG TTA GGA GAC TGA CTG CAA A | 106534983 | 8779 | 60.4 |
| AJ_P9 | 85653646 | G10 | AJ_850 | /5AmMC6/CCC AAT CAG CAC ACG AGT TCT AGT AAA A | 106534984 | 8714 | 58.6 |
| AJ_P9 | 85653647 | G11 | AJ_851 | /5AmMC6/CCC AAA CGT CAC CTA GGT TGG GTT ACA A | 106534985 | 8737 | 62.1 |
| AJ_P9 | 85653648 | G12 | AJ_852 | /5AmMC6/CCC AAA CCT TGT CTC TTA GCC ATG GAA A | 106534986 | 8672 | 60.6 |
| AJ_P9 | 85653649 | H01 | AJ_853 | /5AmMC6/CCC AAA CCT TGT TAC TGT GCT AGA GCA A | 106534987 | 8712 | 60.6 |
| AJ_P9 | 85653650 | H02 | AJ_854 | /5AmMC6/CCC AAA CAG AGT GCT TCC AAC TTC TGA A | 106534988 | 8681 | 60.8 |
| AJ_P9 | 85653651 | H03 | AJ_855 | /5AmMC6/CCC AAT CGT TCA CGA AGT AGG GTT ACA A | 106534989 | 8761 | 60.2 |
| AJ_P9 | 85653652 | H04 | AJ_856 | /5AmMC6/CCC AAA AAC ATG TTC CGT AGT TGC CAA A | 106534990 | 8705 | 60.1 |
| AJ_P9 | 85653653 | H05 | AJ_857 | /5AmMC6/CCC AAT GAC CAC AAC ATA GCA TGT CGA A | 106534991 | 8699 | 60.9 |
| AJ_P9 | 85653654 | H06 | AJ_858 | /5AmMC6/CCC AAG CAT AAA CAC TCT GGA CAG GTA A | 106534992 | 8739 | 60.2 |
| AJ_P9 | 85653655 | H07 | AJ_859 | /5AmMC6/CCC AAG CTA ACA ACC ATC GAG AGT CTA A | 106534993 | 8699 | 59.7 |
| AJ_P9 | 85653656 | H08 | AJ_860 | /5AmMC6/CCC AAG TGA AAC TCA CAC GAG ACT CTA A | 106534994 | 8699 | 59.7 |
| AJ_P9 | 85653657 | H09 | AJ_861 | /5AmMC6/CCC AAG TAA CAA ACC CAT GAG CTG TGA A | 106534995 | 8739 | 60.9 |
| AJ_P9 | 85653658 | H10 | AJ_862 | /5AmMC6/CCC AAG TCG ACA TCA CAG TCA AGG TGA A | 106534996 | 8755 | 61.9 |
| AJ_P9 | 85653659 | H11 | AJ_863 | /5AmMC6/CCC AAG AAC TCT CTC TGC ACA TTG TGA A | 106534997 | 8672 | 60.4 |
| AJ_P9 | 85653660 | H12 | AJ_864 | /5AmMC6/CCC AAC TGC ACA CAT GGT TTC TTT GAA A | 106534998 | 8687 | 60.1 |
| AJ_P10 | 85653662 | A01 | AJ_865 | /5AmMC6/CCC AAT AAA GCA CTT TGA GAG TAC CGA A | 106534999 | 8754 | 58.7 |
| AJ_P10 | 85653663 | A02 | AJ_866 | /5AmMC6/CCC AAA TCG CTT GTT TAA CCT ACT GGA A | 106535000 | 8687 | 59.1 |
| AJ_P10 | 85653664 | A03 | AJ_867 | /5AmMC6/CCC AAC GTT GAG TTT AAG CTA CCA GAA A | 106535001 | 8745 | 59 |
| AJ_P10 | 85653665 | A04 | AJ_868 | /5AmMC6/CCC AAG TTT CAC TAC ACG ACT TCG AGA A | 106535002 | 8681 | 60 |
| AJ_P10 | 85653666 | A05 | AJ_869 | /5AmMC6/CCC AAT GGA GAC AGT CTT CCC TTT GAA A | 106535003 | 8712 | 60.4 |
| AJ_P10 | 85653667 | A06 | AJ_870 | /5AmMC6/CCC AAG TTT CAC TGC ACT TCA AGG TGA A | 106535004 | 8712 | 61.1 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P10 | 85653668A07 | | AJ_871 | /5AmMC6/CCC AAC CAG TCT GGT TCT ACT ACA CGA A | 106535005 | 8657 | 61.2 |
| AJ_P10 | 85653669A08 | | AJ_872 | /5AmMC6/CCC AAA TTC TCG TTC TCA GAG TCA GGA A | 106535006 | 8712 | 59.9 |
| AJ_P10 | 85653670A09 | | AJ_873 | /5AmMC6/CCC AAG TTA CCA ACA CCT GAG AAG CTA A | 106535007 | 8699 | 60.1 |
| AJ_P10 | 85653671A10 | | AJ_874 | /5AmMC6/CCC AAA CTA CTG TCA AAG GAG TAG GCA A | 106535008 | 8779 | 60.1 |
| AJ_P10 | 85653672A11 | | AJ_875 | /5AmMC6/CCC AAG TTC CCA AGA CCT ACA AGC TGA A | 106535009 | 8675 | 62 |
| AJ_P10 | 85653673A12 | | AJ_876 | /5AmMC6/CCC AAT TTA GCC TAA CAG CAA CAG GTA A | 106535010 | 8714 | 59 |
| AJ_P10 | 85653674B01 | | AJ_877 | /5AmMC6/CCC AAA TCT GTT CTC TGC AAA GTC GTA A | 106535011 | 8687 | 59 |
| AJ_P10 | 85653675B02 | | AJ_878 | /5AmMC6/CCC AAA GTC CTT GTC TCA AAC TCA GGA A | 106535012 | 8681 | 60.3 |
| AJ_P10 | 85653676B03 | | AJ_879 | /5AmMC6/CCC AAA TCT TGT GTG TCG AAG CAA CTA A | 106535013 | 8736 | 59.3 |
| AJ_P10 | 85653677B04 | | AJ_880 | /5AmMC6/CCC AAG TGC AAC TGG AGA CAG ACT TTA A | 106535014 | 8770 | 60.4 |
| AJ_P10 | 85653678B05 | | AJ_881 | /5AmMC6/CCC AAA CTG TCT TGT TCG AAC AGC ATA A | 106535015 | 8696 | 59.3 |
| AJ_P10 | 85653679B06 | | AJ_882 | /5AmMC6/CCC AAT TTG TAC ATC GCT TCA TCG GAA A | 106535016 | 8687 | 59.4 |
| AJ_P10 | 85653680B07 | | AJ_883 | /5AmMC6/CCC AAT ACA GAA GGA GTA CCT GAC CTA A | 106535017 | 8739 | 58.9 |
| AJ_P10 | 85653681B08 | | AJ_884 | /5AmMC6/CCC AAT CGC AAA GAA GTA CCA GTT TCA A | 106535018 | 8714 | 59.4 |
| AJ_P10 | 85653682B09 | | AJ_885 | /5AmMC6/CCC AAC TGG TAG ACA TGC ATA GAA GCA A | 106535019 | 8779 | 60.4 |
| AJ_P10 | 85653683B10 | | AJ_886 | /5AmMC6/CCC AAG AGA ACT ACC GTT GTG AAG GCA A | 106535020 | 8795 | 62.2 |
| AJ_P10 | 85653684B11 | | AJ_887 | /5AmMC6/CCC AAT TTC GAG AGT CAC ATC AAC AGA A | 106535021 | 8714 | 58.8 |
| AJ_P10 | 85653685B12 | | AJ_888 | /5AmMC6/CCC AAC GGT AAG GCT ACC TCT TTG TAA A | 106535022 | 8712 | 60.1 |
| AJ_P10 | 85653686C01 | | AJ_889 | /5AmMC6/CCC AAC TAC GCT ACT AAA GTA AAG GCA A | 106535023 | 8723 | 58.5 |
| AJ_P10 | 85653687C02 | | AJ_890 | /5AmMC6/CCC AAC GTG AGT TCG TTA ACT ACC AGA A | 106535024 | 8721 | 60 |
| AJ_P10 | 85653688C03 | | AJ_891 | /5AmMC6/CCC AAT GGT CTA GCA TTC AAC TAC CGA A | 106535025 | 8681 | 60.2 |
| AJ_P10 | 85653689C04 | | AJ_892 | /5AmMC6/CCC AAT GTT TCA GAC CTG ACT ACC TGA A | 106535026 | 8672 | 60 |
| AJ_P10 | 85653690C05 | | AJ_893 | /5AmMC6/CCC AAT AAC AGA ACC CAT GCT CAG GTA A | 106577190 | 8699 | 60.3 |
| AJ_P10 | 85653691C06 | | AJ_894 | /5AmMC6/CCC AAA CAC GTT GCA CTT TAC TTT GGA A | 106535028 | 8687 | 60 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P10 | 85653692C07 | AJ_895 | /5AmMC6/CCC AAT GCT GAC GTA CAC AAA CAA GTA A | 106535029 | 8723 | 59.3 |
| AJ_P10 | 85653693C08 | AJ_896 | /5AmMC6/CCC AAA GCT GTT GCT GTT AAA CCG TAA A | 106535030 | 8736 | 59.9 |
| AJ_P10 | 85653694C09 | AJ_897 | /5AmMC6/CCC AAC ATG TTG TGG TAG CTA CCG AAA A | 106535031 | 8761 | 60.8 |
| AJ_P10 | 85653695C10 | AJ_898 | /5AmMC6/CCC AAA TCT CTG TGG TAG CAT AAC GGA A | 106535032 | 8761 | 60.2 |
| AJ_P10 | 85653696C11 | AJ_899 | /5AmMC6/CCC AAG AGC TCT CGT GTT ACT AAA GTA A | 106535033 | 8736 | 57.8 |
| AJ_P10 | 85653697C12 | AJ_900 | /5AmMC6/CCC AAA GCC TTG GTT GTC AGT CTT AAA A | 106535034 | 8727 | 59.5 |
| AJ_P10 | 85653698D01 | AJ_901 | /5AmMC6/CCC AAG TAC CTC TAC TCT GAC TCA GGA A | 106535035 | 8657 | 60.2 |
| AJ_P10 | 85653699D02 | AJ_902 | /5AmMC6/CCC AAG GCA TAC AAC TCT GAC CTG TCA A | 106535036 | 8666 | 61.9 |
| AJ_P10 | 85653700D03 | AJ_903 | /5AmMC6/CCC AAC CAG TAA ACC AGT GAC TTG CCA A | 106535037 | 8675 | 62.6 |
| AJ_P10 | 85653701D04 | AJ_904 | /5AmMC6/CCC AAG ACT CCT TGG TTC AAC GGT AAA A | 106535038 | 8721 | 60.6 |
| AJ_P10 | 85653702D05 | AJ_905 | /5AmMC6/CCC AAC TTA GGT AGG TAG CAC ACT GAA A | 106535039 | 8770 | 59.7 |
| AJ_P10 | 85653703D06 | AJ_906 | /5AmMC6/CCC AAA GTC CAG AGC ACA TTT CAT AGA A | 106535040 | 8714 | 58.8 |
| AJ_P10 | 85653704D07 | AJ_907 | /5AmMC6/CCC AAG GCT ACA TGT CAC CTA ACC AGA A | 106535041 | 8675 | 61.6 |
| AJ_P10 | 85653705D08 | AJ_908 | /5AmMC6/CCC AAT GTC CAT GAC TTT CCT AAC GGA A | 106535042 | 8672 | 60.4 |
| AJ_P10 | 85653706D09 | AJ_909 | /5AmMC6/CCC AAG CAC ATG GTT CCA CAT AAA CGA A | 106535043 | 8699 | 61.2 |
| AJ_P10 | 85653707D10 | AJ_910 | /5AmMC6/CCC AAG CCA TGT TGC ACA CTA CAA AGA A | 106535044 | 8699 | 61.4 |
| AJ_P10 | 85653708D11 | AJ_911 | /5AmMC6/CCC AAA CGC ATC AAA AGT TAG GGT ACA A | 106535045 | 8739 | 60.9 |
| AJ_P10 | 85653709D12 | AJ_912 | /5AmMC6/CCC AAC CAC TCG TAG TCT ACT AGG AGA A | 106535046 | 8706 | 60.1 |
| AJ_P10 | 85653710E01 | AJ_913 | /5AmMC6/CCC AAA CTG TGT TGT CTC ACT AGA GGA A | 106535047 | 8752 | 59.8 |
| AJ_P10 | 85653711E02 | AJ_914 | /5AmMC6/CCC AAG TAC TCC TAC TCG TAC ATG GCA A | 106535048 | 8657 | 61.1 |
| AJ_P10 | 85653712E03 | AJ_915 | /5AmMC6/CCC AAT AAC ACG AAA GCT TGT GCA TCA A | 106535049 | 8714 | 59.9 |
| AJ_P10 | 85653713E04 | AJ_916 | /5AmMC6/CCC AAT TTC TAG AAC TGT GCT TGC ACA A | 106535050 | 8687 | 59.6 |
| AJ_P10 | 85653714E05 | AJ_917 | /5AmMC6/CCC AAG GTG TAC CTT TGA CCA GTG AGA A | 106535051 | 8777 | 61.7 |
| AJ_P10 | 85653715E06 | AJ_918 | /5AmMC6/CCC AAG TTA CCT CTT GCC ATA CGA GAA A | 106535052 | 8681 | 60.1 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P10 | 85653716E07 | | AJ_919 | /5AmMC6/CCC AAG AAC GTT CTG CTC ATA GCA AAA A | 106535053 | 8714 | 59.6 |
| AJ_P10 | 85653717E08 | | AJ_920 | /5AmMC6/CCC AAA CGC TTC TTC ATT GTA ACA GGA A | 106535054 | 8696 | 59.4 |
| AJ_P10 | 85653718E09 | | AJ_921 | /5AmMC6/CCC AAG AGT CTC GAC TCC TCT ACT AGA A | 106535055 | 8657 | 59.8 |
| AJ_P10 | 85653719E10 | | AJ_922 | /5AmMC6/CCC AAG AGT ACA GAA CCT CAC TTT CGA A | 106535056 | 8690 | 59.8 |
| AJ_P10 | 85653720E11 | | AJ_923 | /5AmMC6/CCC AAG TAC TGC TGA CAC AAC TAA CGA A | 106535057 | 8699 | 60.3 |
| AJ_P10 | 85653721E12 | | AJ_924 | /5AmMC6/CCC AAA GCC TTT GGT AGT CAG ACA GTA A | 106535058 | 8761 | 60.1 |
| AJ_P10 | 85653722F01 | | AJ_925 | /5AmMC6/CCC AAA GGC TAC TCA GAA CAA CTT TGA A | 106535059 | 8714 | 59 |
| AJ_P10 | 85653723F02 | | AJ_926 | /5AmMC6/CCC AAG TAC CTC ACT CAA GCA TCA GGA A | 106535060 | 8675 | 61.6 |
| AJ_P10 | 85653724F03 | | AJ_927 | /5AmMC6/CCC AAA TAG TCT CAG TGT GCT AGT GCA A | 106535061 | 8752 | 60.3 |
| AJ_P10 | 85653725F04 | | AJ_928 | /5AmMC6/CCC AAG TCC ACT TTC TGC ACT AAG GGA A | 106535062 | 8697 | 62 |
| AJ_P10 | 85653726F05 | | AJ_929 | /5AmMC6/CCC AAC AGT GCT TGC AAA CAT CAA AGA A | 106535063 | 8723 | 60.3 |
| AJ_P10 | 85653727F06 | | AJ_930 | /5AmMC6/CCC AAA CTT GTC TCT CTG AGT ACA GGA A | 106535064 | 8712 | 59.5 |
| AJ_P10 | 85653728F07 | | AJ_931 | /5AmMC6/CCC AAA GTT CTC CAC AAG TGT CAG AGA A | 106535065 | 8730 | 60.2 |
| AJ_P10 | 85653729F08 | | AJ_932 | /5AmMC6/CCC AAG TCT TCA CAC TCA GAA CGT GAA A | 106535066 | 8690 | 60.4 |
| AJ_P10 | 85653730F09 | | AJ_933 | /5AmMC6/CCC AAT CCG AAG TTG CGT AGA CTA AAA A | 106535067 | 8754 | 59 |
| AJ_P10 | 85653731F10 | | AJ_934 | /5AmMC6/CCC AAG AAA CAT CGT ACA CAG TCT CGA A | 106535068 | 8699 | 60.1 |
| AJ_P10 | 85653732F11 | | AJ_935 | /5AmMC6/CCC AAG AAC CAT CAC CTG TCA GCA TGA A | 106535069 | 8675 | 62.4 |
| AJ_P10 | 85653733F12 | | AJ_936 | /5AmMC6/CCC AAC GAC ATA CCT AAA GCA TGG TGA A | 106535070 | 8739 | 60.5 |
| AJ_P10 | 85653734G01 | | AJ_937 | /5AmMC6/CCC AAG GTC ACA GCA CTT TCC ACT AGA A | 106535071 | 8666 | 61.9 |
| AJ_P10 | 85653735G02 | | AJ_938 | /5AmMC6/CCC AAC GAG TTA CAC GTT TGC CTA AAA A | 106535072 | 8705 | 59.6 |
| AJ_P10 | 85653736G03 | | AJ_939 | /5AmMC6/CCC AAG TAC GCT AGT CTC TCA CAT AGA A | 106535073 | 8681 | 58.9 |
| AJ_P10 | 85653737G04 | | AJ_940 | /5AmMC6/CCC AAA GTG TCT GAC CAT ACT TAC CGA A | 106535074 | 8681 | 59.9 |
| AJ_P10 | 85653738G05 | | AJ_941 | /5AmMC6/CCC AAC GTT CCA TAC CAA GGA CAT AGA A | 106535075 | 8699 | 60 |
| AJ_P10 | 85653739G06 | | AJ_942 | /5AmMC6/CCC AAG GAC TTC GAC TTC CTA CTA AGA A | 106535076 | 8681 | 59.1 |

TABLE 1-continued

Oligonucleotide Probe Sequences for Custom Microarray
(Table 1 discloses SEQ ID NOS 2-961, respectively, in order of appearance)

| Plate Name | IDT Ref. # | Well Pos. | Seq Name | Sequence | IDT Mfg ID | Calc'd Molec. Weight | $T_m$ |
|---|---|---|---|---|---|---|---|
| AJ_P10 | 85653740G07 | | AJ_943 | /5AmMC6/CCC AAT GAC GTT GTA AAC CTC TCA CGA A | 106535077 | 8681 | 60.5 |
| AJ_P10 | 85653741G08 | | AJ_944 | /5AmMC6/CCC AAG CAC TGT GTA AAC AAC CTT CGA A | 106535078 | 8690 | 61 |
| AJ_P10 | 85653742G09 | | AJ_945 | /5AmMC6/CCC AAC ATG TAG AGA AAC TCT CGA GAA A | 106535079 | 8763 | 58.1 |
| AJ_P10 | 85653743G10 | | AJ_946 | /5AmMC6/CCC AAC AGC TTC CTC ATA GTC TTA GGA A | 106535080 | 8672 | 59.5 |
| AJ_P10 | 85653744G11 | | AJ_947 | /5AmMC6/CCC AAG TCC TAC ACA CAG TCA TAC GGA A | 106535081 | 8675 | 61.3 |
| AJ_P10 | 85653745G12 | | AJ_948 | /5AmMC6/CCC AAG TCC ATA CAT CCG AAC TGT GCA A | 106535082 | 8666 | 62.3 |
| AJ_P10 | 85653746H01 | | AJ_949 | /5AmMC6/CCC AAG AAC TTC CAC TTA GCA TGT GCA A | 106535083 | 8681 | 61 |
| AJ_P10 | 85653747H02 | | AJ_950 | /5AmMC6/CCC AAG GTT CTA CAT CAC GTA CGC AAA A | 106535084 | 8690 | 60.7 |
| AJ_P10 | 85653748H03 | | AJ_951 | /5AmMC6/CCC AAG AGT GCT ACC TTC GTA CAG AAA A | 106535085 | 8730 | 60 |
| AJ_P10 | 85653749H04 | | AJ_952 | /5AmMC6/CCC AAA TAA GTC CTG AAG GAA CGC ATA A | 106535086 | 8763 | 58.8 |
| AJ_P10 | 85653750H05 | | AJ_953 | /5AmMC6/CCC AAG TGC AAC GAG ACC TTT GAC AAA A | 106535087 | 8739 | 61.4 |
| AJ_P10 | 85653751H06 | | AJ_954 | /5AmMC6/CCC AAG CAC TGT TGA AAC CCT TTC GAA A | 106535088 | 8681 | 61.5 |
| AJ_P10 | 85653752H07 | | AJ_955 | /5AmMC6/CCC AAA CTC GTC ACC TTT GGG TAA ACA A | 106535089 | 8681 | 61 |
| AJ_P10 | 85653753H08 | | AJ_956 | /5AmMC6/CCC AAA GCC TTC TTG GTC ATA GAC AGA A | 106535090 | 8721 | 60.2 |
| AJ_P10 | 85653754H09 | | AJ_957 | /5AmMC6/CCC AAC AAC GGT ACT TTG TTG GTA GCA A | 106535091 | 8752 | 61.1 |
| AJ_P10 | 85653755H10 | | AJ_958 | /5AmMC6/CCC AAC ATT CTG GTG TTA CGA ACT GGA A | 106535092 | 8752 | 60.6 |
| AJ_P10 | 85653756H11 | | AJ_959 | /5AmMC6/CCC AAT GAA ACC ATC CAT GTC AGA GCA A | 106535093 | 8699 | 61 |
| AJ_P10 | 85653757H12 | | AJ_960 | /5AmMC6/CCC AAA ACT GAC CAT TGT GGT GTG CAA A | 106535094 | 8761 | 61.9 |

Example 11

Titration or Dilution Series

The ability to perform multiple experiments in parallel enables straightforward exploration of the counting results from samples with a range of starting concentrations or amounts of target, sometimes known as a titration experiment or a dilution series.

Figure 26:
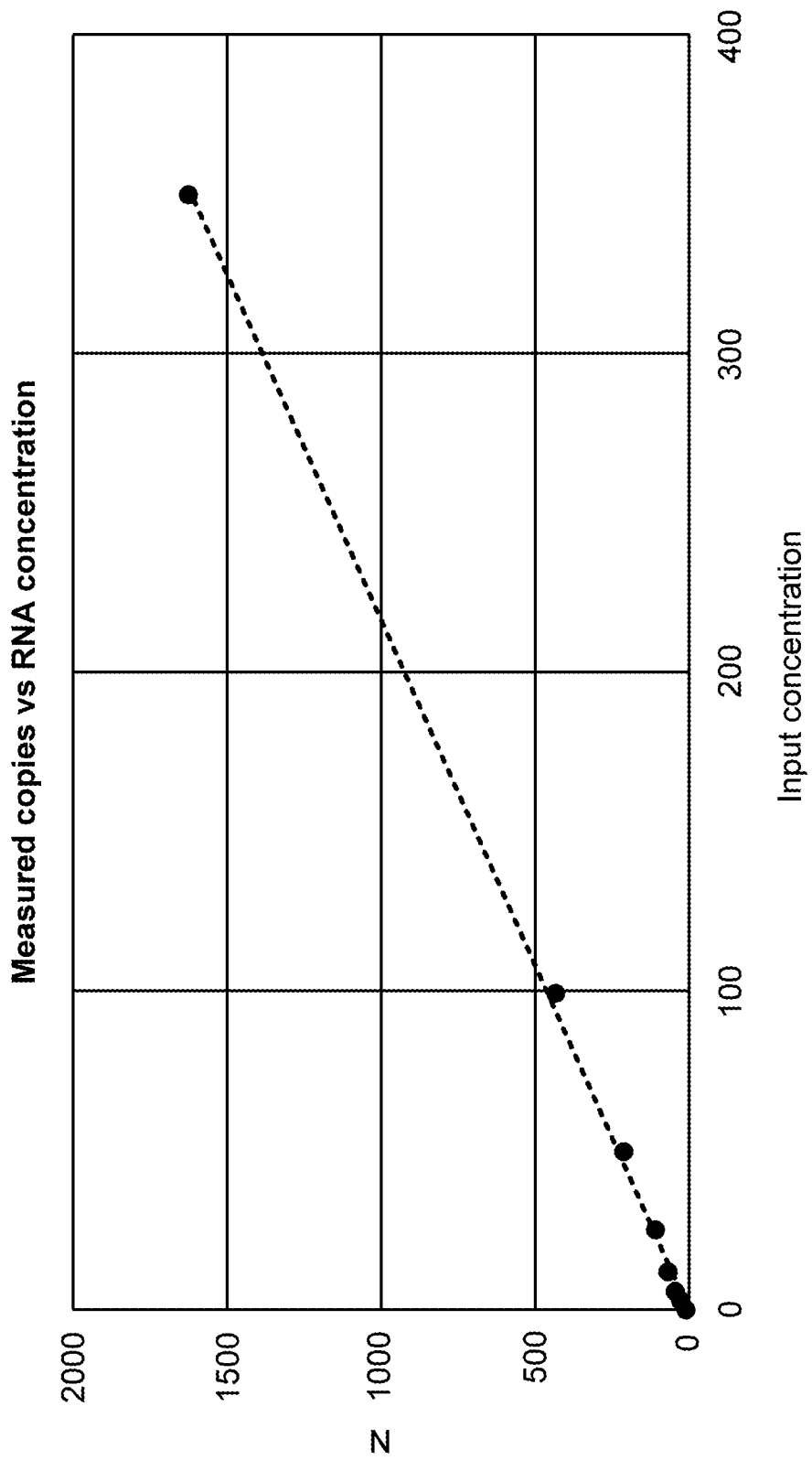
FIG. 26 shows dilution series data for using digital counting of labeled features on an array to measure the number of target RNA molecules in a sample.

An example of dilution series data for a labeled RPLPO gene sequence is shown in FIG. 26. Plotted in the figure is the counting result N for each array where the nominal starting concentration of mRNA in the reaction is shown on the X axis.

Figure 27:
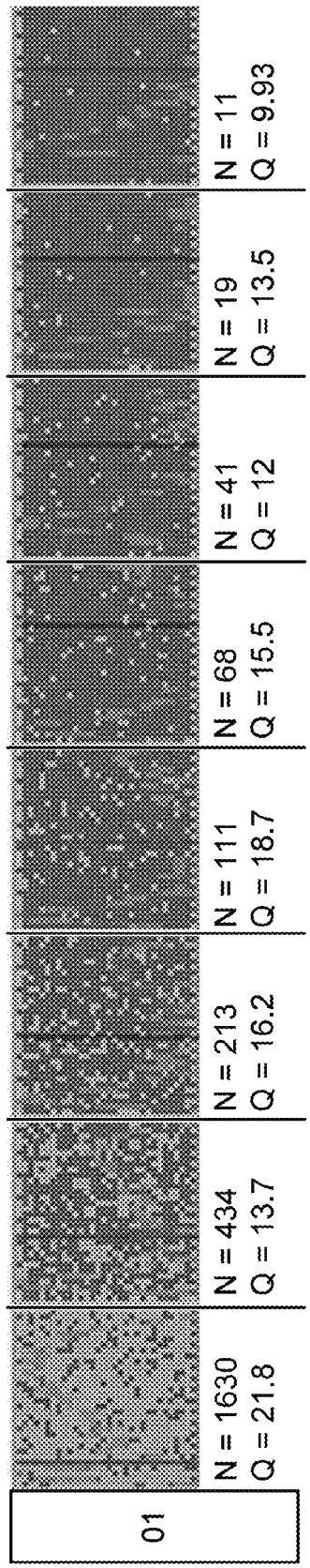
FIG. 27 shows a screenshot of the output data provided by the system software for a dilution series experiment. For each array used in the dilution series experiment, the software displays a histogram of feature intensity data with a blue line indicating the value of the threshold used for counting, overlaid on a digital representation of the array.

Some of the graphical output from the analysis software for the same experiment is shown in FIG. 27. For each array, there is a compound display with the following elements: (i) an intensity histogram (green) for the index spots, (ii) a blue line registered with the histogram, showing the dynamic threshold for spot counting, (iii) a 32×32 grid which is a digital representation of each array. A white site in the grid denotes a spot whose intensity was above the dynamic threshold, and a black site denotes that the intensity was below the dynamic threshold, and (iv) the result N and the quality score Q is reported for each array as text.

While preferred embodiments of the present invention have been shown and described herein, it will be obvious to those skilled in the art that such embodiments may be provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. An array reader system comprising
a computer system comprising a digital processor configured to execute computer-executable instructions to at least:
(a) acquiring image data of a region of an array, wherein the array comprises a plurality of stochastically labeled and non-labeled features, and wherein the features comprise oligonucleotide probes;
(b) measuring a signal intensity and a local background intensity for one of the plurality of stochastically labeled and non-labeled features based on the acquired image data;
(c) calculating a local background corrected signal intensity for the one of the plurality of stochastically labeled and non-labeled features using the signal intensity and the local background intensity measured in (b);
(d) transforming the local background corrected signal intensity calculated in (c) for the one of the plurality of stochastically labeled and non-labeled features to determine the number of stochastically labeled and non-labeled features in the of the array; and
(e) calculating the absolute number of a target molecule based on the number of stochastically labeled and non-labeled features determined in (d) within the region of the array.

2. The array reader system of claim 1, further comprising an optical imaging system that comprises one or more image sensors and an illumination system, wherein the illumination system comprises at least one light source; and
wherein acquiring the image data of the region of the array comprises acquiring the image data of the region of the array from the optical imaging system.

3. The array reader system of claim 1, wherein the array comprises a microarray, microscope slide, or microwell plate.

4. The array reader system of claim 2, wherein the optical imaging system has a magnification of less than 1, equal to 1, or greater than 1.

5. The array reader system of claim 2, wherein the optical imaging system comprises a fluorescence imaging system.

6. The array reader system of claim 2, wherein the optical imaging system comprises a phosphorescence imaging system.

7. The array reader system of claim 2, wherein the optical imaging system comprises an imaging system that operates in a transmitted light, reflected light, or scattered light imaging mode, or combinations thereof.

8. The array reader system of claim 2, wherein the one or more image sensors have a resolution of at least 320×240 pixels.

9. The array reader system of claim 2, wherein the one or more image sensors are CCD image sensors.

10. The array reader system of claim 2, wherein the one or more image sensors are CMOS Image sensors.

11. The array reader system of claim 2, wherein the one or more image sensors comprise one or more circuit boards.

12. The array reader system of claim 2, wherein the optical imaging system further comprises one or more components selected from the group including, but not limited to, a microscope objective, a camera lens, a finite-conjugate lens, an infinite-conjugate lens, a plano-convex lens, a double convex lens, a plano-concave lens, a double concave lens, an achromatic cemented doublet, or a bandpass filter.

13. The array reader system of claim 5, wherein the fluorescence imaging system is designed for use with fluorescein, Cy3, Cy5, or phycoerythrin fluorophores.

14. The array reader system of claim 2, wherein the at least one light source is an LED or LED assembly.

15. The array reader system of claim 2, wherein the at least one light source is electronically synchronized with the image sensor, the at least one light source being turned on when the image sensor is acquiring an image and turned off when the image sensor is not acquiring an image.

16. The array reader system of claim 2, wherein the illumination system is an off-axis illumination system.

17. The array reader system of claim 16, wherein the off-axis illumination system satisfies the Scheimpflug condition.

18. The array reader system of claim 16, wherein the off-axis illumination system does not satisfy the Scheimpflug condition.

19. The array reader system of claim 16, wherein the off-axis illumination subsystem is a Kohler illumination system.

20. The array reader system of claim 16, wherein the off-axis illumination system is an Abbe illumination system.

21. The array reader system of claim 2, wherein the illumination system is an epi-illumination system.

22. The array reader system of claim 21, wherein the epi-illumination system is a Kohler illumination system.

23. The array reader system of claim 21, wherein the epi-illumination system is an Abbe illumination system.

24. The array reader system of claim 2, wherein the illumination system is a trans-illumination system.

25. The array reader system of claim 24, wherein the trans-illumination system is a Kohler illumination system.

26. The array reader system of claim 24, wherein the trans-illumination system is an Abbe illumination system.

27. The array reader system of claim 2, wherein the optical imaging system further comprises a translation stage.

28. The array reader system of claim 27, wherein the translation stage is a single-axis translation stage.

29. The array reader system of claim 27, wherein the translation stage is a dual-axis translation stage.

30. The array reader system of claim 27, wherein the translation stage is a multi-axis translation stage.

31. The array reader system of claim 1, wherein the digital processor is configured to automatically locates features of the array within the acquired image data.

32. The array reader system of claim 1, wherein calculating the local background corrected signal intensity for the one of the plurality of stochastically labeled and non-labeled features using the signal intensity and the local background intensity measured in (b) comprises:
  (i) centering a predefined analysis window on an array feature within an image,
  (ii) calculating an intensity value statistic for signal and background pixels according to a predefined pattern of pixels within the array feature, and
  (iii) utilizing the intensity value statistic for signal and background pixels to calculate the local background corrected signal intensity for the array feature.

33. The array reader system of claim 32, wherein the digital processor is configured to perform a k-means clustering analysis of the background corrected signal intensity values for the array features to determine a dynamic signal intensity threshold for discrimination between the plurality of stochastically labeled and non-labeled features of the array.

34. The array reader system of claim 32, wherein the digital processor is configured to perform a k-medoids clustering analysis of the background corrected signal intensity values for the array features to determine a dynamic signal intensity threshold for discrimination between the plurality of stochastically labeled and non-labeled features of the array.

35. The array reader system of claim 32, wherein the digital processor is configured to perform a mixture model statistical analysis of the background corrected signal intensity values for the array features to determine a dynamic signal intensity threshold for discrimination between the plurality of stochastically labeled and non-labeled features of the array.

36. The array reader system of claim 32, wherein the digital processor is configured to perform an empirical analysis based on sorting of background corrected signal intensity values for the array features to determine a dynamic signal intensity threshold for discrimination between the plurality of stochastically labeled and non-labeled features of the array.

37. The array reader system of claim 32, wherein the digital processor is configured to perform an empirical analysis based on sorting of pairwise differences in background corrected signal intensity values for the array features to determine a dynamic signal intensity threshold for discrimination between the plurality of stochastically labeled and non-labeled features of the array.

38. The array reader system of claim 32, wherein the digital processor is configured to perform one or more statistical analyses of the background corrected signal intensity values for the array features to determine a dynamic signal intensity threshold for discrimination between the plurality of stochastically labeled and non-labeled features of the array, and wherein the one or more statistical analyses are selected from the list comprising k-means clustering, k-medoids clustering, mixture model statistical analysis, an empirical analysis, or any combination thereof.

39. The array reader system of claim 1, wherein calculating the absolute number of the target molecule based on the number of stochastically labeled and non-labeled features determined in (d) within the region of the array comprises calculate the absolute number of the target molecule based on the number of stochastically labeled features, the number of non-labeled features within the region of the array, and the predictions of the Poisson distribution.

40. The array reader system of claim 1, wherein the digital processor is configured to calculate a confidence interval for the number of target molecules.

41. The array reader system of claim 2, wherein the optical imaging system and computer system are combined within a single, stand-alone instrument.

42. The array reader system of claim 2, wherein the optical imaging system and computer system are configured as separate instrument modules.

43. The array reader system of claim 32, wherein the digital processor is configured to perform an analysis of the local background corrected signal intensities for the array features to determine a dynamic signal intensity threshold, and wherein the analysis comprises fitting a model function to the local background corrected signal intensities by varying model parameters.

44. The array reader system of claim 32, wherein the digital processor is configured to perform an analysis of the local background corrected signal intensities for the array features to determine a dynamic signal intensity threshold, and wherein the analysis comprises maximizing a quality metric relating to a statistical difference between feature intensities above the threshold and feature intensities below the threshold.

* * * * *

UNITED STATES PATENT AND TRADEMARK OFFICE
CERTIFICATE OF CORRECTION

PATENT NO. : 9,582,877 B2
APPLICATION NO. : 14/508911
DATED : February 28, 2017
INVENTOR(S) : Glenn Fu It is certified that error appears in the above-identified patent and that said Letters Patent is hereby corrected as shown below:

In the Claims

In Column 481 at Line 61, in Claim 1, change "in the of the array" to --in the region of the array--.

Signed and Sealed this
Twenty-ninth Day of May, 2018

Andrei Iancu
*Director of the United States Patent and Trademark Office*